US012673113B2

(12) United States Patent
Hubbell et al.

(10) Patent No.: US 12,673,113 B2
(45) Date of Patent: Jul. 7, 2026

(54) METHODS AND COMPOSITIONS FOR TREATING CANCER WITH CANCER-TARGETED ADJUVANTS

(71) Applicant: The University of Chicago, Chicago, IL (US)

(72) Inventors: Jeffrey A. Hubbell, Chicago, IL (US); David S. Wilson, Chicago, IL (US); Tiffany M. Marchell, Chicago, IL (US); Laura T. Gray, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 1195 days.

(21) Appl. No.: 17/596,106

(22) PCT Filed: Jun. 3, 2020

(86) PCT No.: PCT/US2020/070112
§ 371 (c)(1),
(2) Date: Dec. 3, 2021

(87) PCT Pub. No.: WO2020/247973
PCT Pub. Date: Dec. 10, 2020

(65) Prior Publication Data
US 2022/0305135 A1 Sep. 29, 2022

Related U.S. Application Data

(60) Provisional application No. 62/856,375, filed on Jun. 3, 2019.

(51) Int. Cl.
*A61K 47/68* (2017.01)
*A61K 39/395* (2006.01)
(Continued)

(52) U.S. Cl.
CPC ...... *A61K 47/6883* (2017.08); *A61K 39/3955* (2013.01); *A61K 47/643* (2017.08);
(Continued)

(58) Field of Classification Search
None
See application file for complete search history.

(56) References Cited

U.S. PATENT DOCUMENTS

2009/0081157 A1 3/2009 Kornbluth et al.
2009/0123467 A1 5/2009 Bedi et al.
(Continued)

FOREIGN PATENT DOCUMENTS

CN 103275220 A 9/2013
WO WO 2013/166110 11/2013
(Continued)

OTHER PUBLICATIONS

Zappasodi et al., Cancer Cell 33, Apr. 9, 2018, pp. 581-597 (Year: 2018).*
(Continued)

*Primary Examiner* — Karl J Puttlitz
(74) *Attorney, Agent, or Firm* — Norton Rose Fulbright US LLP

(57) ABSTRACT

Here, the inventors describe methods and compositions for targeting a TLR agonist to the tumor cell or stroma. Aspects of the disclosure relate to a polypeptide comprising a tumor targeting agent operatively linked to p(Man-TLR). Also disclosed are compositions and methods for treating cancer in a subject comprising administration of the polypeptide comprising the tumor targeting agent linked to p(Man-TLR) to the subject.

11 Claims, 27 Drawing Sheets

Specification includes a Sequence Listing.

(51) Int. Cl.
*A61K 47/64* (2017.01)
*A61P 35/00* (2006.01)

(52) U.S. Cl.
CPC ...... *A61K 47/6803* (2017.08); *A61K 47/6851* (2017.08); *A61P 35/00* (2018.01)

(56) References Cited

U.S. PATENT DOCUMENTS

| | | | |
|---|---|---|---|
| 2014/0256922 | A1 | 9/2014 | David et al. |
| 2015/0110742 | A1 | 4/2015 | Spiegel et al. |
| 2018/0280524 | A1 | 10/2018 | Hubbell et al. |
| 2019/0099485 | A1 | 4/2019 | Swartz et al. |
| 2020/0123228 | A1 | 4/2020 | Hubbell et al. |
| 2021/0040179 | A1 | 2/2021 | Hubbell et al. |
| 2021/0094995 | A1 | 4/2021 | Hubbell et al. |
| 2021/0171642 | A1 | 6/2021 | Hubbell et al. |
| 2021/0244812 | A1 | 8/2021 | Hubbell et al. |

FOREIGN PATENT DOCUMENTS

| | | | |
|---|---|---|---|
| WO | WO 2017/058996 | 4/2017 | |
| WO | WO-2017058996 A1 * | 4/2017 | ........... A61K 31/787 |
| WO | WO 2017/100305 | 6/2017 | |
| WO | WO 2018/195386 | 10/2018 | |
| WO | WO-2018195386 A1 * | 10/2018 | ............. A61K 38/18 |
| WO | WO 2019/006038 | 1/2019 | |
| WO | WO 2020/176478 | 9/2020 | |
| WO | WO 2020/247974 | 12/2020 | |
| WO | WO 2021/016640 | 1/2021 | |

OTHER PUBLICATIONS

Liang et al., Journal of Controlled Release, vol. 209, 2015, pp. 101-109 (Year: 2015).*

Flood et al., J Thromb Haemost. Jul. 2012; 10(7):1417-24 (Year: 2012).*

English translation of Office Communication issued in Chinese Patent Application No. 202080056122.6, dated Aug. 24, 2023.

Extended European Search Report issued in corresponding European Application No. 20818190.9, dated Jun. 9, 2023.

Gadd et al. "Targeted activation of toll-like receptors: conjugation of a toll-like receptor 7 agonist to a monoclonal antibody maintains antigen binding and specificity", *Bioconjugate Chemistry*, vol. 26, No. 8, pp. 1743-1752, 2015.

Bevaart et al., "The High-Affinity lgG Receptor, Fc;RI, Plays a Central Role in Antibody Therapy of Experimental Melanoma" *Cancer Res* 2006; 66: (3), 1261-1264.

Bussard et al., "Tumor-associated stromal cells as key contributors to the tumor microenvironment" *Breast Cancer Research* 2016, 18, 1-11.

International Search Report and Written Opinion issued in Corresponding PCT Application No. PCT/US2020/070112, dated Sep. 10, 2020.

International Search Report and Written Opinion issued in Corresponding PCT Application No. PCT/US2016/054315, dated Dec. 29, 2016.

Li et al., "Overexpression of CD47 predicts poor prognosis and promotes cancer cell invasion in high-grade serous ovarian carcinoma" *Am J Transl Res* 2017, 9(6), 2901-2910.

Majeti et al., "CD47 Is an Adverse Prognostic Factor and Therapeutic Antibody Target on Human Acute Myeloid Leukemia Stem Cells." *Cell* 2009, 138, 286-299.

Morse et al., "Phase I Study Utilizing a Novel Antigen-Presenting Cell-Targeted Vaccine with Toll-like Receptor Stimulation to Induce Immunity to Self-antigens in Cancer Patients" *Clinical Cancer Research* 2011, 17(14), 4844-4853.

Takechi et al., "A melanosomal membrane protein is a cell surface target for melanoma therapy." *Clin. Cancer Res.* 1996, 2, 1837-1842.

Thomson et al., "Pigmentation-Associated Glycoprotein of Human Melanomas and Melanocytes: Definition with a Mouse Monoclonal Antibody" *J. Invest. Dermatol.* 1985, 85, 169-174.

Tong, B. & Wang, M. "CD47 is a novel potent immunotherapy target in human malignancies: current studies and future promises". Future Oncology 2018, 14(21), doi:10.2217/fon-2018-0035.

Wilson et al., "Antigens reversibly conjugated to a polymeric glyco-adjuvant induce protective humoral and cellular immunity" *Natural Materials* 2019, 18, 175-185.

Zhao et al., "Prognostic significance of CD47 in human malignancies: a systematic review and meta-analysis" *Transl Cancer Res* 2018;7(3):609-621.

* cited by examiner

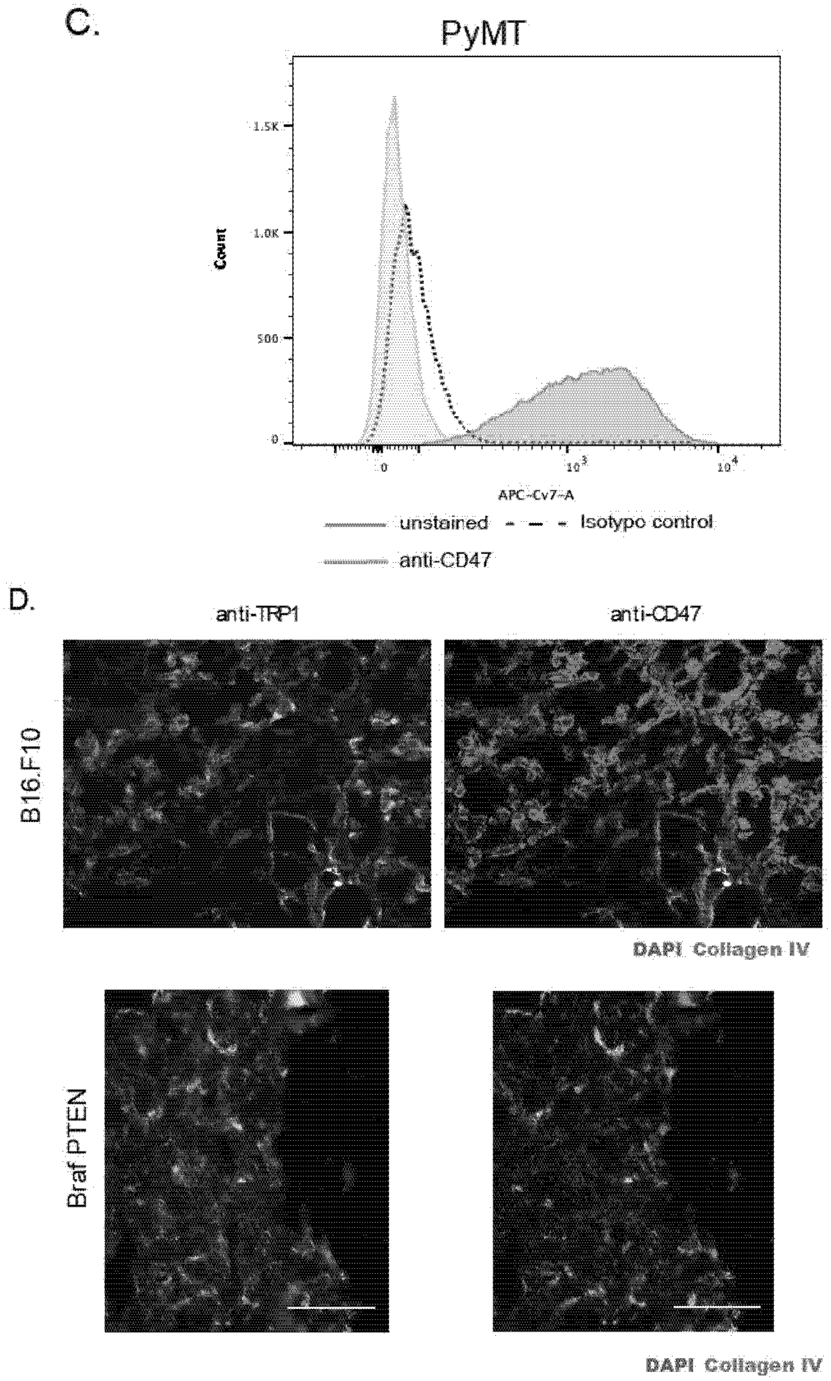
FIG. 1C-D

E.

A
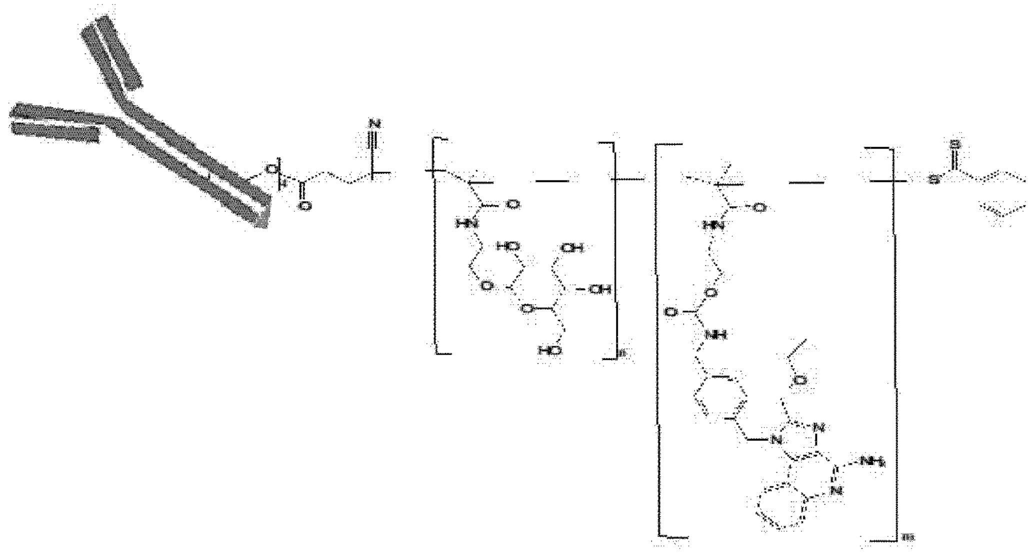
B
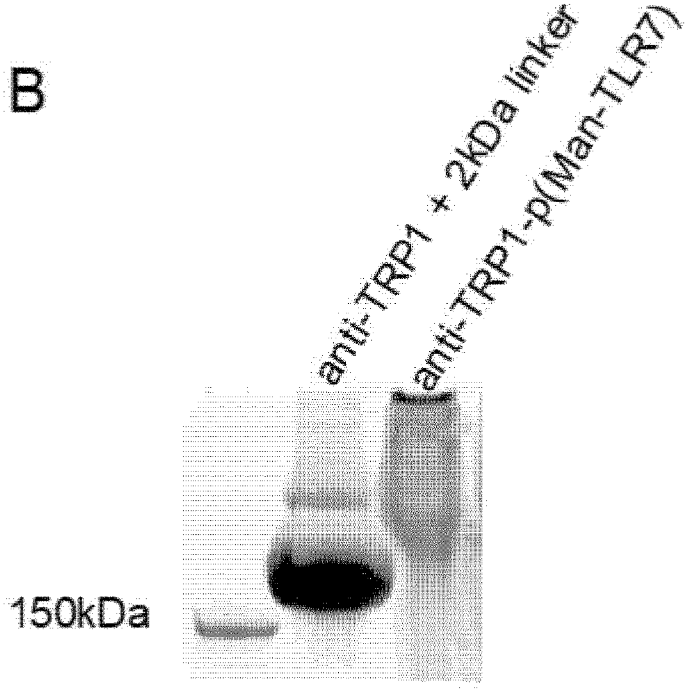
FIG. 2A-B

D.

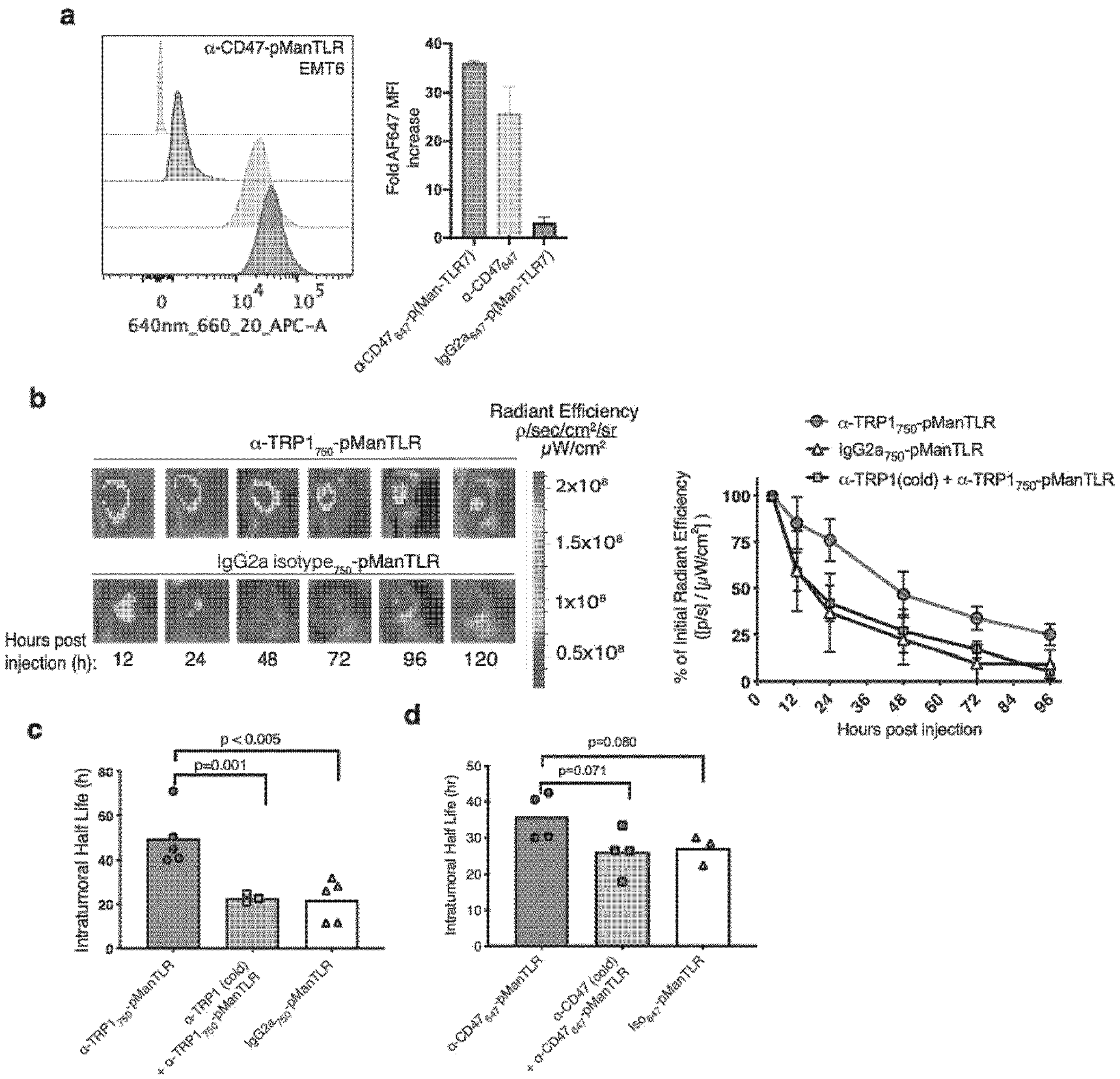
FIG. 3A-D

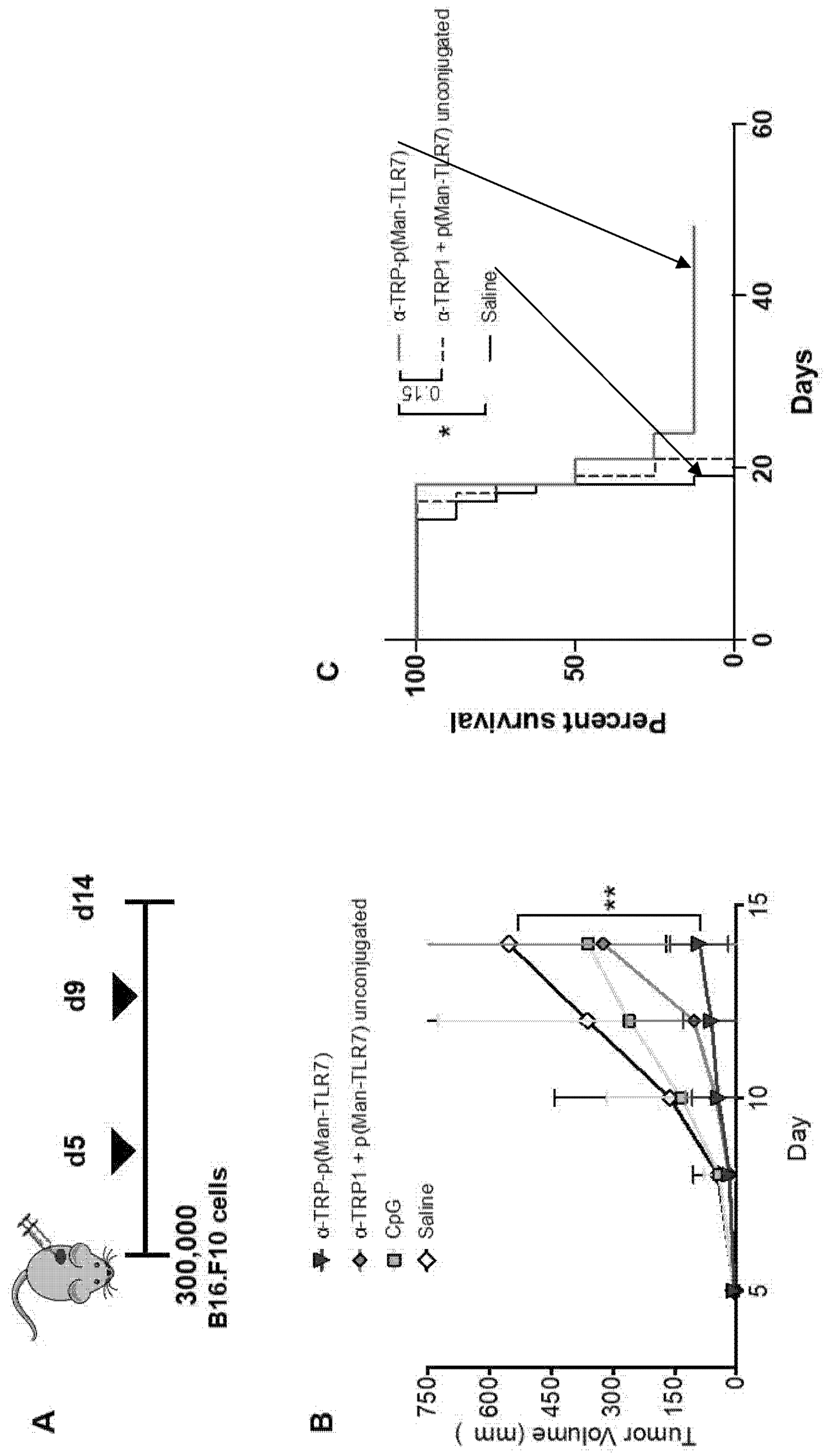
FIG. 4A-C

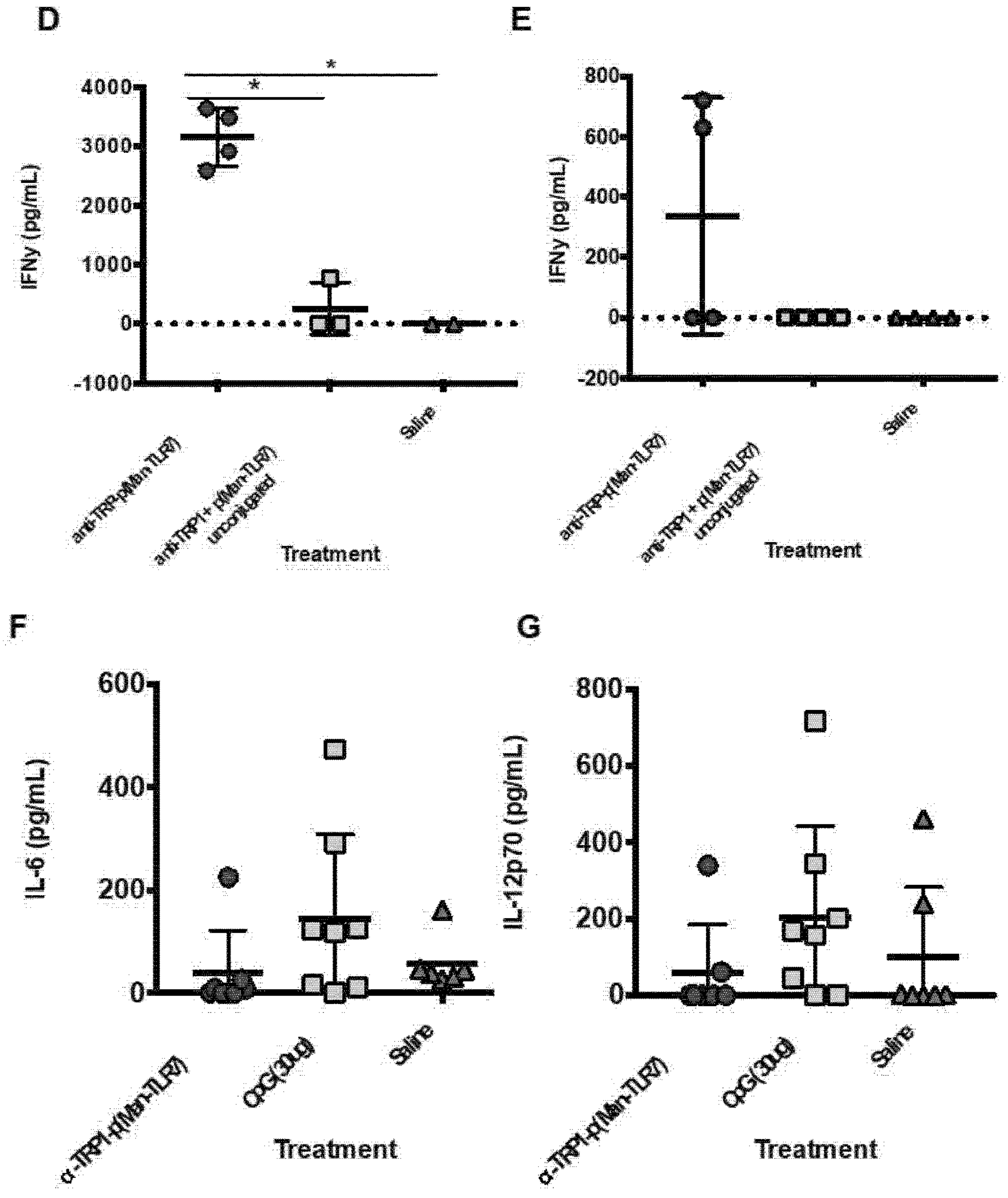
FIG. 4D-G

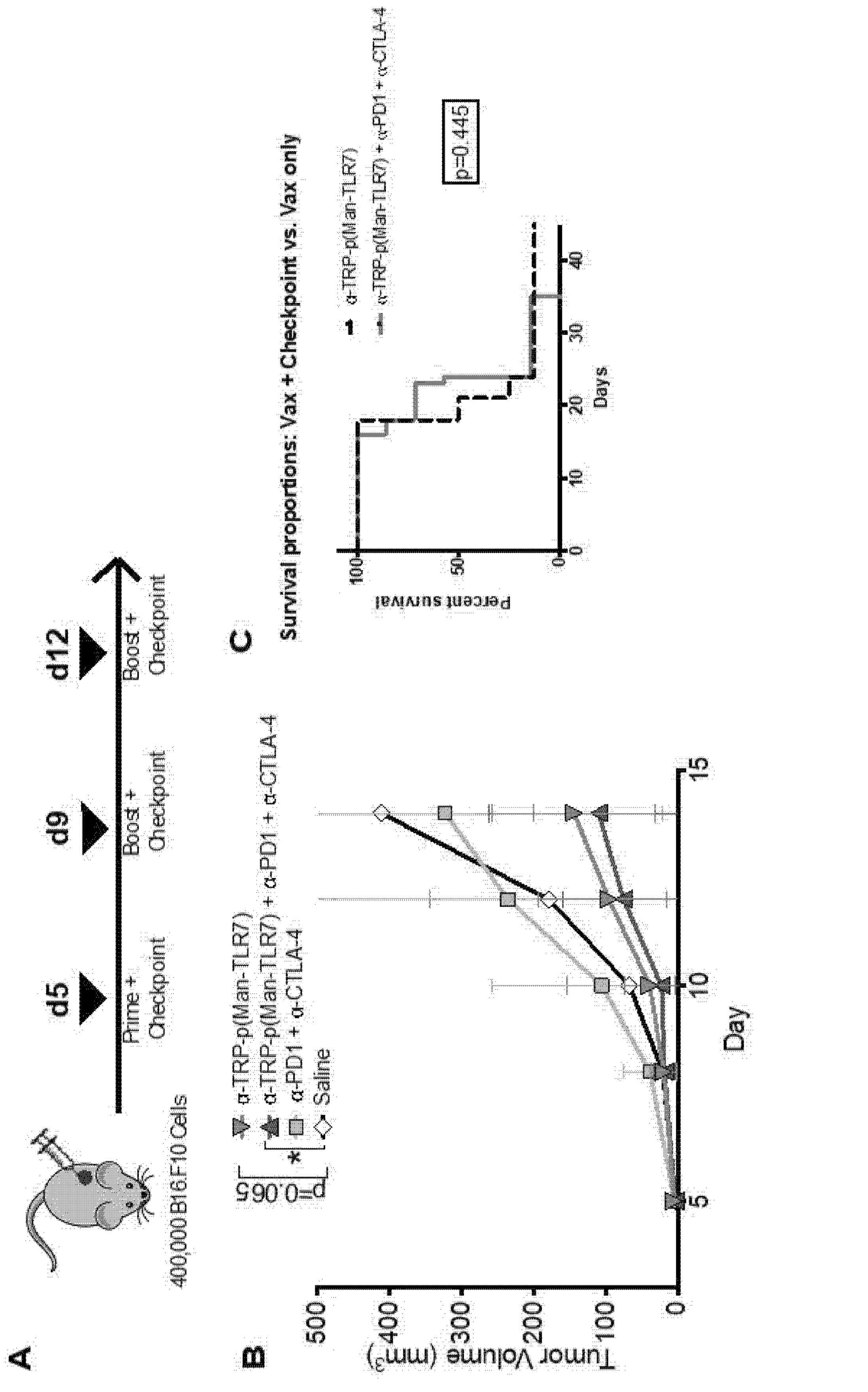
FIG. 5A-C

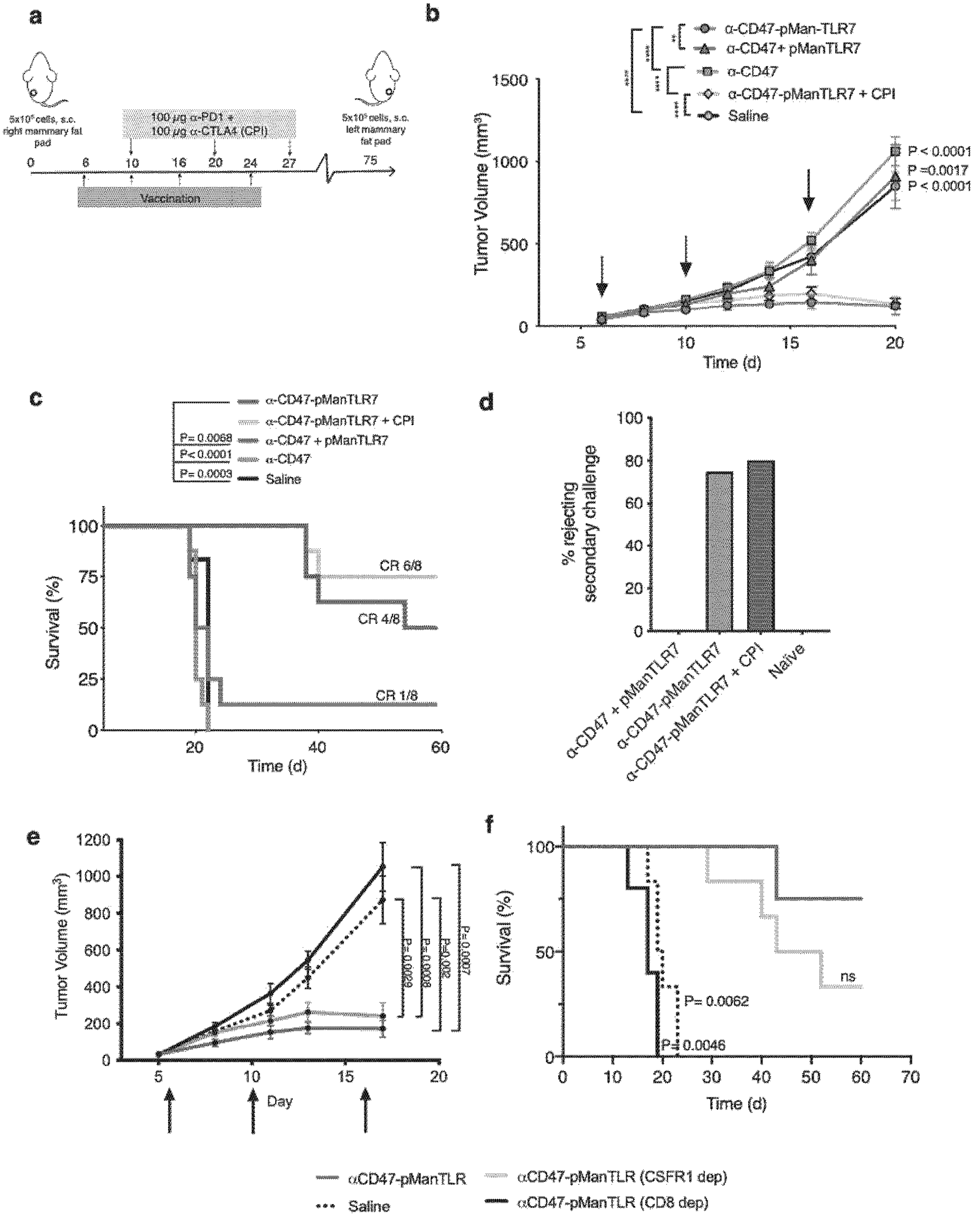
FIG. 6A-F

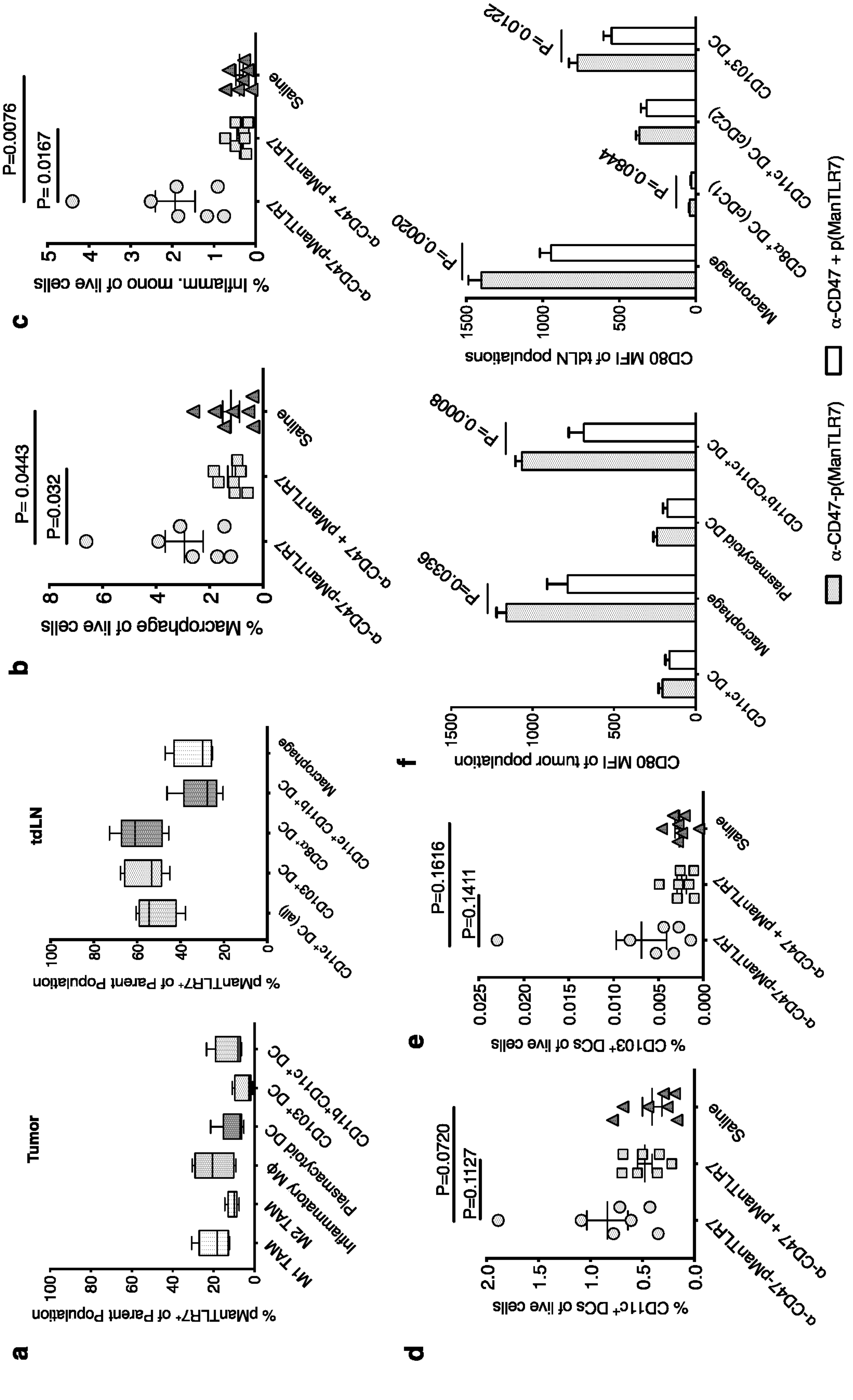
FIG. 7A-F

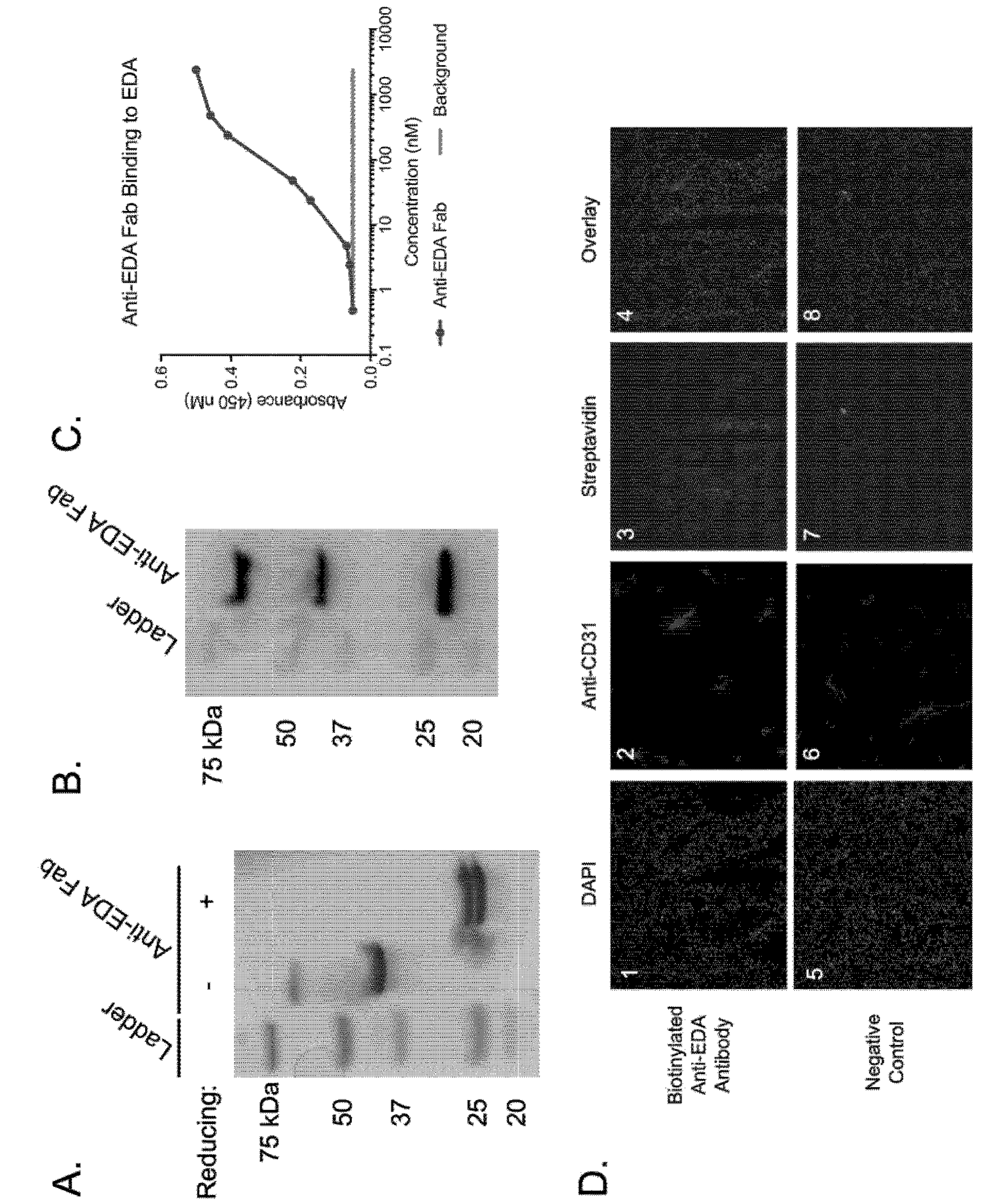
FIG. 8A-D

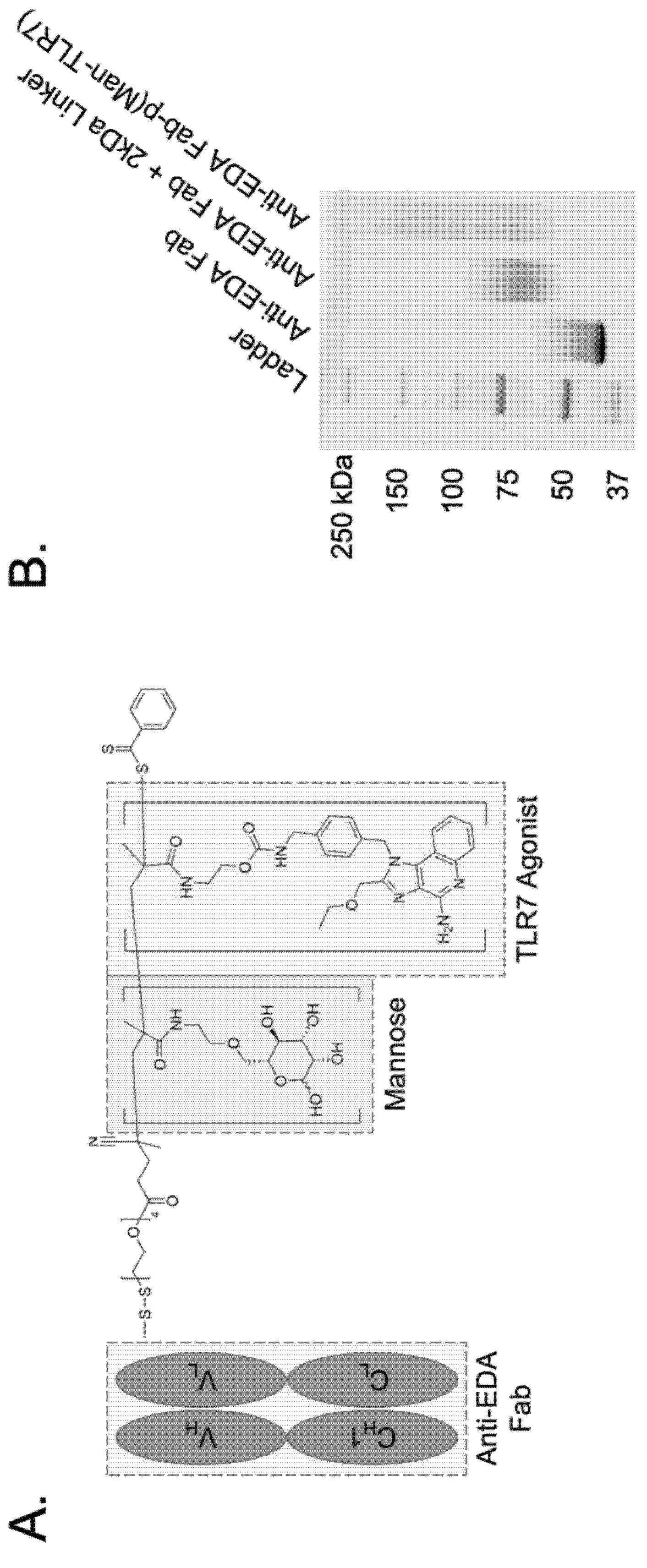
FIG. 9A-B

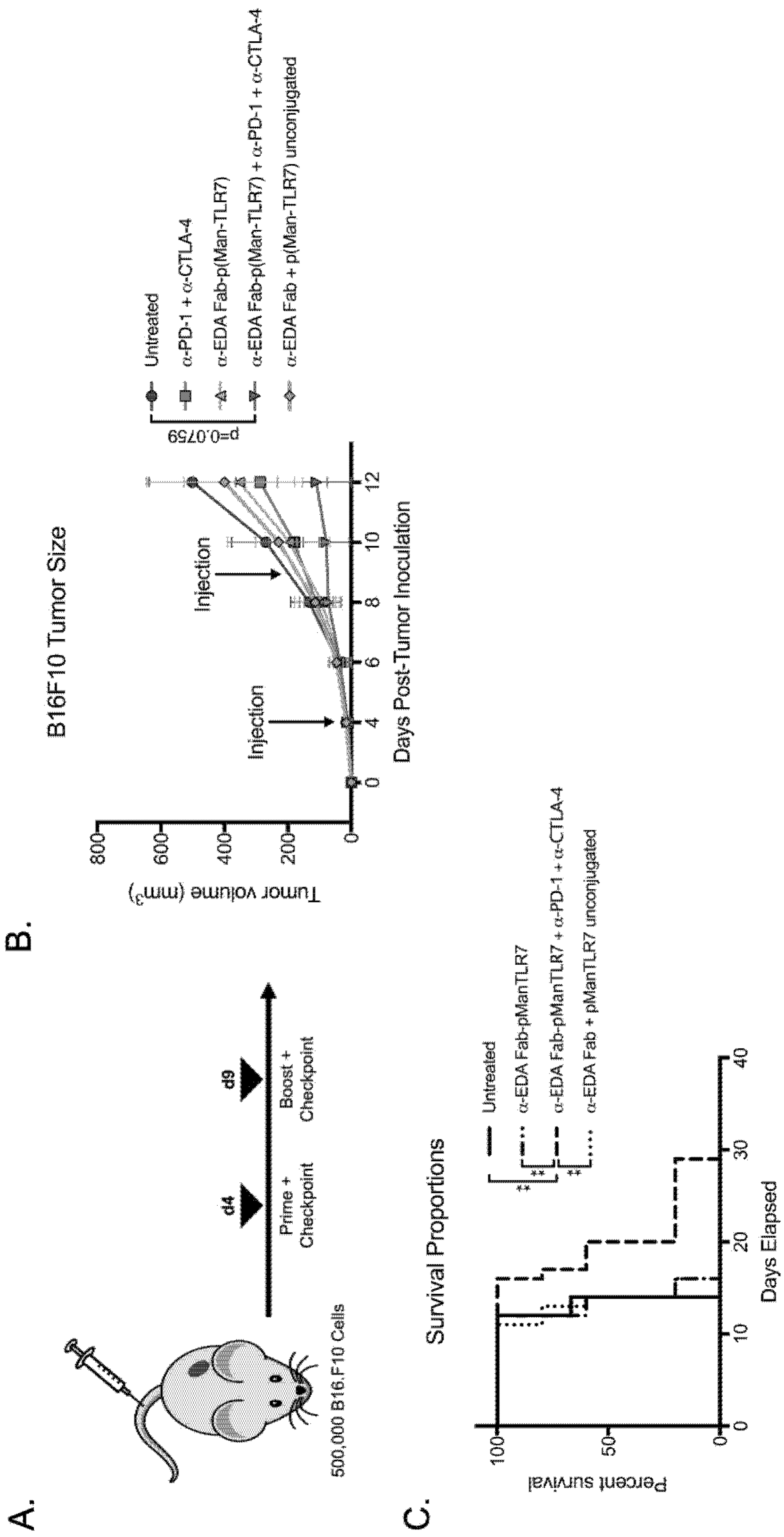
FIG. 10A-C

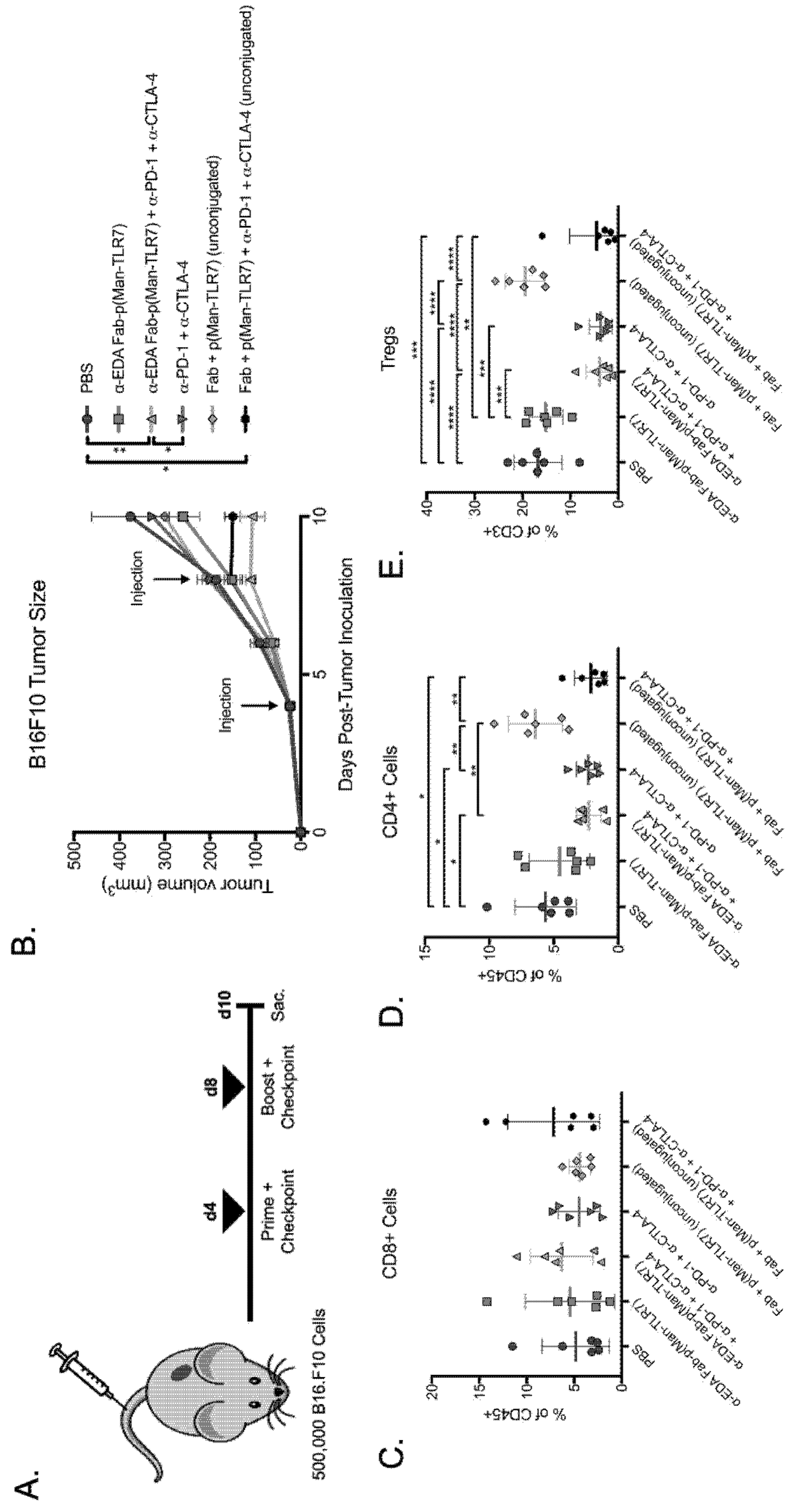
FIG. 11A-E

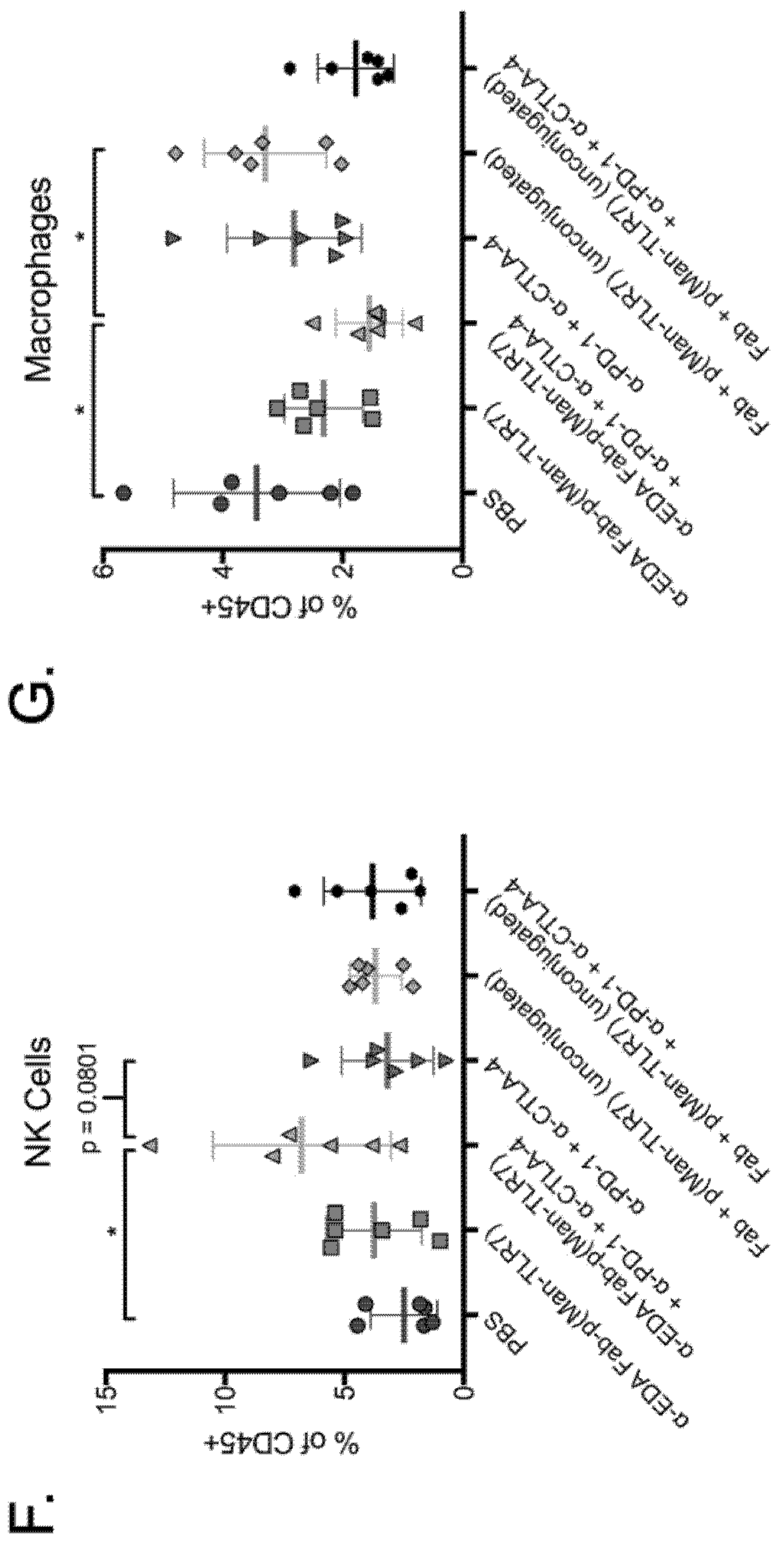
FIG. 11F-G

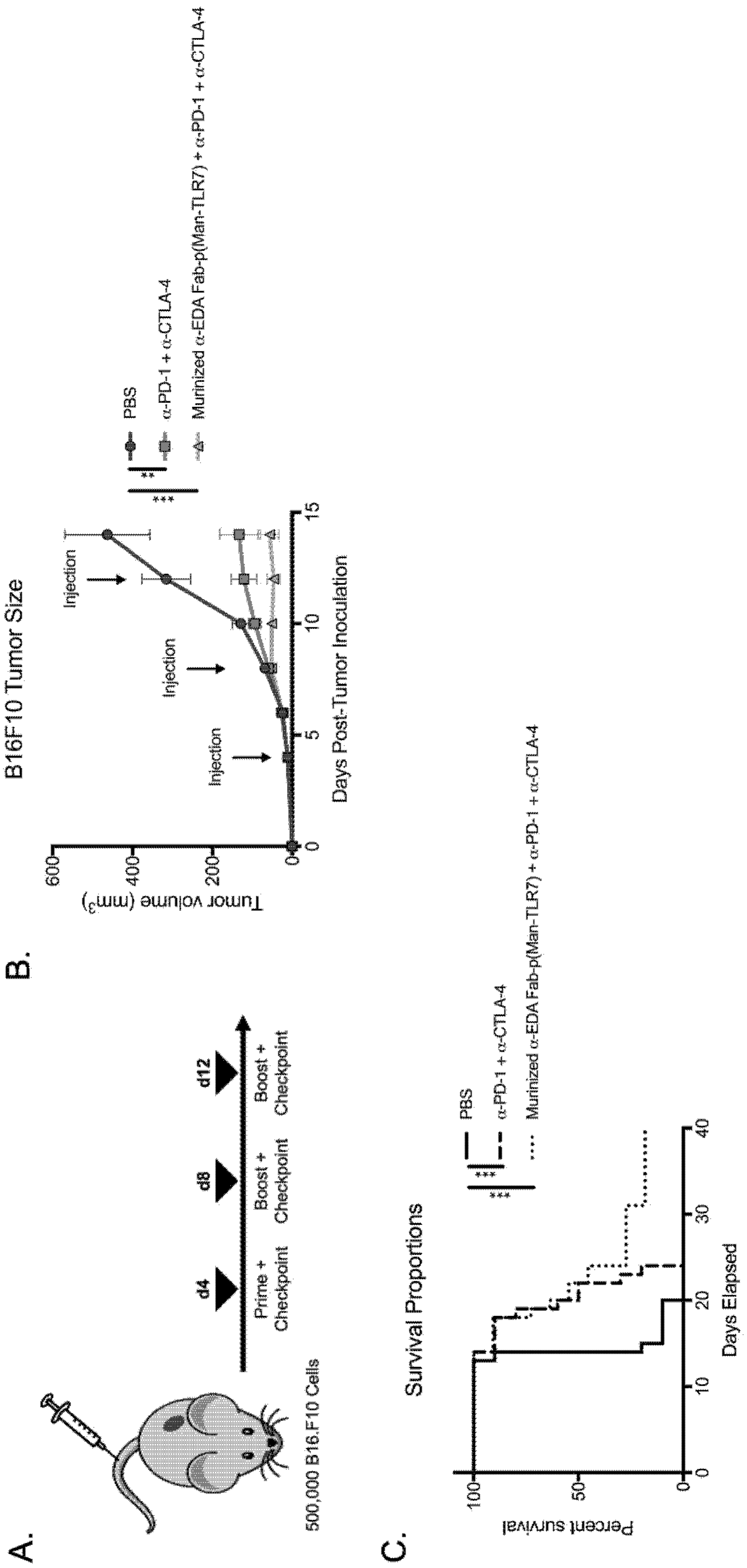
FIG. 12A-C

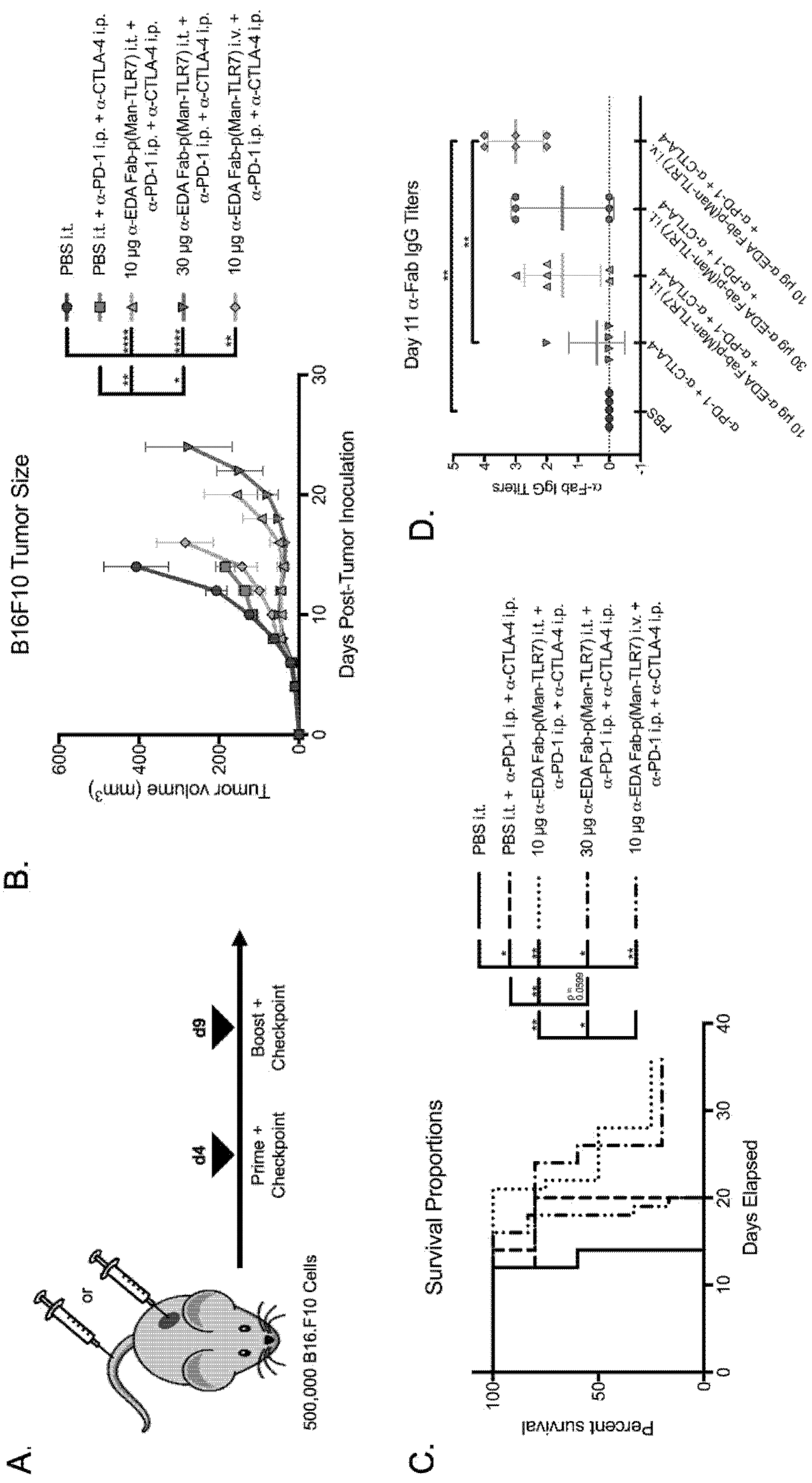
FIG. 13A-D

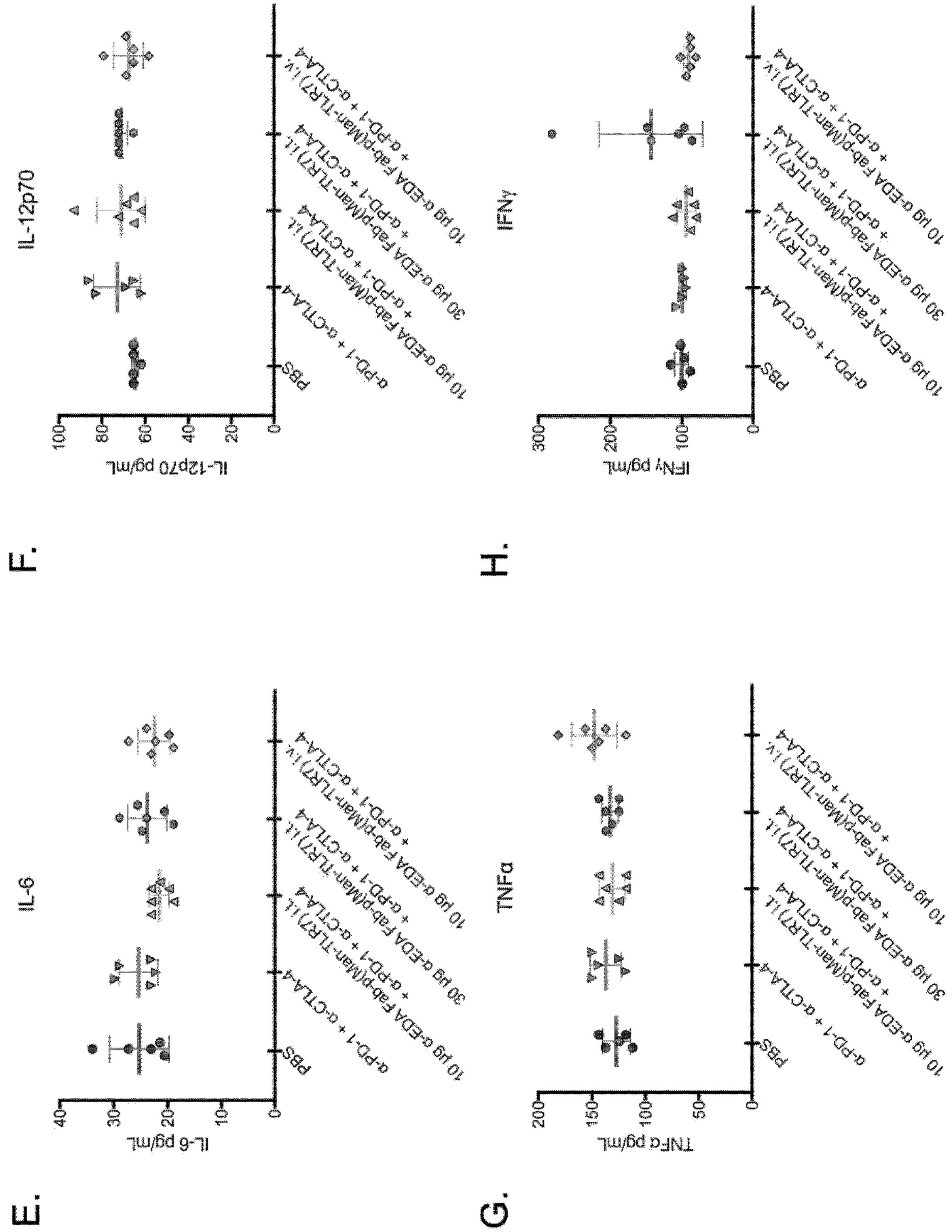
FIG. 13E-H

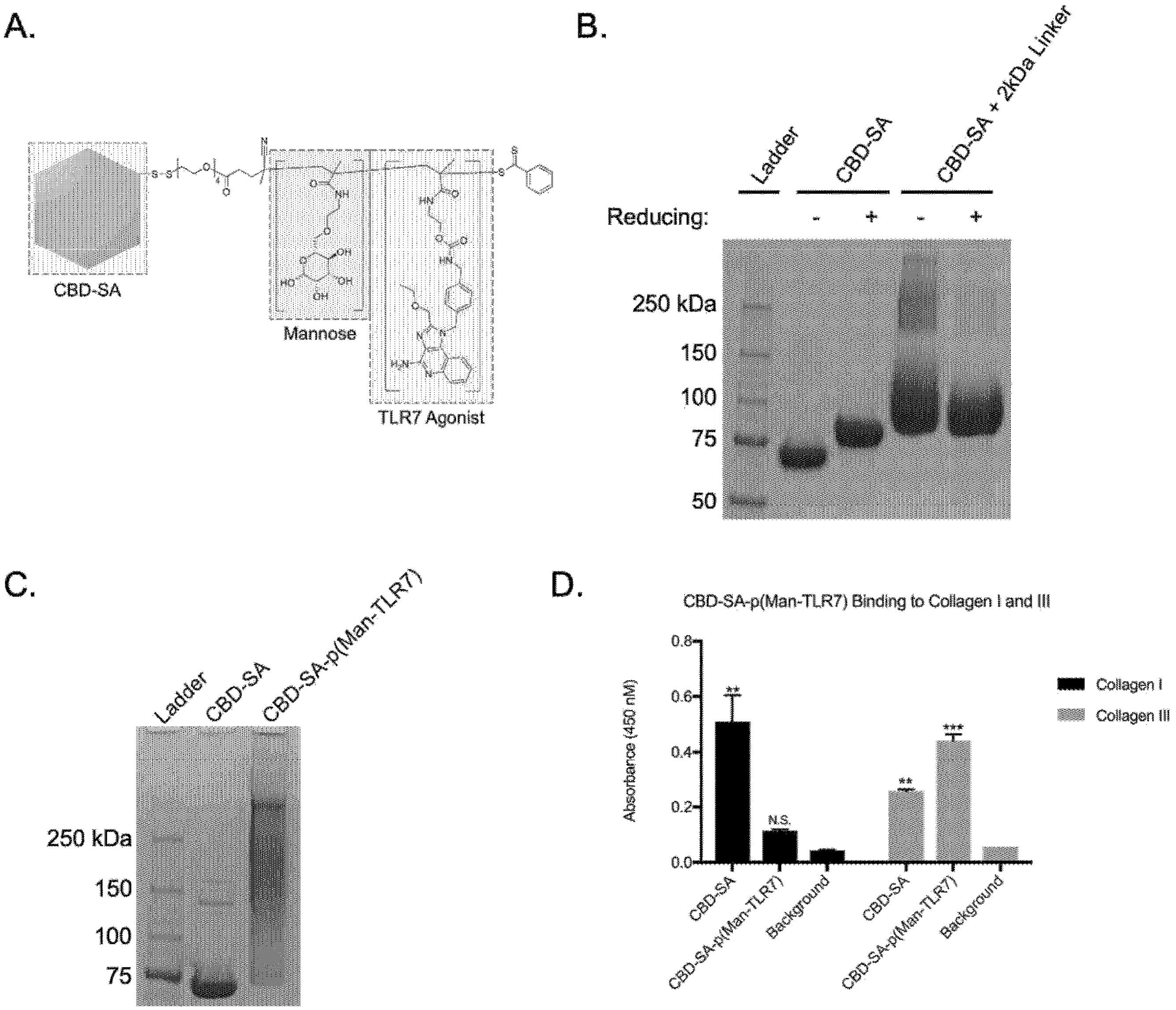
FIG. 14A-D

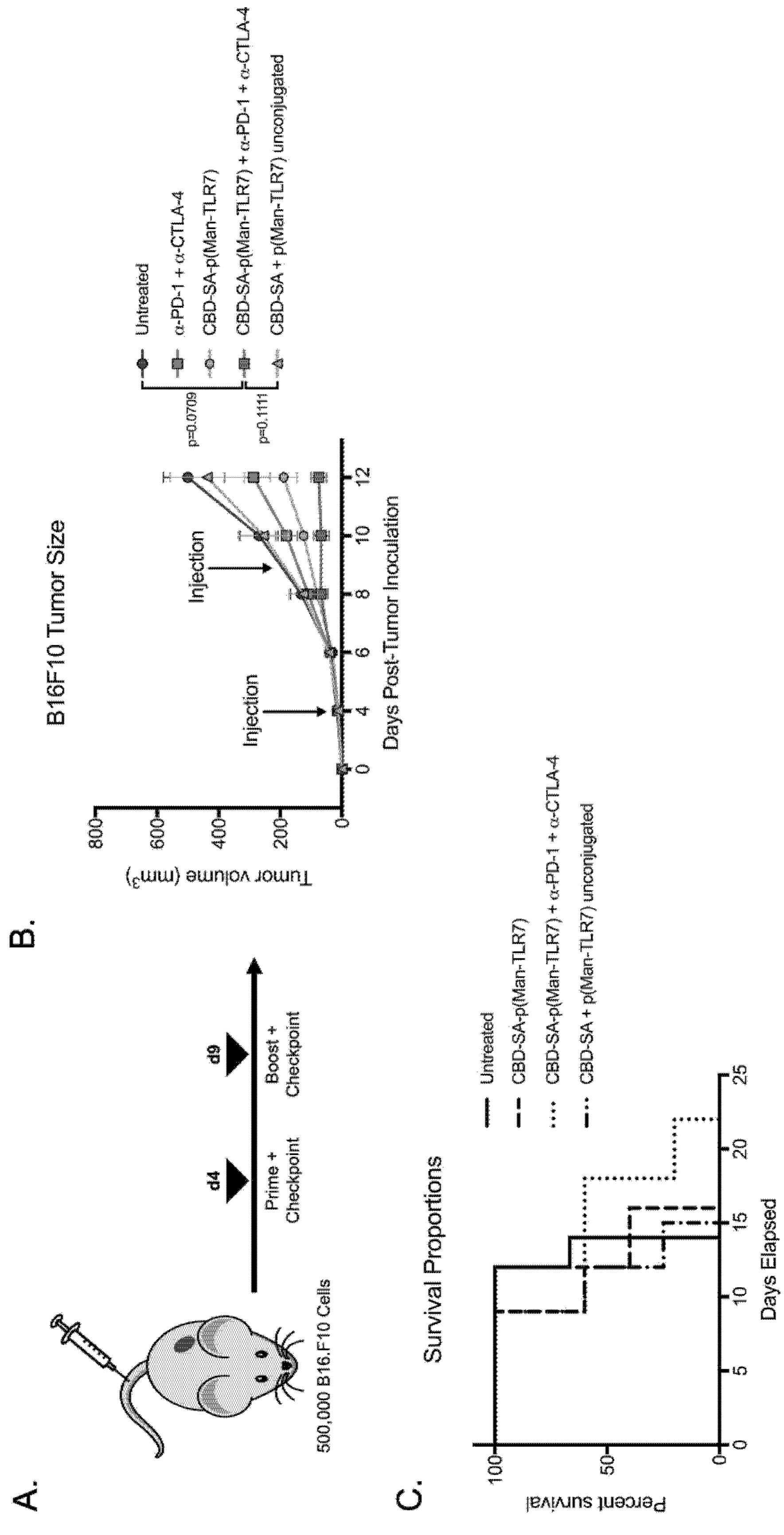
FIG. 15A-C

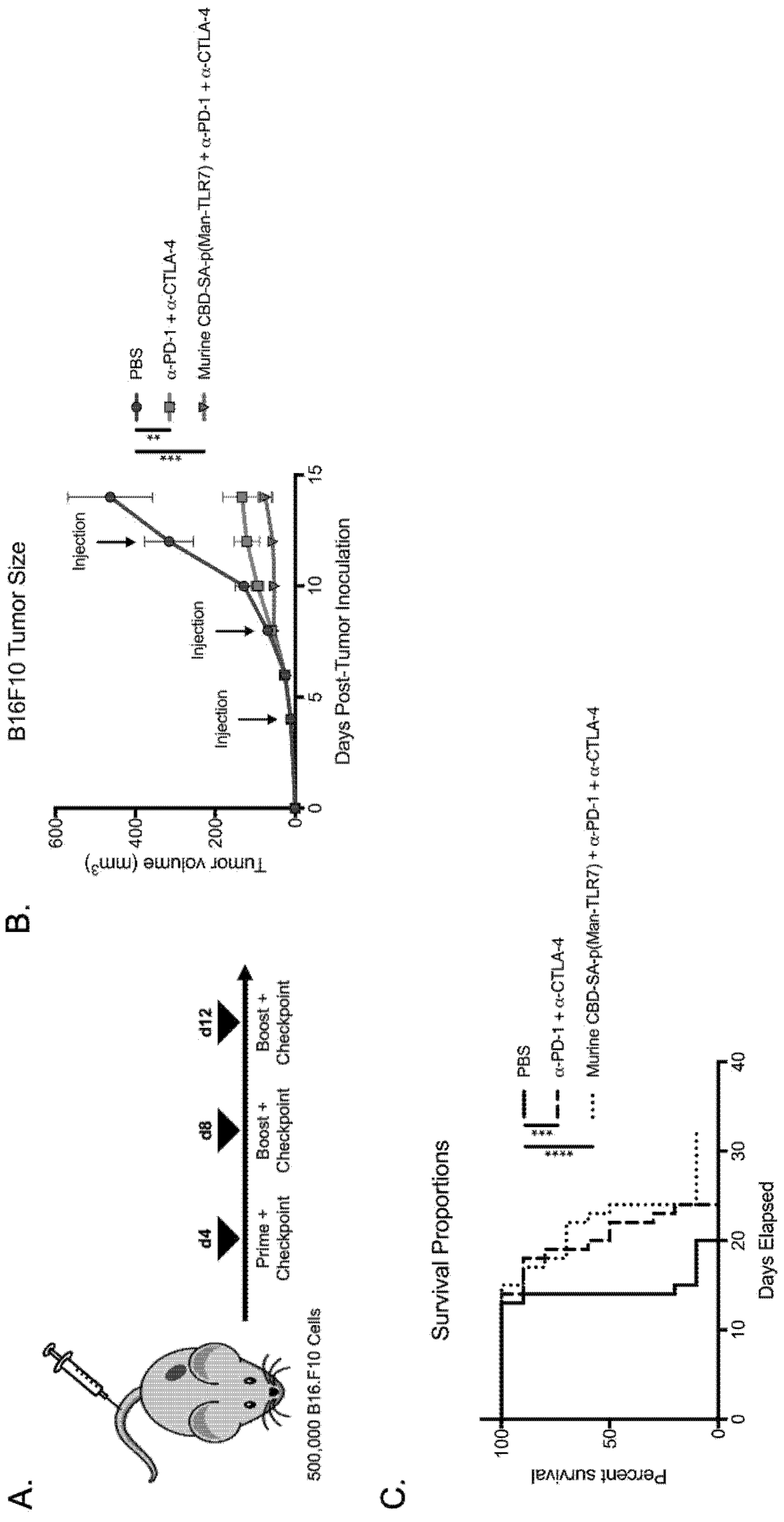
FIG. 16A-C

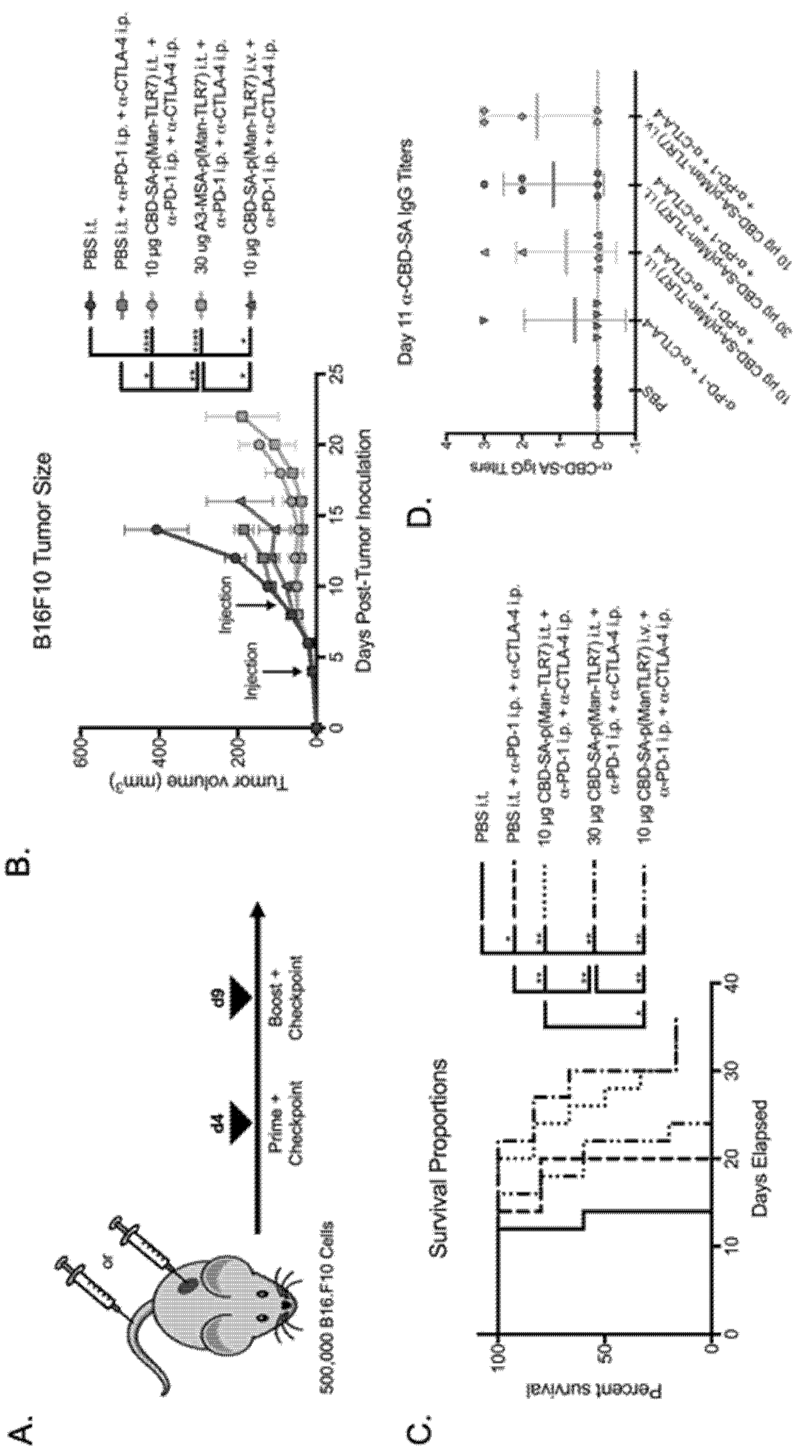
FIG. 17A-D

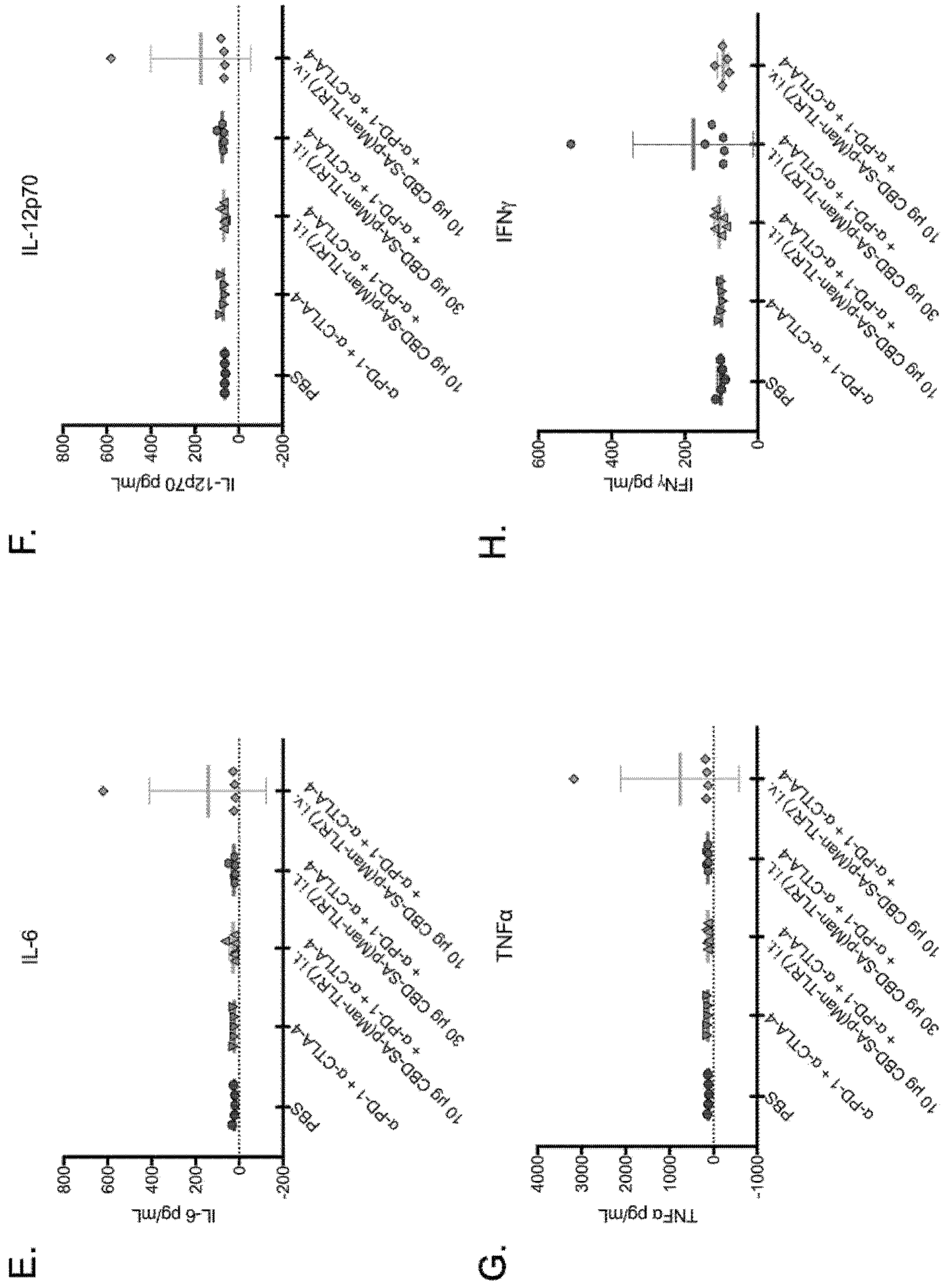
FIG. 17E-H

SEQUENCE LISTING

```
<160> NUMBER OF SEQ ID NOS: 30

<210> SEQ ID NO 1
<211> LENGTH: 205
<212> TYPE: PRT
<213> ORGANISM: Homo sapiens

<400> SEQUENCE: 1

Cys Ser Gly Glu Gly Leu Gln Ile Pro Thr Leu Ser Pro Ala Pro Asp
1               5                   10                  15

Cys Ser Gln Pro Leu Asp Val Ile Leu Leu Leu Asp Gly Ser Ser Ser
            20                  25                  30

Phe Pro Ala Ser Tyr Phe Asp Glu Met Lys Ser Phe Ala Lys Ala Phe
        35                  40                  45

Ile Ser Lys Ala Asn Ile Gly Pro Arg Leu Thr Gln Val Ser Val Leu
    50                  55                  60

Gln Tyr Gly Ser Ile Thr Thr Ile Asp Val Pro Trp Asn Val Val Pro
65                  70                  75                  80

Glu Lys Ala His Leu Leu Ser Leu Val Asp Val Met Gln Arg Glu Gly
                85                  90                  95

Gly Pro Ser Gln Ile Gly Asp Ala Leu Gly Phe Ala Val Arg Tyr Leu
            100                 105                 110

Thr Ser Glu Met His Gly Ala Arg Pro Gly Ala Ser Lys Ala Val Val
        115                 120                 125

Ile Leu Val Thr Asp Val Ser Val Asp Ser Val Asp Ala Ala Ala Asp
    130                 135                 140

Ala Ala Arg Ser Asn Arg Val Thr Val Phe Pro Ile Gly Ile Gly Asp
145                 150                 155                 160

Arg Tyr Asp Ala Ala Gln Leu Arg Ile Leu Ala Gly Pro Ala Gly Asp
                165                 170                 175

Ser Asn Val Val Lys Leu Gln Arg Ile Glu Asp Leu Pro Thr Met Val
            180                 185                 190

Thr Leu Gly Asn Ser Phe Leu His Lys Leu Cys Ser Gly
        195                 200                 205


<210> SEQ ID NO 2
<211> LENGTH: 193
<212> TYPE: PRT
<213> ORGANISM: Unknown
<220> FEATURE:
<223> OTHER INFORMATION: Description of Unknown:
      Collagen binding domain sequence

<400> SEQUENCE: 2

Cys Ser Gln Pro Leu Asp Val Ile Leu Leu Leu Asp Gly Ser Ser Ser
1               5                   10                  15

Phe Pro Ala Ser Tyr Phe Asp Glu Met Lys Ser Phe Ala Lys Ala Phe
            20                  25                  30
```

```
Ile Ser Lys Ala Asn Ile Gly Pro Arg Leu Thr Gln Val Ser Val Leu
        35                  40                  45

Gln Tyr Gly Ser Ile Thr Thr Ile Asp Val Pro Trp Asn Val Val Pro
    50                  55                  60

Glu Lys Ala His Leu Leu Ser Leu Val Asp Val Met Gln Arg Glu Gly
65                  70                  75                  80

Gly Pro Ser Gln Ile Gly Asp Ala Leu Gly Phe Ala Val Arg Tyr Leu
                85                  90                  95

Thr Ser Glu Met His Gly Ala Arg Pro Gly Ala Ser Lys Ala Val Val
            100                 105                 110

Ile Leu Val Thr Asp Val Ser Val Asp Ser Val Asp Ala Ala Ala Asp
        115                 120                 125

Ala Ala Arg Ser Asn Arg Val Thr Val Phe Pro Ile Gly Ile Gly Asp
    130                 135                 140

Arg Tyr Asp Ala Ala Gln Leu Arg Ile Leu Ala Gly Pro Ala Gly Asp
145                 150                 155                 160

Ser Asn Val Val Lys Leu Gln Arg Ile Glu Asp Leu Pro Thr Met Val
                165                 170                 175

Thr Leu Gly Asn Ser Phe Leu His Lys Leu Cys Ser Gly Phe Val Arg
            180                 185                 190

Ile


<210> SEQ ID NO 3
<211> LENGTH: 791
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Cys Ser Gln Pro Leu Asp Val Ile Leu Leu Leu Asp Gly Ser Ser Ser
1               5                   10                  15

Phe Pro Ala Ser Tyr Phe Asp Glu Met Lys Ser Phe Ala Lys Ala Phe
            20                  25                  30

Ile Ser Lys Ala Asn Ile Gly Pro Arg Leu Thr Gln Val Ser Val Leu
        35                  40                  45

Gln Tyr Gly Ser Ile Thr Thr Ile Asp Val Pro Trp Asn Val Val Pro
    50                  55                  60

Glu Lys Ala His Leu Leu Ser Leu Val Asp Val Met Gln Arg Glu Gly
65                  70                  75                  80

Gly Pro Ser Gln Ile Gly Asp Ala Leu Gly Phe Ala Val Arg Tyr Leu
                85                  90                  95

Thr Ser Glu Met His Gly Ala Arg Pro Gly Ala Ser Lys Ala Val Val
            100                 105                 110

Ile Leu Val Thr Asp Val Ser Val Asp Ser Val Asp Ala Ala Ala Asp
        115                 120                 125

Ala Ala Arg Ser Asn Arg Val Thr Val Phe Pro Ile Gly Ile Gly Asp
    130                 135                 140

Arg Tyr Asp Ala Ala Gln Leu Arg Ile Leu Ala Gly Pro Ala Gly Asp
145                 150                 155                 160

Ser Asn Val Val Lys Leu Gln Arg Ile Glu Asp Leu Pro Thr Met Val
                165                 170                 175

Thr Leu Gly Asn Ser Phe Leu His Lys Leu Cys Ser Gly Phe Val Arg
            180                 185                 190
```

-continued

```
Ile Gly Gly Gly Ser Gly Gly Gly Ser Glu Ala His Lys Ser Glu Ile
        195                 200                 205

Ala His Arg Tyr Asn Asp Leu Gly Glu Gln His Phe Lys Gly Leu Val
    210                 215                 220

Leu Ile Ala Phe Ser Gln Tyr Leu Gln Lys Cys Ser Tyr Asp Glu His
225                 230                 235                 240

Ala Lys Leu Val Gln Glu Val Thr Asp Phe Ala Lys Thr Cys Val Ala
                245                 250                 255

Asp Glu Ser Ala Ala Asn Cys Asp Lys Ser Leu His Thr Leu Phe Gly
            260                 265                 270

Asp Lys Leu Cys Ala Ile Pro Asn Leu Arg Glu Asn Tyr Gly Glu Leu
        275                 280                 285

Ala Asp Cys Cys Thr Lys Gln Glu Pro Glu Arg Asn Glu Cys Phe Leu
    290                 295                 300

Gln His Lys Asp Asp Asn Pro Ser Leu Pro Pro Phe Glu Arg Pro Glu
305                 310                 315                 320

Ala Glu Ala Met Cys Thr Ser Phe Lys Glu Asn Pro Thr Thr Phe Met
                325                 330                 335

Gly His Tyr Leu His Glu Val Ala Arg Arg His Pro Tyr Phe Tyr Ala
            340                 345                 350

Pro Glu Leu Leu Tyr Tyr Ala Glu Gln Tyr Asn Glu Ile Leu Thr Gln
        355                 360                 365

Cys Cys Ala Glu Ala Asp Lys Glu Ser Cys Leu Thr Pro Lys Leu Asp
    370                 375                 380

Gly Val Lys Glu Lys Ala Leu Val Ser Ser Val Arg Gln Arg Met Lys
385                 390                 395                 400

Cys Ser Ser Met Gln Lys Phe Gly Glu Arg Ala Phe Lys Ala Trp Ala
                405                 410                 415

Val Ala Arg Leu Ser Gln Thr Phe Pro Asn Ala Asp Phe Ala Glu Ile
            420                 425                 430

Thr Lys Leu Ala Thr Asp Leu Thr Lys Val Asn Lys Glu Cys Cys His
        435                 440                 445

Gly Asp Leu Leu Glu Cys Ala Asp Asp Arg Ala Glu Leu Ala Lys Tyr
    450                 455                 460

Met Cys Glu Asn Gln Ala Thr Ile Ser Ser Lys Leu Gln Thr Cys Cys
465                 470                 475                 480

Asp Lys Pro Leu Leu Lys Lys Ala His Cys Leu Ser Glu Val Glu His
                485                 490                 495

Asp Thr Met Pro Ala Asp Leu Pro Ala Ile Ala Ala Asp Phe Val Glu
            500                 505                 510

Asp Gln Glu Val Cys Lys Asn Tyr Ala Glu Ala Lys Asp Val Phe Leu
        515                 520                 525

Gly Thr Phe Leu Tyr Glu Tyr Ser Arg Arg His Pro Asp Tyr Ser Val
    530                 535                 540

Ser Leu Leu Leu Arg Leu Ala Lys Lys Tyr Glu Ala Thr Leu Glu Lys
545                 550                 555                 560

Cys Cys Ala Glu Ala Asn Pro Pro Ala Cys Tyr Gly Thr Val Leu Ala
                565                 570                 575

Glu Phe Gln Pro Leu Val Glu Glu Pro Lys Asn Leu Val Lys Thr Asn
            580                 585                 590

Cys Asp Leu Tyr Glu Lys Leu Gly Glu Tyr Gly Phe Gln Asn Ala Ile
        595                 600                 605

Leu Val Arg Tyr Thr Gln Lys Ala Pro Gln Val Ser Thr Pro Thr Leu
```

-continued

```
    610                 615                 620

Val Glu Ala Ala Arg Asn Leu Gly Arg Val Gly Thr Lys Cys Cys Thr
625                 630                 635                 640

Leu Pro Glu Asp Gln Arg Leu Pro Cys Val Glu Asp Tyr Leu Ser Ala
                645                 650                 655

Ile Leu Asn Arg Val Cys Leu Leu His Glu Lys Thr Pro Val Ser Glu
            660                 665                 670

His Val Thr Lys Cys Cys Ser Gly Ser Leu Val Glu Arg Arg Pro Cys
        675                 680                 685

Phe Ser Ala Leu Thr Val Asp Glu Thr Tyr Val Pro Lys Glu Phe Lys
    690                 695                 700

Ala Glu Thr Phe Thr Phe His Ser Asp Ile Cys Thr Leu Pro Glu Lys
705                 710                 715                 720

Glu Lys Gln Ile Lys Lys Gln Thr Ala Leu Ala Glu Leu Val Lys His
                725                 730                 735

Lys Pro Lys Ala Thr Ala Glu Gln Leu Lys Thr Val Met Asp Asp Phe
            740                 745                 750

Ala Gln Phe Leu Asp Thr Cys Cys Lys Ala Ala Asp Lys Asp Thr Cys
        755                 760                 765

Phe Ser Thr Glu Gly Pro Asn Leu Val Thr Arg Cys Lys Asp Ala Leu
    770                 775                 780

Ala His His His His His His
785                 790


<210> SEQ ID NO 4
<211> LENGTH: 2813
<212> TYPE: PRT
<213> ORGANISM: Homo sapiens

<400> SEQUENCE: 4

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190
```

-continued

```
Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
```

```
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
    930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                1005

Ser Ser  Asn Leu Gln Val Glu  Glu Asp Pro Val Asp  Phe Gly Asn
    1010                1015                1020

Ser Trp  Lys Val Ser Ser Gln  Cys Ala Asp Thr Arg  Lys Val Pro
    1025                1030                1035
```

```
Leu Asp  Ser Ser Pro Ala Thr  Cys His Asn Asn Ile  Met Lys Gln
    1040                 1045                 1050

Thr Met  Val Asp Ser Ser Cys  Arg Ile Leu Thr Ser  Asp Val Phe
    1055                 1060                 1065

Gln Asp  Cys Asn Lys Leu Val  Asp Pro Glu Pro Tyr  Leu Asp Val
    1070                 1075                 1080

Cys Ile  Tyr Asp Thr Cys Ser  Cys Glu Ser Ile Gly  Asp Cys Ala
    1085                 1090                 1095

Cys Phe  Cys Asp Thr Ile Ala  Ala Tyr Ala His Val  Cys Ala Gln
    1100                 1105                 1110

His Gly  Lys Val Val Thr Trp  Arg Thr Ala Thr Leu  Cys Pro Gln
    1115                 1120                 1125

Ser Cys  Glu Glu Arg Asn Leu  Arg Glu Asn Gly Tyr  Glu Cys Glu
    1130                 1135                 1140

Trp Arg  Tyr Asn Ser Cys Ala  Pro Ala Cys Gln Val  Thr Cys Gln
    1145                 1150                 1155

His Pro  Glu Pro Leu Ala Cys  Pro Val Gln Cys Val  Glu Gly Cys
    1160                 1165                 1170

His Ala  His Cys Pro Pro Gly  Lys Ile Leu Asp Glu  Leu Leu Gln
    1175                 1180                 1185

Thr Cys  Val Asp Pro Glu Asp  Cys Pro Val Cys Glu  Val Ala Gly
    1190                 1195                 1200

Arg Arg  Phe Ala Ser Gly Lys  Lys Val Thr Leu Asn  Pro Ser Asp
    1205                 1210                 1215

Pro Glu  His Cys Gln Ile Cys  His Cys Asp Val Val  Asn Leu Thr
    1220                 1225                 1230

Cys Glu  Ala Cys Gln Glu Pro  Gly Gly Leu Val Val  Pro Pro Thr
    1235                 1240                 1245

Asp Ala  Pro Val Ser Pro Thr  Thr Leu Tyr Val Glu  Asp Ile Ser
    1250                 1255                 1260

Glu Pro  Pro Leu His Asp Phe  Tyr Cys Ser Arg Leu  Leu Asp Leu
    1265                 1270                 1275

Val Phe  Leu Leu Asp Gly Ser  Ser Arg Leu Ser Glu  Ala Glu Phe
    1280                 1285                 1290

Glu Val  Leu Lys Ala Phe Val  Val Asp Met Met Glu  Arg Leu Arg
    1295                 1300                 1305

Ile Ser  Gln Lys Trp Val Arg  Val Ala Val Val Glu  Tyr His Asp
    1310                 1315                 1320

Gly Ser  His Ala Tyr Ile Gly  Leu Lys Asp Arg Lys  Arg Pro Ser
    1325                 1330                 1335

Glu Leu  Arg Arg Ile Ala Ser  Gln Val Lys Tyr Ala  Gly Ser Gln
    1340                 1345                 1350

Val Ala  Ser Thr Ser Glu Val  Leu Lys Tyr Thr Leu  Phe Gln Ile
    1355                 1360                 1365

Phe Ser  Lys Ile Asp Arg Pro  Glu Ala Ser Arg Ile  Thr Leu Leu
    1370                 1375                 1380

Leu Met  Ala Ser Gln Glu Pro  Gln Arg Met Ser Arg  Asn Phe Val
    1385                 1390                 1395

Arg Tyr  Val Gln Gly Leu Lys  Lys Lys Lys Val Ile  Val Ile Pro
    1400                 1405                 1410

Val Gly  Ile Gly Pro His Ala  Asn Leu Lys Gln Ile  Arg Leu Ile
    1415                 1420                 1425
```

-continued

```
Glu Lys  Gln Ala Pro Glu Asn  Lys Ala Phe Val Leu  Ser Ser Val
    1430                 1435                 1440

Asp Glu  Leu Glu Gln Gln Arg  Asp Glu Ile Val Ser  Tyr Leu Cys
    1445                 1450                 1455

Asp Leu  Ala Pro Glu Ala Pro  Pro Pro Thr Leu Pro  Pro Asp Met
    1460                 1465                 1470

Ala Gln  Val Thr Val Gly Pro  Gly Leu Leu Gly Val  Ser Thr Leu
    1475                 1480                 1485

Gly Pro  Lys Arg Asn Ser Met  Val Leu Asp Val Ala  Phe Val Leu
    1490                 1495                 1500

Glu Gly  Ser Asp Lys Ile Gly  Glu Ala Asp Phe Asn  Arg Ser Lys
    1505                 1510                 1515

Glu Phe  Met Glu Glu Val Ile  Gln Arg Met Asp Val  Gly Gln Asp
    1520                 1525                 1530

Ser Ile  His Val Thr Val Leu  Gln Tyr Ser Tyr Met  Val Thr Val
    1535                 1540                 1545

Glu Tyr  Pro Phe Ser Glu Ala  Gln Ser Lys Gly Asp  Ile Leu Gln
    1550                 1555                 1560

Arg Val  Arg Glu Ile Arg Tyr  Gln Gly Gly Asn Arg  Thr Asn Thr
    1565                 1570                 1575

Gly Leu  Ala Leu Arg Tyr Leu  Ser Asp His Ser Phe  Leu Val Ser
    1580                 1585                 1590

Gln Gly  Asp Arg Glu Gln Ala  Pro Asn Leu Val Tyr  Met Val Thr
    1595                 1600                 1605

Gly Asn  Pro Ala Ser Asp Glu  Ile Lys Arg Leu Pro  Gly Asp Ile
    1610                 1615                 1620

Gln Val  Val Pro Ile Gly Val  Gly Pro Asn Ala Asn  Val Gln Glu
    1625                 1630                 1635

Leu Glu  Arg Ile Gly Trp Pro  Asn Ala Pro Ile Leu  Ile Gln Asp
    1640                 1645                 1650

Phe Glu  Thr Leu Pro Arg Glu  Ala Pro Asp Leu Val  Leu Gln Arg
    1655                 1660                 1665

Cys Cys  Ser Gly Glu Gly Leu  Gln Ile Pro Thr Leu  Ser Pro Ala
    1670                 1675                 1680

Pro Asp  Cys Ser Gln Pro Leu  Asp Val Ile Leu Leu  Leu Asp Gly
    1685                 1690                 1695

Ser Ser  Ser Phe Pro Ala Ser  Tyr Phe Asp Glu Met  Lys Ser Phe
    1700                 1705                 1710

Ala Lys  Ala Phe Ile Ser Lys  Ala Asn Ile Gly Pro  Arg Leu Thr
    1715                 1720                 1725

Gln Val  Ser Val Leu Gln Tyr  Gly Ser Ile Thr Thr  Ile Asp Val
    1730                 1735                 1740

Pro Trp  Asn Val Val Pro Glu  Lys Ala His Leu Leu  Ser Leu Val
    1745                 1750                 1755

Asp Val  Met Gln Arg Glu Gly  Gly Pro Ser Gln Ile  Gly Asp Ala
    1760                 1765                 1770

Leu Gly  Phe Ala Val Arg Tyr  Leu Thr Ser Glu Met  His Gly Ala
    1775                 1780                 1785

Arg Pro  Gly Ala Ser Lys Ala  Val Val Ile Leu Val  Thr Asp Val
    1790                 1795                 1800

Ser Val  Asp Ser Val Asp Ala  Ala Ala Asp Ala Ala  Arg Ser Asn
    1805                 1810                 1815

Arg Val  Thr Val Phe Pro Ile  Gly Ile Gly Asp Arg  Tyr Asp Ala
```

-continued

```
    1820                1825                1830

Ala Gln  Leu Arg Ile Leu Ala  Gly Pro Ala Gly Asp  Ser Asn Val
    1835                1840                1845

Val Lys  Leu Gln Arg Ile Glu  Asp Leu Pro Thr Met  Val Thr Leu
    1850                1855                1860

Gly Asn  Ser Phe Leu His Lys  Leu Cys Ser Gly Phe  Val Arg Ile
    1865                1870                1875

Cys Met  Asp Glu Asp Gly Asn  Glu Lys Arg Pro Gly  Asp Val Trp
    1880                1885                1890

Thr Leu  Pro Asp Gln Cys His  Thr Val Thr Cys Gln  Pro Asp Gly
    1895                1900                1905

Gln Thr  Leu Leu Lys Ser His  Arg Val Asn Cys Asp  Arg Gly Leu
    1910                1915                1920

Arg Pro  Ser Cys Pro Asn Ser  Gln Ser Pro Val Lys  Val Glu Glu
    1925                1930                1935

Thr Cys  Gly Cys Arg Trp Thr  Cys Pro Cys Val Cys  Thr Gly Ser
    1940                1945                1950

Ser Thr  Arg His Ile Val Thr  Phe Asp Gly Gln Asn  Phe Lys Leu
    1955                1960                1965

Thr Gly  Ser Cys Ser Tyr Val  Leu Phe Gln Asn Lys  Glu Gln Asp
    1970                1975                1980

Leu Glu  Val Ile Leu His Asn  Gly Ala Cys Ser Pro  Gly Ala Arg
    1985                1990                1995

Gln Gly  Cys Met Lys Ser Ile  Glu Val Lys His Ser  Ala Leu Ser
    2000                2005                2010

Val Glu  Leu His Ser Asp Met  Glu Val Thr Val Asn  Gly Arg Leu
    2015                2020                2025

Val Ser  Val Pro Tyr Val Gly  Gly Asn Met Glu Val  Asn Val Tyr
    2030                2035                2040

Gly Ala  Ile Met His Glu Val  Arg Phe Asn His Leu  Gly His Ile
    2045                2050                2055

Phe Thr  Phe Thr Pro Gln Asn  Asn Glu Phe Gln Leu  Gln Leu Ser
    2060                2065                2070

Pro Lys  Thr Phe Ala Ser Lys  Thr Tyr Gly Leu Cys  Gly Ile Cys
    2075                2080                2085

Asp Glu  Asn Gly Ala Asn Asp  Phe Met Leu Arg Asp  Gly Thr Val
    2090                2095                2100

Thr Thr  Asp Trp Lys Thr Leu  Val Gln Glu Trp Thr  Val Gln Arg
    2105                2110                2115

Pro Gly  Gln Thr Cys Gln Pro  Ile Leu Glu Glu Gln  Cys Leu Val
    2120                2125                2130

Pro Asp  Ser Ser His Cys Gln  Val Leu Leu Leu Pro  Leu Phe Ala
    2135                2140                2145

Glu Cys  His Lys Val Leu Ala  Pro Ala Thr Phe Tyr  Ala Ile Cys
    2150                2155                2160

Gln Gln  Asp Ser Cys His Gln  Glu Gln Val Cys Glu  Val Ile Ala
    2165                2170                2175

Ser Tyr  Ala His Leu Cys Arg  Thr Asn Gly Val Cys  Val Asp Trp
    2180                2185                2190

Arg Thr  Pro Asp Phe Cys Ala  Met Ser Cys Pro Pro  Ser Leu Val
    2195                2200                2205

Tyr Asn  His Cys Glu His Gly  Cys Pro Arg His Cys  Asp Gly Asn
    2210                2215                2220
```

-continued

```
Val Ser  Ser Cys Gly Asp His  Pro Ser Glu Gly Cys  Phe Cys Pro
    2225                 2230                 2235

Pro Asp  Lys Val Met Leu Glu  Gly Ser Cys Val Pro  Glu Glu Ala
    2240                 2245                 2250

Cys Thr  Gln Cys Ile Gly Glu  Asp Gly Val Gln His  Gln Phe Leu
    2255                 2260                 2265

Glu Ala  Trp Val Pro Asp His  Gln Pro Cys Gln Ile  Cys Thr Cys
    2270                 2275                 2280

Leu Ser  Gly Arg Lys Val Asn  Cys Thr Thr Gln Pro  Cys Pro Thr
    2285                 2290                 2295

Ala Lys  Ala Pro Thr Cys Gly  Leu Cys Glu Val Ala  Arg Leu Arg
    2300                 2305                 2310

Gln Asn  Ala Asp Gln Cys Cys  Pro Glu Tyr Glu Cys  Val Cys Asp
    2315                 2320                 2325

Pro Val  Ser Cys Asp Leu Pro  Pro Val Pro His Cys  Glu Arg Gly
    2330                 2335                 2340

Leu Gln  Pro Thr Leu Thr Asn  Pro Gly Glu Cys Arg  Pro Asn Phe
    2345                 2350                 2355

Thr Cys  Ala Cys Arg Lys Glu  Glu Cys Lys Arg Val  Ser Pro Pro
    2360                 2365                 2370

Ser Cys  Pro Pro His Arg Leu  Pro Thr Leu Arg Lys  Thr Gln Cys
    2375                 2380                 2385

Cys Asp  Glu Tyr Glu Cys Ala  Cys Asn Cys Val Asn  Ser Thr Val
    2390                 2395                 2400

Ser Cys  Pro Leu Gly Tyr Leu  Ala Ser Thr Ala Thr  Asn Asp Cys
    2405                 2410                 2415

Gly Cys  Thr Thr Thr Thr Cys  Leu Pro Asp Lys Val  Cys Val His
    2420                 2425                 2430

Arg Ser  Thr Ile Tyr Pro Val  Gly Gln Phe Trp Glu  Glu Gly Cys
    2435                 2440                 2445

Asp Val  Cys Thr Cys Thr Asp  Met Glu Asp Ala Val  Met Gly Leu
    2450                 2455                 2460

Arg Val  Ala Gln Cys Ser Gln  Lys Pro Cys Glu Asp  Ser Cys Arg
    2465                 2470                 2475

Ser Gly  Phe Thr Tyr Val Leu  His Glu Gly Glu Cys  Cys Gly Arg
    2480                 2485                 2490

Cys Leu  Pro Ser Ala Cys Glu  Val Val Thr Gly Ser  Pro Arg Gly
    2495                 2500                 2505

Asp Ser  Gln Ser Ser Trp Lys  Ser Val Gly Ser Gln  Trp Ala Ser
    2510                 2515                 2520

Pro Glu  Asn Pro Cys Leu Ile  Asn Glu Cys Val Arg  Val Lys Glu
    2525                 2530                 2535

Glu Val  Phe Ile Gln Gln Arg  Asn Val Ser Cys Pro  Gln Leu Glu
    2540                 2545                 2550

Val Pro  Val Cys Pro Ser Gly  Phe Gln Leu Ser Cys  Lys Thr Ser
    2555                 2560                 2565

Ala Cys  Cys Pro Ser Cys Arg  Cys Glu Arg Met Glu  Ala Cys Met
    2570                 2575                 2580

Leu Asn  Gly Thr Val Ile Gly  Pro Gly Lys Thr Val  Met Ile Asp
    2585                 2590                 2595

Val Cys  Thr Thr Cys Arg Cys  Met Val Gln Val Gly  Val Ile Ser
    2600                 2605                 2610
```

Gly Phe Lys Leu Glu Cys Arg Lys Thr Thr Cys Asn Pro Cys Pro
2615 2620 2625

Leu Gly Tyr Lys Glu Glu Asn Asn Thr Gly Glu Cys Cys Gly Arg
2630 2635 2640

Cys Leu Pro Thr Ala Cys Thr Ile Gln Leu Arg Gly Gly Gln Ile
2645 2650 2655

Met Thr Leu Lys Arg Asp Glu Thr Leu Gln Asp Gly Cys Asp Thr
2660 2665 2670

His Phe Cys Lys Val Asn Glu Arg Gly Glu Tyr Phe Trp Glu Lys
2675 2680 2685

Arg Val Thr Gly Cys Pro Pro Phe Asp Glu His Lys Cys Leu Ala
2690 2695 2700

Glu Gly Gly Lys Ile Met Lys Ile Pro Gly Thr Cys Cys Asp Thr
2705 2710 2715

Cys Glu Glu Pro Glu Cys Asn Asp Ile Thr Ala Arg Leu Gln Tyr
2720 2725 2730

Val Lys Val Gly Ser Cys Lys Ser Glu Val Glu Val Asp Ile His
2735 2740 2745

Tyr Cys Gln Gly Lys Cys Ala Ser Lys Ala Met Tyr Ser Ile Asp
2750 2755 2760

Ile Asn Asp Val Gln Asp Gln Cys Ser Cys Cys Ser Pro Thr Arg
2765 2770 2775

Thr Glu Pro Met Gln Val Ala Leu His Cys Thr Asn Gly Ser Val
2780 2785 2790

Val Tyr His Glu Val Leu Asn Ala Met Glu Cys Lys Cys Ser Pro
2795 2800 2805

Arg Lys Cys Ser Lys
2810

<210> SEQ ID NO 5
<211> LENGTH: 10
<212> TYPE: PRT
<213> ORGANISM: Bos sp.

<400> SEQUENCE: 5

Leu Arg Glu Leu His Leu Asn Asn Asn Cys
1 5 10

<210> SEQ ID NO 6
<211> LENGTH: 10
<212> TYPE: PRT
<213> ORGANISM: Homo sapiens

<400> SEQUENCE: 6

Leu Arg Glu Leu His Leu Asp Asn Asn Cys
1 5 10

<210> SEQ ID NO 7
<211> LENGTH: 344
<212> TYPE: PRT
<213> ORGANISM: Homo sapiens

<400> SEQUENCE: 7

Cys Gly Pro Phe Gln Gln Arg Gly Leu Phe Asp Phe Met Leu Glu Asp
1 5 10 15

Glu Ala Ser Gly Ile Gly Pro Glu Val Pro Asp Asp Arg Asp Phe Glu
20 25 30

Pro Ser Leu Gly Pro Val Cys Pro Phe Arg Cys Gln Cys His Leu Arg

-continued

```
        35                  40                  45

Val Val Gln Cys Ser Asp Leu Gly Leu Asp Lys Val Pro Lys Asp Leu
    50                  55                  60

Pro Pro Asp Thr Thr Leu Leu Asp Leu Gln Asn Asn Lys Ile Thr Glu
65                  70                  75                  80

Ile Lys Asp Gly Asp Phe Lys Asn Leu Lys Asn Leu His Ala Leu Ile
                85                  90                  95

Leu Val Asn Asn Lys Ile Ser Lys Val Ser Pro Gly Ala Phe Thr Pro
            100                 105                 110

Leu Val Lys Leu Glu Arg Leu Tyr Leu Ser Lys Asn Gln Leu Lys Glu
        115                 120                 125

Leu Pro Glu Lys Met Pro Lys Thr Leu Gln Glu Leu Arg Ala His Glu
    130                 135                 140

Asn Glu Ile Thr Lys Val Arg Lys Val Thr Phe Asn Gly Leu Asn Gln
145                 150                 155                 160

Met Ile Val Ile Glu Leu Gly Thr Asn Pro Leu Lys Ser Ser Gly Ile
                165                 170                 175

Glu Asn Gly Ala Phe Gln Gly Met Lys Lys Leu Ser Tyr Ile Arg Ile
            180                 185                 190

Ala Asp Thr Asn Ile Thr Ser Ile Pro Gln Gly Leu Pro Pro Ser Leu
        195                 200                 205

Thr Glu Leu His Leu Asp Gly Asn Lys Ile Ser Arg Val Asp Ala Ala
    210                 215                 220

Ser Leu Lys Gly Leu Asn Asn Leu Ala Lys Leu Gly Leu Ser Phe Asn
225                 230                 235                 240

Ser Ile Ser Ala Val Asp Asn Gly Ser Leu Ala Asn Thr Pro His Leu
                245                 250                 255

Arg Glu Leu His Leu Asp Asn Asn Lys Leu Thr Arg Val Pro Gly Gly
            260                 265                 270

Leu Ala Glu His Lys Tyr Ile Gln Val Val Tyr Leu His Asn Asn Asn
        275                 280                 285

Ile Ser Val Val Gly Ser Ser Asp Phe Cys Pro Pro Gly His Asn Thr
    290                 295                 300

Lys Lys Ala Ser Tyr Ser Gly Val Ser Leu Phe Ser Asn Pro Val Gln
305                 310                 315                 320

Tyr Trp Glu Ile Gln Pro Ser Thr Phe Arg Cys Val Tyr Val Arg Ser
                325                 330                 335

Ala Ile Gln Leu Gly Asn Tyr Lys
            340
```

<210> SEQ ID NO 8
<211> LENGTH: 196
<212> TYPE: PRT
<213> ORGANISM: Unknown
<220> FEATURE:
<223> OTHER INFORMATION: Description of Unknown:
ECM sequence

<400> SEQUENCE: 8

```
Cys Ser Gln Pro Leu Asp Val Ile Leu Leu Leu Asp Gly Ser Ser Ser
1               5                   10                  15

Phe Pro Ala Ser Tyr Phe Asp Glu Met Lys Ser Phe Ala Lys Ala Phe
            20                  25                  30

Ile Ser Lys Ala Asn Ile Gly Pro Arg Leu Thr Gln Val Ser Val Leu
        35                  40                  45
```

```
Gln Tyr Gly Ser Ile Thr Thr Ile Asp Val Pro Trp Asn Val Val Pro
    50                  55                  60

Glu Lys Ala His Leu Leu Ser Leu Val Asp Val Met Gln Arg Glu Gly
65                  70                  75                  80

Gly Pro Ser Gln Ile Gly Asp Ala Leu Gly Phe Ala Val Arg Tyr Leu
                85                  90                  95

Thr Ser Glu Met His Gly Ala Arg Pro Gly Ala Ser Lys Ala Val Val
            100                 105                 110

Ile Leu Val Thr Asp Val Ser Val Asp Ser Val Asp Ala Ala Ala Asp
        115                 120                 125

Ala Ala Arg Ser Asn Arg Val Thr Val Phe Pro Ile Gly Ile Gly Asp
    130                 135                 140

Arg Tyr Asp Ala Ala Gln Leu Arg Ile Leu Ala Gly Pro Ala Gly Asp
145                 150                 155                 160

Ser Asn Val Val Lys Leu Gln Arg Ile Glu Asp Leu Pro Thr Met Val
                165                 170                 175

Thr Leu Gly Asn Ser Phe Leu His Lys Leu Cys Ser Gly Phe Val Arg
            180                 185                 190

Ile Cys Thr Gly
        195


<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Gly Ser Gly Gly Gly Ser
1               5


<210> SEQ ID NO 10
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 “Gly Gly Gly
      Ser” repeating units
<220> FEATURE:
<223> OTHER INFORMATION: See specification as filed for detailed
      description of substitutions and preferred embodiments

<400> SEQUENCE: 10

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40


<210> SEQ ID NO 11
<211> LENGTH: 609
<212> TYPE: PRT
<213> ORGANISM: Unknown
<220> FEATURE:
<223> OTHER INFORMATION: Description of Unknown:
```

Albumin peptide sequence

<400> SEQUENCE: 11

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Lys Thr Thr Leu Glu Lys Cys
    370                 375                 380

Cys Ala Ala Ala Asp Pro His Glu Cys Tyr Ala Lys Val Phe Asp Glu
385                 390                 395                 400
```

-continued

```
Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Arg Ala Ala Leu Gly
        595                 600                 605

Leu


<210> SEQ ID NO 12
<211> LENGTH: 584
<212> TYPE: PRT
<213> ORGANISM: Unknown
<220> FEATURE:
<223> OTHER INFORMATION: Description of Unknown:
      Albumin peptide sequence

<400> SEQUENCE: 12

Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
            20                  25                  30

Lys Cys Ser Tyr Asp Glu His Ala Lys Leu Val Gln Glu Val Thr Asp
        35                  40                  45

Phe Ala Lys Thr Cys Val Ala Asp Glu Ser Ala Ala Asn Cys Asp Lys
    50                  55                  60

Ser Leu His Thr Leu Phe Gly Asp Lys Leu Cys Ala Ile Pro Asn Leu
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
        115                 120                 125

Glu Asn Pro Thr Thr Phe Met Gly His Tyr Leu His Glu Val Ala Arg
    130                 135                 140
```

-continued

```
Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg Gln Arg Met Lys Cys Ser Ser Met Gln Lys Phe Gly Glu
        195                 200                 205

Arg Ala Phe Lys Ala Trp Ala Val Ala Arg Leu Ser Gln Thr Phe Pro
    210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

Arg Ala Glu Leu Ala Lys Tyr Met Cys Glu Asn Gln Ala Thr Ile Ser
            260                 265                 270

Ser Lys Leu Gln Thr Cys Cys Asp Lys Pro Leu Leu Lys Lys Ala His
        275                 280                 285

Cys Leu Ser Glu Val Glu His Asp Thr Met Pro Ala Asp Leu Pro Ala
    290                 295                 300

Ile Ala Ala Asp Phe Val Glu Asp Gln Glu Val Cys Lys Asn Tyr Ala
305                 310                 315                 320

Glu Ala Lys Asp Val Phe Leu Gly Thr Phe Leu Tyr Glu Tyr Ser Arg
                325                 330                 335

Arg His Pro Asp Tyr Ser Val Ser Leu Leu Leu Arg Leu Ala Lys Lys
            340                 345                 350

Tyr Glu Ala Thr Leu Glu Lys Cys Cys Ala Glu Ala Asn Pro Pro Ala
        355                 360                 365

Cys Tyr Gly Thr Val Leu Ala Glu Phe Gln Pro Leu Val Glu Glu Pro
    370                 375                 380

Lys Asn Leu Val Lys Thr Asn Cys Asp Leu Tyr Glu Lys Leu Gly Glu
385                 390                 395                 400

Tyr Gly Phe Gln Asn Ala Ile Leu Val Arg Tyr Thr Gln Lys Ala Pro
                405                 410                 415

Gln Val Ser Thr Pro Thr Leu Val Glu Ala Ala Arg Asn Leu Gly Arg
            420                 425                 430

Val Gly Thr Lys Cys Cys Thr Leu Pro Glu Asp Gln Arg Leu Pro Cys
        435                 440                 445

Val Glu Asp Tyr Leu Ser Ala Ile Leu Asn Arg Val Cys Leu Leu His
    450                 455                 460

Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
                485                 490                 495

Tyr Val Pro Lys Glu Phe Lys Ala Glu Thr Phe Thr Phe His Ser Asp
            500                 505                 510

Ile Cys Thr Leu Pro Glu Lys Glu Lys Gln Ile Lys Lys Gln Thr Ala
        515                 520                 525

Leu Ala Glu Leu Val Lys His Lys Pro Lys Ala Thr Ala Glu Gln Leu
    530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
```

-continued

```
                565                 570                 575

Thr Arg Cys Lys Asp Ala Leu Ala
            580


<210> SEQ ID NO 13
<211> LENGTH: 608
<212> TYPE: PRT
<213> ORGANISM: Unknown
<220> FEATURE:
<223> OTHER INFORMATION: Description of Unknown:
      Albumin peptide sequence

<400> SEQUENCE: 13

Met Lys Trp Val Thr Phe Leu Leu Leu Leu Phe Val Ser Gly Ser Ala
1               5                   10                  15

Phe Ser Arg Gly Val Phe Arg Arg Glu Ala His Lys Ser Glu Ile Ala
            20                  25                  30

His Arg Tyr Asn Asp Leu Gly Glu Gln His Phe Lys Gly Leu Val Leu
        35                  40                  45

Ile Ala Phe Ser Gln Tyr Leu Gln Lys Cys Ser Tyr Asp Glu His Ala
    50                  55                  60

Lys Leu Val Gln Glu Val Thr Asp Phe Ala Lys Thr Cys Val Ala Asp
65                  70                  75                  80

Glu Ser Ala Ala Asn Cys Asp Lys Ser Leu His Thr Leu Phe Gly Asp
                85                  90                  95

Lys Leu Cys Ala Ile Pro Asn Leu Arg Glu Asn Tyr Gly Glu Leu Ala
            100                 105                 110

Asp Cys Cys Thr Lys Gln Glu Pro Glu Arg Asn Glu Cys Phe Leu Gln
        115                 120                 125

His Lys Asp Asp Asn Pro Ser Leu Pro Pro Phe Glu Arg Pro Glu Ala
    130                 135                 140

Glu Ala Met Cys Thr Ser Phe Lys Glu Asn Pro Thr Thr Phe Met Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Gln Tyr Asn Glu Ile Leu Thr Gln Cys
            180                 185                 190

Cys Ala Glu Ala Asp Lys Glu Ser Cys Leu Thr Pro Lys Leu Asp Gly
        195                 200                 205

Val Lys Glu Lys Ala Leu Val Ser Ser Val Arg Gln Arg Met Lys Cys
    210                 215                 220

Ser Ser Met Gln Lys Phe Gly Glu Arg Ala Phe Lys Ala Trp Ala Val
225                 230                 235                 240

Ala Arg Leu Ser Gln Thr Phe Pro Asn Ala Asp Phe Ala Glu Ile Thr
                245                 250                 255

Lys Leu Ala Thr Asp Leu Thr Lys Val Asn Lys Glu Cys Cys His Gly
            260                 265                 270

Asp Leu Leu Glu Cys Ala Asp Asp Arg Ala Glu Leu Ala Lys Tyr Met
        275                 280                 285

Cys Glu Asn Gln Ala Thr Ile Ser Ser Lys Leu Gln Thr Cys Cys Asp
    290                 295                 300

Lys Pro Leu Leu Lys Lys Ala His Cys Leu Ser Glu Val Glu His Asp
305                 310                 315                 320

Thr Met Pro Ala Asp Leu Pro Ala Ile Ala Ala Asp Phe Val Glu Asp
                325                 330                 335
```

```
Gln Glu Val Cys Lys Asn Tyr Ala Glu Ala Lys Asp Val Phe Leu Gly
            340                 345                 350

Thr Phe Leu Tyr Glu Tyr Ser Arg Arg His Pro Asp Tyr Ser Val Ser
        355                 360                 365

Leu Leu Leu Arg Leu Ala Lys Lys Tyr Glu Ala Thr Leu Glu Lys Cys
    370                 375                 380

Cys Ala Glu Ala Asn Pro Pro Ala Cys Tyr Gly Thr Val Leu Ala Glu
385                 390                 395                 400

Phe Gln Pro Leu Val Glu Glu Pro Lys Asn Leu Val Lys Thr Asn Cys
                405                 410                 415

Asp Leu Tyr Glu Lys Leu Gly Glu Tyr Gly Phe Gln Asn Ala Ile Leu
            420                 425                 430

Val Arg Tyr Thr Gln Lys Ala Pro Gln Val Ser Thr Pro Thr Leu Val
        435                 440                 445

Glu Ala Ala Arg Asn Leu Gly Arg Val Gly Thr Lys Cys Cys Thr Leu
    450                 455                 460

Pro Glu Asp Gln Arg Leu Pro Cys Val Glu Asp Tyr Leu Ser Ala Ile
465                 470                 475                 480

Leu Asn Arg Val Cys Leu Leu His Glu Lys Thr Pro Val Ser Glu His
                485                 490                 495

Val Thr Lys Cys Cys Ser Gly Ser Leu Val Glu Arg Arg Pro Cys Phe
            500                 505                 510

Ser Ala Leu Thr Val Asp Glu Thr Tyr Val Pro Lys Glu Phe Lys Ala
        515                 520                 525

Glu Thr Phe Thr Phe His Ser Asp Ile Cys Thr Leu Pro Glu Lys Glu
    530                 535                 540

Lys Gln Ile Lys Lys Gln Thr Ala Leu Ala Glu Leu Val Lys His Lys
545                 550                 555                 560

Pro Lys Ala Thr Ala Glu Gln Leu Lys Thr Val Met Asp Asp Phe Ala
                565                 570                 575

Gln Phe Leu Asp Thr Cys Cys Lys Ala Ala Asp Lys Asp Thr Cys Phe
            580                 585                 590

Ser Thr Glu Gly Pro Asn Leu Val Thr Arg Cys Lys Asp Ala Leu Ala
        595                 600                 605


<210> SEQ ID NO 14
<211> LENGTH: 584
<212> TYPE: PRT
<213> ORGANISM: Unknown
<220> FEATURE:
<223> OTHER INFORMATION: Description of Unknown:
      Albumin peptide sequence

<400> SEQUENCE: 14

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95
```

-continued

```
Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Lys Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510
```

```
Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Arg Ala Ala Leu Gly
            580


<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Gly Ser
1


<210> SEQ ID NO 16
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Val Met
            20                  25                  30

Lys Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115


<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Met Lys Met Ser
1               5
```

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

```
Ala Ile Ser Gly Ser Gly Gly Ser Thr Tyr Tyr Ala Asp Ser Val Lys
1               5                   10                  15

Gly
```

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

```
Ser Thr His Leu Tyr Leu Phe Asp Tyr
1               5
```

<210> SEQ ID NO 20
<211> LENGTH: 104
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Ser
            100
```

<210> SEQ ID NO 21
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Ala
            20                  25                  30

Phe Leu Ala Trp Tyr Gln Gln Lys Pro Gly Gln Ala Pro Arg Leu Leu
```

-continued 35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Met Arg Gly Arg Pro
85 90 95

Pro Thr Phe Gly Gln Gly Thr Lys Val Glu Ile Lys
100 105

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Arg Ala Ser Gln Ser Val Ser Asn Ala Phe Leu Ala
1 5 10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Gly Ala Ser Ser Arg Ala Thr
1 5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Gln Gln Met Arg Gly Arg Pro Pro Thr
1 5

<210> SEQ ID NO 25
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

Arg Ala Asp Ala Ala Pro Thr Val Ser Ile Phe Pro Pro Ser Ser Glu
1 5 10 15

Gln Leu Thr Ser Gly Gly Ala Ser Val Val Cys Phe Leu Asn Asn Phe
20 25 30

Tyr Pro Lys Asp Ile Asn Val Lys Trp Lys Ile Asp Gly Ser Glu Arg
35 40 45

Gln Asn Gly Val Leu Asn Ser Trp Thr Asp Gln Asp Ser Lys Asp Ser
50 55 60

```
Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105


<210> SEQ ID NO 26
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys
            100


<210> SEQ ID NO 27
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 28
<211> LENGTH: 120
<212> TYPE: PRT
<213> ORGANISM: Artificial Sequence
<220> FEATURE:
```

-continued

```
<223> OTHER INFORMATION: Description of Artificial Sequence: Synthetic
      polypeptide
<220> FEATURE:
<221> NAME/KEY: MISC_FEATURE
<222> LOCATION: (1)..(120)
<223> OTHER INFORMATION: This sequence may encompass 3-30 "Gly Gly Gly
      Ser" repeating units
<220> FEATURE:
<223> OTHER INFORMATION: See specification as filed for detailed
      description of substitutions and preferred embodiments

<400> SEQUENCE: 28

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Ser Gly Gly Gly Ser
        35                  40                  45

Gly Gly Gly Ser Gly Gly Gly Ser Gly Gly Gly Ser Gly Gly Gly Ser
    50                  55                  60

Gly Gly Gly Ser Gly Gly Gly Ser Gly Gly Gly Ser Gly Gly Gly Ser
65                  70                  75                  80

Gly Gly Gly Ser Gly Gly Gly Ser Gly Gly Gly Ser Gly Gly Gly Ser
                85                  90                  95

Gly Gly Gly Ser Gly Gly Gly Ser Gly Gly Gly Ser Gly Gly Gly Ser
            100                 105                 110

Gly Gly Gly Ser Gly Gly Gly Ser
        115                 120


<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Glu Gly Ser Arg Asn Gln Asp Trp Leu
1               5


<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 30

His His His His His His
1               5
```

METHODS AND COMPOSITIONS FOR TREATING CANCER WITH CANCER-TARGETED ADJUVANTS

CROSS-REFERENCE TO RELATED APPLICATIONS

This application is a national phase application under 35 U.S.C. § 371 of International Application No. PCT/US2020/070112 filed Jun. 3, 2020, which claims the benefit of priority of U.S. Provisional Patent Application No. 62/856,375 filed Jun. 3, 2019, which are hereby incorporated by reference in their entirety.

BACKGROUND

II. Field of the Invention

The invention generally relates to the field of medicine. More particularly, it concerns compositions and methods involving nucleotide constructs, proteins, and drug carriers for treating cancers.

III. Background

Generating a robust adaptive immune response against cancer-specific antigens plays a major role in tumor eradication. The advent of checkpoint blockade antibodies, which help T cells overcome the immunosuppressive tumor environment by reinvigorating the T cells' efficacy, has been a breakthrough cancer treatment for extending survival time for patients with metastatic melanoma. Despite its success, immunotherapy provides durable clinical results in only a minority of patients, for only a subset of cancers. It is well established that the extent of T cell infiltration into the tumor is highly predictive of patient responses to immunotherapy. Many patients lack the pre-existing anti-tumor immunity to reinvigorate, or have dominantly immunosuppressive tumors. For these populations, few effective therapies exist for initiating T cell responses, expanding tumor-reactive cells, or making the tumor microenvironment more inflammatory.

Cancer vaccines are one form of immunotherapy by which tumor proteins, or antigens, are used to activate cellular and humoral immune responses against cancer. Typically, these vaccines are comprised of specific antigens along with immunostimulatory molecules, termed adjuvants. The adjuvant activates antigen presenting cells (APCs), licensing them to activate cancer-recognizing T cells.

To overcome the multiple immune evasion mechanisms cancer cells use to avoid attack, cancer vaccines must activate a large enough immune response to multiple tumor antigens. Lack of strong, clinically approved adjuvants combined with the difficulty of identifying cancer-specific antigens pose major barriers to successful cancer vaccination. Despite the success of various therapeutic cancer vaccine approaches in preclinical murine models, few have accomplished the necessary breadth and magnitude of cellular and humoral responses required for tumor control. In translation to the clinical treatment of cancer, many vaccines ultimately fail to activate sufficient magnitude and functionality of cytotoxic CD8+ T cell responses required for therapeutic efficacy. There remains a critical need for additional methods to induce the cellular immune responses against cancer cells required for tumor control.

SUMMARY OF INVENTION

Here, the inventors describe methods and compositions for targeting a TLR agonist to the tumor cell or stroma. Accordingly, aspects of the disclosure relate to a polypeptide comprising a tumor targeting agent operatively linked to p(Man-TLR7).

p(Man-TLR7) is a copolymer having the following structure:

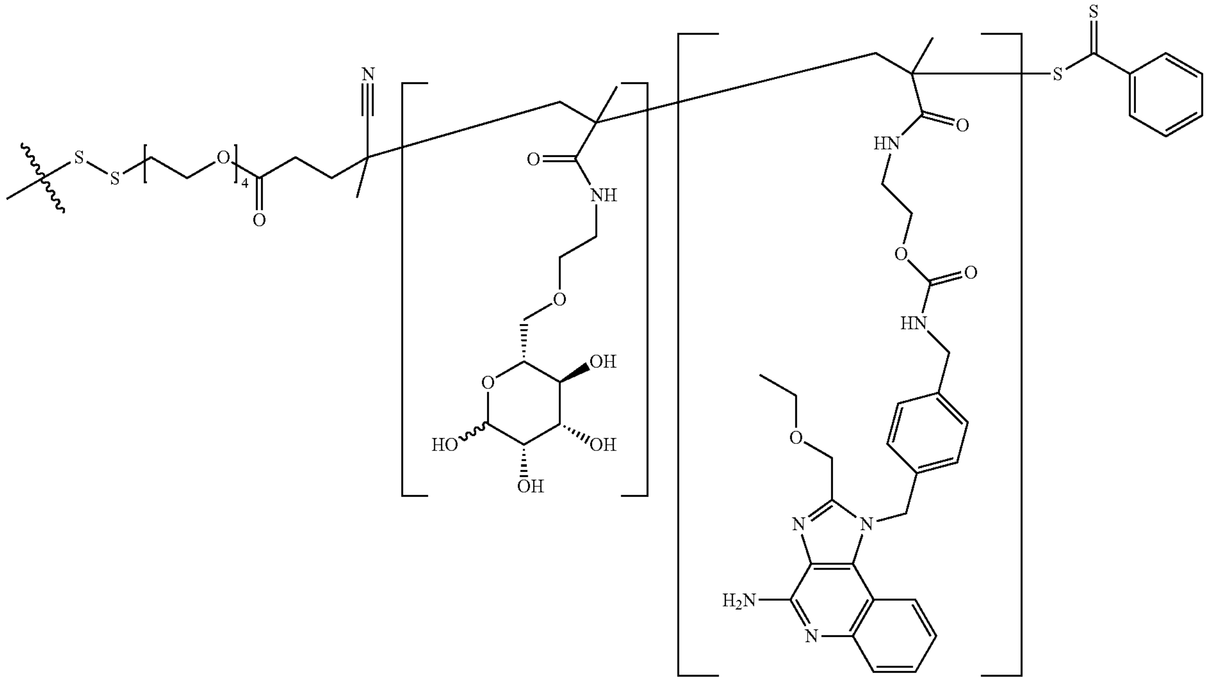

wherein the wavy line indicates attachment to a molecule, such as a tumor targeting agent, as described herein.

Further aspects of the disclosure relate to a polypeptide comprising a a tumor targeting agent operatively linked to a TLR agonist. Further aspects relate to a composition comprising a polypeptide of the disclosure. Further aspects relate to a method for treating cancer in a subject comprising administering a polypeptide or composition of the disclosure. Further aspects relate to a method for targeting a TLR agonist to a tumor in a subject comprising administering a polypeptide or composition of the disclosure. Further aspects relate to a method for increasing the accumulation of a TLR agonist in a tumor in a subject, the method comprising administering a polypeptide or a composition of the disclosure to the subject. Yet further aspects relate to a method for treating a tumor, such as a tumor in a subject, the method comprising administering a polypeptide or a composition of the disclosure to the tumor or subject. In some aspects, the method is for inhibiting tumor growth or tumor progression. The inhibition may be at least, at most, or about 10, 20, 30, 40, 50, 60, 70, 80, 90, 95, 99, or 100% (or any derivable range therein).

The term "operatively linked" refers to a covalent or non-covalent attachment. In some embodiments, the attachment is covalent. In some embodiments, the attachment is non-covalent. In some embodiments, the TLR agonist and/or albumin is covalently linked to the tumor targeting agent. In some embodiments, the TLR agonist is non-covalently linked to the tumor targeting agent.

In some embodiments, the TLR agonist comprises a copolymer and wherein the copolymer comprises the structure (I):

(I)

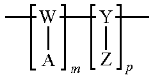

wherein A is absent or comprises at least one group that binds an Antigen Presenting Cell (APC) mannose receptor; Z comprises at least one Toll-Like Receptor (TLR) agonist; W and Y, are each independently a monomer unit of a polymer; m is 10 to 150 (or any integer derivable therein); and p is 1 to 20 (or any integer derivable therein).

In some embodiments, the TLR agonist comprises the TLR agonist having the general structure (VI):

(VI)

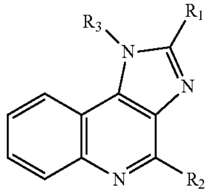

where $R_1$ and $R_2$ are each independently a hydrogen atom, a halogen, an alkyl group, a substituted alkyl group, a heteroalkyl group, a substituted heteroalkyl group, a cycloalkyl group, a substituted cycloalkyl group, a heterocycloalkyl group, a substituted heterocycloalkyl group, an aryl group, or a substituted aryl group; and $R_3$ is a ligand comprising a polymerizable group Y'. It is specifically contemplated that one or more of these species may be excluded in an embodiment.

In some embodiments, the TLR agonist comprises a TLR7 agonist. In some embodiments, the TLR agonist is a TLR7/8 agonist. In some embodiments, the TLR agonist is a TLR agonist as described herein. In some embodiments, the tumor targeting agent targets the tumor cell. In some embodiments, the tumor targeting agent specifically binds to a protein or peptide expressed or located on the surface of the tumor cell. In some embodiments, the tumor targeting agent targets the stroma. In some embodiments, the tumor targeting agent is non-specific to the tumor cell, which indicates that the agent does not specifically bind to the tumor cell.

In some embodiments, the tumor targeting agent binds to collagen. In some embodiments, the tumor targeting agent comprises an antibody or an antigen-binding fragment thereof. In some embodiments, the antibody or antigen-binding fragment comprises a stroma targeting antibody or stroma-binding fragment thereof. In some embodiments, the antibody or binding fragment specifically binds to fibronectin, alternatively spliced domains of fibronectin, collagens, tenascins, periostins, a syndecans, a proteoglycans, or a tumor stroma cell-specific antigen. In some embodiments, the tumor targeting agent comprises a Fab or antibody that specifically binds to an alternatively spliced domain of fibronectin comprising extra domain A (EDA). The table below provides exemplary EDA Fab and antibody embodiments useful in the methods and compositions of the disclosure.

| Description | Sequence | SEQ ID NO: |
|---|---|---|
| | Murinized anti-EDA Fab Sequence | |
| VH | EVQLLESGGGLVQPGGSLRLSCAASGFTFSVMKMSWVRQAP GKGLEWVSAISGSGGSTYYADSVKGRFTISRDNSKNTLYLQ MNSLRAEDTAVYYCAKSTHLYLFDYWGQGTLVTVSS | 16 |
| HCDR1 | VMKMS | 17 |
| HCDR2 | AISGSGGSTYYADSVKG | 18 |
| HCDR3 | STHLYLFDY | 19 |
| CH | AKTTPPSVYPLAPGSAAQTNSMVTLGCLVKGYFPEPVTVTW NSGSLSSGVHTFPAVLQSDLYTLSSSVTVPSSTWPSETVTCNV AHPASSTKVDKKIVPRDCGS | 20 |

-continued

| Description | Sequence | SEQ ID NO: |
|---|---|---|
| Vk | EIVLTQSPGTLSLSPGERATLSCRASQSVSNAFLAWYQQKPG QAPRLLIYGASSRATGIPDRFSGSGSGTDFTLTISRLEPEDFA VYYCQQMRGRPPTFGQGTKVEIK | 21 |
| LCDR1 | RASQSVSNAFLA | 22 |
| LCDR2 | GASSRAT | 23 |
| LCDR3 | QQMRGRPPT | 24 |
| Ck | RADAAPTVSIFPPSSEQLTSGGASVVCFLNNFYPKDINVKWKI DGSERQNGVLNSWTDQDSKDSTYSMSSTLTLTKDEYERHNS YTCEATHKTSTSPIVKSFNRNEC | 25 |
| | Human Anti-EDA Fab Sequence | |
| VH | EVQLLESGGGLVQPGGSLRLSCAASGFTFSVMKMSWVRQAP GKGLEWVSAISGSGGSTYYADSVKGRFTISRDNSKNTLYLQ MNSLRAEDTAVYYCAKSTHLYLFDYWGQGTLVTVSS | 16 |
| HCDR1 | VMKMS | 17 |
| HCDR2 | AISGSGGSTYYADSVKG | 18 |
| HCDR3 | STHLYLFDY | 19 |
| CH | ASTKGPSVFPLAPSSKSTSGGTAALGCLVKDYFPEPVTVSWN SGALTGVHTFPAVLQSSGLYSLSSVVTVPSSSLGTQTYICNV NHKPSNTKVDKRVEPKSC | 26 |
| Vk | EIVLTQSPGTLSLSPGERATLSCRASQSVSNAFLAWYQQKPG QAPRLLIYGASSRATGIPDRFSGSGSGTDFTLTISRLEPEDFA VYYCQQMRGRPPTFGQGTKVEIK | 21 |
| LCDR1 | RASQSVSNAFLA | 22 |
| LCDR2 | GASSRAT | 23 |
| LCDR3 | QQMRGRPPT | 24 |
| Ck | RTVAAPSVFIFPPSDEQLKSGTASVVCLLNNFYPREAKVQWK VDNALQSGNSQESVTEQDSKDSTYSLSSTLTLSKADYEKHK VYACEVTHQGLSSPVTKSFNRGEC | 27 |

In some embodiments, the EDA antibody, EDA Fab, or EDA antigen binding fragment comprises a heavy chain variable region comprising a HCDR1, HCDR2, and/or HCDR3 with an amino acid sequence that is at least 80% identical to SEQ ID NOS:17-19, respectively, and a light chain variable region comprising a LCDR1, LCDR2, and/or LCDR3 with an amino acid sequence that is at least 80% identical to SEQ ID NOS:22-24, respectively. In some embodiments, the EDA antibody, EDA Fab, or EDA antigen binding fragment comprises a heavy chain variable region comprising a HCDR1, HCDR2, and/or HCDR3 with an amino acid sequence having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NOS:17-19, respectively, and a light chain variable region comprising a LCDR1, LCDR2, and/or LCDR3 with an amino acid sequence having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NOS:22-24, respectively. In some embodiments, the EDA antibody, EDA Fab, or EDA antigen binding fragment comprises a heavy chain variable region comprising a HCDR1, HCDR2, and/or HCDR3 with the amino acid sequence of SEQ ID NOS:17-19, respectively, and a light chain variable region comprising a LCDR1, LCDR2, and/or LCDR3 with the amino acid sequence of SEQ ID NOS:22-24, respectively.

In some embodiments, the EDA antibody, EDA Fab, or EDA antigen binding fragment comprises a heavy chain variable region comprising an amino acid sequence with at least 80% sequence identity to SEQ ID NO:16 and/or a light chain variable region comprising an amino acid sequence with at least 80% sequence identity to SEQ ID NO:21. In some embodiments, the EDA antibody, EDA Fab, or EDA antigen binding fragment comprises a heavy chain variable region comprising an amino acid sequence with at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:16 and/or a light chain variable region comprising an amino acid sequence with at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:21. In some embodiments, the EDA antibody, EDA Fab, or EDA antigen binding fragment comprises a heavy chain variable region comprising the amino acid sequence of SEQ ID NO:16 and/or a light chain variable region comprising the amino acid sequence of SEQ ID NO:21.

In some embodiments the EDA antibody, EDA Fab, or EDA antigen binding fragment comprises a heavy chain constant region comprising an amino acid sequence with at least 80% sequence identity to SEQ ID NO:26 and/or a light chain constant region comprising an amino acid sequence with at least 80% sequence identity to SEQ ID NO:27. In some embodiments the EDA antibody, EDA Fab, or EDA antigen binding fragment comprises a heavy chain constant region comprising an amino acid sequence with at least 80% sequence identity to SEQ ID NO:20 and/or a light chain constant region comprising an amino acid sequence with at least 80% sequence identity to SEQ ID NO:25. In some embodiments the EDA antibody, EDA Fab, or EDA antigen binding fragment comprises a heavy chain constant region comprising an amino acid sequence with at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:26 and/or a light chain constant region comprising an amino acid sequence with at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:27. In some embodiments the EDA antibody, EDA Fab, or EDA antigen binding fragment comprises a heavy chain constant region comprising an amino acid sequence with at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:20 and/or a light chain constant region comprising an amino acid sequence with at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:25. In some embodiments the EDA antibody, EDA Fab, or EDA antigen binding fragment comprises a heavy chain constant region comprising the amino acid sequence of SEQ ID NO:26 and/or a light chain constant region comprising the amino acid sequence of SEQ ID NO:27. In some embodiments the EDA antibody, EDA Fab, or EDA antigen binding fragment comprises a heavy chain constant region comprising the amino acid sequence of SEQ ID NO:20 and/or a light chain constant region comprising the amino acid sequence of SEQ ID NO:25.

A CDR may also comprise 1, 2, 3, 4, 5, 6, 7, 8, 9, 10, 11, 12, 13, 14, 15, 16, 16, 18, 19, 20, 21, 22, 23, or more contiguous amino acid residues (or any range derivable therein) flanking one or both sides of a particular CDR sequence; therefore, there may be one or more additional amino acids at the N-terminal or C-terminal end of a particular CDR sequence, such as those shown in SEQ ID NOS:17-19 and 22-24. In some embodiments, the CDR may comprise a fragment of the amino acid sequences shown in SEQ ID NOS:17-19 and 22-24. In some embodiments, the CDR may comprise a fragment of SEQ ID NO:16 or 21, such as a fragment that comprises amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, (or any derivable range therein) to amino acid 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, or 118 of SEQ ID NO:16 and 21.

In some embodiments, the tumor targeting agent comprises an antibody or antigen binding fragment thereof that specifically binds to a tumor-associated antigen or cancer antigen. The cancer antigen may be any cancer antigen that is described herein. In some embodiments, the cancer antigen comprises a cancer antigen that is specific for the subject. In some embodiments, the subject has been determined to have cancer cells that express the cancer antigen. In some embodiments, the method further comprises determining whether cells in a biological sample from the subject express a cancer antigen. In some embodiments, the tumor targeting agent specifically binds to CD47 or TRP1.

In some embodiments, the tumor targeting agent comprises a collagen binding domain. In some embodiments, the polypeptide comprises a collagen binding domain from decorin or von Willebrand factor (vWF). In some embodiments, the collagen binding domain comprises a polypeptide with at least 80% identity to SEQ ID NO:1 or a fragment thereof. In some embodiments, the collagen binding domain comprises a polypeptide with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% identity to SEQ ID NO:1-8 (or any range derivable therein), or a fragment thereof. In some embodiments, the collagen binding domain is at the amino end of the albumin polypeptide and/or TLR agonist. In some embodiments, the collagen binding domain is at the carboxy end of the albumin polypeptide and/or TLR agonist. The phrase "at the amino end" or "at the carboxy end" refers to the relative position of one polypeptide to another. For example, when one polypeptide is "at the amino end" it is linked to the N-terminal amine group of the other polypeptide. However, there may be intervening sequences between the two polypeptides, agents, or domains. Similarly, a polypeptide "at the carboxy end" refers to a polypeptide linked to the carboxy terminus of another polypeptide or domain. In some embodiments, the TLR agonist is linked to the amino terminus of the collagen binding domain or tumor targeting agent. In some embodiments, the TLR agonist is linked to the carboxy terminus of the collagen binding domain or tumor targeting agent.

In some embodiments, the polypeptide comprises a linker between the albumin polypeptide and the collagen binding domain or the tumor targeting agent. In some embodiments, the linker comprises glycine and serine amino acid residues. In some embodiments, the linker comprises GGGS (SEQ ID NO: 15), (GGGS)n (SEQ ID NO: 28), or $(GGGS)_2$ (SEQ ID NO: 9), and n can be 3, 4, 5, 6, 7, 8, 9, 10, 11, 12, 13, 14, 15, 16, 17, 18, 19, 20, 21, 22, 23, 24, 25, 26, 27, 28, 29, 30 or more (or any range derivable therein). In some embodiments, the linker comprises a linker described herein.

In some embodiments, the polypeptide is not operatively linked to a particle, nanovesicle, or liposome. In some embodiments, the polypeptide is not operatively linked to a nanoparticle or a solid support, such as a microplate or bead. In some embodiments, the composition does not comprise a liposome, particle, or nanovescicle. In some embodiments, the composition does not comprise a nanoparticle or a solid support, such as a microplate or a bead. In some embodiments, the polypeptide and/or composition does not further comprise an antigen, such as a cancer antigen.

In some embodiments, the polypeptide comprises at least two collagen binding domains. In some embodiments, the polypeptide comprises at least 2, 3, 4, 5, 6, 7, or 8 collagen binding domains (or any range derivable therein). The collagen binding domains may be in tandem or at both the amino and carboxy terminus of the albumin polypeptide.

In some embodiments, the polypeptide is covalently linked to an albumin polypeptide. In some embodiments, the albumin polypeptide comprises a polypeptide with at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to one of SEQ ID Nos: 11-14.

In some embodiments, the ratio of TLR agonist to tumor targeting agent is 3:1. In some embodiments, the ratio of TLR agonist to tumor targeting agent is at least, at most, or exactly 0.5:1, 1:1, 1.5:1, 2:1, 2.5:1, 3:1, 3.5:1, 4:1, 4.5:1, 5:1, 5.5:1, 6:1, 7:1, 8:1, 9:1, or 10:1 (or any derivable range therein). In some embodiments, the ratio of albumin polypeptide to tumor targeting agent is 1:1, 2:1, 3:1, 4:1, 1:2, 1:3, 1:4, 4:1, 3:1, or 2:1 (or any range derivable therein).

In some embodiments, the molar ratio of the tumor targeting agent to TLR7 agonist is 1:5. In some embodiments, the molar ratio of the tumor targeting agent to TLR7 agonist is at least, at most, or exactly 0.5:1, 1:1, 1.5:1, 2:1, 2.5:1, 3:1, 3.5:1, 4:1, 4.5:1, 5:1, 5.5:1, 6:1, 7:1, 8:1, 9:1, or 10:1 (or any derivable range therein).

In some embodiments, the subject has cancer. In some embodiments, the cancer comprises melanoma, lymphoma, bladder, breast, mammary carcinoma, or colon cancer. In some embodiments, the cancer comprises melanoma. In some embodiments, the cancer comprises a mammary carcinoma. In some embodiments, the cancer comprises breast cancer. In some embodiments, the cancer is a cancer described herein.

In some embodiments, the method further comprises administration of one or more additional cancer therapies. In some embodiments, the cancer therapy comprises an immunotherapy. In some embodiments, the cancer therapy comprises an additional therapy described herein. In some embodiments, the subject has or will receive an immunotherapy. In some embodiments, the immunotherapy is administered before, after, or concurrent with the polypeptide. In some embodiments, the immunotherapy comprises checkpoint inhibitor therapy. In some embodiments, the checkpoint inhibitor therapy comprises a PD-1 antibody, a CTLA4 antibody, or both. In some embodiments, the checkpoint inhibitor therapy comprises a PD-L1 antibody.

In some embodiments, the polypeptide or composition is administered systemically. In some embodiments, the polypeptide or composition is administered by intravenous injection. In some embodiments, the polypeptide or composition is administered by intraperitoneal injection. In some embodiments, the polypeptide and additional therapy is administered in the same composition. In some embodiments, the polypeptide and additional therapy are administered in separate compositions. In some embodiments, compositions of the disclosure further comprise one or more immune checkpoint inhibitors. In some embodiments, compositions of the disclosure comprise a PD1 antibody. In some embodiments, compositions of the disclosure comprise a CTLA4 antibody. In some embodiments, compositions of the disclosure comprise a PD-1 and CTLA4 antibody. In some embodiments, the polypeptide or composition is administered intratumorally or peritumorally. In some embodiments, the polypeptide or composition is administered by a route of administration described herein.

In some embodiments, the method further comprises administration of an additional cancer therapy. In some embodiments, the subject has or will receive an immunotherapy. In some embodiments, the subject has been determined to be non-responsive to the immunotherapy. In some embodiments, the subject has refractory cancer. In some embodiments, the subject is one that experienced toxicity associated with the previous therapy or previous immunotherapy. In some embodiments, the method further comprises administration of an immunotherapy. In some embodiments, he immunotherapy is administered before, after, or concurrent with the polypeptide. In some embodiments, the immunotherapy comprises checkpoint inhibitor therapy. In some embodiments, the checkpoint inhibitor therapy comprises mono checkpoint inhibitor therapy, which indicates that only one checkpoint inhibitor is administered. In some embodiments, the checkpoint inhibitor therapy comprises combination checkpoint inhibitor therapy, which indicates that at least two checkpoint inhibitors, such as an inhibitor to PD-1 and an inhibitor to CTLA-4 is administered. In some embodiments, the checkpoint inhibitor therapy comprises a PD-1 antibody. In some embodiments, the checkpoint inhibitor therapy comprises one or more checkpoint inhibitors described herein.

In some embodiments, the administered dose of the TLR agonist is less than the minimum effective dose of the TLR agonist unlinked to the tumor targeting agent. In some embodiments, the administered dose of the TLR agonist is at least 10, 20, 30, 40, 50, 60, 70, 80, or 90% (or any derivable range therein) less than the minimum effective dose of the TLR agonist unlinked to the tumor targeting agent. In some embodiments, the administered dose of the TLR agonist is less than the minimum effective dose of the TLR agonist unlinked to the tumor targeting agent linked to the albumin polypeptide. In some embodiments, the administered dose of the TLR agonist is at least 10, 20, 30, 40, 50, 60, 70, 80, or 90% (or any derivable range therein) less than the minimum effective dose of the TLR agonist unlinked to the tumor targeting agent and albumin polypeptide. In some embodiments, the subject has been previously treated with an adjuvant. In some embodiments, the subject has been determined to be non-responsive to the previous treatment or wherein the wherein the subject experienced non-specific toxicity to the previous treatment. In some embodiments, the subject experience greater than 2, 3, 4, or 5 immune related adverse events in response to the prior therapy.

The terms "protein", "polypeptide" and "peptide" are used interchangeably herein when referring to a gene product.

The terms "subject," "mammal," and "patient" are used interchangeably. In some embodiments, the subject is a mammal. In some embodiments, the subject is a human. In some embodiments, the subject is a mouse, rat, rabbit, dog, donkey, or a laboratory test animal such as fruit fly, zebrafish, etc. In some embodiments, the subject is a non-human primate.

In some embodiments, the patient has been previously treated for the cancer. In some embodiments, the subject was resistant to the previous cancer treatment. In some embodiments, the subject was determined to be a poor responder to the previous cancer treatment.

It is contemplated that the methods and compositions include exclusion of any of the embodiments described herein.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z,"

"x or (y and z)," or "x or y or z." Is specifically contemplated that x, y, or z may be specifically excluded from an embodiment.

Throughout this application, the term "about" is used according to its plain and ordinary meaning in the area of cell biology to indicate that a value includes the standard deviation of error for the device or method being employed to determine the value.

The term "comprising," which is synonymous with "including," "containing," or "characterized by," is inclusive or open-ended and does not exclude additional, unrecited elements or method steps. The phrase "consisting of" excludes any element, step, or ingredient not specified. The phrase "consisting essentially of" limits the scope of described subject matter to the specified materials or steps and those that do not materially affect its basic and novel characteristics. It is contemplated that embodiments described in the context of the term "comprising" may also be implemented in the context of the term "consisting of" or "consisting essentially of."

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. Aspects of an embodiment set forth in the Examples are also embodiments that may be implemented in the context of embodiments discussed elsewhere in a different Example or elsewhere in the application, such as in the Summary of Invention, Detailed Description of the Embodiments, Claims, and description of Figure Legends.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-E. Selection of monoclonal tumor-binding antibody components (anti-TRP1 and anti-CD47) for in situ vaccination of various transplantable and autologous murine tumor models. a. B16F10 cells were incubated with Cy7-labeled anti-TRP1, anti-CD47, mouse IgG2a isotype control antibodies at 30 μg/mL or with 5 μg/mL antibody as pManTLR7 conjugate for 20 min at 4C. Cells were washed before analysis by flow cytometry. b. EMT6 or c. PyMT cells were incubated with Cy7-labeled anti-CD47 or mouse IgG2a isotype control antibody at 30 μg/mL for 20 min at 4° C., washed, and fluorescent signal was analyzed via flow cytometry. d. Frozen tissue sections of B16F10 tumor or BP tumor were stained with anti-TRP1-Cy7, anti-CD47, and biotinylated anti-collagen IV antibodies. Primary staining of antibodies was detected via Alexa Fluor 647 anti-rat Ab (Invitrogen) and 750-conjugated streptavidin (BioLegend). Slides mounted with ProLong gold antifade mountant with DAPI (Invitrogen) were then imaged on a confocal microscope. Scale bar shows 70 μm. e. Mice bearing 80 mm3 B16F10 tumors were treated intratumorally with Cy7-labeled anti-TRP1, anti-CD47, mouse IgG2a isotype control antibodies and imaged at various timepoints post treatment. Tumors were imaged via IVIS Spectrum fluorescent imaging system. Quantitative analysis of fluorescent signal of the tumors treated with fluorescently labeled conjugates was performed using radiant efficiency to calculate protein content. Data represented as mean±SEM for n=5 mice. Paired t-test, Bonferroni-Dunn post hoc test correction. * P<0.05, P<0.01, *P<0.001, **** P<0.0001, # indicates significance between anti-Trp1 and isotype control antibodies.

FIG. 2A-D. pManTLR7 is conjugated to tumor-binding antibodies. a. Representative schematic of antibody-pManTLR7 polymer, composed of mannose and TLR7 monomers. b. Gel electrophoresis analysis of i. free antibody, ii. anti-TRP1-Linker, iii. anti-TRP1-pManTLR7. The experiment was repeated at least twice with similar results. c. MALDI-TOF-MS analysis of TRP1 antibody alone (left) and after conjugation to 2 kDa Dithiol pyridyl-PEG-BCN linker. Molecular weight changed used to calculate the amount of linker per antibody molecule and subsequent estimation of the number of pManTLR7 polymers per antibody of final product. d. B16F10 cells were stained with Alexa Fluor-647 labeled mouse IgG2a isotype control antibody, anti-TRP1, or anti-TRP1-pManTLR7 conjugate, washed, and cell fluorescence was analyzed via flow cytometry FIG. 3A-D. Antibody-pmanTLR7 conjugates prolong tumor retention in an antigen-specific manner. (a) EMT6 tumor cells stained with fluorescently labeled anti-$CD47_{647}$-pManTLR7 conjugates or anti-$CD47_{647}$ antibody alone, with equivalent amounts of fluorescently labeled antibody. Fluorescence of bound antibody to EMT6 tumor cells were assessed via flow cytometry. (b) Tumor bearing mice imaged 4 hrs post injection with fluorescent dye-labelled conjugates of $aCD47_{647}$-pManTLR7 or $aTRP1_{647}$-pManTLR7 or IgG2a isotype $control_{647}$-pManTLR7 conjugates and imaged via IVIS to measure loss of fluorescent signal over time. ROIs were drawn around tumor and loss of tumor fluorescence was calculated with respect to % initial (4 hr) fluorescent signal. Intratumoral half-life was calculated using phase decay curve fitting of Radiant Efficiency loss over time in B16F10 (c) and EMT6 (d) tumor-bearing mice. Experiments were repeated twice with pooled results shown for (c, d).

FIG. 4A-G. anti-TRP1-pManTLR7 treatment reduces B16F10 melanoma growth rate and systemic exposure to TLR7. a. Mice were inoculated with B16F10 cells on day 0 and vaccinated every 4 days, starting on day 5 with 30 μg of TLR7 as anti-TRP1-pManTLR7, equivalent amount unconjugated mix of anti-TRP1 and pManTLR7, 30 μg of CpG, or saline (vehicle). b, c, f, and g are from experimental setup where mice were inoculated with 300,000 cells. d and e are from identical treatment schedule and dosing, except mice were inoculated with 400,000 cells and sacrificed on day 14. All treatments were administered intratumorally. b. Tumor volumes over time until the first mouse died [n=8, mean±SD] c. Percent survival until endpoint. Concentration of IFNγ secretion in supernatant after restimulation of cells from d, tumor-draining lymph node and e, spleen with gp100 tumor peptide for 3 days, as determined by ELISA [n=5, mean±SD]. 24 hours post vaccination blood plasma was collected, and concentrations of systemic f, IL-6 and g, IL-12p70 was determined by ELISA [n=8, mean±SD]. Log-rank (Mantel-Cox) test was performed for survival curves. Statistical analysis were done using ANOVA and Bonferroni post-hoc test correction. Kruskal-Wallis test followed by Dunn's multiple comparison was used in b due to nonparametic data. *P<0.05, ** P<0.01.

FIG. 5A-D. anti-TRP1-pManTLR7 vaccination does not synergize with anti-CTLA4 and anti-PD1 checkpoint blockade therapy. a. Mice were inoculated with B16F10 cells on day 0 and vaccinated every 4 days, starting on day 5 with 30 μg of TLR7 as anti-TRP1-pManTLR7 alone or in combination with anti-PD1+anti-CTLA4 antibodies (100 μg of each, administered intraperitoneally), anti-PD1+anti-CTLA4 alone, or saline (vehicle). b. Tumor volumes over time until the first mouse died [n=8, mean±SD] c. Percent survival. Concentration of IFNγ secretion in supernatant after restimulation of cells from d, tumor-draining lymph node with gp100 tumor peptide for 3 days, as determined by ELISA [n=5, mean±SD]. Log-rank (Mantel-Cox) test was performed for survival curves. Statistical analysis were done using ANOVA and Bonferroni post-hoc test correction. *P<0.05, **P<0.01.

FIG. 6A-F. Vaccination efficacy in immunologically excluded tumor model EMT6. (a) Treatment schedule for EMT6 tumor-bearing mice. Mice were dosed 3 times at 4 day interval than 1× 8 days later with vaccine or control treatment as shown. For combination with checkpoint inhibitor antibodies (Anti-CTLA4+anti-PD1, 100 ug each) mice were treated i.p. For anti-CD47 alone, mice were treated intratumorally with equivalent dose of anti-CD47 antibody was administered as contained in full anti-CD47-pManTLR7 conjugate. BALB/C mice (n=8) were inoculated with $5\times10^5$ EMT6 murine breast cancer cells then treated with 20 μg of TLR7 as aCD47-p(Man-TLR7), aCD47+pManTLR7 mixed, or saline as shown. Checkpoint blockade antibodies anti-PD1 and anti-CTLA4, 100 ug each were administered i.p. Mice were followed up for tumor growth over time. Mean tumor volume ±SEM (b) and the Kaplan-Meier survival curves (c) are shown. (g) Surviving mice were re-challenged with $5\times10^5$ EMT6 cells in the abscopal mammary fat pad 30 days after tumor clearance (day 90 post initial tumor inoculation) to assess circulating memory responses. (e) EMT6 tumor bearing mice were vaccinated following the same schedule shown in (a) and additionally treated with either isotype control Ab (no cell depletion), anti-CSF1R, or anti-CD8a depleting antibodies i.p. starting one day prior to first vaccination. Mean tumor volume ±SEM (e) and the Kaplan-Meier survival curves (f) are shown.

FIG. 7A-C. tAb-pManTLR7 is endocytosed by multiple APC subsets and activates DCs and macrophages in tumor and draining lymph node. (a) Percentage of anti-$CD47_{647}$-pManTLR+ cells of DC populations and macrophages in the tumor and tumor-draining lymph node 24 hours after intratumoral injection. APC subsets defined as CD11c+ all: $CD11c^+CD11b^-$, $CD103^+$ DC: $CD11c^+CD11b^-$ $CD103^+$, $CD8^+$DC: $CD11c^+CD11b^-$ $CD8a^+$, $CD11c^+CD11b^+$DCs, Macrophage: $CD11b^+F480^+$, M1 macrophage: $CD11b^+$ $F480^+CD80^+$, M2 macrophage: $CD11b^+F480^+CD206^+$. (n=5, mean±SD). Percentage of live macrophages (b), inflammatory monocytes ($CD11b^+Ly6C^{hi}$)(c), $CD11c^+$DC, and $CD103^+$ DCs in tumor draining lymph node 24 hours after vaccination with anti-CD47-pManTLR7, anti-CD47+pManTLR7, or saline. (n=7, mean±SD) (c) Activation of cell populations in tumor (left) and tumor draining lymph node. Cell populations defined by same markers as in (a), including Plasmacytoid DC: $CD11c^+B220^+$. For (b, c) statistical differences were determined via two-tailed t-test. Experiments were repeated twice with similar results.

FIG. 8A-D. Production of tumor stroma-binding antibody fragment (anti-EDA) for vaccination of various transplantable and autologous murine tumor models. a. Gel electrophoresis of the anti-EDA Fab produced in HEK293 cells after purification under non-reducing (i.) and reducing conditions (ii.). Expected size is 47 kDa. An additional band at just under 75 kDa also appears that is eliminated under reducing conditions. This experiment was repeated at least twice with similar results. b. Western blot of the anti-EDA Fab with detection using an anti-human IgG antibody. c. ELISA testing binding of anti-EDA Fab to EDA, as described in Materials and Methods section. Measured $K_d$ was 50.9 nM. d. Frozen tissue sections of B16F10 tumor were stained with rat anti-mouse CD31 (panels 1-8) and biotinylated mouse anti-EDA (panels 1-4 only) antibodies. Primary staining of antibodies was detected via Alexa Fluor 647-conjugated anti-rat IgG (panels 1-8) and Alexa Fluor 488-conjugated streptavadin (panels 1-8). Slides mounted with ProLong gold antifade mountant with DAPI (Invitrogen) and were then imaged on an IX83 microscope (Olympus). Images were processed using ImageJ software (NIH).

FIG. 9A-B. p(Man-TLR7) is conjugated to anti-EDA Fab. a. Representative schematic of anti-EDA Fab conjugated to the p(Man-TLR7) polymer, composed of mannose and TLR7 monomers. b. Gel electrophoresis analysis of i. free anti-EDA Fab, ii. anti-EDA Fab-linker, iii. anti-EDA Fab-p (Man-TLR7). The experiment was repeated at least twice with similar results.

FIG. 10A-C. Anti-EDA Fab-p(Man-TLR7) vaccination synergizes with anti-CTLA-4 and anti-PD-1 checkpoint blockade therapy to reduce B16F10 melanoma growth rate. a. Mice were inoculated with 500,000 B16F10 cells on day 0 and vaccinated at days 4 and 9 post-tumor inoculation with 10 μg of TLR7 as human anti-EDA Fab-p(Man-TLR7) alone (n=4) or in combination with anti-PD-1+anti-CTLA-4 antibodies (100 μg of each, administered intravenously), equivalent amounts of an unconjugated mix of human anti-EDA Fab and p(Man-TLR7), or anti-PD-1+anti-CTLA-4 alone. Additionally, one group of mice was left untreated as a control (n=3). All treatments were administered intravenously via the tail vein. n=5 for all groups, except where noted. b. Tumor volumes over time until the first mouse died [mean±SD]. c. Percent survival until endpoint. Log-rank (Mantel-Cox) test was performed for survival curves. Statistical analysis on tumor growth curves was done using one-way ANOVA followed by Tukey's multiple comparisons test at day 12. *P<0.05, **P<0.01.

FIG. 11A-G. Immune cell analysis following anti-EDA Fab-p(Man-TLR7) vaccination. a. Mice (n=6) were inoculated with 500,000 B16F10 cells on day 0 and vaccinated at days 4 and 8 post-tumor inoculation with 30 μg of TLR7 as human anti-EDA Fab-p(Man-TLR7) alone or in combination with anti-PD-1+anti-CTLA-4 antibodies (100 μg of each), equivalent amounts of an unconjugated mix of human anti-EDA Fab and p(Man-TLR7) with or without the checkpoint antibodies, anti-PD-1+anti-CTLA-4 alone, or PBS. Checkpoint antibodies were administered intraperitoneally. All other treatments were administered intravenously. Mice were then sacrificed at day 10, and the tumors were harvested. b. Tumor volumes over time [mean±SD]. c-g. Flow cytometric analysis on the harvested tumors. Cell types are defined as follows: (c) $CD8^+$ T cells: $CD45^+CD3^+CD8^+$; (d) $CD4^+$ T cells: $CD45^+CD3^+CD4^+$; (e) Tregs: $CD45^+CD3^+$ $CD4^+CD25^+Foxp3^+$; (f) NK cells: $CD45^+CD3^-NK1.1^+$; (g) Macrophages: $CD45^+CD19^-Gr1^-F4/80^+$. All statistical analyses were done using ANOVA with Tukey's test. *P<0.05, P<0.01, *P<0.001, ****P<0.0001.

FIG. 12A-C. Vaccination with murinized anti-EDA Fab-p(Man-TLR7) synergizes with anti-CTLA-4 and anti-PD-1 checkpoint blockade therapy to reduce B16F10 melanoma growth rate. a. Mice (n=10) were inoculated with 500,000 B16F10 cells on day 0 and vaccinated at days 4, 8, and 12 post-tumor inoculation with 30 μg of TLR7 as murinized anti-EDA Fab-p(Man-TLR7) in combination with anti-PD-1+anti-CTLA-4 antibodies (100 μg of each), anti-PD-1+anti-CTLA-4 alone, or PBS. Checkpoint antibodies were administered intraperitoneally. All other treatments were administered intravenously. b. Tumor volumes over time until the first mouse died [mean±SD]. c. Percent survival until endpoint. Log-rank (Mantel-Cox) test was performed for survival curves. Statistical analysis on tumor growth curves was done using one-way ANOVA followed by Tukey's multiple comparisons test at day 12. *P<0.05, P<0.01, *P<0.001.

FIG. 13A-H. Intratumoral administration of EDA targeted-p(Man-TLR7) vaccination results in improved anti-tumor efficacy as compared to intravenous administration. a. Mice (n=5-6) were inoculated with 500,000 B16F10 cells on day 0 and vaccinated at days 4 and 9 post-tumor inoculation with 10 or 30 μg of TLR7 as murinized anti-EDA Fab-p (Man-TLR7) in combination with anti-PD-1+anti-CTLA-4 antibodies (100 μg of each), anti-PD-1+anti-CTLA-4 alone, or PBS. Checkpoint antibodies were administered intraperitoneally. Other treatments were administered intravenously or intratumorally, as indicated. b. Tumor volumes over time until the first mouse died in each group [mean±SD]. c. Percent survival until endpoint. d. Blood was collected 11 days post-tumor inoculation, and titers of IgGs against the anti-EDA Fab in the plasma were assessed by ELISA. e-h. Blood was collected 11 days post-tumor inoculation, and levels of IL-6 (e), IL-12p70 (f), TNFα (g), and IFNγ (h) in the serum were assessed by ELISA. Log-rank (Mantel-Cox) test was performed for survival curves. Statistical analysis on tumor growth curves was done using one-way ANOVA followed by Tukey's multiple comparisons test at day 12. *P<0.05, P<0.01, *P<0.001, ****P<0.0001.

FIG. 14A-D. p(Man-TLR7) is conjugated to CBD-SA. a. Representative schematic of CBD-SA conjugated to the p(Man-TLR7) polymer, composed of mannose and TLR7 monomers. b. Gel electrophoresis analysis of free CBD-SA and CBD-SA-linker under reducing and non-reducing conditions. The experiment was repeated at least twice with similar results. c. Gel electrophoresis analysis of free CBD-SA and CBD-SA-p(Man-TLR7). The experiment was repeated at least twice with similar results. d. ELISA testing binding of CBD-SA and CBD-SA-p(Man-TLR7) to collagen I and collagen III, as described in Materials and Methods section. Statistical analysis was done using one-way ANOVA followed by Tukey's multiple comparisons test. Significance shown is comparing the background absorbance with the absorbance from either CBD-SA or CBD-SA-p(Man-TLR7). *P<0.05, P<0.01, *P<0.001, N.S.=not significant.

FIG. 15A-C. CBD-SA-p(Man-TLR7) vaccination synergizes with anti-CTLA-4 and anti-PD-1 checkpoint blockade therapy to reduce B16F10 melanoma growth rate. a. Mice were inoculated with 500,000 B16F10 cells on day 0 and vaccinated at days 4 and 9 post-tumor inoculation with 10 μg of TLR7 as CBD-SA-p(Man-TLR7) alone (n=3) or in combination with anti-PD-1+anti-CTLA-4 antibodies (100 μg of each, administered intravenously, n=3), equivalent amounts of an unconjugated mix of CBD-SA and p(Man-TLR7) (n=4), or anti-PD-1+anti-CTLA-4 alone (n=5). Additionally, one group of mice was left untreated as a control (n=3). All treatments were administered intravenously via the tail vein. n is indicated for all groups. b. Tumor volumes over time until the first mouse died [mean±SEM]. c. Percent survival until endpoint. Log-rank (Mantel-Cox) test was performed for survival curves. Statistical analysis on tumor growth curves was done using one-way ANOVA followed by Tukey's multiple comparisons test at day 12.

FIG. 16A-C. Vaccination with murine CBD-SA-p(Man-TLR7) synergizes with anti-CTLA-4 and anti-PD-1 checkpoint blockade therapy to reduce B16F10 melanoma growth rate. a. Mice (n=10) were inoculated with 500,000 B16F10 cells on day 0 and vaccinated at days 4, 8, and 12 post-tumor inoculation with 30 μg of TLR7 as murine CBD-SA-p(Man-TLR7) in combination with anti-PD-1+anti-CTLA-4 antibodies (100 μg of each), anti-PD-1+anti-CTLA-4 alone, or PBS. Checkpoint antibodies were administered intraperitoneally. All other treatments were administered intravenously. b. Tumor volumes over time until the first mouse died [mean±SD]. c. Percent survival until endpoint. Log-rank (Mantel-Cox) test was performed for survival curves. Statistical analysis on tumor growth curves was done using one-way ANOVA followed by Tukey's multiple comparisons test at day 12. *P<0.05, P<0.01, *P<0.001, ****P<0.0001.

FIG. 17A-H. Intratumoral administration of collagen targeted-p(Man-TLR7) vaccination results in improved anti-tumor efficacy as compared to intravenous administration. a. Mice (n=5-6) were inoculated with 500,000 B16F10 cells on day 0 and vaccinated at days 4 and 9 post-tumor inoculation with 10 or 30 μg of TLR7 as murine CBD-SA-p(Man-TLR7) in combination with anti-PD-1+anti-CTLA-4 antibodies (100 μg of each), anti-PD-1+anti-CTLA-4 alone, or PBS. Checkpoint antibodies were administered intraperitoneally. Other treatments were administered intravenously or intratumorally, as indicated. b. Tumor volumes over time until the first mouse died in each group [mean±SD]. c. Percent survival until endpoint. d. Blood was collected 11 days post-tumor inoculation, and titers of IgGs against CBD-SA in the plasma were assessed by ELISA. e-h. Blood was collected 11 days post-tumor inoculation, and levels of IL-6 (e), IL-12p70 (f), TNFα (g), and IFNγ (h) in the serum were assessed by ELISA. Log-rank (Mantel-Cox) test was performed for survival curves. Statistical analysis on tumor growth curves was done using one-way ANOVA followed by Tukey's multiple comparisons test at day 12. *P<0.05, P<0.01, *P<0.001, ****P<0.0001.

DETAILED DESCRIPTION

Figure 1A:
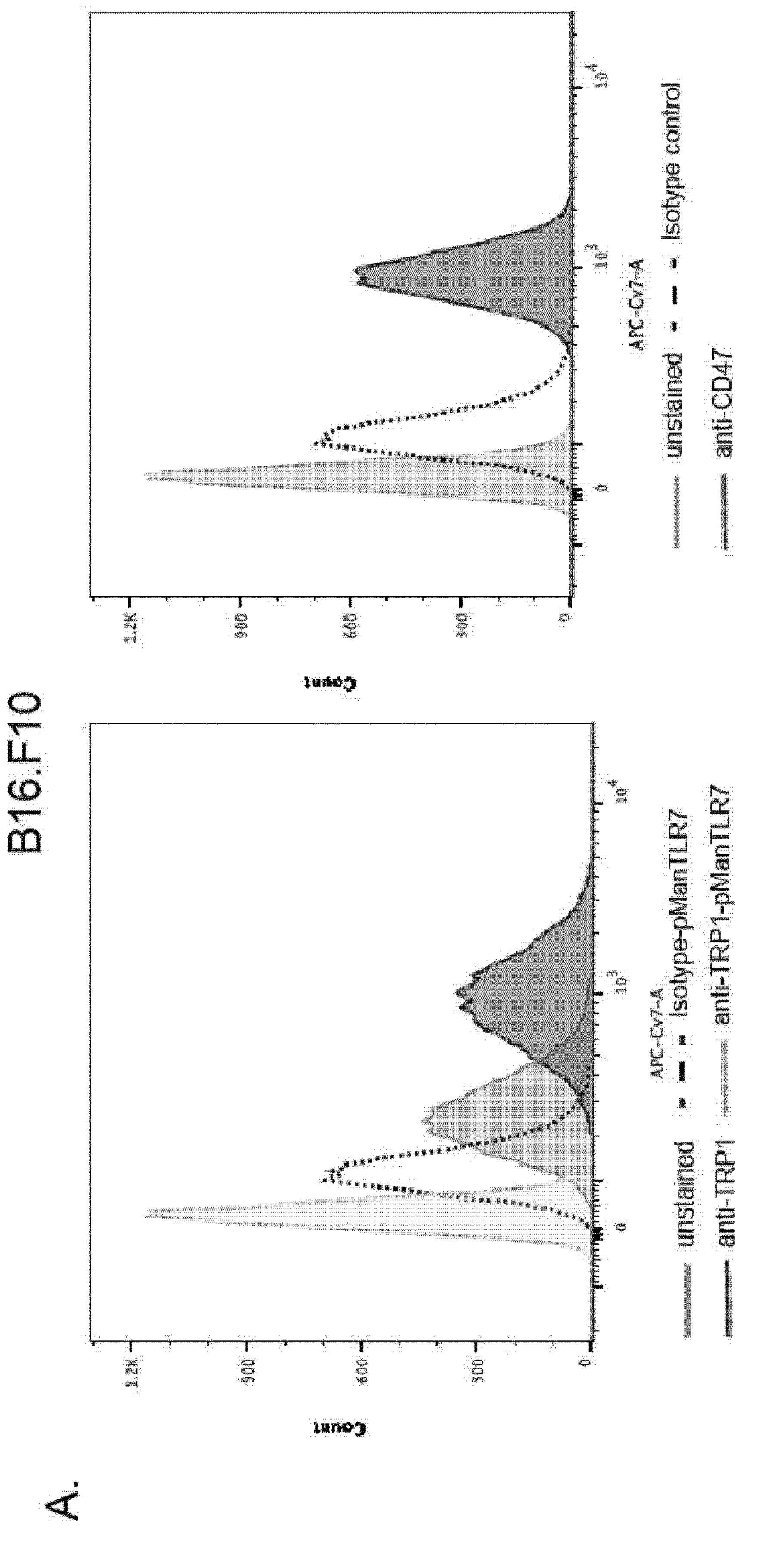
Figure 1B:
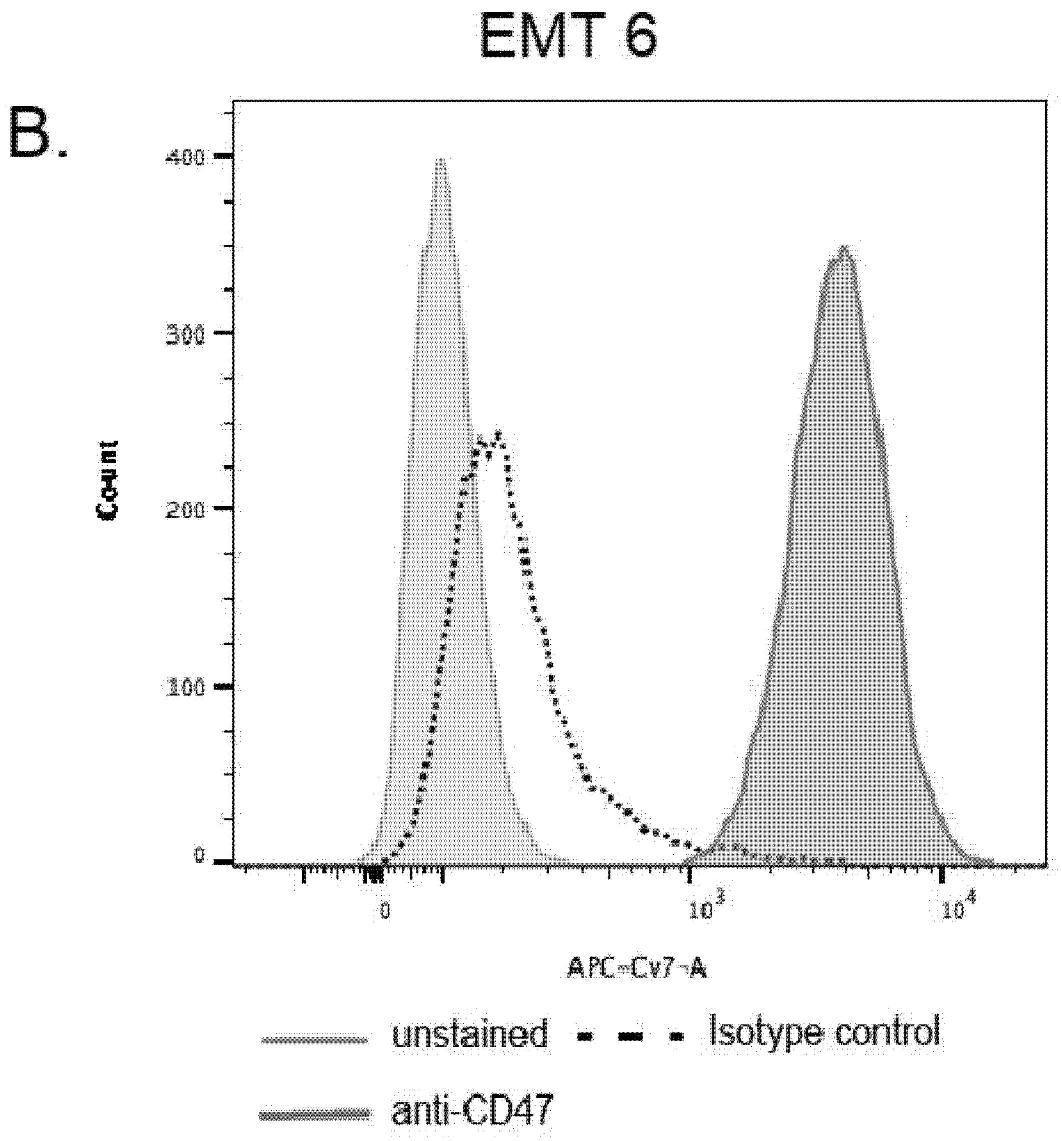

Here the inventors demonstrate the creation of therapeutic cancer vaccines using a TLR7 agonist adjuvant conjugated to a tumor- or matrix-binding moieties, optimizing the adjuvant as an in situ vaccine where the tumor itself is utilized as source of antigen to which immune responses are generated. The compositions and methods of the disclosure are useful for delivering the adjuvant to the tumor and prolonging tumor retention of the adjuvant to increase APC activation within the tumor microenvironment and enhance T cell priming in the tumor draining lymph node. By increasing intratumoral APC activation, the inventors' vaccination will shift the tumor immune environment from suppressive to inflammatory. The cytokines produced by activated APCs will create a proinflammatory cytokine milieu which will improve T cell functionality within the tumor, as well as enhance T cell priming in the tumor draining lymph node. Extended duration and magnitude of inflammatory conditions to the draining lymph node more closely mimics natural infections and previous studies have reported prolonged antigen availability and delivery to immune cells improves vaccination efficacy through T follicular helper cell differentiation, appropriate T cell polarization, and humoral responses. Furthermore, prolonged inflammation with adjuvant and antigen has been shown to improve T cell memory differentiation and clonal expansion. Together, the inventors' vaccination strategy seeks to provides an optimal immunostimulatory context for the priming of naïve T cells against cancer antigens and improved functionality of T cells within the tumor microenvironment.

I. DEFINITIONS

The term "each independently" is used herein to indicate that the choices can be identical or different, i.e., in the case of R groups, for example, the term "each independently" indicates that the R groups (e.g., R1, R2) can be identical (e.g., R1 and R2 may both be substituted alkyl groups) or different (e.g., R1 may be an alkyl group and R2 may be an alkoxy group) specified otherwise, a named R group will have the structure recognized in the art as corresponding to R groups with that name. For the purposes of illustration, representative R groups are defined herein. These definitions are intended to supplement and illustrate, not preclude, the definitions known to those of skill in the art.

The term "aliphatic group" denotes an acyclic or cyclic, saturated or unsaturated hydrocarbon group excluding aromatic compounds. "Substituted aliphatic group" refers to an aliphatic group as just described in which one or more hydrogen atoms attached to carbon of the aliphatic group is replaced by any other group, such as halogen, aryl, substituted aryl, heteroaryl, substituted heteroaryl, cycloalkyl, alkoxy, amino, ester, amide, alcohol, and combinations thereof.

The term "alkyl group" denotes a monovalent linear or branched saturated hydrocarbon group of 1 to 12 carbon atoms. In certain embodiments, an alkyl group has 1 to 7 carbon atoms, and in more particular embodiments 1 to 4 carbon atoms. Non-limiting examples of alkyl groups include methyl, ethyl, propyl, isopropyl, n-butyl, iso-butyl, and sec-butyl. Particular alkyl groups include methyl, ethyl, propyl and isopropyl. More particular alkyl groups are methyl, ethyl and propyl.

The term "substituted alkyl group" refers to an alkyl group as just described in which one or more hydrogen atoms attached to at least one carbon of the alkyl group is replaced by any other group, such as halogen, aryl, substituted aryl, heteroaryl, substituted heteroaryl, cycloalkyl, alkoxy, amino, ester, amide, alcohol, and combinations thereof.

The term "cycloalkyl group" denotes a cyclized alkyl group, for example cyclopropyl, cyclobutyl, cyclopentyl, cyclohexyl, etc.

The term "substituted cycloalkyl group" refers to a cycloalkyl group as just described in which one or more hydrogen atoms attached to at least one carbon of the cycloalkyl group is replaced by another group, such as halogen, alkyl, substituted alkyl, aryl, substituted aryl, cycloalkyl, substituted cycloalkyl, heterocycloalkyl, heteroaryl, substituted heteroaryl, alkoxy, aryloxy, boryl, phosphino, amino, thio, ester, amide, alcohol and combinations thereof.

The term "heteroalkyl group" refers to an alkyl or a substituted alkyl group as described above in which one or more carbon atoms are replaced with a heteroatom from the group consisting of N, O, P, B, S, Si, Se and Ge. The bond between the carbon atom and the heteroatom may be saturated or unsaturated. Examples include an alkoxy group such as methoxy, ethoxy, propoxy, iso-propoxy, butoxy or t-butoxy, an alkoxyalkyl group such as methoxymethyl, ethoxymethyl, 1-methoxyethyl, 1-ethoxyethyl, 2-methoxyethyl or 2-ethoxyethyl, an alkylamino group such as methylamino, ethylamino, propylamino, isopropylamino, dimethylamino or diethylamino, an alkylthio group such as methylthio, ethylthio or isopropylthio or a cyano group. Thus, an alkyl group substituted with a group such as heterocycloalkyl, substituted heterocycloalkyl, heteroaryl, substituted heteroaryl, alkoxy, aryloxy, boryl, phosphino, amino, imino, or thio is within the scope of the term heteroalkyl group.

The term "heterocycloalkyl group" refers to a cycloalkyl group as described, but in which one or more or all carbon atoms of the unsaturated group are replaced by a heteroatom from the group consisting of N, O, P, B, S, Si, Se and Ge. Suitable heterocycloalkyl groups include, for example, piperazinyl, morpholinyl, tetrahydropyranyl, tetrahydrofuranyl, piperidinyl and pyrrolidinyl.

The term "substituted heterocycloalkyl group" refers to a heterocycloalkyl group as just described, but in which one or more hydrogen atoms on any atom of the heterocycloalkyl group is replaced by another group such as a halogen, alkyl, substituted alkyl, aryl, substituted aryl, cycloalkyl, substituted cycloalkyl, heterocycloalkyl, heteroaryl, substituted heteroaryl, alkoxy, aryloxy, boryl, phosphino, amino, thio, and combinations thereof.

The term "aryl group" refers to an aromatic substituent, which may be a single aromatic ring or multiple aromatic rings which are fused together, linked covalently, or linked to a common group such as a methylene or ethylene moiety. The common linking group may also be a carbonyl as in benzophenone or a heteroatom, such as oxygen in the case of diphenylether or nitrogen in the case of diphenylamine. The aromatic ring(s) may include phenyl, naphthyl, biphenyl, diphenylether, diphenylamine and benzophenone among others. In certain embodiments, aryl groups have between 1 and 50 carbon atoms, 1 and 9 carbon atoms, or 1 and 6 carbon atoms.

The term "substituted aryl group" refers to an aryl group as just described in which one or more hydrogen atoms attached to any carbon atom is replaced by one or more functional groups such as alkyl, substituted alkyl, cycloalkyl, substituted cycloalkyl, heterocycloalkyl, substituted heterocycloalkyl, halogen, halogenated alkyl (e.g., CF3), hydroxy, amino, phosphino, alkoxy, amino, thio and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. Specific example of substituted aryl groups include perfluorophenyl, chlorophenyl, 3,5-dimethylphenyl, 2,6-diisopropylphenyl and the like.

The term "heteroaryl group" refers to aromatic ring(s) in which one or more carbon atoms of the aromatic ring(s) are replaced by a heteroatom(s) such as nitrogen, oxygen, boron, selenium, phosphorus, silicon or sulfur. Heteroaryl group refers to structures that may be a single aromatic ring, multiple aromatic ring(s), or one or more aromatic rings coupled to one or more nonaromatic ring(s). In structures having multiple rings, the rings can be fused together, linked covalently, or linked to a common group such as a methylene or ethylene moiety. The common linking group may also be a carbonyl as in phenyl pyridyl ketone. Rings such as thiophene, pyridine, oxazole, isoxazole, thiazole, isothiazole, isophthalimide, pyrazole, indole, pyridine, pyrimidine, pyrazine, furan, etc. or benzo-fused analogues of these rings are defined by the term "heteroaryl group."

The term "substituted heteroaryl group" refers to a heteroaryl group as just described in which one or more hydrogen atoms on any atom of the heteroaryl moiety is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heteroaryl groups include, for example, 4-N,N-dimethylaminopyridine.

The term "alkoxy group" refers to the —OZ' radical, where Z' is selected from the group consisting of alkyl, substituted alkyl, cycloalkyl, substituted cycloalkyl, heterocycloalkyl, substituted heterocycloalkyl, silyl groups and combinations thereof as described herein. Suitable alkoxy groups include, for example, methoxy, ethoxy, benzyloxy, t-butoxy, and the like. A related term is "aryloxy" where Z' is selected from the group consisting of aryl, substituted aryl, heteroaryl, substituted heteroaryl, and combinations thereof. Examples of suitable aryloxy groups include phenoxy, substituted phenoxy, 2-pyridinoxy, 8-quinalinoxy and the like.

The term "alkoxyalkyl group" denotes an alkyl group where at least one of the hydrogen atoms of the alkyl group has been replaced by an alkoxy group. Exemplary alkoxyalkyl groups include methoxymethyl, ethoxymethyl, methoxyethyl, ethoxyethyl, methoxypropyl, ethoxypropyl and isopropoxymethyl. Particular alkoxyalkyl groups include methoxymethyl, methoxyethyl and ethoxymethyl.

The term "alkoxyalkoxy group" denotes an alkoxy group wherein at least one of the hydrogen atoms of the alkoxy group has been replaced by another alkoxy group. Examples of alkoxyalkoxy groups include methoxymethoxy, ethoxymethoxy, methoxyethoxy, ethoxyethoxy, methoxypropoxy and ethoxypropoxy. Particular alkoxyalkoxy groups include methoxymethoxy and methoxyethoxy.

The term "alkoxyalkoxyalkyl group" denotes an alkyl group wherein at least one of the hydrogen atoms of the alkyl group has been replaced by an alkoxyalkoxy group. Examples of alkoxyalkoxyalkyl groups include methoxymethoxymethyl, ethoxymethoxymethyl, methoxyethoxymethyl, ethoxyethoxymethyl, methoxypropoxymethyl, ethoxypropoxymethyl, methoxymethoxyethyl, ethoxymethoxyethyl, methoxyethoxyethyl, ethoxyethoxyethyl, methoxypropoxyethyl and ethoxypropoxyethyl.

The term "amino group" refers to the group —NZ'Z", where each of Z' and Z" is each independently selected from hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, alkyloxyalkyl, aryloxy, and combinations thereof.

The term "halogen" means fluoro, chloro, bromo, or iodo, preferably fluoro or chloro.

The term "carbonyl" denotes a —C═O or —C(O)— group.

The term "hydroxy" or "alcohol" denotes a —OH group.

The term "cyano" denotes a —C≡T group

The term "azide" denotes a —N3 group.

The compounds and polymers of the present invention may have asymmetric centers. Compounds and polymers of the present invention containing an asymmetrically substituted atom may be isolated in optically active or racemic forms. According to the Cahn-Ingold-Prelog Convention the asymmetric carbon atom can be of the "R" or "S" configuration. It is well known in the art how to prepare optically active forms, such as by resolution of materials. All chiral, diastereomeric, meso, racemic forms are within the scope of this invention, unless the specific stereochemistry or isomeric form is specifically indicated.

Additionally, as used herein the term C1-C6 alkyl and terms derived therefrom includes all the possible isomeric forms of said C1-C6 alkyl group. Furthermore, the heteroaryl include all the positional isomers. Furthermore, all polymorphic forms and hydrates of monomer (VI), copolymers (I), (IV), (VII), or polymer (VIII) are within the scope of this invention.

The terms "compound" and "a compound of the invention" and "compound of the present invention" and the like, and their plural forms include the embodiment of formula (III) and (VI) and the other more particular embodiments encompassed by copolymers (I), (IV), (VII), or polymer (VIII) described herein and exemplified compounds described herein or a pharmaceutically acceptable salt of each of these embodiments. All references to compounds, include all isotopes of the atoms contained therein, including isotopically-labeled compounds.

The terms "polymer" and "a polymer of the invention" and "polymer of the present invention" and the like, and their plural forms include the embodiment of formula (VIII) and the other more particular embodiments encompassed by monomer (VI), copolymers (I), (IV) and (VII) described herein and exemplified compounds and polymers described herein or a pharmaceutically acceptable salt of each of these embodiments. All references to polymers, include all isotopes of the atoms contained therein, including isotopically-labeled polymers.

The compounds and polymers of the present invention may exist as tautomers. All tautomeric forms of the compounds of the invention are contemplated to be within the scope of the present invention.

The compositions also include the prodrugs of monomer (VI), copolymers (I), (IV), (VII), or polymer (VIII). The term prodrug is intended to represent covalently bonded carriers, which are capable of releasing the active ingredient of monomer (VI), copolymers (I), (IV), (VII), or polymer (VIII) respectively, when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups in vivo or by routine manipulation. Prodrugs of monomer (VI), copolymers (I), (IV), (VII), or polymer (VIII) include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups), amides (e.g., trifluoroacetylamino, acetylamino, and the like), and the like.

A "pharmaceutically acceptable salt" of a compound means a salt that is pharmaceutically acceptable and that possesses the desired pharmacological activity of the parent compound. Non-limiting examples of such salts include acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are nontoxic. Additional information on suitable pharmaceutically acceptable salts can be found in Remington's Pharmaceutical Sciences, 17th ed., Mack Publishing Company, Easton, Pa., 1985, which is incorporated herein by reference.

An "antigen" includes any substance that may be specifically bound by an antibody molecule. Thus, the term "antigen" encompasses biologic molecules including, but not limited to, simple intermediary metabolites, sugars, lipids, amino acids, and hormones, as well as macromolecules such as complex carbohydrates, phopholipids, nucleic acids, peptides, and proteins, for example ovalbumin (OVA). In certain embodiments, the antigen is one that is related to the infection or disease to be treated. In specific embodiments, the antigen is from an infectious agent or from a tumor or cancer cell. The antigen may be all or part of a molecule from an infectious agent or tumor/cancer cell. In particular embodiments, the antigen is one in which an immune response is desired or intended.

The term "polymer" refers to a molecule composed of repeating structural units connected by covalent chemical bonds often characterized by a substantial number of repeating units (e.g., equal to or greater than 10 repeating units and often equal to or greater than 50 repeating units and often equal to or greater than 100 repeating units) and a high molecular weight (e.g., greater than or equal to 50,000 Da). Polymers are commonly the polymerization product of one or more monomer precursors. The term polymer includes homopolymers, or polymers consisting essentially of a single repeating monomer subunit. The term polymer also includes copolymers which are formed when two or more different types of monomers are linked in the same polymer. Copolymers may comprise two or more monomer subunits, and include random, block, alternating, segmented, grafted, tapered and other copolymers. Useful polymers include organic polymers that are water miscible for vaccine administration.

An "oligomer" refers to a molecule composed of repeating structural units connected by covalent chemical bonds often characterized by a number of repeating units less than that of a polymer (e.g., equal to or less than 10 repeating units) and a lower molecular weights (e.g., less than or equal to about 50,000 Da) than polymers. Oligomers may be the polymerization product of one or more monomer precursors.

It is specifically contemplated that any of m, o, p, p' or the number of monomers are integers and may be, be at least, or be at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 20000, 30000, 40000, 50000, 60000, 70000, 80000, 90000 or more, or any range derivable therein.

The term "operatively linked" refers to a situation where two components are combined to form the active complex prior to binding at the target site. For example, a molecule conjugated to one-half of a biotin-streptavidin complex and an antigen complexed to the other one-half of the biotin-streptavidin complex are operatively linked through complexation of the biotin and streptavidin molecules. The term operatively linked is also intended to refer to covalent or chemical linkages that conjugate two molecules together.

II. POLYPEPTIDES

A. Targeting Agent

1. Collagen Binding Domain

In some embodiments, the tumor targeting agent comprises a collagen binding peptide. In some embodiments, the polypeptide comprises a collagen binding domain from decorin. In some embodiments, the collagen binding domain comprises a decorin peptide such as LRELHLNNNC (SEQ ID NO:5), which is derived from bovine or LRELHLDNNC (SEQ ID NO:6), which is derived from human.

In some embodiments, the collagen binding domain comprises a peptide fragment from human decorin, which is represented by the following amino acid sequence:

(SEQ ID NO: 7)
CGPFQQRGLFDFMLEDEASGIGPEVPDDRDFEPSLGPVCPFRCQCHLRVV
QCSDLGLDKVPKDLPPDTTLLDLQNNKITEIKDGDFKNLKNLHALILVNN
KISKVSPGAFTPLVKLERLYLSKNQLKELPEKMPKTLQELRAHENEITKV
RKVTFNGLNQMIVIELGTNPLKSSGIENGAFQGMKKLSYIRIADTNITSI
PQGLPPSLTELHLDGNKISRVDAASLKGLNNLAKLGLSFNSISAVDNGSL
ANTPHLRELHLDNNKLTRVPGGLAEHKYIQVVYLHNNNISVVGSSDFCPP
GHNTKKASYSGVSLFSNPVQYWEIQPSTFRCVYVRS AIQLGNYK.

In some embodiments, the collagen binding peptide is a peptide from von Willebrand factor (vWF). The sequence of human vWF comprises the following:

(SEQ ID NO: 4)
MIPARFAGVLLALALILPGTLCAEGTRGRSSTARCSLFGSDFVNTFDGSM
YSFAGYCSYLLAGGCQKRSFSIIGDFQNGKRVSLSVYLGEFFDIHLFVNG
TVTQGDQRVSMPYASKGLYLETEAGYYKLSGEAYGFVARIDGSGNFQVLL
SDRYFNKTCGLCGNFNIFAEDDFMTQEGTLTSDPYDFANSWALSSGEQWC
ERASPPSSSCNISSGEMQKGLWEQCQLLKSTSVFARCHPLVDPEPFVALC
EKTLCECAGGLECACPALLEYARTCAQEGMVLYGWTDHSACSPVCPAGME
YRQCVSPCARTCQSLHINEMCQERCVDGCSCPEGQLLDEGLCVESTECPC
VHSGKRYPPGTSLSRDCNTCICRNSQWICSNEECPGECLVTGQSHFKSFD
NRYFTFSGICQYLLARDCQDHSFSIVIETVQCADDRDAVCTRSVTVRLPG
LHNSLVKLKHGAGVAMDGQDVQLPLLKGDLRIQHTVTASVRLSYGEDLQM
DWDGRGRLLVKLSPVYAGKTCGLCGNYNGNQGDDFLTPSGLAEPRVEDFG
NAWKLHGDCQDLQKQHSDPCALNPRMTRFSEEACAVLTSPTFEACHRAVS
PLPYLRNCRYDVCScSDGRECLCGALASYAAACAGRGVRVAWREPGRCEL
NCPKGQVYLQCGTPCNLTCRSLSYPDEECNEACLEGCFCPPGLYMDERGD
CVPKAQCPCYYDGEIFQPEDIFSDHHTMCYCEDGFMHCTMSGVPGSLLPD
AVLSSPLSHRSKRSLSCRPPMVKLVCPADNLRAEGLECTKTCQNYDLECM
SMGCVSGCLCPPGMVRHENRCVALERCPCFHQGKEYAPGETVKIGCNTCV
CRDRKWNCTDHVCDATCSTIGMAHYLTFDGLKYLFPGECQYVLVQDYCGS
NPGTFRILVGNKGCSHPSVKCKKRVTILVEGGEIELFDGEVNVKRPMKDE
THFEVVESGRYIILLLGKALSVVWDRHLSISVVLKQTYQEKVCGLCGNFD
GIQNNDLTSSNLQVEEDPVDFGNSWKVSSQCADTRKVPLDSSPATCHNNI
MKQTMVDSSCRILTSDVFQDCNKLVDPEPYLDVCIYDTCSCESIGDCACF
CDTIAAYAHVCAQHGKVVTWRTATLCPQSCEERNLRENGYECEWRYNSCA
PACQVTCQHPEPLACPVQCVEGCHAHCPPGKILDELLQTCVDPEDCPVCE
VAGRRFASGKKVTLNPSDPEHCQICHCDVVNLTCEACQEPGGLVVPPTDA
PVSPTTLYVEDISEPPLHDFYCSRLLDLVFLLDGSSRLSEAEFEVLKAFV
VDMMERLRISQKWVRVAVVEYHDGSHAYIGLKDRKRPSELRRIASQVKYA

-continued
GSQVASTSEVLKYTLFQIFSKIDRPEASRITLLLMASQEPQRMSRNFVRY
VQGLKKKKVIVIPVGIGPHANLKQIRLIEKQAPENKAFVLSSVDELEQQR
DEIVSYLCDLAPEAPPPTLPPDMAQVTVGPGLLGVSTLGPKRNSMVLDVA
FVLEGSDKIGEADFNRSKEFMEEVIQRMDVGQDSIHVTVLQYSYMVTVEY
PFSEAQSKGDILQRVREIRYQGGNRTNTGLALRYLSDHSFLVSQGDREQA
PNLVYMVTGNPASDEIKRLPGDIQVVPIGVGPNANVQELERIGWPNAPIL
IQDFETLPREAPDLVLQRCCSGEGLQIPTLSPAPDCSQPLDVILLLDGSS
SFPASYFDEMKSFAKAFISKANIGPRLTQVSVLQYGSITTIDVPWNVVPE
KAHLLSLVDVMQREGGPSQIGDALGFAVRYLTSEMHGARPGASKAVVILV
TDVSVDSVDAAADAARSNRVTVFPIGIGDRYDAAQLRILAGPAGDSNVVK
LQRIEDLPTMVTLGNSFLHKLCSGFVRICMDEDGNEKRPGDVWTLPDQCH
TVTCQPDGQTLLKSHRVNCDRGLRPSCPNSQSPVKVEETCGCRWTCPCVC
TGSSTRHIVTFDGQNFKLTGSCSYVLFQNKEQDLEVILHNGACSPGARQG
CMKSIEVKHSALSVELHSDMEVTVNGRLVSVPYVGGNMEVNVYGAIMHEV
RFNHLGHIFTFTPQNNEFQLQLSPKTFASKTYGLCGICDENGANDFMLRD
GTVTTDWKTLVQEWTVQRPGQTCQPILEEQCLVPDSSHCQVLLLPLFAEC
HKVLAPATFYAICQQDSCHQEQVCEVIASYAHLCRTNGVCVDWRTPDFCA
MSCPPSLVYNHCEHGCPRHCDGNVSSCGDHPSEGCFCPPDKVMLEGSCVP
EEACTQCIGEDGVQHQFLEAWVPDHQPCQICTCLSGRKVNCTTQPCPTAK
APTCGLCEVARLRQNADQCCPEYECVCDPVSCDLPPVPHCERGLQPTLTN
PGECRPNETCACRKEECKRVSPPSCPPHRLPTLRKTQCCDEYECACNCVN
STVSCPLGYLASTATNDCGCTTTTCLPDKVCVHRSTIYPVGQFWEEGCDV
CTCTDMEDAVMGLRVAQCSQKPCEDSCRSGFTYVLHEGECCGRCLPSACE
VVTGSPRGDSQSSWKSVGSQWASPENPCLINECVRVKEEVFIQQRNVSCP
QLEVPVCPSGEQLSCKTSACCPSCRCERMEACMLNGTVIGPGKTVMIDVC
TTCRCMVQVGVISGFKLECRKTTCNPCPLGYKEENNTGECCGRCLPTACT
IQLRGGQINITLKRDETLQDGCDTHFCKVNERGEYFWEKRVTGCPPFDEH
KCLAEGGKIMKIPGTCCDTCEEPECNDITARLQYVKVGSCKSEVEVDIHY
CQGKCASKAMYSIDINDVQDQCSCCSPTRTEPMQVALHCTNGSVVYHEVL
NAMECKCSPRKCSK.

In some embodiments, the peptide is from the vWF A3 domain. The VWF A3 domain is derived from the human sequence, residues 1670-1874 (907-1111 of mature VWF) and has the following sequence:

(SEQ ID NO: 1)
CSGEGLQIPTLSPAPDCSQPLDVILLLDGSSSFPASYFDEMKSFAKAFIS
KANIGPRLTQVSVLQYGSITTIDVPWNVVPEKAHLLSLVDVMQREGGPSQ
IGDALGFAVRYLTSEMEHGARPGASKAVVILVTDVSVDSVDAAADAARSN
RVTVFPIGIGDRYDAAQLRILAGPAGDSNVVKLQRIEDLPTMVTLGNSFL
HKLCSG.

In some embodiments, the ECM-peptide comprises all or a fragment of vWF A3, which is represented by the following amino acid sequences:

(SEQ ID NO: 8)
CSQPLDVILLLDGSSSFPASYFDEMKSFAKAFISKANIGPRLTQVSVLQY
GSITTIDVPWNVVPEKAHLLSLVDVMQREGGPSQIGDALGFAVRYLTSEM
HGARPGASKAVVILVTDVSVDSVDAAADAARSNRVTVFPIGIGDRYDAAQ
LRILAGPAGDSNVVKLQRIEDLPTMVTLGNSFLHKLCSGFVRICTG.

In some embodiments, the collagen binding domain comprises a polypeptide with the following sequence:

(SEQ ID NO: 2)
CSQPLDVILLLDGSSSFPASYFDEMKSFAKAFISKANIGPRLTQVSVLQY
GSITTIDVPWNVVPEKAHLLSLVDVMQREGGPSQIGDALGFAVRYLTSEM
HGARPGASKAVVILVTDVSVDSVDAAADAARSNRVTVFPIGIGDRYDAAQ
LRILAGPAGDSNVVKLQRIEDLPTMVTLGNSFLHKLCSGFVRI

In some embodiments, the polypeptide comprises a collagen binding domain albumin polypeptide having the following sequence:

(SEQ ID NO: 3)
CSQPLDVILLLDGSSSFPASYFDEMKSFAKAFISKANIGPRLTQVSVLQY
GSITTIDVPWNVVPEKAHLLSLVDVMQREGGPSQIGDALGFAVRYLTSEM
HGARPGASKAVVILVTDVSVDSVDAAADAARSNRVTVFPIGIGDRYDAAQ
LRILAGPAGDSNVVKLQRIEDLPTMVTLGNSFLHKLCSGFVRIGGGSGGG
SEAHKSEIAHRYNDLGEQHFKGLVLIAFSQYLQKCSYDEHAKLVQEVTDF
AKTCVADESAANCDKSLHTLFGDKLCAIPNLRENYGELADCCTKQEPERN
ECFLQHKDDNPSLPPFERPEAEAMCTSFKENPTTFMGHYLHEVARRHPYF
YAPELLYYAEQYNEILTQCCAEADKESCLTPKLDGVKEKALVSSVRQRMK
CSSMQKFGERAFKAWAVARLSQTFPNADFAEITKLATDLTKVNKECCHGD
LLECADDRAELAKYMCENQATISSKLQTCCDKPLLKKAHCLSEVEHDTMP
ADLPAIAADFVEDQEVCKNYAEAKDVFLGTFLYEYSRRHPDYSVSLLLRL
AKKYEATLEKCCAEANPPACYGTVLAEFQPLVEEPKNLVKTNCDLYEKLG
EYGFQNAILVRYTQKAPQVSTPTLVEAARNLGRVGTKCCTLPEDQRLPCV
EDYLSAILNRVCLLHEKTPVSEHVTKCCSGSLVERRPCFSALTVDETYVP
KEFKAETFTFHSDICTLPEKEKQIKKQTALAELVKHKPKATAEQLKTVMD
DFAQFLDTCCKAADKDTCFSTEGPNLVTRCKDALAHHHHHH

Exemplary peptides include all or part of any one of SEQ ID NO:1-4 or 11-14. The collagen binding domain may be a polypeptide with 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to a polypeptide of the disclosure, such as to SEQ ID NO: 1-8.

2. Antibodies and Antigen-Binding Fragments

Aspects of the disclosure relate to antibodies or fragments thereof as tumor targeting agents that bind to tumor stroma or to cancer antigens/tumor-associated antigens. The term "antibody" refers to an intact immunoglobulin of any isotype, or a fragment thereof that can compete with the intact antibody for specific binding to the target antigen, and includes chimeric, humanized, fully human, and bispecific antibodies. In some embodiments, the antibody is a mouse antibody. In some embodiments, the antibody is a monoclonal or polyclonal antibody. As used herein, the terms "antibody" or "immunoglobulin" are used interchangeably and refer to any of several classes of structurally related proteins that function as part of the immune response of an animal, including IgG, IgD, IgE, IgA, IgM, and related proteins, as well as polypeptides comprising antibody CDR domains that retain antigen-binding activity.

The term "antigen" refers to a molecule or a portion of a molecule capable of being bound by a selective binding agent, such as an antibody. An antigen may possess one or more epitopes that are capable of interacting with different antibodies.

The term "epitope" includes any region or portion of molecule capable eliciting an immune response by binding to an immunoglobulin or to a T-cell receptor. Epitope determinants may include chemically active surface groups such as amino acids, sugar side chains, phosphoryl or sulfonyl groups, and may have specific three-dimensional structural characteristics and/or specific charge characteristics. Generally, antibodies specific for a particular target antigen will preferentially recognize an epitope on the target antigen within a complex mixture.

The epitope regions of a given polypeptide can be identified using many different epitope mapping techniques that are well known in the art, including: x-ray crystallography, nuclear magnetic resonance spectroscopy, site-directed mutagenesis mapping, protein display arrays, see, e.g., Epitope Mapping Protocols, (Johan Rockberg and Johan Nilvebrant, Ed., 2018) Humana Press, New York, N.Y. Such techniques are known in the art and described in, e.g., U.S. Pat. No. 4,708,871; Geysen et al. Proc. Natl. Acad. Sci. USA 81:3998-4002 (1984); Geysen et al. Proc. Natl. Acad. Sci. USA 82:178-182 (1985); Geysen et al. Molec. Immunol. 23:709-715 (1986 See, e.g., Epitope Mapping Protocols, supra. Additionally, antigenic regions of proteins can also be predicted and identified using standard antigenicity and hydropathy plots.

An intact antibody is generally composed of two full-length heavy chains and two full-length light chains, but in some instances may include fewer chains, such as antibodies naturally occurring in camelids that may comprise only heavy chains. Antibodies as disclosed herein may be derived solely from a single source or may be "chimeric," that is, different portions of the antibody may be derived from two different antibodies. For example, the variable or CDR regions may be derived from a rat or murine source, while the constant region is derived from a different animal source, such as a human. The antibodies or binding fragments may be produced in hybridomas, by recombinant DNA techniques, or by enzymatic or chemical cleavage of intact antibodies. Unless otherwise indicated, the term "antibody" includes derivatives, variants, fragments, and muteins thereof, examples of which are described below (Sela-Culang et al. Front Immunol. 2013; 4: 302; 2013)

The term "light chain" includes a full-length light chain and fragments thereof having sufficient variable region sequence to confer binding specificity. A full-length light chain has a molecular weight of around 25,000 Daltons and includes a variable region domain (abbreviated herein as VL), and a constant region domain (abbreviated herein as CL). There are two classifications of light chains, identified as kappa (κ) and lambda (λ). The term "VL fragment" means a fragment of the light chain of a monoclonal antibody that includes all or part of the light chain variable region, including CDRs. A VL fragment can further include light chain constant region sequences. The variable region domain of the light chain is at the amino-terminus of the polypeptide.

The term "heavy chain" includes a full-length heavy chain and fragments thereof having sufficient variable region sequence to confer binding specificity. A full-length heavy chain has a molecular weight of around 50,000 Daltons and includes a variable region domain (abbreviated herein as VH), and three constant region domains (abbreviated herein as CH1, CH2, and CH3). The term "VH fragment" means a fragment of the heavy chain of a monoclonal antibody that includes all or part of the heavy chain variable region, including CDRs. A VH fragment can further include heavy chain constant region sequences. The number of heavy chain constant region domains will depend on the isotype. The VH domain is at the amino-terminus of the polypeptide, and the CH domains are at the carboxy-terminus, with the CH3 being closest to the —COOH end. The isotype of an antibody can be IgM, IgD, IgG, IgA, or IgE and is defined by the heavy chains present of which there are five classifications: mu (μ), delta (δ), gamma (γ), alpha (α), or epsilon (ε) chains, respectively. IgG has several subtypes, including, but not limited to, IgG1, IgG2, IgG3, and IgG4. IgM subtypes include IgM1 and IgM2. IgA subtypes include IgA1 and IgA2.

Antibodies can be whole immunoglobulins of any isotype or classification, chimeric antibodies, or hybrid antibodies with specificity to two or more antigens. They may also be fragments (e.g., F(ab')2, Fab', Fab, Fv, and the like), including hybrid fragments. An immunoglobulin also includes natural, synthetic, or genetically engineered proteins that act like an antibody by binding to specific antigens to form a complex. The term antibody includes genetically engineered or otherwise modified forms of immunoglobulins.

The term "monomer" means an antibody containing only one Ig unit. Monomers are the basic functional units of antibodies. The term "dimer" means an antibody containing two Ig units attached to one another via constant domains of the antibody heavy chains (the Fc, or fragment crystallizable, region). The complex may be stabilized by a joining (J) chain protein. The term "multimer" means an antibody containing more than two Ig units attached to one another via constant domains of the antibody heavy chains (the Fc region). The complex may be stabilized by a joining (J) chain protein.

The term "bivalent antibody" means an antibody that comprises two antigen-binding sites. The two binding sites may have the same antigen specificities, or they may be bi-specific, meaning the two antigen-binding sites have different antigen specificities.

Bispecific antibodies are a class of antibodies that have two paratopes with different binding sites for two or more distinct epitopes. In some embodiments, bispecific antibodies can be biparatopic, wherein a bispecific antibody may specifically recognize a different epitope from the same antigen. In some embodiments, bispecific antibodies can be constructed from a pair of different single domain antibodies termed "nanobodies". Single domain antibodies are sourced and modified from cartilaginous fish and camelids. Nanobodies can be joined together by a linker using techniques typical to a person skilled in the art; such methods for selection and joining of nanobodies are described in PCT Publication No. WO2015044386A1, No. WO2010037838A2, and Bever et al., Anal Chem. 86:7875-7882 (2014), each of which are specifically incorporated herein by reference in their entirety.

Bispecific antibodies can be constructed as: a whole IgG, Fab'2, Fab'PEG, a diabody, or alternatively as scFv. Diabodies and scFvs can be constructed without an Fc region, using only variable domains, potentially reducing the effects of anti-idiotypic reaction. Bispecific antibodies may be produced by a variety of methods including, but not limited to, fusion of hybridomas or linking of Fab' fragments. See, e.g., Songsivilai and Lachmann, Clin. Exp. Immunol. 79:315-321 (1990); Kostelny et al., J. Immunol. 148:1547-1553 (1992), each of which are specifically incorporated by reference in their entirety.

In certain aspects, the antigen-binding domain may be multispecific or heterospecific by multimerizing with VH and VL region pairs that bind a different antigen. For example, the antibody may bind to, or interact with, (a) a cell surface antigen, (b) an Fc receptor on the surface of an effector cell, or (c) at least one other component. Accordingly, aspects may include, but are not limited to, bispecific, trispecific, tetraspecific, and other multispecific antibodies or antigen-binding fragments thereof that are directed to epitopes and to other targets, such as Fc receptors on effector cells.

In some embodiments, multispecific antibodies can be used and directly linked via a short flexible polypeptide chain, using routine methods known in the art. One such example is diabodies that are bivalent, bispecific antibodies in which the VH and VL domains are expressed on a single polypeptide chain, and utilize a linker that is too short to allow for pairing between domains on the same chain, thereby forcing the domains to pair with complementary domains of another chain creating two antigen binding sites. The linker functionality is applicable for embodiments of triabodies, tetrabodies, and higher order antibody multimers. (see, e.g., Hollinger et al., Proc Natl. Acad. Sci. USA 90:6444-6448 (1993); Polijak et al., Structure 2:1121-1123 (1994); Todorovska et al., J. Immunol. Methods 248:47-66 (2001)).

Bispecific diabodies, as opposed to bispecific whole antibodies, may also be advantageous because they can be readily constructed and expressed in *E. coli*. Diabodies (and other polypeptides such as antibody fragments) of appropriate binding specificities can be readily selected using phage display (WO94/13804) from libraries. If one arm of the diabody is kept constant, for instance, with a specificity directed against a protein, then a library can be made where the other arm is varied and an antibody of appropriate specificity selected. Bispecific whole antibodies may be made by alternative engineering methods as described in Ridgeway et al., (Protein Eng., 9:616-621, 1996) and Krah et al., (N Biotechnol. 39:167-173, 2017), each of which is hereby incorporated by reference in their entirety.

Heteroconjugate antibodies are composed of two covalently linked monoclonal antibodies with different specificities. See, e.g., U.S. Pat. No. 6,010,902, incorporated herein by reference in its entirety.

The part of the Fv fragment of an antibody molecule that binds with high specificity to the epitope of the antigen is referred to herein as the "paratope." The paratope consists of the amino acid residues that make contact with the epitope of an antigen to facilitate antigen recognition. Each of the two Fv fragments of an antibody is composed of the two variable domains, VH and VL, in dimerized configuration. The primary structure of each of the variable domains includes three hypervariable loops separated by, and flanked by, Framework Regions (FR). The hypervariable loops are the regions of highest primary sequences variability among the antibody molecules from any mammal. The term hypervariable loop is sometimes used interchangeably with the term "Complementarity Determining Region (CDR)." The length of the hypervariable loops (or CDRs) varies between antibody molecules. The framework regions of all antibody molecules from a given mammal have high primary sequence similarity/consensus. The consensus of framework regions can be used by one skilled in the art to identify both the framework regions and the hypervariable loops (or CDRs) which are interspersed among the framework regions. The hypervariable loops are given identifying names which distinguish their position within the polypeptide, and on which domain they occur. CDRs in the VL domain are identified as L1, L2, and L3, with L1 occurring at the most distal end and L3 occurring closest to the CL domain. The CDRs may also be given the names CDR-1, CDR-2, and CDR-3. The L3 (CDR-3) is generally the region of highest variability among all antibody molecules produced by a given organism. The CDRs are regions of the polypeptide chain arranged linearly in the primary structure, and separated from each other by Framework Regions. The amino terminal (N-terminal) end of the VL chain is named FR1. The region identified as FR2 occurs between L1 and L2 hypervariable loops. FR3 occurs between L2 and L3 hypervariable loops, and the FR4 region is closest to the CL domain. This structure and nomenclature is repeated for the VH chain, which includes three CDRs identified as H1, H2 and H3. The majority of amino acid residues in the variable domains, or Fv fragments (VH and VL), are part of the framework regions (approximately 85%). The three dimensional, or tertiary, structure of an antibody molecule is such that the framework regions are more internal to the molecule and provide the majority of the structure, with the CDRs on the extenal surface of the molecule.

Several methods have been developed and can be used by one skilled in the art to identify the exact amino acids that constitute each of these regions. This can be done using any of a number of multiple sequence alignment methods and algorithms, which identify the conserved amino acid residues that make up the framework regions, therefore identifying the CDRs that may vary in length but are located between framework regions. Three commonly used methods have been developed for identification of the CDRs of antibodies: Kabat (as described in T. T. Wu and E. A. Kabat, "AN ANALYSIS OF THE SEQUENCES OF THE VARIABLE REGIONS OF BENCE JONES PROTEINS AND MYELOMA LIGHT CHAINS AND THEIR IMPLICATIONS FOR ANTIBODY COMPLEMENTARITY," J Exp Med, vol. 132, no. 2, pp. 211-250, August 1970); Chothia (as described in C. Chothia et al., "Conformations of immunoglobulin hypervariable regions," Nature, vol. 342, no. 6252, pp. 877-883, December 1989); and IMGT (as described in M.-P. Lefranc et al., "IMGT unique numbering for immunoglobulin and T cell receptor variable domains and Ig superfamily V-like domains," Developmental & Comparative Immunology, vol. 27, no. 1, pp. 55-77, January 2003). These methods each include unique numbering systems for the identification of the amino acid residues that constitute the variable regions. In most antibody molecules, the amino acid residues that actually contact the epitope of the antigen occur in the CDRs, although in some cases, residues within the framework regions contribute to antigen binding.

One skilled in the art can use any of several methods to determine the paratope of an antibody. These methods include: 1) Computational predictions of the tertiary structure of the antibody/epitope binding interactions based on the chemical nature of the amino acid sequence of the antibody variable region and composition of the epitope; 2) Hydrogen-deuterium exchange and mass spectroscopy; 3) Polypeptide fragmentation and peptide mapping approaches in which one generates multiple overlapping peptide fragments from the full length of the polypeptide and evaluates the binding affinity of these peptides for the epitope; 4) Antibody Phage Display Library analysis in which the antibody Fab fragment encoding genes of the mammal are expressed by bacteriophage in such a way as to be incorporated into the coat of the phage. This population of Fab expressing phage are then allowed to interact with the antigen which has been immobilized or may be expressed in by a different exogenous expression system. Non-binding Fab fragments are washed away, thereby leaving only the specific binding Fab fragments attached to the antigen. The binding Fab fragments can be readily isolated and the genes which encode them determined. This approach can also be used for smaller regions of the Fab fragment including Fv fragments or specific VH and VL domains as appropriate.

In certain aspects, affinity matured antibodies are enhanced with one or more modifications in one or more CDRs thereof that result in an improvement in the affinity of the antibody for a target antigen as compared to a parent antibody that does not possess those alteration(s). Certain affinity matured antibodies will have nanomolar or picomolar affinities for the target antigen. Affinity matured antibodies are produced by procedures known in the art, e.g., Marks et al., Bio/Technology 10:779 (1992) describes affinity maturation by VH and VL domain shuffling, random mutagenesis of CDR and/or framework residues employed in phage display is described by Rajpal et al., PNAS. 24: 8466-8471 (2005) and Thie et al., Methods Mol Biol. 525:309-22 (2009) in conjugation with computation methods as demonstrated in Tiller et al., Front. Immunol. 8:986 (2017).

Chimeric immunoglobulins are the products of fused genes derived from different species; "humanized" chimeras generally have the framework region (FR) from human immunoglobulins and one or more CDRs are from a non-human source.

In certain aspects, portions of the heavy and/or light chain are identical or homologous to corresponding sequences from another particular species or belonging to a particular antibody class or subclass, while the remainder of the chain(s) is identical or homologous to corresponding sequences in antibodies derived from another species or belonging to another antibody class or subclass, as well as fragments of such antibodies, so long as they exhibit the desired biological activity. U.S. Pat. No. 4,816,567; and Morrison et al., Proc. Natl. Acad. Sci. USA 81:6851 (1984). For methods relating to chimeric antibodies, see, e.g., U.S. Pat. No. 4,816,567; and Morrison et al., Proc. Natl. Acad. Sci. USA 81:6851-6855 (1985), each of which are specifically incorporated herein by reference in their entirety. CDR grafting is described, for example, in U.S. Pat. Nos. 6,180,370, 5,693,762, 5,693,761, 5,585,089, and 5,530,101, which are all hereby incorporated by reference for all purposes.

In some embodiments, minimizing the antibody polypeptide sequence from the non-human species optimizes chimeric antibody function and reduces immunogenicity. Specific amino acid residues from non-antigen recognizing regions of the non-human antibody are modified to be homologous to corresponding residues in a human antibody or isotype. One example is the "CDR-grafted" antibody, in which an antibody comprises one or more CDRs from a particular species or belonging to a specific antibody class or subclass, while the remainder of the antibody chain(s) is identical or homologous to a corresponding sequence in antibodies derived from another species or belonging to another antibody class or subclass. For use in humans, the V region composed of CDR1, CDR2, and partial CDR3 for both the light and heavy chain variance region from a non-human immunoglobulin, are grafted with a human antibody framework region, replacing the naturally occurring antigen receptors of the human antibody with the non-human CDRs. In some instances, corresponding non-human residues replace framework region residues of the human immunoglobulin. Furthermore, humanized antibodies may comprise residues that are not found in the recipient antibody or in the donor antibody to further refine performance. The humanized antibody may also comprise at least a portion of an immunoglobulin constant region (Fc), typically that of a human immunoglobulin. See, e.g., Jones et al., Nature 321:522 (1986); Riechmann et al., Nature 332:323 (1988); Presta, Curr. Op. Struct. Biol. 2:593 (1992); Vaswani and Hamilton, Ann. Allergy, Asthma and Immunol. 1:105 (1998); Harris, Biochem. Soc. Transactions 23; 1035 (1995); Hurle and Gross, Curr. Op. Biotech. 5:428 (1994); Verhoeyen et al., Science 239:1534-36 (1988).

Intrabodies are intracellularly localized immunoglobulins that bind to intracellular antigens as opposed to secreted antibodies, which bind antigens in the extracellular space.

Polyclonal antibody preparations typically include different antibodies against different determinants (epitopes). In order to produce polyclonal antibodies, a host, such as a rabbit or goat, is immunized with the antigen or antigen fragment, generally with an adjuvant and, if necessary, coupled to a carrier. Antibodies to the antigen are subsequently collected from the sera of the host. The polyclonal antibody can be affinity purified against the antigen rendering it monospecific.

Monoclonal antibodies or "mAb" refer to an antibody obtained from a population of homogeneous antibodies from an exclusive parental cell, e.g., the population is identical except for naturally occurring mutations that may be present in minor amounts. Each monoclonal antibody is directed against a single antigenic determinant.

a. Antigen-Binding Fragments

Certain aspects relate to antibody fragments, such as antibody fragments that bind to tumor cells or tumor stroma. The term functional antibody fragment includes antigen-binding fragments of an antibody that retain the ability to specifically bind to an antigen. These fragments are constituted of various arrangements of the variable region heavy chain (VH) and/or light chain (VL); and in some embodiments, include constant region heavy chain 1 (CH1) and light chain (CL). In some embodiments, they lack the Fc region constituted of heavy chain 2 (CH2) and 3 (CH3) domains. Embodiments of antigen binding fragments and the modifications thereof may include: (i) the Fab fragment type constituted with the VL, VH, CL, and CH1 domains; (ii) the Fd fragment type constituted with the VH and CH1 domains; (iii) the Fv fragment type constituted with the VH and VL domains; (iv) the single domain fragment type, dAb, (Ward, 1989; McCafferty et al., 1990; Holt et al., 2003) constituted with a single VH or VL domain; (v) isolated complementarity determining region (CDR) regions. Such terms are described, for example, in Harlow and Lane, Antibodies: A Laboratory Manual, Cold Spring Harbor Laboratory, N Y (1989); Molec. Biology and Biotechnology: A Comprehensive Desk Reference (Myers, R. A. (ed.), New York: VCH Publisher, Inc.); Huston et al., Cell Biophysics, 22:189-224 (1993); Pluckthun and Skerra, Meth. Enzymol., 178:497-515 (1989) and in Day, E. D., Advanced Immunochemistry, 2d ed., Wiley-Liss, Inc. New York, N.Y. (1990); Antibodies, 4:259-277 (2015). The citations in this paragraph are all incorporated by reference.

Antigen-binding fragments also include fragments of an antibody that retain exactly, at least, or at most 1, 2, or 3 complementarity determining regions (CDRs) from a light chain variable region. Fusions of CDR-containing sequences to an Fc region (or a CH2 or CH3 region thereof) are included within the scope of this definition including, for example, scFv fused, directly or indirectly, to an Fc region are included herein.

The term Fab fragment means a monovalent antigen-binding fragment of an antibody containing the VL, VH, CL and CH1 domains. The term Fab' fragment means a monovalent antigen-binding fragment of a monoclonal antibody that is larger than a Fab fragment. For example, a Fab' fragment includes the VL, VH, CL and CH1 domains and all or part of the hinge region. The term F(ab')2 fragment means a bivalent antigen-binding fragment of a monoclonal antibody comprising two Fab' fragments linked by a disulfide bridge at the hinge region. An F(ab')2 fragment includes, for example, all or part of the two VH and VL domains, and can further include all or part of the two CL and CH1 domains.

The term Fd fragment means a fragment of the heavy chain of a monoclonal antibody, which includes all or part of the VH, including the CDRs. An Fd fragment can further include CH1 region sequences.

The term Fv fragment means a monovalent antigen-binding fragment of a monoclonal antibody, including all or part of the VL and VH, and absent of the CL and CH1 domains. The VL and VH include, for example, the CDRs. Single-chain antibodies (sFv or scFv) are Fv molecules in which the VL and VH regions have been connected by a flexible linker to form a single polypeptide chain, which forms an antigen-binding fragment. Single chain antibodies are discussed in detail in International Patent Application Publication No. WO 88/01649 and U.S. Pat. Nos. 4,946,778 and 5,260,203, the disclosures of which are herein incorporated by reference. The term (scFv)2 means bivalent or bispecific sFv polypeptide chains that include oligomerization domains at their C-termini, separated from the sFv by a hinge region (Pack et al. 1992). The oligomerization domain comprises self-associating a-helices, e.g., leucine zippers, which can be further stabilized by additional disulfide bonds. (scFv)2 fragments are also known as "miniantibodies" or "minibodies."

A single domain antibody is an antigen-binding fragment containing only a VH or the VL domain. In some instances, two or more VH regions are covalently joined with a peptide linker to create a bivalent domain antibody. The two VH regions of a bivalent domain antibody may target the same or different antigens.

b. Fragment Crystallizable Region, Fc

An Fc region contains two heavy chain fragments comprising the CH2 and CH3 domains of an antibody. The two heavy chain fragments are held together by two or more disulfide bonds and by hydrophobic interactions of the CH3 domains. The term "Fc polypeptide" as used herein includes native and mutein forms of polypeptides derived from the Fc region of an antibody. Truncated forms of such polypeptides containing the hinge region that promotes dimerization are included.

c. Polypeptides with antibody CDRs & Scaffolding Domains that Display the CDRs

Antigen-binding peptide scaffolds, such as complementarity-determining regions (CDRs), are used to generate protein-binding molecules in accordance with the embodiments. Generally, a person skilled in the art can determine the type of protein scaffold on which to graft at least one of the CDRs. It is known that scaffolds, optimally, must meet a number of criteria such as: good phylogenetic conservation; known three-dimensional structure; small size; few or no post-transcriptional modifications; and/or be easy to produce, express, and purify. Skerra, J Mol Recognit, 13:167-87 (2000).

The protein scaffolds can be sourced from, but not limited to: fibronectin type III FN3 domain (known as "monobodies"), fibronectin type III domain 10, lipocalin, anticalin, Z-domain of protein A of *Staphylococcus aureus*, thioredoxin A or proteins with a repeated motif such as the "ankyrin repeat", the "armadillo repeat", the "leucine-rich repeat" and the "tetratricopeptide repeat". Such proteins are described in US Patent Publication Nos. 2010/0285564, 2006/0058510, 2006/0088908, 2005/0106660, and PCT Publication No. WO2006/056464, each of which are specifically incorporated herein by reference in their entirety. Scaffolds derived from toxins from scorpions, insects, plants, mollusks, etc., and the protein inhibiters of neuronal NO synthase (PIN) may also be used.

d. Tumor Associated Antigens

Certain aspects of the disclosure include methods and compositions concerning targeting molecules that specifically bind to tumor associated antigens, including segments, fragments, or epitopes of polypeptides, peptides, nucleic acids, carbohydrates, lipids and other molecules that provoke or induce an antigenic response, generally referred to as antigens, tumor-associated antigen, or cancer antigen. In one embodiment, the antigen is a peptide. In one embodiment, the antigen is a protein. In particular, antigens, or antigenic segments or fragments of such antigens, which lead to the destruction of a cell via an immune response, can be identified and used in the methods and compositions described herein. In some embodiments, the antigen is one that is on the surface of a cancer cell.

The targeting agent may be an antibody or antigen binding fragment that specifically binds to a cancer antigen. The cancer antigen can be any type of cancer antigen known in the art. The cancer antigen may be an epithelial cancer antigen, (e.g., breast, gastrointestinal, lung), a prostate specific cancer antigen (PSA) or prostate specific membrane antigen (PSMA), a bladder cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, a head and neck cancer antigen, a melanoma specific antigen, or a colorectal cancer antigen.

In one embodiment, the cancer antigen is a melanoma cancer antigen. Melanoma cancer antigens are useful for treating melanoma. Non-limiting exemplary melanoma cancer antigens include MART-1 (e.g., MART-1 26-35 peptide, MART-1 27-35 peptide); MART-1/Melan A; pMel17; pMel17/gp100; gp100 (e.g., gp 100 peptide 280-288, gp 100 peptide 154-162, gp 100 peptide 457-467); TRP-1; TRP-2; NY-ESO-1; p16; beta-catenin; mum-1; and the like.

Further examples of cancer antigens include, for example, 5T4, 707-AP (707 alanine proline), 9D7, AFP (alpha-fetoprotein), AlbZIP HPG1, alpha5beta1-Integrin, alpha5beta6-Integrin, alpha-methylacyl-coenzyme A racemase, ART-4 (adenocarcinoma antigen recognized by T cells 4), B7H4, BAGE-1 (B antigen), BCL-2, BING-4, CA 15-3/CA 27-29, CA 19-9, CA 72-4, CA125, calreticulin, CAMEL (CTL-recognized antigen on melanoma), CASP-8 (caspase-8), cathepsin B, cathepsin L, CD19, CD20, CD22, CD25, CD30, CD33, CD40, CD52, CD55, CD56, CD80, CEA (carcinoembryonic antigen), CLCA2 (calcium-activated chloride channel-2), CML28, Coactosin-like protein, Collagen XXIII, COX-2, CT-9/BRD6 (bromodomain testis-specific protein), Cten (C-terminal tensin-like protein), cyclin B1, cyclin D1, cyp-B (cyclophilin B), CYPB1 (cytochrom P450 1B1), DAM-10/MAGE-B1 (differentiation antigen melanoma 10), DAM-6/MAGE-B2 (differentiation antigen melanoma 6), EGFR/Her1, EMMPRIN (tumor cell-associated extracellular matrix metalloproteinase inducer/), EpCam (epithelial cell adhesion molecule), EphA2 (ephrin type-A receptor 2), EphA3 (ephrin type-A receptor 3), ErbB3, EZH2 (enhancer of Zeste homolog 2), FGF-5 (fibroblast growth factor-5), FN (fibronectin), Fra-1 (Fos-related antigen-1), G250/CALX (glycoprotein 250), GAGE-1 (G antigen 1), GAGE-2 (G antigen 2), GAGE-3 (G antigen 3), GAGE-4 (G antigen 4), GAGE-5 (G antigen 5), GAGE-6 (G antigen 6), GAGE-7b (G antigen 7b), GAGE-8 (G antigen 8), GDEP (gene differentially expressed in prostate), GnT-V (N-acetylglucosaminyltransferase V), gp100 (glycoprotein 100 kDa), GPC3 (glypican 3), HAGE (helicase antigen), HAST-2 (human signet ring tumor-2), hepsin, Her2/neu/ErbB2 (human epidermal receptor-2/neurological), HERV-K-MEL, HNE (human neutrophil elastase), homeobox NKX 3.1, HOM-TES-14/SCP-1, HOM-TES-85, HPV-E6, HPV-E7, HST-2, hTERT (human telomerase reverse transcriptase), iCE (intestinal carboxyl esterase), IGF-1R, IL-13Ra2 (interleukin 13 receptor alpha 2 chain), IL-2R, IL-5, immature laminin receptor, kallikrein 2, kallikrein 4, Ki67, KIAA0205, KK-LC-1 (Kita-kyushu lung cancer antigen 1), KM-FIN-1, LAGE-1 (L antigen), livin, MAGE-A1 (melanoma antigen-A1), MAGE-A10 (melanoma antigen-A10), MAGE-A12 (melanoma antigen-A12), MAGE-A2 (melanoma antigen-A2), MAGE-A3 (melanoma antigen-A3), MAGE-A4 (melanoma antigen-A4), MAGE-A6 (melanoma antigen-A6), MAGE-A9 (melanoma-antigen-A9), MAGE-B1 (melanoma-antigen-B1), MAGE-B10 (melanoma-antigen-B10), MAGE-B16 (melanoma-antigen-B16), MAGE-B17 (melanoma-antigen-B17), MAGE-B2 (melanoma-antigen-B2), MAGE-B3 (melanoma-antigen-B3), MAGE-B4 (melanoma-antigen-B4), MAGE-B5 (melanoma-antigen-B5), MAGE-B6 (melanoma-antigen-B6), MAGE-C1 (melanoma-antigen-C1), MAGE-C2 (melanoma-antigen-C2), MAGE-C3 (melanoma-antigen-C3), MAGE-D1 (melanoma-antigen-D1), MAGE-D2 (melanoma-antigen-D2), MAGE-D4 (melanoma-antigen-D4), MAGE-E1 (melanoma-antigen-E1), MAGE-E2 (melanoma-antigen-E2), MAGE-F1 (melanoma-antigen-F1), MAGE-H1 (melanoma-antigen-H1), MAGEL2 (MAGE-like 2), mammaglobin A, MART-1/Melan-A (melanoma antigen recognized by T cells-1/melanoma antigen A), MART-2 (melanoma antigen recognized by T cells-2), matrix protein 22, MC1R (melanocortin 1 receptor), M-CSF (macrophage colony-stimulating factor gene), mesothelin, MG50/PXDN, MMP 11 (M-phase phosphoprotein 11), MN/CA IX-antigen, MRP-3 (multidrug resistance-associated protein 3), MUC1 (mucin 1), MUC2 (mucin 2), NA88-A (NA cDNA clone of patient M88), N-acetylglucosaminyltransferase-V, Neo-PAP (Neo-poly(A) polymerase), NGEP, NMP22, NPM/ALK (nucleophosmin/anaplastic lymphoma kinase fusion protein), NSE (neuron-specific enolase), NY-ESO-1 (New York esophageous 1), NY-ESO-B, OA1 (ocular albinism type 1 protein), OFA-iLRP (oncofetal antigen-immature laminin receptor), OGT (O-linked N-acetylglucosamine transferase gene), OS-9, osteocalcin, osteopontin, p15 (protein 15), p15, p190 minor bcr-abl, p53, PAGE-4 (prostate GAGE-like protein-4), PAI-1 (plasminogen acitvator inhibitor 1), PAI-2 (plasminogen acitvator inhibitor 2), PAP (prostate acic phosphatase), PART-1, PATE, PDEF, Pim-1-Kinase, Pin1 (Propyl isomerase), POTE, PRAIVIE (preferentially expressed antigen of melanoma), prostein, proteinase-3, PSA (prostate-specific antigen), PSCA, PSGR, PSM, PSMA (prostate-specific membrane antigen), RAGE-1 (renal antigen), RHAMM/CD168 (receptor for hyaluronic acid mediated motility), RU1 (renal ubiquitous 1), RU2 (renal ubiquitous 1), S-100, SAGE (sarcoma antigen), SART-1 (squamous antigen rejecting tumor 1), SART-2 (squamous antigen rejecting tumor 1), SART-3 (squamous antigen rejecting tumor 1), SCC (squamous cell carcinoma antigen), Sp17 (sperm protein 17), SSX-1 (synovial sarcoma X breakpoint 1), SSX-2/HOM-MEL-40 (synovial sarcoma X breakpoint), SSX-4 (synovial sarcoma X breakpoint 4), STAMP-1, STEAP (six transmembrane epithelial antigen prostate), surviving, survivin-2B (intron 2-retaining survivin), TA-90, TAG-72, TARP, TGFb (TGFbeta), TGFbRII (TGFbeta receptor II), TGM-4 (prostate-specific transglutaminase), TRAG-3 (taxol resistant associated protein 3), TRG (testin-related gene), TRP-1 (tyrosine related protein 1), TRP-2/6b (TRP-2/novel exon 6b), TRP-2/INT2 (TRP-2/intron 2), Trp-p8, Tyrosinase, UPA (urokinase-type plasminogen activator), VEGF (vascular endothelial growth factor), VEGFR-2/FLK-1 (vascular endothelial growth factor receptor-2), WT1 (Wilm' tumor gene), or may comprise e.g. mutant antigens expressed in cancer diseases selected from the group comprising, without being limited thereto, alpha-actinin-4/m, ARTC1/m, bcr/abl (breakpoint cluster region-Abelson fusion protein), beta-Catenin/m (beta-Catenin), BRCA1/m, BRCA2/m, CASP-5/m, CASP-8/m, CDC27/m (cell-division-cycle 27), CDK4/m (cyclin-dependent kinase 4), CDKN2A/m, CML66, COA-1/m, DEK-CAN (fusion protein), EFTUD2/m, ELF2/m (Elongation factor 2), ETV6-AML1 (Ets variant gene6/acute myeloid leukemia 1 gene fusion protein), FN1/m (fibronectin 1), GPNMB/m, HLA-A*0201-R170I (arginine to isoleucine exchange at residue 170 of the alpha-helix of the alpha2-domain in the HLA-A2 gene), HLA-A11/m, HLA-A2/m, HSP70-2M (heat shock protein 70-2 mutated), KIAA0205/m, K-Ras/m, LDLR-FUT (LDR-Fucosyltransferase fusion protein), MART2/m, ME1/m, MUM-1/m (melanoma ubiquitous mutated 1), MUM-2/m (melanoma ubiquitous mutated 2), MUM-3/m (melanoma ubiquitous mutated 3), Myosin class I/m, neo-PAP/m, NFYC/m, N-Ras/m, OGT/m, OS-9/m, p53/m, Pml/RARa (promyelocytic leukemia/retinoic acid receptor alpha), PRDXS/m, PTPRK/m (receptor-type protein-tyrosine phosphatase kappa), RBAF600/m, SIRT2/m, SYT-SSX-1 (synaptotagmin I/synovial sarcoma X fusion protein), SYT-SSX-2 (synaptotagmin I/synovial sarcoma X fusion protein), TEL-AML1 (translocation Ets-family leukemia/acute myeloid leukemia 1 fusion protein), TGFbRII (TGFbeta receptor II), and TPI/m (triosephosphate isomerase).

B. Linker

A linker sequence may be included in the polypeptides. For example, a linker having at least, at most, or exactly 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids (or any derivable range therein) may separate the tumor targeting agent, TLR agonist, copolymer, and/or albumin. In some embodiments, there is a linker between the albumin polypeptide and the tumor targeting agent.

In some embodiments, the albumin polypeptide, TLR agonist, copolymer, collagen binding domain, tumor targeting agent, and/or antibody are covalently linked. For example, the TLR agonist may be covalently linked to the collagen binding domain or antibody or antigen-binding fragment. In some embodiments, the collagen binding domain is covalently linked to the albumin polypeptide. In some embodiments, a linker is between the TLR agonist and the targeting agent and/or the albumin polypeptide. In some embodiments, the albumin polypeptide is covalently linked to the targeting agent. In some embodiments, a linker is between the albumin polypeptide and the targeting agent. In some embodiments, the linker comprises a bifunctional linker. Linkers, such as amino acid or peptidimimetic sequences may be inserted between the peptide and/or antibody or antibody fragment sequence. Linkers may have one or more properties that include a flexible conformation, an inability to form an ordered secondary structure or a hydrophobic or charged character which could promote or interact with either domain. Examples of amino acids typically found in flexible protein regions may include Gly, Asn and Ser. For example, a suitable peptide linker may be or comprise GGGS (SEQ ID NO:15), GGGSGGGS (SEQ ID NO:9) or (GGGS)n (SEQ ID NO:10), wherein n=1, 2, 3, 4, 5, 6, 7, 8, 9, or 10 (or any range derivable therein). Other near neutral amino acids, such as Thr and Ala, may also be used in the linker sequence. The length of the linker sequence may vary without significantly affecting the function or activity of the fusion protein (see, e.g., U.S. Pat. No. 6,087,329). In a particular aspect, the linker may be at least, at most, or exactly 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 amino acid residues (or any range derivable therein). Examples of linkers may also include chemical moieties and conjugating agents, such as sulfo-succinimidyl derivatives (sulfo-SMCC, sulfo-SMPB), disuccinimidyl suberate (DSS), disuccinimidyl glutarate (DSG) and disuccinimidyl tartrate (DST). Examples of linkers further comprise a linear carbon chain, such as CN (where N=1-100 carbon atoms). In some embodiments, the linker can be a dipeptide linker, such as a valine-citrulline (val-cit), a phenylalanine-lysine (phe-lys) linker, or maleimidocapronic-valine-citruline-p-aminobenzyloxycarbonyl (vc) linker. In some embodiments, the linker is sulfosuccinimidyl-4-[N-maleimidomethyl]cyclohexane-1-carboxylate (smcc). Sulfo-smcc conjugation occurs via a maleimide group which reacts with sulfhydryls (thiols, —SH), while its sulfo-NHS ester is reactive toward primary amines (as found in lysine and the protein or peptide N-terminus). Further, the linker may be maleimidocaproyl (mc). In some embodiments, the covalent linkage may be achieved through the use of Traut's reagent.

C. Albumin

In some embodiments, the albumin polypeptide is from mouse. In some embodiments, the albumin polypeptide is from humans.

In some embodiments, the albumin polypeptide may comprise a polypeptide or fragment with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to a polypeptide having the following sequence:

(SEQ ID NO: 11)
MKWVTFISLLFLFSSAYSRGVFRRDAHKSEVAHRFKDLGEENFKALVLIA
FAQYLQQCPFEDHVKLVNEVTEFAKTCVADESAENCDKSLHTLFGDKLCT
VATLRETYGEMADCCAKQEPERNECFLQHKDDNPNLPRLVRPEVDVMCTA
FHDNEETFLKKYLYEIARRHPYFYAPELLFFAKRYKAAFTECCQAADKAA
CLLPKLDELRDEGKASSAKQRLKCASLQKFGERAFKAWAVARLSQRFPKA
EFAEVSKLVTDLTKVHTECCHGDLLECADDRADLAKYICENQDSISSKLK
ECCEKPLLEKSHCIAEVENDEMPADLPSLAADFVESKDVCKNYAEAKDVF
LGMFLYEYARRHPDYSVVLLLRLAKTYKTTLEKCCAAADPHECYAKVFDE
FKPLVEEPQNLIKQNCELFEQLGEYKFQNALLVRYTKKVPQVSTPTLVEV
SRNLGKVGSKCCKHPEAKRMPCAEDYLSVVLNQLCVLHEKTPVSDRVTKC
CTESLVNRRPCFSALEVDETYVPKEFNAETFTFHADICTLSEKERQIKKQ
TALVELVKHKPKATKEQLKAVMDDFAAFVEKCCKADDKETCFAEEGKKLV
AASRAALGL.

In some embodiments, the albumin polypeptide may comprise a polypeptide or fragment with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to a polypeptide having the following sequence:

(SEQ ID NO: 12)
EAHKSEIAHRYNDLGEQHFKGLVLIAFSQYLQKCSYDEHAKLVQEVTDFA
KTCVADESAANCDKSLHTLFGDKLCAIPNLRENYGELADCCTKQEPERNE
CFLQHKDDNPSLPPFERPEAEAMCTSFKENPTTFMGHYLHEVARRHPYFY
APELLYYAEQYNEILTQCCAEADKESCLTPKLDGVKEKALVSSVRQRMKC
SSMQKFGERAFKAWAVARLSQTFPNADFAEITKLATDLTKVNKECCHGDL
LECADDRAELAKYMCENQATISSKLQTCCDKPLLKKAHCLSEVEHDTMPA
DLPAIAADFVEDQEVCKNYAEAKDVFLGTFLYEYSRRHPDYSVSLLLRLA
KKYEATLEKCCAEANPPACYGTVLAEFQPLVEEPKNLVKTNCDLYEKLGE
YGFQNAILVRYTQKAPQVSTPTLVEAARNLGRVGTKCCTLPEDQRLPCVE
DYLSAILNRVCLLHEKTPVSEHVTKCCSGSLVERRPCFSALTVDETYVPK
EFKAETFTFHSDICTLPEKEKQIKKQTALAELVKHKPKATAEQLKTVMDD
FAQFLDTCCKAADKDTCFSTEGPNLVTRCKDALA.

In some embodiments, the albumin polypeptide may comprise a polypeptide or fragment with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to a polypeptide having the following sequence:

(SEQ ID NO: 13)
MKWVTFLLLLFVSGSAFSRGVERREAHKSEIAHRYNDLGEQHFKGLVLIA
FSQYLQKCSYDEHAKLVQEVTDFAKTCVADESAANCDKSLHTLFGDKLCA
IPNLRENYGELADCCTKQEPERNECFLQHKDDNPSLPPFERPEAEAMCTS
FKENPTTFMGHYLHEVARRHPYFYAPELLYYAEQYNEILTQCCAEADKES

-continued
CLTPKLDGVKEKALVSSVRQRMKCSSMQKFGERAFKAWAVARLSQTFPNA
DFAEITKLATDLTKVNKECCHGDLLECADDRAELAKYMCENQATISSKLQ
TCCDKPLLKKAHCLSEVEHDTMPADLPAIAADFVEDQEVCKNYAEAKDVF
LGTFLYEYSRRHPDYSVSLLLRLAKKYEATLEKCCAEANPPACYGTVLAE
FQPLVEEPKNLVKTNCDLYEKLGEYGFQNAILVRYTQKAPQVSTPTLVEA
ARNLGRVGTKCCTLPEDQRLPCVEDYLSAILNRVCLLHEKTPVSEHVTKC
CSGSLVERRPCFSALTVDETYVPKEFKAETFTEHSDICTLPEKEKQIKKQ
TALAELVKHKPKATAEQLKTVMDDFAQFLDTCCKAADKDTCFSTEGPNLV
TRCKDALA.

In some embodiments, the albumin polypeptide may comprise a polypeptide or fragment with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to a polypeptide having the following sequence:

(SEQ ID NO: 14)
DAHKSEVAHREKDLGEENFKALVLIAFAQYLQQCPFEDHVKLVNEVTEFA
KTCVADESAENCDKSLHTLFGDKLCTVATLRETYGEMADCCAKQEPERNE
CFLQHKDDNPNLPRLVRPEVDVMCTAFHDNEETFLKKYLYEIARRHPYFY
APELLFFAKRYKAAFTECCQAADKAACLLPKLDELRDEGKASSAKQRLKC
ASLQKFGERAFKAWAVARLSQRFPKAEFAEVSKLVTDLTKVHTECCHGDL
LECADDRADLAKYICENQDSISSKLKECCEKPLLEKSHCIAEVENDEMPA
DLPSLAADEVESKDVCKNYAEAKDVFLGMFLYEYARRHPDYSVVLLLRLA
KTYKTTLEKCCAAADPHECYAKVEDEFKPLVEEPQNLIKQNCELFEQLGE
YKFQNALLVRYTKKVPQVSTPTLVEVSRNLGKVGSKCCKHPEAKRMPCAE
DYLSVVLNQLCVLHEKTPVSDRVTKCCTESLVNRRPCFSALEVDETYVPK
EFNAETFTFHADICTLSEKERQIKKQTALVELVKHKPKATKEQLKAVNID
DFAAFVEKCCKADDKETCFAEEGKKLVAASRAALG.

D. TLR Agonists

1. Copolymers Comprising TLR Agonist

In one embodiment there is disclosed a copolymer having the structure (I):

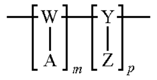

(I)

where A is absent or includes at least one group that binds an Antigen Presenting Cell (APC) mannose receptor or includes mannose-binding C-type lectin; Z includes at least one Toll-Like Receptor (TLR) agonist; W and Y, are each independently a monomer unit of a polymer; m is from 1 to 100000, from 5 to 50000, from 5 to 10000, from 5 to 1000, from 10 to 500. In some embodiments, m is from 10 to 150, and p is from 1 to 100000, from 1 to 50000, from 1 to 10000, from 1 to 1000, from 1 to 100, from 1 to 50, and from 1 to 20. It is understood that m and p are integers. In one aspect A is a mannose-containing compound that can be derived from mannose and N-(2-hydroxyethyl)methacrylamide. In another aspect of copolymer (I), Z has the general structure (II):

(II)

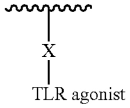

where X is a linker bonded to the TLR agonist and Y. X can be a heteroatom, an aliphatic group, a substituted aliphatic group, an alkoxy group, a heteroalkyl group, a substituted heteroalkyl group, an aryl group, a substituted aryl group, a benzyl group, a substituted benzyl group, a heteroaryl group, a substituted heteroaryl group, any combination thereof or a covalent bond. In a particular aspect, the TLR agonist is a TLR7 agonist, a TLR8 agonist, a TLR7/8 agonist, or any combination thereof and the TLR agonist has the general structure (III):

(III)

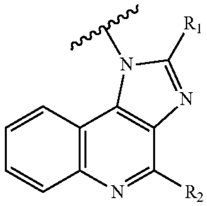

where $R_1$ and $R_2$ are each independently a hydrogen atom, a halogen, an alkyl group, a substituted alkyl group, a heteroalkyl group, a substituted heteroalkyl group, a cycloalkyl group, a substituted cycloalkyl group, a heterocycloalkyl group, a substituted heterocycloalkyl group, an aryl group, a substituted aryl group, a heteroaryl group, a substituted heteroaryl group, an alkoxy group, an alkoxyalkyl group, an alkoxyalkoxy group, and alkoxyalkoxyalkyl group, an amino group, or a hydroxyl group. In one aspect, $R_2$ is a free amine ($—NH_2$) and $R_1$ is an alkyl group or an alkoxy group, and preferably the alkoxyalkyl group is ethoxymethyl ($—CH_2OCH_2CH_3$). In one example, X (Structure (II)) is a substituted benzyl group and Z is:

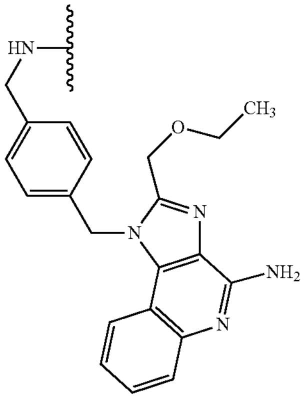 [SMILES: *NCc1ccc(Cn2c(COCC)nc3c(N)nc4ccccc4c32)cc1]

In another example, X is a substituted benzyl group and Z is:

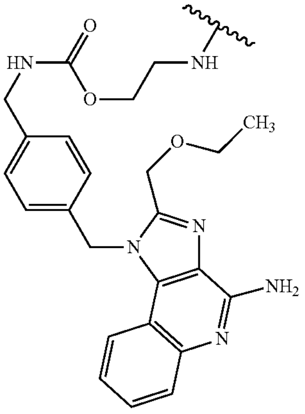 [SMILES: *NCCOC(=O)NCc1ccc(Cn2c(COCC)nc3c(N)nc4ccccc4c32)cc1]

In another aspect of TLR agonist of structure (III), R2 is a free amine (—NH2) and R1 is a C1-C6 alkyl group, preferably n-butyl. In one example, X is a substituted heteroalkyl group and Z is:

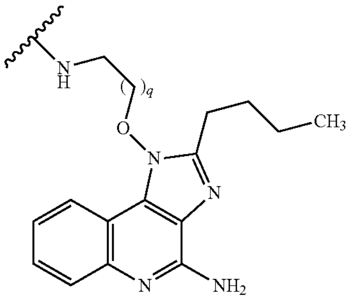

where q is from about 1 to 100, from about 1 to 50, from about 2 to 20, and preferably from about 2 to 9.

In another embodiment, the copolymer includes end units, wherein the end units are each independently a residue of the polymer, a linker, an immunomodulating agent, or combinations thereof, and the copolymer has the general structure (IV):

(IV)

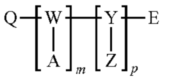

where E and Q are end units, wherein E and Q are each independently a residue of the polymer, a linker, an immunomodulating agent, or any combination thereof. In one aspect, at least one of E or Q is at least one linker. The linker can be an azide containing linker. The azide containing linker can be:

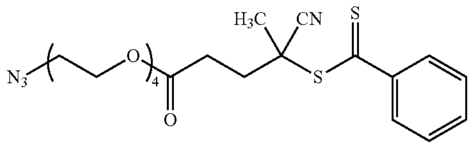

In another aspect, E or Q is an immunomodulating agent and the immunomodulating agent is an antigen, a TLR, or any combination thereof. In certain aspects, the immunomodulating agent is an antigen covalently attached to the polymer by a linker, wherein the linker is a self-immolating linker and the linker is:

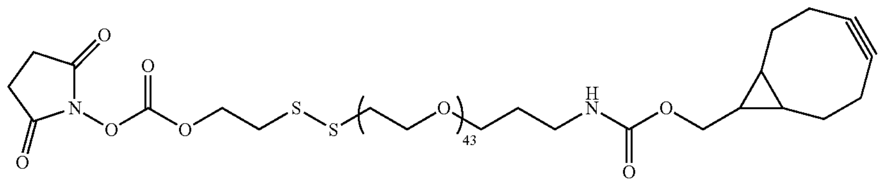

In yet another aspect, W and Y are each independently monomer units of a polyacrylate, such as poly(acrylic acid) or poly(methacrylic acid) or poly(hydrxyproply methacrylate), a polyacrylamide, a saturated polyolefin, a polyamide, such as poly(acrylamide) or poly(methacrylamide), a peptide, a polypeptide, an unsaturated olefin formed by ring opening metathesis polymerization, a siloxane, a polysiloxane, a polyether, a polysaccharide, a polyoxazoline, such as poly(ethyloxazoline), a polyimine, such as poly(ethylenimine), a polyvinyl derivative, such as poly(vinyl alcohol) and poly(vinyl pyrrolidone), or any combination thereof, and copolymer (I) is:

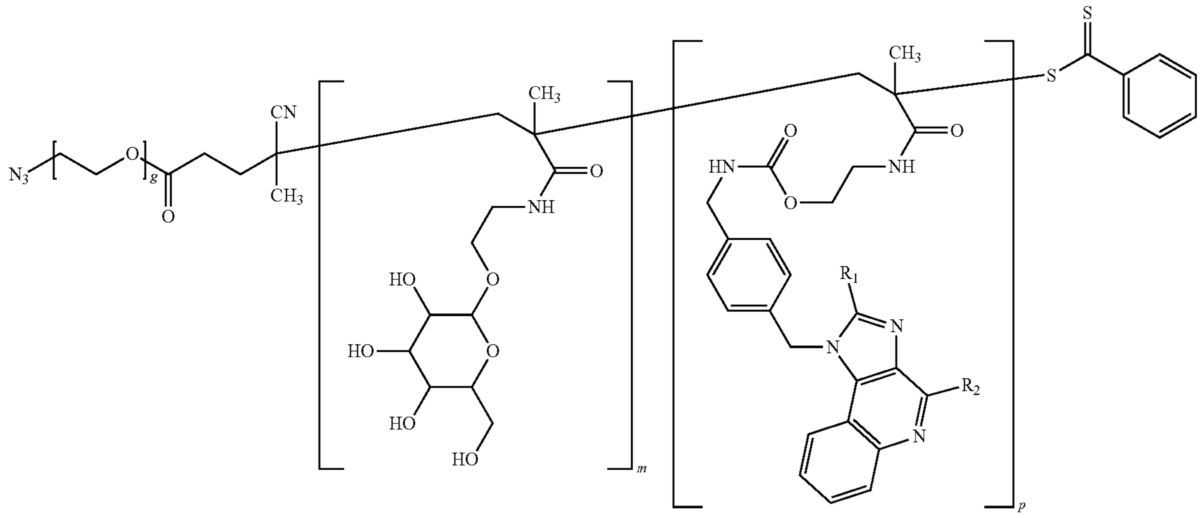

where m is from 1 to 100,000, p is from 1 to 100,000, and g is from 1 to 100.

In one example, R1 is ethoxymethyl (—CH2OCH2CH3) and R2 is a free amine (—NH2). In another example, copolymer (I) is:

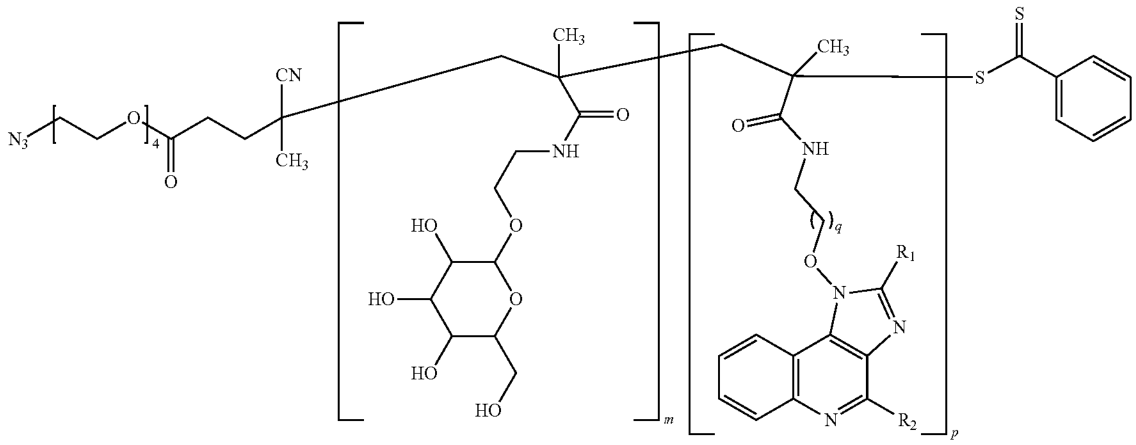

where q is from 1 to 100, from 1 to 50, from 2 to 20, and from 2 to 9. In one example, $R_1$ is n-butyl or ethoxymethyl (—$CH_2OCH_2CH_3$) and $R_2$ is a free amine (—$NH_2$). The ratio of p:m for copolymer (I) as described herein ranges from about 10:90 to about 20:80 and any range therebetween, including 11:89, 12:88, 13:87, 14:86, 15:85, 16:84, 17:83, 18:82, and 19:81, preferably about 16:84. The average molecular weight ranges from about 30 to about 80 kDa and any weight therebetween, including about 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, and 79, (and any range derivable therein); in one embodiment the average molecule weight is about 34 kDa.

In some embodiments, copolymer (I) can further include a repeating unit (V):

(V)

where Y" is a monomer unit of a polymer bonded to W or Y; Z' comprises at least one TLR agonist; and p' is from 1 to 100000, from 1 to 50000, from 1 to 10000, from 1 to 1000, from 1 to 100, from 1 to 50, and in specific embodiments, p' is from 1 to 20. Y' can be a monomer unit of polyacrylate, such as poly(acrylic acid) or poly(methacrylic acid) or poly(hydrxyproply methacrylate), a polyacrylamide, a saturated polyolefin, a polyamide, such as poly(acrylamide) or poly(methacrylamide), a peptide, a polypeptide, an unsaturated olefin formed by ring opening metathesis polymerization, a siloxane, a polysiloxane, a polyether, a polysaccharide, a polyoxazoline, such as poly(ethyloxazoline), a polyimine, such as poly(ethylenimine), a polyvinyl derivative, such as poly(vinyl alcohol) and poly(vinyl pyrrolidone), or any combination thereof.

Also disclosed herein are compositions that include the copolymers as described above. In one embodiment, the compositions further include an antigen and the antigen can be operatively linked to copolymer (I), (IV), or (V). Alternatively the antigen can be covalently linked to the compound by a linker or non-covalently linked to the polymer. In some aspects of the composition, the antigen is covalently linked to the copolymer using a bifunctional linker having functional groups selected from amines, azides, alkynes, and N-succinimidyl carbonates. In a particular aspect, the linker is a self-immolating linker and can be:

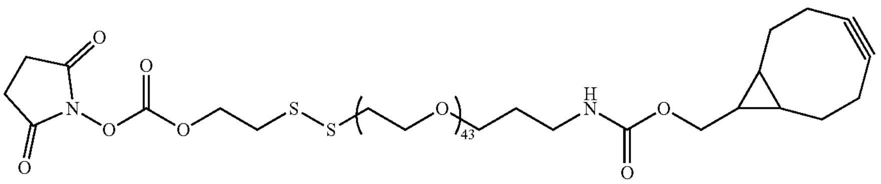

In other embodiments, there is disclosed a monomer having a general structure of (VI):

(VI)

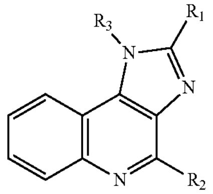

where $R_1$ and $R_2$ are each independently a hydrogen atom, a halogen, an alkyl group, a substituted alkyl group, a heteroalkyl group, a substituted heteroalkyl group, a cycloalkyl group, a substituted cycloalkyl group, a heterocycloalkyl group, a substituted heterocycloalkyl group, an aryl group, a substituted aryl group; and $R_3$ is a ligand comprising a polymerizable group Y'. In one example, $R_2$ is a free amine ($—NH_2$) and $R_1$ is an alkyl group or an alkoxy group, preferably $R_1$ is a $C_1$ to $C_6$ alkyl group or a n-butyl group or alternatively $R_1$ is an ethoxymethyl group ($—CH_2OCH_2CH_3$). In another example, the $R_3$ ligand of the monomer further contains a heteroatom, an aliphatic group, a substituted aliphatic group, an alkoxy group, a heteroalkyl group, a substituted heteroalkyl group, an aryl group, a substituted aryl group, a benzyl group, a substituted benzyl group, a heteroaryl group, a substituted heteroaryl group. In one embodiment, the $R_3$ ligand is a substituted benzyl group and $R_3$ has the general structure of:

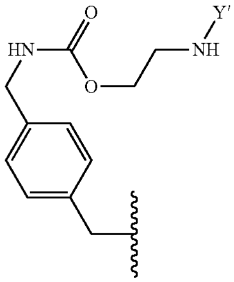

In one aspect, Y' includes an olefin and the monomer (VI) is:

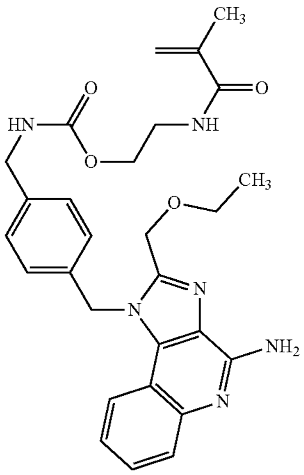 [SMILES: C=C(C)C(=O)NCCOC(=O)NCc1ccc(Cn2c(COCC)nc3c(N)nc4ccccc4c32)cc1]

In another embodiment, the R3 ligand is OR5, where R5 is a substituted aliphatic group that includes Y', and monomer (VI) has the general structure of:

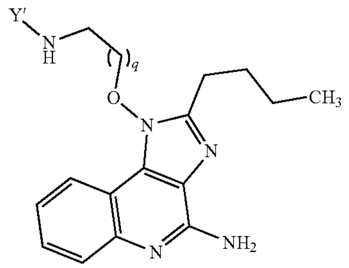

where q is from 1 to 100, from 1 to 50, from about 2 to 20, or from 2 to 9. In one aspect, Y' includes an olefin and the monomer (VI) is:

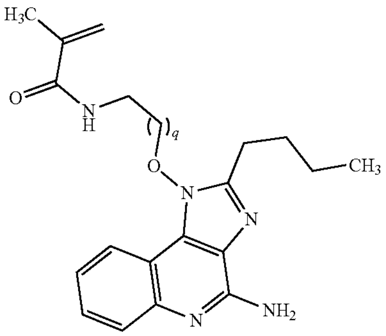

In some embodiments, a copolymer containing monomer (VI) is disclosed. The copolymer can further include a second monomeric unit, where the second monomeric group includes at least one group that binds to an APC mannose receptor coupled to a polymerizable group. In this instance, the copolymer has a general structure of (VII):

(VII)

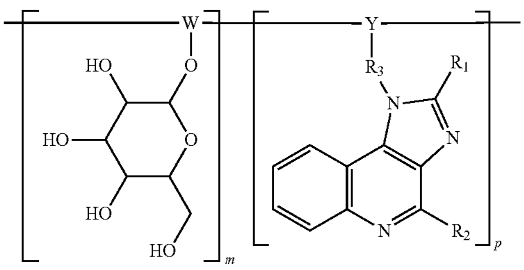

where W is a monomeric unit of a polymer; Y is a monomeric unit of the polymerizable group Y'; m is from 1 to 100000, from 5 to 50000, from 5 to 10000, from 5 to 1000, from 10 to 500, and from 10 to 150, and p is from 1 to 100000, from 1 to 50000, from 1 to 10000, from 1 to 1000, from 1 to 100, from 1 to 50, and from 1 to 20. In a particular aspect, W is a derivative of derivative of N-(2-hydroxyethyl) methacrylamides. Copolymer (VII) may further contain an antigen and the antigen can be covalently bound to the copolymer.

In other embodiments, a polymer containing monomer (VI) is disclosed. The polymer is formed via the polymerization of Y' and the polymer has a general structure of (VIII):

(VIII)

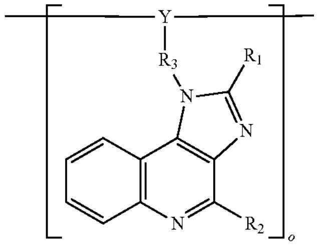

where o is from 2 to 100000, from 2 to 50000, from 2 to 10000, from 2 to 1000, from 2 to 100, from 2 to 50, or from 2 to 20, and Y is the product of polymerizing Y'. In one instance polymer (VIII) is:

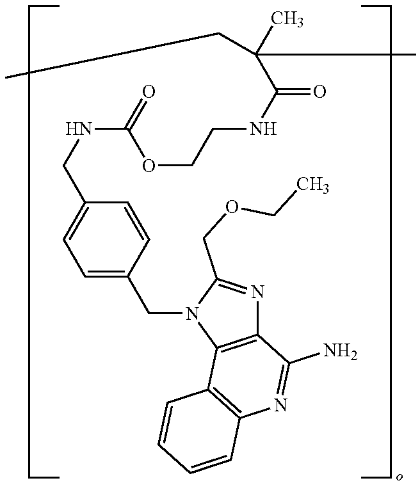

In another instance polymer (VIII) is:

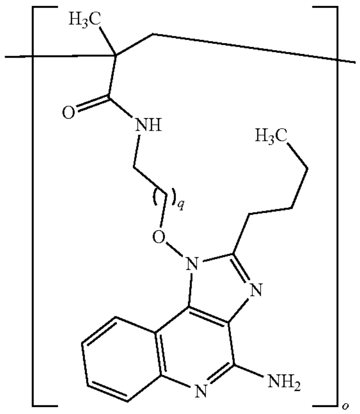

where q is from 1 to 100, from 1 to 50, from 2 to 20, or from 2 to 9. In one aspect, polymer (VIII) can be operatively linked to an APC-targeting molecule and the APC-targeting molecule can be a mannose-containing compound. In a particular aspect, polymer (VIII) is covalently linked to the mannose-containing compound and the mannose-containing compound is derived from mannose and N-(2-hydroxyethyl) methacrylamide. Polymer (VIII) can also be covalently linked to the mannose-containing compound to form a copolymer and the copolymer has the general structure of (VII):

(VII)

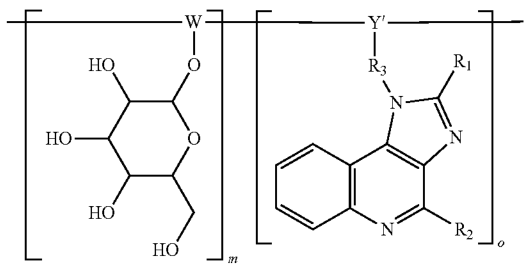

where W is a polymerizable unit; and m is from 1 to 100000, from 5 to 50000, from 5 to 10000, from 5 to 1000, from 10 to 500, or from 10 to 150. Polymer (VII) may also further include an antigen and the antigen may be covalently bound. In a further aspect, any of the copolymers described above may be a block copolymer, an alternating copolymer or a random copolymer.

In one application, linkers include compounds for molecular conjugation reactions to provide structural stability or assistance in protein-protein, protein-peptide, protein-polymer, polymer-small molecule, peptide/protein-small molecule interactions, immobilization for assays or purification, as well as various peptide-nucleic acid and nucleic acid-nucleic acid conjugations, among many others. Typically, linkers contain functional groups, such as primary amines, sulfhydryls, acids, alcohols, azides, alkynes and halides. Specifically, maleimide (sulfhydryl reactive) and succinimidyl ester (NETS) or isothiocyanate (ITC) groups that react with amines may find use in the current embodiments.

In one embodiment, a bifunctional linker can be used as a latent spacer between a therapeutic or diagnostic moiety and a polymer. In one aspect, the latency is selected such that a first linking group (functional group) of the bifunctional linker can be selectively conjugated in the presence of a second linking group. In another aspect, the latency can be selected such that after both linking groups on the bifunctional linker are conjugated one group can be selectively cleaved. For example, the hydrolysis of the spacer-polymer bond can be rate limiting in the release of the therapeutic or diagnostic moiety from the polymeric prodrug. Cleavage and release of the therapeutic or diagnostic moiety from the polymeric prodrug can occur in vivo, for example by an enzymatic or non-enzymatic hydrolysis mechanism using linking groups such as ester, carbonate, carbamate, imine (hydrazone), amide, maleimide, succinimidyl, vinylsulfone, conjugated C=C double bond, epoxy, aldehyde, ketone, silane or siloxane functionalities. It is within the purview of those skilled in the art to appreciate the release of a therapeutic or diagnostic moiety from polymeric prodrugs employing aqueous hydrolysis depends on a multitude of factors like hydration of the linkage, the nature of the leaving group and steric crowding around the linkage. Substrate specificity, hydrophilicity, and steric crowding all influence the release from enzyme susceptible linkages and subtle changes made to the specific embodiments disclosed herein can still obtain the same result without departed from the spirit and scope of the invention. In certain aspects, the bifunctional linkers can be first conjugated with the copolymers and polymers of the current invention through a first functional group on the bifunctional linker and then the product can be further conjugated through a second functional group on the bifunctional linker. Once both functional groups of the bifunctional linker are conjugated, the portion derived from the bifunctional linker can be referred to as a linking group or linker. Exemplary compounds used as bifunctional linkers in the preparation of the polymeric conjugated vaccines of the current invention including any of the above mentioned functional groups can include alkyne-PEG5-acid, N-alloc-1,4-butandiamine hydrochloride, N-alloc-1,6-hexanediamine hydrochloride, allyl(4-methoxyphenyl)dimethylsilane, 6-(allyloxycarbonylamino)-1-hexanol, 3-(allyloxycarbonylamino)-1-propanol, 4-aminobutyraldehyde diethyl acetal, (E)-N-(2-aminoethyl)-4-{2-[4-(3-azidopropoxy)phenyl]diazenyl}benzamide hydrochloride, N-(2-aminoethyl)maleimide trifluoroacetate salt, amino-PEG4-alkyne, benzyl N-(3-hydroxypropyl)carbamate, 4-(Boc-amino)-1-butanol, 4-(Boc-amino)butyl bromide, 2-(Boc-amino)ethanethiol, 2-[2-(Boc-amino)ethoxy]ethoxyacetic acid, (dicyclohexylammonium) salt, 2-(Boc-amino)ethyl bromide, 6-(Boc-amino)-1-hexanol, 21-(Boc-amino)-4,7,10,13,16,19-hexaoxaheneicosanoic acid, 6-(Boc-amino)hexyl bromide, 5-(Boc-amino)-1-pentanol, 3-(Boc-amino)-1-propanol, 3-(Boc-amino)propyl bromide, 15-(Boc-amino)-4,7,10,13-tetraoxapentadecanoic acid, N-Boc-1,4-butanediamine, N-Boc-cadaverine, N-Boc-ethanolamine, N-Boc-ethylenediamine, N-Boc-2,2'-(ethylenedioxy)diethylamine, N-Boc-1,6-hexanediamine, N-Boc-1,6-hexanediamine hydrochloride, N-Boc-4-isothiocyanatoaniline, N-Boc-4-isothiocyanatobutylamine, N-Boc-2-isothiocyanatoethylamine, N-Boc-3-isothiocyanatopropylamine, N-Boc-N-methylethylenediamine, N-Boc-m-phenylenediamine, N-Boc-p-phenylenediamine, 2-(4-Boc-1-piperazinyl)acetic acid, N-Boc-1,3-propanediamine, N-Boc-1,3-propanediamine, N-Boc-N'-succinyl-4,7,10-trioxa-1,13-tridecanediamine, N-Boc-4,7,10-trioxa-1,13-tridecanediamine, N-(4-Bromobutyl)phthalimide, 4-bromobutyric acid, 4-bromobutyryl chloride, 4-bromobutyryl chloride, N-(2-bromoethyl)phthalimide, 6-bromo-1-hexanol, 3-(bromomethyl)benzoic acid N-succinimidylester, 4-(bromomethyl)phenyl isothiocyanate, 8-bromooctanoic acid, 8-bromo-1-octanol, 4-(2-bromopropionyl)phenoxyacetic acid, N-(3-bromopropyl)phthalimide, 4-(tert-Butoxymethyl)benzoic acid, tert-butyl 2-(4-{[4-(3-azidopropoxy)phenyl]azo}benzamido)ethylcarbamate, 2-[2-(tert-butyldimethylsilyloxy)ethoxy]ethanamine, tert-butyl 4-hydroxybutyrate, chloral hydrate, 4-(2-chloropropionyl)phenylacetic acid, 1,11-diamino-3,6,9-trioxaundecane, di-Boc-cystamine, diethylene glycol monoallyl ether, 3,4-Dihydro-2H-pyran-2-methanol, 4-[(2,4-Dimethoxyphenyl)(Fmoc-amino)methyl]phenoxyacetic acid, 4-(Diphenylhydroxymethyl)benzoic acid, 4-(Fmoc-amino)-1-butanol, 2-(Fmoc-amino)ethanol, 2-[2-(Fmoc-amino)ethoxy]ethylamine hydrochloride, 2-(Fmoc-amino)ethyl bromide, 6-(Fmoc-amino)-1-hexanol, 5-(Fmoc-amino)-1-pentanol, 3-(Fmoc-amino)-1-propanol, 3-(Fmoc-amino)propyl bromide, N-Fmoc-2-bromoethylamine, N-Fmoc-1,4-butanediamine hydrobromide, N-Fmoc-cadaverine hydrobromide, N-Fmoc-ethylenediamine hydrobromide, N-Fmoc-1,6-hexanediamine hydrobromide, N-Fmoc-1,3-propanediamine hydrobromide, N-Fmoc-N"-succinyl-4,7,10-trioxa-1,13-tridecanediamine, (3-Formyl-1-indolyl)acetic acid 6-Guanidinohexanoic acid 4-Hydroxybenzyl alcohol N-(4-hydroxybutyl)trifluoroacetamide, 4'-hydroxy-2,4-dimethoxybenzophenone, N-(2-hydroxy ethyl)maleimide, 4-[4-(1-hydroxy ethyl)-2-methoxy-5-nitrophenoxy]butyric acid, N-(2-hydroxy ethyl)trifluoroacetamide, N-(6-hydroxyhexyl)trifluoroacetamide, 4-hydroxy-2-methoxybenzaldehyde, 4-hydroxy-3-methoxybenzyl alcohol, 4-(hydroxymethyl)benzoic acid, 4-hydroxymethyl-3-methoxyphenoxyacetic acid, 4-(4-hydroxymethyl-3-methoxyphenoxy)butyric acid, 4-(hydroxymethyl)phenoxyacetic acid, 3-(4-hydroxymethylphenoxy)propionic acid, N-(5-hydroxypentyl)trifluoroacetamide, 4-(4'-hydroxyphenylazo)benzoic acid, N-(3-hydroxypropyl)trifluoroacetamide, 2-maleimidoethyl mesylate, 4-mercapto-1-butanol, 6-mercapto-1-hexanol, phenacyl 4-(bromomethyl)phenylacetate, phenacyl 4-(bromomethyl)phenyl acetate, 4-sulfamoylbenzoic acid, 4-sulfamoylbutyric acid, N-trityl-1,2-ethanediamine hydrobromide, 4-(Z-amino)-1-butanol, 6-(Z-amino)-1-hexanol, 5-(Z-amino)-1-pentanol, N—Z-1,4-butanediamine hydrochloride, N—Z-ethanolamine, N—Z-ethylenediamine hydrochloride, N—Z-ethylenediamine hydrochloride, N—Z-1,6-hexanediamine hydrochloride, N—Z-1,5-pentanediamine hydrochloride, and N—Z-1,3-propanediamine hydrochloride. Non-limiting examples of trifunctional linkers used to link three separate molecules together include N1,N4-bis-Boc-spermidine, N1,N5-bis-Boc-spermidine, N-Boc-diethanolamine, N1-Boc-2,2'-iminodiethylamine, N-Boc-iminodipropionic acid, N1-Boc-3,3'-iminodipropylamine, N,N"-Di-Z-diethylenetriamine. In specific aspects, the bifunctional linker contains a radical conjugation functional group, such as found in 2-(2-(2-(2-azidoethoxy)ethoxy)ethoxy)ethyl 4-cyano-4-(phenylcarbonothioylthio)pentanoate that can be first conjugated with monomers in a polymerization reaction (i.e., reversible addition-fragmentation chain transfer (RAFT) polymerization) to afford an azide functionalized agent. The azide agent can then be used in subsequent conjugation reactions to prepare polymer conjugate vaccines or polymer conjugate vaccine precursors. A non-limiting example of a commercial source of the above mentioned bifunctional and trifunctional linkers is Sigma Aldrich® (U.S.A).

In other embodiments, polymeric compositions using methods of site-specific controlled release of antigens are disclosed. These polymers and methods provide the impetus for a diverse range of applications spanning drug delivery, biological and chemical sensors, and diagnostics. One such novel substrate-polymer coupling moiety that finds use in the current embodiments includes self-immolating linkers. Self-immolating linkers utilize polymeric release of a stable bond between protecting and leaving groups, which becomes labile upon activation, leading to the rapid disassembly of the parent polymer by electronic cascade, dendrimer or polymer disassembly, or chemical amplified release. Chemical amplifiers are structures that translate a single bond-breaking event into release of numerous chemical outputs. In this way, a single bond cleavage input reaction (e.g., a reaction triggered by an analyte, a photon, or an enzyme) can be translated into the release of numerous output chemical cargoes. Outputs can take the form of reporting molecules (e.g., fluorescent dyes), biomolecules, antigens, or drugs. The current embodiments include self-immolating linker technologies comprising a trigger, linker and effector units such as those used in non-toxic prodrugs to enhance the selectivity in cancer chemotherapy, i.e., using monoclonal antibodies to specifically deliver highly potent, conjugated small molecule therapeutics to cancer cells. In another aspect, a self-immolating linker such as PABC or PAB (para-aminobenzyloxycarbonyl) and derivatives are self-immolating electronic cascade linkers formed by linking a carboxy terminus and para-aminobenzyl of PAB or derivative and are cleavable under enzymatic, hydrolytic, or other metabolic conditions. The aromatic para-amine becomes electron-donating and initiates an electronic cascade that leads to the expulsion of the leaving group by 1,6-elimination and fragmentation, which can become a free-amine antigen after elimination of carbon dioxide. In one example cathepsin B is an intracellular ubiquitous cysteine protease except in pathological conditions, such as metastatic tumors or rheumatoid arthritis. PABC and derivative conjugates produced with cathepsin B-cleavable linkers are stable in circulation. Upon cleavage of a peptide bond adjacent to the PABC, i.e., by an intracellular enzyme, the free-amine antigen is released. In another aspect, cis-aconityl amides formed with cis-aconityl anhydride can also release free-amine antigens by an electronic mechanism inspired by the hydrolysis of phthalamic acid protected amides under acidic conditions (pH 5). The 2-nitroimidazol-5-ylmethyl group may also find use in the current embodiment as a fragmenting antigen unit.

The self-immolating linkers in certain current embodiments function through reductive cleavage of linking disulfide bond that activates a trigger on the linker that causes snapback 1,4-intramolecular cyclization, carbon dioxide elimination, and release of the free antigen. One example includes a disulfide-bearing 4-mercaptopentanoate linker for antibody-maytansinoid conjugates of maytansinoids (DM1 and DM4). Other self-immolating linkers are envisioned that use disulfide cleavage in combination with a 1,6-elimination mechanism using ester or ethane-1,1-diol 4-oxymethyl-phenoxy-linked derivatives as shown below:

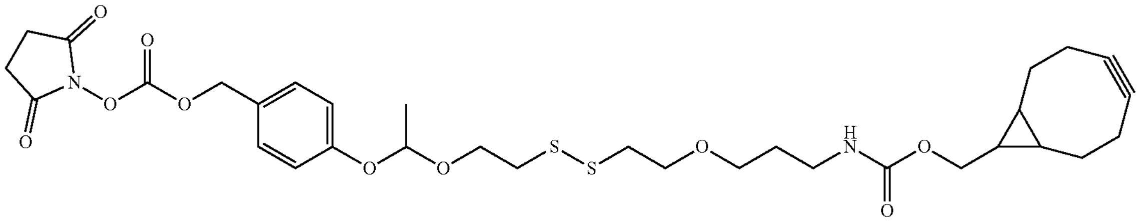

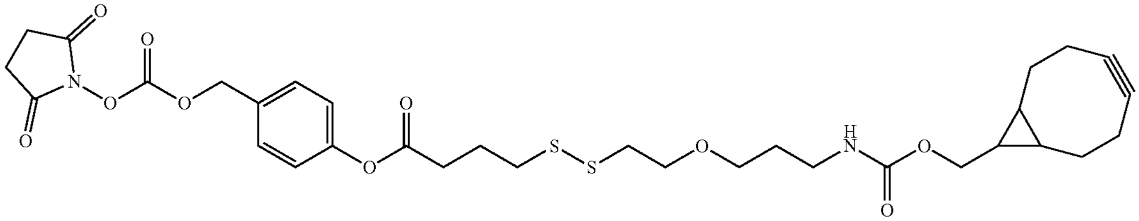

In specific aspects, the self-immolating linkers of the current invention contain functional groups that allow conjugation through stepwise reactions to link an azide functional group to an amine of an antigen.

Without limitation to theory, the current invention also encompasses all cleavable linkers used in chemical biology classified according to their cleavage conditions by enzymes, nucleophilic/basic reagents, reducing agents, photo-irradiation, electrophilic/acidic reagents, organometallic and metal reagents, or oxidizing reagents.

2. Compounds of Formula (VI)

In some embodiments, the TLR agonist comprises a compound of formula VI as described below. In one embodiment, low toxicity, small molecule Toll-Like Receptor (TLR)-7 and/or TLR-8 imidazoquinoline ligands are provided as vaccine adjuvants with decreased hydrophobicity (cLogP) and increased activity for use in vaccine formulations. In one embodiment, the TLR7 agonist, TLR8 agonist, or TLR7/8 agonist monomer has the general structure (VI):

(VI)

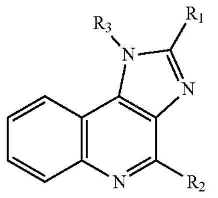

where $R_1$ and $R_2$ are each independently a hydrogen atom, a halogen, an alkyl group, a substituted alkyl group, a heteroalkyl group, a substituted heteroalkyl group, a cycloalkyl group, a substituted cycloalkyl group, a heterocycloalkyl group, a substituted heterocycloalkyl group, an aryl group, or a substituted aryl group; and $R_3$ is a ligand comprising a polymerizable group Y'.

Non-limiting examples of imidazoquinoline compounds of general structure (VI) for use in the current embodiments that are easily derived using various commercially available acid chlorides (e.g., substituting for (14) in the synthetic protocol described herein in FIG. 2, step vi) include 2-methacrylamidoethyl 4-((4-amino-2-methyl-1H-imidazo[4,5-c]quinolin-1-yl)methyl)benzylcarbamate, 2-methacrylamidoethyl 4-((4-amino-2-ethyl-1H-imidazo[4,5-c]quinolin-1-yl)methyl)benzylcarbamate, 2-methacrylamidoethyl 4-((4-amino-2-propyl-1H-imidazo[4,5-c]quinolin-1-yl)methyl)benzylcarbamate, 2-methacrylamidoethyl 4-((4-amino-2-isopropyl-1H-imidazo[4,5-c]quinolin-1-yl)methyl)benzylcarbamate, 2-methacrylamidoethyl 4-((4-amino-2-cyclopropyl-1H-imidazo[4,5-c]quinolin-1-yl)methyl)benzylcarbamate, 2-methacrylamidoethyl 4-((4-amino-2-butyl-1H-imidazo[4,5-c]quinolin-1-yl)methyl)benzylcarbamate, 2-methacrylamidoethyl 4-((4-amino-2-isobutyl-1H-imidazo[4,5-c]quinolin-1-yl)methyl)benzylcarbamate, 2-methacrylamidoethyl 4-((4-amino-2-sec-butyl-1H-imidazo[4,5-c]quinolin-1-yl)methyl)

benzylcarbamate, 2-methacrylamidoethyl 4-((4-amino-2-cyclobutyl-1H-imidazo[4,5-c]quinolin-1-yl)methyl)benzylcarbamate, 2-methacrylamidoethyl 4-((4-amino-2-(oxetan-2-yl)-1H-imidazo[4,5-c]quinolin-1-yl)methyl) benzylcarbamate, 2-methacrylamidoethyl 4-((4-amino-2-(oxetan-3-yl)-1H-imidazo[4,5-c]quinolin-1-yl)methyl) benzylcarbamate, 2-methacrylamidoethyl 4-((4-amino-2-cyclopentyl-1H-imidazo[4,5-c]quinolin-1-yl)methyl) benzylcarbamate, 2-methacrylamidoethyl 4-((4-amino-2-(tetrahydrofuran-3-yl)-1H-imidazo[4,5-c]quinolin-1-yl) methyl)benzylcarbamate, 2-methacrylamidoethyl 4-((4-amino-2-(tetrahydrofuran-2-yl)-1H-imidazo[4,5-c]quinolin-1-yl)methyl)benzylcarbamate, 2-methacrylamidoethyl 4-((4-amino-2-(2-methoxyethyl)-1H-imidazo[4,5-c]quinolin-1-yl)methyl)benzylcarbamate, 2-methacrylamidoethyl 4-((4-amino-2-(ethoxymethyl)-1H-imidazo[4,5-c]quinolin-1-yl)methyl)benzylcarbamate (TLR-7-oxyethyl-methacrylamide(TLR-MA, 3)), 2-methacrylamidoethyl 4-((4-amino-2-((2-methoxyethoxy)methyl)-1H-imidazo[4,5-c]quinolin-1-yl)methyl)benzylcarbamate, 4-amino-1-(4-(((2-methacrylamidoethoxy)carbonylamino)methyl)benzyl)-1H-imidazo[4,5-c]quinoline-2-carboxylic acid, methyl 4-amino-1-(4-(((2-methacrylamidoethoxy)carbonylamino) methyl)benzyl)-1H-imidazo[4,5-c]quinoline-2-carboxylate, ethyl 4-amino-1-(4-(((2-methacrylamidoethoxy)carbonylamino)methyl)benzyl)-1H-imidazo[4,5-c]quinoline-2-carboxylate, 2-(4-amino-1-(4-(((2-methacrylamidoethoxy) carbonylamino)methyl)benzyl)-1H-imidazo[4,5-c]quinolin-2-yl)acetic acid, methyl 2-(4-amino-1-(4-(((2-methacrylamidoethoxy)carbonylamino)methyl)benzyl)-1H-imidazo[4,5-c]quinolin-2-yl)acetate, ethyl 2-(4-amino-1-(4-(((2-methacrylamidoethoxy)carbonylamino)methyl) benzyl)-1H-imidazo[4,5-c]quinolin-2-yl)acetate, 3-(4-amino-1-(4-(((2-methacrylamidoethoxy)carbonylamino) methyl)benzyl)-1H-imidazo[4,5-c]quinolin-2-yl)propanoic acid, methyl 3-(4-amino-1-(4-(((2-methacrylamidoethoxy) carbonylamino)methyl)benzyl)-1H-imidazo[4,5-c]quinolin-2-yl)propanoate, ethyl 3-(4-amino-1-(4-(((2-methacrylamidoethoxy)carbonylamino)methyl)benzyl)-1H-imidazo[4,5-c]quinolin-2-yl)propanoate, 2-methacrylamidoethyl 4-((4-amino-2-(thiazol-2-yl)-1H-imidazo[4,5-c]quinolin-1-yl) methyl)benzylcarbamate, 2-methacrylamidoethyl 4-((4-amino-2-(thiazol-5-yl)-1H-imidazo[4,5-c]quinolin-1-yl) methyl)benzylcarbamate, 2-methacrylamidoethyl 4-((4-amino-2-(isothiazol-5-yl)-1H-imidazo[4,5-c]quinolin-1-yl) methyl)benzylcarbamate, 2-methacrylamidoethyl 4-((4-amino-2-(isothiazol-3-yl)-1H-imidazo[4,5-c]quinolin-1-yl) methyl)benzylcarbamate, 2-methacrylamidoethyl 4-((4-amino-2-(isothiazol-4-yl)-1H-imidazo[4,5-c]quinolin-1-yl) methyl)benzylcarbamate, 2-methacrylamidoethyl 4-((4-amino-2-(thiazol-4-yl)-1H-imidazo[4,5-c]quinolin-1-yl) methyl)benzylcarbamate, 2-methacrylamidoethyl 4-((4-amino-2-(oxazol-4-yl)-1H-imidazo[4,5-c]quinolin-1-yl) methyl)benzylcarbamate, 2-methacrylamidoethyl 4-((4-amino-2-(isoxazol-4-yl)-1H-imidazo[4,5-c]quinolin-1-yl) methyl)benzylcarbamate, 2-methacrylamidoethyl 4-((4-amino-2-(isoxazol-3-yl)-1H-imidazo[4,5-c]quinolin-1-yl) methyl)benzylcarbamate, 2-methacrylamidoethyl 4-((4-amino-2-(furan-2-yl)-1H-imidazo[4,5-c]quinolin-1-yl) methyl)benzylcarbamate, 2-methacrylamidoethyl 4-((4-amino-2-(furan-3-yl)-1H-imidazo[4,5-c]quinolin-1-yl) methyl)benzylcarbamate, 2-methacrylamidoethyl 4-((4-amino-2-(thiophen-3-yl)-1H-imidazo[4,5-c]quinolin-1-yl) methyl)benzylcarbamate, 2-methacrylamidoethyl 4-((4-amino-2-(thiophen-2-yl)-1H-imidazo[4,5-c]quinolin-1-yl) methyl)benzylcarbamate, 2-methacrylamidoethyl 4-((4-amino-2-(oxazol-2-yl)-1H-imidazo[4,5-c]quinolin-1-yl) methyl)benzylcarbamate, 2-methacrylamidoethyl 4-((4-amino-2-(oxazol-5-yl)-1H-imidazo[4,5-c]quinolin-1-yl) methyl)benzylcarbamate, 2-methacrylamidoethyl 4-((4-amino-2-(isoxazol-5-yl)-1H-imidazo[4,5-c]quinolin-1-yl) methyl)benzylcarbamate, 2-methacrylamidoethyl 4-((4-amino-2-(pyridin-2-yl)-1H-imidazo[4,5-c]quinolin-1-yl) methyl)benzylcarbamate, 2-methacrylamidoethyl 4-((4-amino-2-(pyridin-3-yl)-1H-imidazo[4,5-c]quinolin-1-yl) methyl)benzylcarbamate, 2-methacrylamidoethyl 4-((4-amino-2-(pyridin-4-yl)-1H-imidazo[4,5-c]quinolin-1-yl) methyl)benzylcarbamate, 2-methacrylamidoethyl 4-((4-amino-2-(pyrimidin-4-yl)-1H-imidazo[4,5-c]quinolin-1-yl) methyl)benzylcarbamate, 2-methacrylamidoethyl 4-((4-amino-2-(pyrazin-2-yl)-1H-imidazo[4,5-c]quinolin-1-yl) methyl)benzylcarbamate, 2-methacrylamidoethyl 4-((4-amino-2-(pyridazin-3-yl)-1H-imidazo[4,5-c]quinolin-1-yl) methyl)benzylcarbamate, 2-methacrylamidoethyl 4-((4-amino-2-(pyridazin-4-yl)-1H-imidazo[4,5-c]quinolin-1-yl) methyl)benzylcarbamate, 2-methacrylamidoethyl 4-((4-amino-2-(pyrimidin-5-yl)-1H-imidazo[4,5-c]quinolin-1-yl) methyl)benzylcarbamate, and derivatives thereof. Also disclosed are compounds of formula (1) where R3=OR5. Exemplary imidazoquinoline derivatives further include: N-(3-(4-amino-2-(ethoxymethyl)-1H-imidazo[4,5-c]quinolin-1-yloxy)propyl)methacrylamide, N-(4-(4-amino-2-(ethoxymethyl)-1H-imidazo[4,5-c]quinolin-1-yloxy)butyl) methacrylamide, N-(4-(4-amino-2-(ethoxymethyl)-1H-imidazo[4,5-c]quinolin-1-yloxy)pentyl)methacrylamide, N-(4-(4-amino-2-(ethoxymethyl)-1H-imidazo[4,5-c]quinolin-1-yloxy)hexyl)methacrylamide, N-(4-(4-amino-2-(ethoxymethyl)-1H-imidazo[4,5-c]quinolin-1-yloxy)heptyl) methacrylamide, N-(4-(4-amino-2-(ethoxymethyl)-1H-imidazo[4,5-c]quinolin-1-yloxy)octyl)methacrylamide, N-(4-(4-amino-2-(ethoxymethyl)-1H-imidazo[4,5-c]quinolin-1-yloxy)nonyl)methacrylamide, N-(4-(4-amino-2-(ethoxymethyl)-1H-imidazo[4,5-c]quinolin-1-yloxy)decyl) methacrylamide, as well as those N—O bond containing structures containing the above mentioned 4- and 2-position imidazoquinoline substitutions and derivatives thereof. The 4-amino group in common to the above mentioned variously 2-substituted imidazoquinoline derivatives installed in FIG. 2 (step vii) could be any other nucleophile capable of a nucleophilic aromatic substitution (SNAr) reaction with 4-substituted heteroaryl chloride, for example hydroxide, methylamine, dimethylamine, ethylamine, methylethylamine, propylamine, azetidine, cyclopropylamine, pyrrolidine, etc. Alternatively the 4-substituted heteroaryl chloride may be replaced with hydrogen by a hydro or radical dehalogenation reaction or participate as a coupling partner in a transition metal catalyzed carbon-carbon bond formation reaction.

In select embodiments of the current disclosure, any of the disclosed TLR agonist monomers can be linked with another monomer that contains at least one group that binds to an Antigen Presenting Cell (APC) mannose receptor as polymers, homopolymers, copolymers, copolymeric blends, terpolymers, quaterpolymers, or oligomers, etc., and can be present in compositions and conjugated to, for example, antigens. Any of the copolymers may be a block copolymer, an alternating copolymer or a random copolymer. Preferably the compounds, copolymers, and polymers of the present invention are hydrophilic. Non-limiting examples of water-soluble polymers that may find use in the current embodiments include polyacrylates, such as poly(acrylic acid) or poly(methacrylic acid) or poly(hydrxypropyl methacrylate), polyamides, such as poly(acrylamide) or poly(methacrylamide), polysaccharides, polyoxazoline, such as poly(ethyloxazoline), polyimine, such as poly(ethylenimine), and polyvinyl derivatives, such as a poly(vinylalcohol) or poly (vinylpyrrolidone). Linking of monomers to form polymers, homopolymers, copolymers, polymeric blends, terpolymers, quaterpolymers, or oligomers and conjugation to, for instance, antigens as disclosed in the current embodiments, may be accomplished using synthetic organic techniques using polymerizable and linking groups which would be readily apparent to one of ordinary skill in the art, based on the present disclosure. Non-limiting examples of making the compounds, copolymers, and polymers of the present invention are provided in the Examples section.

3. Other TLR Agonists

In some embodiments, the copolymer of formula I is operably linked to a TLR agonist. In some embodiments, the TLR agonist is a compound of general formula (VI), as described herein. In some embodiments, the TLR agonist is one known in the art and/or described herein. The TLR agonists may include an agonist to TLR1 (e.g., peptidoglycan or triacyl lipoproteins), TLR2 (e.g., lipoteichoic acid; peptidoglycan from *Bacillus subtilis, E. coli* 0111:B4, *Escherichia coli* K12, or *Staphylococcus aureus*; atypical lipopolysaccharide (LPS) such as Leptospirosis LPS and *Porphyromonas gingivalis* LPS; a synthetic diacylated lipoprotein such as FSL-1 or Pam2CSK4; lipoarabinomannan or lipomannan from *M. smegmatis*; triacylated lipoproteins such as Pam3CSK4; lipoproteins such as MALP-2 and MALP-404 from *mycoplasma; Borrelia burgdorferi* OspA; Porin from *Neisseria meningitidis* or *Haemophilus influenza; Propionibacterium acnes* antigen mixtures; *Yersinia* LcrV; lipomannan from *Mycobacterium* or *Mycobacterium tuberculosis; Trypanosoma cruzi* GPI anchor; *Schistosoma mansoni* lysophosphatidylserine; *Leishmania major* lipophosphoglycan (LPG); *Plasmodium falciparum* glycophosphatidylinositol (GPI); zymosan; antigen mixtures from *Aspergillus fumigatus* or *Candida albicans*; and measles hemagglutinin), TLR3 (e.g., double-stramded RNA, polyadenylic-polyuridylic acid (Poly(A:U)); polyinosine-polycytidylic acid (Poly(I:C)); polyinosine-polycytidylic acid high molecular weight (Poly(I:C) HMW); and polyinosine-polycytidylic acid low molecular weight (Poly (I:C) LMW)), TLR4 (e.g., LPS from *Escherichia coli* and *Salmonella* species); TLR5 (e.g., Flagellin from *B. subtilis, P. aeruginosa*, or *S. typhimurium*), TLR8 (e.g., single stranded RNAs such as ssRNA with 6UUAU repeats, RNA homopolymer (ssPolyU naked), HIV-1 LTR-derived ssRNA (ssRNA40), or ssRNA with 2 GUCCUUCAA repeats (ssRNA-DR)), TLR7 (e.g., imidazoquinoline compound imiquimod, Imiquimod VacciGrade™, Gardiquimod VacciGrade™, or Gardiquimod™; adenine analog CL264; base analog CL307; guanosine analog loxoribine; TLR7/8 (e.g., thiazoquinoline compound CL075; imidazoquinoline compound CLO97, R848, or R848 VacciGrade™), TLR9 (e.g., CpG ODNs); and TLR11 (e.g., *Toxoplasma gondii* Profilin). In certain embodiments, the TLR agonist is a specific agonist listed above. In further embodiments, the TLR agonist is one that agonizes either one TLR or two TLRs specifically.

In some embodiments, the TLR agonist is a TLR7, TLR8, or a TLR7/8 agonist. The TLR agonist may be multiple (polymerized) molecules of the same TLR agonist or may be a mixture of linked different TLR agonists. The TLR agonist may be linked or polymerized by methods known in the art and/or described herein. In some embodiments, the compound (e.g., TLR agonist) is water soluble. Water solubility affects the shelf-life, stability, and pharmaceutical composition of the compound. Due to the structure of TLR7 and TLR8, most TLR7 and/or TLR8 agonists are poorly soluble in water. However, the compounds of Formula (I) have the advantage of water solubility.

III. ADDITIONAL THERAPIES

A. Immunotherapy

In some embodiments, the methods comprise administration of a cancer immunotherapy. Cancer immunotherapy (sometimes called immuno-oncology, abbreviated IO) is the use of the immune system to treat cancer. Immunotherapies can be categorized as active, passive or hybrid (active and passive). These approaches exploit the fact that cancer cells often have molecules on their surface that can be detected by the immune system, known as tumor-associated antigens (TAAs); they are often proteins or other macromolecules (e.g. carbohydrates). Active immunotherapy directs the immune system to attack tumor cells by targeting TAAs. Passive immunotherapies enhance existing anti-tumor responses and include the use of monoclonal antibodies, lymphocytes and cytokines. Immunotherapies useful in the methods of the disclosure are described below.

1. Checkpoint Inhibitors and Combination Treatment

Embodiments of the disclosure may include administration of immune checkpoint inhibitors (also referred to as checkpoint inhibitor therapy), which are further described below.

b. PD-1, PDL1, and PDL2 inhibitors

PD-1 can act in the tumor microenvironment where T cells encounter an infection or tumor. Activated T cells upregulate PD-1 and continue to express it in the peripheral tissues. Cytokines such as IFN-gamma induce the expression of PDL1 on epithelial cells and tumor cells. PDL2 is expressed on macrophages and dendritic cells. The main role of PD-1 is to limit the activity of effector T cells in the periphery and prevent excessive damage to the tissues during an immune response. Inhibitors of the disclosure may block one or more functions of PD-1 and/or PDL1 activity.

Alternative names for "PD-1" include CD279 and SLEB2. Alternative names for "PDL1" include B7-H1, B7-4, CD274, and B7-H. Alternative names for "PDL2" include B7-DC, Btdc, and CD273. In some embodiments, PD-1, PDL1, and PDL2 are human PD-1, PDL1 and PDL2.

In some embodiments, the PD-1 inhibitor is a molecule that inhibits the binding of PD-1 to its ligand binding partners. In a specific aspect, the PD-1 ligand binding partners are PDL1 and/or PDL2. In another embodiment, a PDL1 inhibitor is a molecule that inhibits the binding of PDL1 to its binding partners. In a specific aspect, PDL1 binding partners are PD-1 and/or B7-1. In another embodiment, the PDL2 inhibitor is a molecule that inhibits the binding of PDL2 to its binding partners. In a specific aspect, a PDL2 binding partner is PD-1. The inhibitor may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 inhibitors for use in the methods and compositions provided herein are known in the art such as described in U.S. Patent Application Nos. US2014/0294898, US2014/022021, and US2011/0008369, all incorporated herein by reference.

In some embodiments, the PD-1 inhibitor is an anti-PD-1 antibody (e.g., a human antibody, a humanized antibody, or a chimeric antibody). In some embodiments, the anti-PD-1 antibody is selected from the group consisting of nivolumab, pembrolizumab, and pidilizumab. In some embodiments, the PD-1 inhibitor is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PDL1 inhibitor comprises AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. Pidilizumab, also known as CT-011, hBAT, or hBAT-1, is an anti-PD-1 antibody described in WO2009/101611. AMP-224, also known as B7-DCIg, is a PDL2-Fc fusion soluble receptor described in WO2010/027827 and WO2011/066342. Additional PD-1 inhibitors include MEDI0680, also known as AMP-514, and REGN2810.

In some embodiments, the immune checkpoint inhibitor is a PDL1 inhibitor such as Durvalumab, also known as MEDI4736, atezolizumab, also known as MPDL3280A, avelumab, also known as MSB00010118C, MDX-1105, BMS-936559, or combinations thereof. In certain aspects, the immune checkpoint inhibitor is a PDL2 inhibitor such as rHIgM12B7.

In some embodiments, the inhibitor comprises the heavy and light chain CDRs or VRs of nivolumab, pembrolizumab, or pidilizumab. Accordingly, in one embodiment, the inhibitor comprises the CDR1, CDR2, and CDR3 domains of the VH region of nivolumab, pembrolizumab, or pidilizumab, and the CDR1, CDR2 and CDR3 domains of the VL region of nivolumab, pembrolizumab, or pidilizumab. In another embodiment, the antibody competes for binding with and/or binds to the same epitope on PD-1, PDL1, or PDL2 as the above-mentioned antibodies. In another embodiment, the antibody has at least about 70, 75, 80, 85, 90, 95, 97, or 99% (or any derivable range therein) variable region amino acid sequence identity with the above-mentioned antibodies.

c. CTLA-4, B7-1, and B7-2

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to B7-1 (CD80) or B7-2 (CD86) on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to B7-1 and B7-2 on antigen-presenting cells. CTLA-4 transmits an inhibitory signal to T cells, whereas CD28 transmits a stimulatory signal. Intracellular CTLA-4 is also found in regulatory T cells and may be important to their function. T cell activation through the T cell receptor and CD28 leads to increased expression of CTLA-4, an inhibitory receptor for B7 molecules. Inhibitors of the disclosure may block one or more functions of CTLA-4, B7-1, and/or B7-2 activity. In some embodiments, the inhibitor blocks the CTLA-4 and B7-1 interaction. In some embodiments, the inhibitor blocks the CTLA-4 and B7-2 interaction.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al., 1998; can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001/014424, WO2000/037504, and U.S. Pat. No. 8,017,114; all incorporated herein by reference.

A further anti-CTLA-4 antibody useful as a checkpoint inhibitor in the methods and compositions of the disclosure is ipilimumab (also known as 10D1, MDX-010, MDX-101, and Yervoy®) or antigen binding fragments and variants thereof (see, e.g., WOO 1/14424).

In some embodiments, the inhibitor comprises the heavy and light chain CDRs or VRs of tremelimumab or ipilimumab. Accordingly, in one embodiment, the inhibitor comprises the CDR1, CDR2, and CDR3 domains of the VH region of tremelimumab or ipilimumab, and the CDR1, CDR2 and CDR3 domains of the VL region of tremelimumab or ipilimumab. In another embodiment, the antibody competes for binding with and/or binds to the same epitope on PD-1, B7-1, or B7-2 as the above-mentioned antibodies. In another embodiment, the antibody has at least about 70, 75, 80, 85, 90, 95, 97, or 99% (or any derivable range therein) variable region amino acid sequence identity with the above-mentioned antibodies.

2. Inhibition of Co-Stimulatory Molecules

In some embodiments, the immunotherapy comprises an inhibitor of a co-stimulatory molecule. In some embodiments, the inhibitor comprises an inhibitor of B7-1 (CD80), B7-2 (CD86), CD28, ICOS, OX40 (TNFRSF4), 4-1BB (CD137; TNFRSF9), CD40L (CD40LG), GITR (TNFRSF18), TIM3, LAG3, VISTA, and combinations thereof. Inhibitors include inhibitory antibodies, polypeptides, compounds, and nucleic acids.

3. Dendritic Cell Therapy

Dendritic cell therapy provokes anti-tumor responses by causing dendritic cells to present tumor antigens to lymphocytes, which activates them, priming them to kill other cells that present the antigen. Dendritic cells are antigen presenting cells (APCs) in the mammalian immune system. In cancer treatment they aid cancer antigen targeting. One example of cellular cancer therapy based on dendritic cells is sipuleucel-T.

One method of inducing dendritic cells to present tumor antigens is by vaccination with autologous tumor lysates or short peptides (small parts of protein that correspond to the protein antigens on cancer cells). These peptides are often given in combination with adjuvants (highly immunogenic substances) to increase the immune and anti-tumor responses. Other adjuvants include proteins or other chemicals that attract and/or activate dendritic cells, such as granulocyte macrophage colony-stimulating factor (GM-CSF).

Dendritic cells can also be activated in vivo by making tumor cells express GM-CSF. This can be achieved by either genetically engineering tumor cells to produce GM-CSF or by infecting tumor cells with an oncolytic virus that expresses GM-CSF.

Another strategy is to remove dendritic cells from the blood of a patient and activate them outside the body. The dendritic cells are activated in the presence of tumor antigens, which may be a single tumor-specific peptide/protein or a tumor cell lysate (a solution of broken down tumor cells). These cells (with optional adjuvants) are infused and provoke an immune response.

Dendritic cell therapies include the use of antibodies that bind to receptors on the surface of dendritic cells. Antigens can be added to the antibody and can induce the dendritic cells to mature and provide immunity to the tumor.

4. CAR-T Cell Therapy

Chimeric antigen receptors (CARs, also known as chimeric immunoreceptors, chimeric T cell receptors or artificial T cell receptors) are engineered receptors that combine a new specificity with an immune cell to target cancer cells. Typically, these receptors graft the specificity of a monoclonal antibody onto a T cell. The receptors are called chimeric because they are fused of parts from different sources. CAR-T cell therapy refers to a treatment that uses such transformed cells for cancer therapy.

The basic principle of CAR-T cell design involves recombinant receptors that combine antigen-binding and T-cell activating functions. The general premise of CAR-T cells is to artificially generate T-cells targeted to markers found on cancer cells. Scientists can remove T-cells from a person, genetically alter them, and put them back into the patient for them to attack the cancer cells. Once the T cell has been engineered to become a CAR-T cell, it acts as a "living drug". CAR-T cells create a link between an extracellular ligand recognition domain to an intracellular signalling molecule which in turn activates T cells. The extracellular ligand recognition domain is usually a single-chain variable fragment (scFv). An important aspect of the safety of CAR-T cell therapy is how to ensure that only cancerous tumor cells are targeted, and not normal cells. The specificity of CAR-T cells is determined by the choice of molecule that is targeted.

Exemplary CAR-T therapies include Tisagenlecleucel (Kymriah) and Axicabtagene ciloleucel (Yescarta). In some embodiments, the CAR-T therapy targets CD19.

5. Cytokine Therapy

Cytokines are proteins produced by many types of cells present within a tumor. They can modulate immune responses. The tumor often employs them to allow it to grow and reduce the immune response. These immune-modulating effects allow them to be used as drugs to provoke an immune response. Two commonly used cytokines are interferons and interleukins.

Interferons are produced by the immune system. They are usually involved in anti-viral response, but also have use for cancer. They fall in three groups: type I (IFN$\alpha$ and IFN$\beta$), type II (IFN$\gamma$) and type III (IFN$\lambda$).

Interleukins have an array of immune system effects. IL-2 is an exemplary interleukin cytokine therapy. Also contemplated within the scope of the disclosure is the administration of chemokine therapy as an immunotherapy useful in the methods of the disclosure.

6. Adoptive T-Cell Therapy

Adoptive T cell therapy is a form of passive immunization by the transfusion of T-cells (adoptive cell transfer). They are found in blood and tissue and usually activate when they find foreign pathogens. Specifically they activate when the T-cell's surface receptors encounter cells that display parts of foreign proteins on their surface antigens. These can be either infected cells, or antigen presenting cells (APCs). They are found in normal tissue and in tumor tissue, where they are known as tumor infiltrating lymphocytes (TILs). They are activated by the presence of APCs such as dendritic cells that present tumor antigens. Although these cells can attack the tumor, the environment within the tumor is highly immunosuppressive, preventing immune-mediated tumor death. [60]

Multiple ways of producing and obtaining tumor targeted T-cells have been developed. T-cells specific to a tumor antigen can be removed from a tumor sample (TILs) or filtered from blood. Subsequent activation and culturing is performed ex vivo, with the results reinfused. Activation can take place through gene therapy, or by exposing the T cells to tumor antigens.

It is contemplated that a cancer treatment may exclude any of the cancer treatments described herein. Furthermore, embodiments of the disclosure include patients that have been previously treated for a therapy described herein, are currently being treated for a therapy described herein, or have not been treated for a therapy described herein. In some embodiments, the patient is one that has been determined to be resistant to a therapy described herein. In some embodiments, the patient is one that has been determined to be sensitive to a therapy described herein.

B. Oncolytic Virus

In some embodiments, the additional therapy comprises an oncolytic virus. An oncolytic virus is a virus that preferentially infects and kills cancer cells. As the infected cancer cells are destroyed by oncolysis, they release new infectious virus particles or virions to help destroy the remaining tumor. Oncolytic viruses are thought not only to cause direct destruction of the tumor cells, but also to stimulate host anti-tumor immune responses for long-term immunotherapy C. Polysaccharides In some embodiments, the additional therapy comprises polysaccharides. Certain compounds found in mushrooms, primarily polysaccharides, can up-regulate the immune system and may have anti-cancer properties. For example, beta-glucans such as lentinan have been shown in laboratory studies to stimulate macrophage, NK cells, T cells and immune system cytokines and have been investigated in clinical trials as immunologic adjuvants.

D. Neoantigens

In some embodiments, the additional therapy comprises neoantigen administration. Many tumors express mutations. These mutations potentially create new targetable antigens (neoantigens) for use in T cell immunotherapy. The presence of CD8+ T cells in cancer lesions, as identified using RNA sequencing data, is higher in tumors with a high mutational burden. The level of transcripts associated with cytolytic activity of natural killer cells and T cells positively correlates with mutational load in many human tumors.

E. Chemotherapies

In some embodiments, the additional therapy comprises a chemotherapy. Suitable classes of chemotherapeutic agents include (a) Alkylating Agents, such as nitrogen mustards (e.g., mechlorethamine, cylophosphamide, ifosfamide, melphalan, chlorambucil), ethylenimines and methylmelamines (e.g., hexamethylmelamine, thiotepa), alkyl sulfonates (e.g., busulfan), nitrosoureas (e.g., carmustine, lomustine, chlorozoticin, streptozocin) and triazines (e.g., dicarbazine), (b) Antimetabolites, such as folic acid analogs (e.g., methotrexate), pyrimidine analogs (e.g., 5-fluorouracil, floxuridine, cytarabine, azauridine) and purine analogs and related materials (e.g., 6-mercaptopurine, 6-thioguanine, pentostatin), (c) Natural Products, such as vinca alkaloids (e.g., vinblastine, vincristine), epipodophylotoxins (e.g., etoposide, teniposide), antibiotics (e.g., dactinomycin, daunorubicin, doxorubicin, bleomycin, plicamycin and mitoxanthrone), enzymes (e.g., L-asparaginase), and biological response modifiers (e.g., Interferon-α), and (d) Miscellaneous Agents, such as platinum coordination complexes (e.g., cisplatin, carboplatin), substituted ureas (e.g., hydroxyurea), methylhydiazine derivatives (e.g., procarbazine), and adreocortical suppressants (e.g., taxol and mitotane). In some embodiments, cisplatin is a particularly suitable chemotherapeutic agent.

Cisplatin has been widely used to treat cancers such as, for example, metastatic testicular or ovarian carcinoma, advanced bladder cancer, head or neck cancer, cervical cancer, lung cancer or other tumors. Cisplatin is not absorbed orally and must therefore be delivered via other routes such as, for example, intravenous, subcutaneous, intratumoral or intraperitoneal injection. Cisplatin can be used alone or in combination with other agents, with efficacious doses used in clinical applications including about 15 mg/m2 to about 20 mg/m2 for 5 days every three weeks for a total of three courses being contemplated in certain embodiments. In some embodiments, the amount of cisplatin delivered to the cell and/or subject in conjunction with the construct comprising an Egr-1 promoter operably linked to a polynucleotide encoding the therapeutic polypeptide is less than the amount that would be delivered when using cisplatin alone.

Other suitable chemotherapeutic agents include antimicrotubule agents, e.g., Paclitaxel ("Taxol") and doxorubicin hydrochloride ("doxorubicin"). The combination of an Egr-1 promoter/TNFα construct delivered via an adenoviral vector and doxorubicin was determined to be effective in overcoming resistance to chemotherapy and/or TNF-α, which suggests that combination treatment with the construct and doxorubicin overcomes resistance to both doxorubicin and TNF-α.

Doxorubicin is absorbed poorly and is preferably administered intravenously. In certain embodiments, appropriate intravenous doses for an adult include about 60 mg/m2 to about 75 mg/m2 at about 21-day intervals or about 25 mg/m2 to about 30 mg/m2 on each of 2 or 3 successive days repeated at about 3 week to about 4 week intervals or about 20 mg/m2 once a week. The lowest dose should be used in elderly patients, when there is prior bone-marrow depression caused by prior chemotherapy or neoplastic marrow invasion, or when the drug is combined with other myelopoietic suppressant drugs.

Nitrogen mustards are another suitable chemotherapeutic agent useful in the methods of the disclosure. A nitrogen mustard may include, but is not limited to, mechlorethamine (HN2), cyclophosphamide and/or ifosfamide, melphalan (L-sarcolysin), and chlorambucil. Cyclophosphamide (CYTOXAN®) is available from Mead Johnson and NEOSTAR® is available from Adria), is another suitable chemotherapeutic agent. Suitable oral doses for adults include, for example, about 1 mg/kg/day to about 5 mg/kg/day, intravenous doses include, for example, initially about 40 mg/kg to about 50 mg/kg in divided doses over a period of about 2 days to about 5 days or about 10 mg/kg to about 15 mg/kg about every 7 days to about 10 days or about 3 mg/kg to about 5 mg/kg twice a week or about 1.5 mg/kg/day to about 3 mg/kg/day. Because of adverse gastrointestinal effects, the intravenous route is preferred. The drug also sometimes is administered intramuscularly, by infiltration or into body cavities.

Additional suitable chemotherapeutic agents include pyrimidine analogs, such as cytarabine (cytosine arabinoside), 5-fluorouracil (fluouracil; 5-FU) and floxuridine (fluorode-oxyuridine; FudR). 5-FU may be administered to a subject in a dosage of anywhere between about 7.5 to about 1000 mg/m2. Further, 5-FU dosing schedules may be for a variety of time periods, for example up to six weeks, or as determined by one of ordinary skill in the art to which this disclosure pertains.

Gemcitabine diphosphate (GEMZAR®, Eli Lilly & Co., "gemcitabine"), another suitable chemotherapeutic agent, is recommended for treatment of advanced and metastatic pancreatic cancer, and will therefore be useful in the present disclosure for these cancers as well.

The amount of the chemotherapeutic agent delivered to the patient may be variable. In one suitable embodiment, the chemotherapeutic agent may be administered in an amount effective to cause arrest or regression of the cancer in a host, when the chemotherapy is administered with the construct. In other embodiments, the chemotherapeutic agent may be administered in an amount that is anywhere between 2 to 10,000 fold less than the chemotherapeutic effective dose of the chemotherapeutic agent. For example, the chemotherapeutic agent may be administered in an amount that is about 20 fold less, about 500 fold less or even about 5000 fold less than the chemotherapeutic effective dose of the chemotherapeutic agent. The chemotherapeutics of the disclosure can be tested in vivo for the desired therapeutic activity in combination with the construct, as well as for determination of effective dosages. For example, such compounds can be tested in suitable animal model systems prior to testing in humans, including, but not limited to, rats, mice, chicken, cows, monkeys, rabbits, etc. In vitro testing may also be used to determine suitable combinations and dosages, as described in the examples.

F. Radiotherapy

In some embodiments, the additional therapy or prior therapy comprises radiation, such as ionizing radiation. As used herein, "ionizing radiation" means radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art.

In some embodiments, the amount of ionizing radiation is greater than 20 Gy and is administered in one dose. In some embodiments, the amount of ionizing radiation is 18 Gy and is administered in three doses. In some embodiments, the amount of ionizing radiation is at least, at most, or exactly 2, 4, 6, 8, 10, 15, 16, 17, 18, 19, 20, 21, 22, 23, 24, 25, 26, 27, 18, 19, 30, 31, 32, 33, 34, 35, 36, 37, 38, 39, 40, 41, 42, 43, 44, 45, 46, 47, 48, 49, or 40 Gy (or any derivable range therein). In some embodiments, the ionizing radiation is administered in at least, at most, or exactly 1, 2, 3, 4, 5, 6, 7, 8, 9, or 10 doses (or any derivable range therein). When more than one dose is administered, the does may be about 1, 4, 8, 12, or 24 hours or 1, 2, 3, 4, 5, 6, 7, or 8 days or 1, 2, 3, 4, 5, 6, 7, 8, 9, 10, 12, 14, or 16 weeks apart, or any derivable range therein.

In some embodiments, the amount of IR may be presented as a total dose of IR, which is then administered in fractionated doses. For example, in some embodiments, the total dose is 50 Gy administered in 10 fractionated doses of 5 Gy each. In some embodiments, the total dose is 50-90 Gy, administered in 20-60 fractionated doses of 2-3 Gy each. In some embodiments, the total dose of IR is at least, at most, or about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 125, 130, 135, 140, or 150 (or any derivable range therein). In some embodiments, the total dose is administered in fractionated doses of at least, at most, or exactly 1, 2, 3, 4, 5, 6, 7, 8, 9, 10, 12, 14, 15, 20, 25, 30, 35, 40, 45, or 50 Gy (or any derivable range therein. In some embodiments, at least, at most, or exactly 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 fractionated doses are administered (or any derivable range therein). In some embodiments, at least, at most, or exactly 1, 2, 3, 4, 5, 6, 7, 8, 9, 10, 11, or 12 (or any derivable range therein) fractionated doses are administered per day. In some embodiments, at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 (or any derivable range therein) fractionated doses are administered per week.

G. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

H. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. NUCLEIC ACIDS

In certain embodiments, there are recombinant nucleic acids encoding the polypeptides described herein.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or fewer in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide. It also is contemplated that a particular polypeptide may be encoded by nucleic acids containing variations having slightly different nucleic acid sequences but, nonetheless, encode the same or substantially similar protein (see above).

In particular embodiments, there are isolated nucleic acid segments and recombinant vectors incorporating nucleic acid sequences that encode a polypeptides (e.g., a polymerase, RNA polymerase, one or more truncated polymerase domains or interaction components that are polypeptides) that drive gene transcription dependent on polymerase activity from the polymerase domains when the interaction components interact. The term "recombinant" may be used in conjunction with a polypeptide or the name of a specific polypeptide, and this generally refers to a polypeptide produced from a nucleic acid molecule that has been manipulated in vitro or that is a replication product of such a molecule.

The nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain embodiments, there are polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence provided herein using the methods described herein (e.g., BLAST analysis using standard parameters). In certain aspects, the isolated polynucleotide will comprise a nucleotide sequence encoding a polypeptide that has at least 90%, preferably 95% and above, identity to an amino acid sequence described herein, over the entire length of the sequence; or a nucleotide sequence complementary to said isolated polynucleotide.

A. Vectors

Polypeptides may be encoded by a nucleic acid molecule. The nucleic acid molecule can be in the form of a nucleic acid vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). Vectors may be used in a host cell to produce a polymerase, RNA polymerase, one or more truncated polymerase domains or interaction components that are fused, attached or linked to the one or more truncated RNA polymerase domains.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

B. Cells

The disclosure provides methods for modifying a target RNA of interest, in particular in prokaryotic cells, eukaryotic cells, tissues, organs, or organisms, more in particular in mammalian cells, tissues, organs, or organisms. The target RNA may be comprised in a nucleic acid molecule within a cell. In some embodiments, the target RNA is in a eukaryotic cell, such as a mammalian cell or a plant cell. The mammalian cell many be a human, non-human primate, bovine, porcine, rodent or mouse cell. The cell may be a non-mammalian eukaryotic cell such as poultry, fish or shrimp. The plant cell may be of a crop plant such as cassava, corn, sorghum, wheat, or rice. The plant cell may also be of an algae, tree or vegetable. The modulation of the RNA induced in the cell by the methods, systems, and compositions of the disclosure may be such that the cell and progeny of the cell are altered for improved production of biologic products such as an antibody, starch, alcohol or other desired cellular output. The modulation of the RNA induced in the cell may be such that the cell and progeny of the cell include an alteration that changes the biologic product produced.

The mammalian cell may be a human or non-human mammal, e.g., primate, bovine, ovine, porcine, canine, rodent, Leporidae such as monkey, cow, sheep, pig, dog, rabbit, rat or mouse cell. The cell may be a non-mammalian eukaryotic cell such as poultry bird (e.g., chicken), vertebrate fish (e.g., salmon) or shellfish (e.g., oyster, clam, lobster, shrimp) cell. The cell may also be a plant cell. The plant cell may be of a monocot or dicot or of a crop or grain plant such as cassava, com, sorghum, soybean, wheat, oat or rice. The plant cell may also be of an algae, tree or production plant, fruit or vegetable (e.g., trees such as citrus trees, e.g., orange, grapefruit or lemon trees; peach or nectarine trees; apple or pear trees; nut trees such as almond or walnut or pistachio trees; nightshade plants; plants of the genus *Brassica*; plants of the genus *Lactuca*; plants of the genus *Spinacia*; plants of the genus *Capsicum*; cotton, tobacco, asparagus, carrot, cabbage, broccoli, cauliflower, tomato, eggplant, pepper, lettuce, spinach, strawberry, blueberry, raspberry, blackberry, grape, coffee, cocoa, etc.).

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

C. Expression Systems

Numerous expression systems exist that comprise at least a part or all of the compositions discussed above. Prokaryote- and/or eukaryote-based systems can be employed for use with an embodiment to produce nucleic acid sequences, or their cognate polypeptides, proteins and peptides. For example, the vectors, fusion proteins, RNA hairpin binding proteins, RNA targeting molecules, RNA regulatory domain, and accessory proteins of the disclosure may utilize an expression system, such as an inducible or constitutive expression system. Many such systems are commercially and widely available. In some embodiments, the expression system comprises Freestyle™ HEK293-F cells, which are available commercially from Gibco.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems, other examples of expression systems include STRATAGENE®'s COMPLETE CONTROL Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

V. PROTEINACEOUS COMPOSITIONS

The polypeptides or polynucleotides of the disclosure such as those comprising or encoding for a tumor targeting agent linked to a TLR agonist and/or albumin, may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more variant amino acids or nucleic acid substitutions or be at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% similar, identical, or homologous with at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids or nucleic acids, or any range derivable therein, of SEQ ID Nos:1-27.

The polypeptides or polynucleotides of the disclosure such as those comprising or encoding for a tumor targeting agent linked to a TLR agonist and/or albumin, may include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of SEQ ID NO:1-27.

In some embodiments, the polypeptide comprises amino acids 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 (or any derivable range therein) of SEQ ID NOs: 1-27.

In some embodiments, the polypeptide comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 (or any derivable range therein) contiguous amino acids of SEQ ID NOs: 1-27.

In some embodiments, the polypeptide comprises at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 (or any derivable range therein) contiguous amino acids of any of SEQ ID NOs:1-27 and starts at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 of any of SEQ ID NO:1-27.

In some embodiments, the polypeptide comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 (or any derivable range therein) contiguous amino acids of SEQ ID NOs:1-27 that are at least, at most, or exactly 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% similar, identical, or homologous with one of SEQ ID NOS:1-27.

The polypeptides of the disclosure may include at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 substitutions.

The substitution may be at amino acid position or nucleic acid position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 of one of SEQ ID NO:1-27.

The polypeptides described herein may be of a fixed length of at least, at most, or exactly 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more amino acids (or any derivable range therein).

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria, eukaryotic cells, yeast, or mammalian cells. It is also contemplated that bacteria containing such a variant may be implemented in compositions and methods. Consequently, a protein need not be isolated.

The term "functionally equivalent codon" is used herein to refer to codons that encode the same amino acid, such as the six codons for arginine or serine, and also refers to codons that encode biologically equivalent amino acids.

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create an equivalent, or even an improved, second-generation molecule. For example, certain amino acids may be substituted for other amino acids in a protein structure without appreciable loss of interactive binding capacity. Structures such as, for example, an enzymatic catalytic domain or interaction components may have amino acid substituted to maintain such function. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity.

In other embodiments, alteration of the function of a polypeptide is intended by introducing one or more substitutions. For example, certain amino acids may be substituted for other amino acids in a protein structure with the intent to modify the interactive binding capacity of interaction components. Structures such as, for example, protein interaction domains, nucleic acid interaction domains, and catalytic sites may have amino acids substituted to alter such function. Since it is the interactive capacity and nature of a protein that defines that protein's biological functional activity, certain amino acid substitutions can be made in a protein sequence, and in its underlying DNA coding sequence, and nevertheless produce a protein with different properties. It is thus contemplated by the inventors that various changes may be made in the DNA sequences of genes with appreciable alteration of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

In specific embodiments, all or part of proteins described herein can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence that encodes a peptide or polypeptide is inserted into an expression vector, transformed or transfected into an appropriate host cell and cultivated under conditions suitable for expression.

One embodiment includes the use of gene transfer to cells, including microorganisms, for the production and/or presentation of proteins. The gene for the protein of interest may be transferred into appropriate host cells followed by culture of cells under the appropriate conditions. A nucleic acid encoding virtually any polypeptide may be employed. The generation of recombinant expression vectors, and the elements included therein, are discussed herein. Alternatively, the protein to be produced may be an endogenous protein normally synthesized by the cell used for protein production.

VI. COMBINATION THERAPY

The compositions and related methods of the present disclosure, particularly administration of a polypeptide comprising a tumor targeting agent linked to a TLR agonist may also be used in combination with the administration of additional therapies such as the additional therapeutics described herein or in combination with other traditional therapeutics known in the art.

The therapeutic compositions and treatments disclosed herein may precede, be co-current with and/or follow another treatment or agent by intervals ranging from minutes to weeks. In embodiments where agents are applied separately to a cell, tissue or organism, one would generally ensure that a significant period of time did not expire between the time of each delivery, such that the therapeutic agents would still be able to exert an advantageously combined effect on the cell, tissue or organism. For example, in such instances, it is contemplated that one may contact the cell, tissue or organism with two, three, four or more agents or treatments substantially simultaneously (i.e., within less than about a minute). In other aspects, one or more therapeutic agents or treatments may be administered or provided within 1 minute, 5 minutes, 10 minutes, 20 minutes, 30 minutes, 45 minutes, 60 minutes, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 1 week, 2 weeks, 3 weeks, 4 weeks, 5 weeks, 6 weeks, 7 weeks, or 8 weeks or more, and any range derivable therein, prior to and/or after administering another therapeutic agent or treatment.

Various combination regimens of the therapeutic agents and treatments may be employed. Non-limiting examples of such combinations are shown below, wherein a therapeutic agent such as a composition disclosed herein is "A" and a second agent, such as an additional agent, chemotherapeutic, or checkpoint inhibitor described herein or known in the art is "B".

| | | | | | | |
|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

In some embodiments, more than one course of therapy may be employed. It is contemplated that multiple courses may be implemented.

VII. THERAPEUTIC METHODS

The current methods and compositions relate to methods for treating cancer. In some embodiments, the cancer comprises a solid tumor. In some embodiments, the cancer is non-lymphatic. In some embodiments, the cancer is melanoma, lymphoma, bladder, breast, or colon cancer.

The compositions of the disclosure may be used for in vivo, in vitro, or ex vivo administration. The route of administration of the composition may be, for example, intratumoral, intracutaneous, subcutaneous, intravenous, intralymphatic, and intraperitoneal administrations. In some embodiments, the administration is intratumoral or intralymphatic or peri-tumoral. In some embodiments, the compositions are administered directly into a cancer tissue or a lymph node.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

The cancers amenable for treatment include, but are not limited to, tumors of all types, locations, sizes, and characteristics. The methods and compositions of the disclosure are suitable for treating, for example, pancreatic cancer, colon cancer, acute myeloid leukemia, adrenocortical carcinoma, AIDS-related cancers, AIDS-related lymphoma, anal cancer, appendix cancer, astrocytoma, childhood cerebellar or cerebral basal cell carcinoma, bile duct cancer, extrahepatic bladder cancer, bone cancer, osteosarcoma/malignant fibrous histiocytoma, brainstem glioma, brain tumor, cerebellar astrocytoma brain tumor, cerebral astrocytoma/malignant glioma brain tumor, ependymoma brain tumor, medulloblastoma brain tumor, supratentorial primitive neuroectodermal tumors brain tumor, visual pathway and hypothalamic glioma, breast cancer, specific breast cancers such as ductal carcinoma in situ, invasive ductal carcinoma, tubular carcinoma of the breast, medullary carcinoma of the breast, mucinous carcinoma of the breast, papillary carcinoma of the breast, cribriform carcinoma of the breast, invasive lobular carcinoma, inflammatory breast cancer, lobular carcinoma in situ, male breast cancer, paget's disease of the nipple, phyllodes tumors of the breast, recurrent and/or metastatic breast, cancer, luminal A or B breast cancer, triple-negative/basal-like breast cancer, and HER2-enriched breast cancer, lymphoid cancer, bronchial adenomas/carcinoids, tracheal cancer, Burkitt lymphoma, carcinoid tumor, childhood carcinoid tumor, gastrointestinal carcinoma of unknown primary, central nervous system lymphoma, primary cerebellar astrocytoma, childhood cerebral astrocytoma/malignant glioma, childhood cervical cancer, childhood cancers, chronic lymphocytic leukemia, chronic myelogenous leukemia, chronic myeloproliferative disorders, cutaneous T-cell lymphoma, desmoplastic small round cell tumor, endometrial cancer, ependymoma, esophageal cancer, Ewing's, childhood extragonadal Germ cell tumor, extrahepatic bile duct cancer, eye cancer, retinoblastoma, gallbladder cancer, gastric (stomach) cancer, gastrointestinal carcinoid tumor, gastrointestinal stromal tumor (GIST), germ cell tumor: extracranial, extragonadal, or ovarian, gestational trophoblastic tumor, glioma of the brain stem, glioma, childhood cerebral astrocytoma, childhood visual pathway and hypothalamic glioma, gastric carcinoid, hairy cell leukemia, head and neck cancer, heart cancer, hepatocellular (liver) cancer, Hodgkin lymphoma, hypopharyngeal cancer, hypothalamic and visual pathway glioma, childhood intraocular melanoma, islet cell carcinoma (endocrine pancreas), kaposi sarcoma, kidney cancer (renal cell cancer), laryngeal cancer, leukemia, acute lymphoblastic (also called acute lymphocytic leukemia) leukemia, acute myeloid (also called acute myelogenous leukemia) leukemia, chronic lymphocytic (also called chronic lymphocytic leukemia) leukemia, chronic myelogenous (also called chronic myeloid leukemia) leukemia, hairy cell lip and oral cavity cancer, liposarcoma, liver cancer (primary), non-small cell lung cancer, small cell lung cancer, lymphomas, AIDS-related lymphoma, Burkitt lymphoma, cutaneous T-cell lymphoma, Hodgkin lymphoma, Non-Hodgkin (an old classification of all lymphomas except Hodgkin's) lymphoma, primary central nervous system lymphoma, Waldenstrom macroglobulinemia, malignant fibrous histiocytoma of bone/osteosarcoma, childhood medulloblastoma, intraocular (eye) melanoma, merkel cell carcinoma, adult malignant mesothelioma, childhood mesothelioma, metastatic squamous neck cancer, mouth cancer, multiple endocrine neoplasia syndrome, multiple myeloma/plasma cell neoplasm, mycosis fungoides, myelodysplastic syndromes, myelodysplastic/myeloproliferative diseases, chronic myelogenous leukemia, adult acute myeloid leukemia, childhood acute myeloid leukemia, multiple myeloma, chronic myeloproliferative disorders, nasal cavity and paranasal sinus cancer, nasopharyngeal carcinoma, neuroblastoma, oral cancer, oropharyngeal cancer, osteosarcoma/malignant, fibrous histiocytoma of bone, ovarian cancer, ovarian epithelial cancer (surface epithelial-stromal tumor), ovarian germ cell tumor, ovarian low malignant potential tumor, pancreatic cancer, islet cell paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, childhood pituitary adenoma, plasma cell neoplasia/multiple myeloma, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma, childhood Salivary gland cancer Sarcoma, Ewing family of tumors, Kaposi sarcoma, soft tissue sarcoma, uterine sezary syndrome sarcoma, skin cancer (nonmelanoma), skin cancer (melanoma), skin carcinoma, Merkel cell small cell lung cancer, small intestine cancer, soft tissue sarcoma, squamous cell carcinoma. squamous neck cancer with occult primary, metastatic stomach cancer, supratentorial primitive neuroectodermal tumor, childhood T-cell lymphoma, testicular cancer, throat cancer, thymoma, childhood thymoma, thymic carcinoma, thyroid cancer, urethral cancer, uterine cancer, endometrial uterine sarcoma, vaginal cancer, visual pathway and hypothalamic glioma, childhood vulvar cancer, and wilms tumor (kidney cancer).

VIII. PHARMACEUTICAL COMPOSITIONS AND METHODS

In some embodiments, pharmaceutical compositions are administered to a subject. Different aspects involve administering an effective amount of a composition to a subject. In some embodiments, a composition comprising an inhibitor may be administered to the subject or patient to treat cancer or reduce the size of a tumor. Additionally, such compounds can be administered in combination with an additional cancer therapy.

Compositions can be formulated for parenteral administration, e.g., formulated for injection via the intravenous, transcatheter injection, intraarterial injection, intramuscular, subcutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and, the preparations can also be emulsified. The preparation of such formulations will be known to those of skill in the art in light of the present disclosure. Other routes of administration include intratumoral, peri-tumoral, intralymphatic, injection into cancer tissue, and injection into lymph nodes. In some embodiments, the administration is systemic.

Other routes of administration are also contemplated. For example, the constructs and agents may be administered in association with a carrier. In some embodiments, the carrier is a nanoparticle or microparticle. In some embodiments, the nanoparticle or microparticle is a tumor directed nanoparticle or microparticle. For example, the carrier may further comprise a targeting moiety that directs the carrier to the tumor. The targeting moiety may be a binding agent (e.g. antibody, including scFv, etc. or other antigen binding agent) that specifically recognizes tumor cells. In some embodiments, the construct is enclosed within the carrier. In some embodiments, the construct is covalently or non-covalently attached to the surface of the carrier. In some embodiments, the carrier is a liposome. In further embodiments, a carrier molecule described herein is excluded.

Particles can have a structure of variable dimension and known variously as a microsphere, microparticle, nanoparticle, nanosphere, or liposome. Such particulate formulations can be formed by covalent or non-covalent coupling of the construct to the particle. In some embodiments, particles described herein are excluded.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent.

As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts or the quaternary ammonium salts of the parent compound formed, for example, from non-toxic inorganic or organic acids. The pharmaceutically acceptable salts can be synthesized from the parent compound which contains a basic or acidic moiety by conventional chemical methods.

Some variation in dosage will necessarily occur depending on the condition of the subject. The person responsible for administration will, in any event, determine the appropriate dose for the individual subject. An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the effects desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

Typically, for a human adult (weighing approximately 70 kilograms), from about 0.1 mg to about 3000 mg (including all values and ranges there between), or from about 5 mg to about 1000 mg (including all values and ranges there between), or from about 10 mg to about 100 mg (including all values and ranges there between), of a compound are administered. It is understood that these dosage ranges are by way of example only, and that administration can be adjusted depending on the factors known to the skilled artisan.

In certain embodiments, a subject is administered about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or μg/kg or micrograms/kg/minute or mg/kg/min or micrograms/kg/hour or mg/kg/hour, or any range derivable therein.

A dose may be administered on an as needed basis or every 1, 2, 3, 4, 5, 6, 7, 8, 9, 10, 11, 12, 18, or 24 hours, or 1, 2, 3, 4, 5, 6, 7, 8, 9, 10, 11, 12, 13, 14, 15, 16, 17, 18, 19, or 20 days (or any range derivable therein) or 1, 2, 3, 4, 5, 6, 7, 8, 9, or times per day (or any range derivable therein). A dose may be first administered before or after signs of a condition. In some embodiments, the patient is administered a first dose of a regimen 1, 2, 3, 4, 5, 6, 7, 8, 9, 10, 11, 12 hours (or any range derivable therein) or 1, 2, 3, 4, or 5 days after the patient experiences or exhibits signs or symptoms of the condition (or any range derivable therein). The patient may be treated for 1, 2, 3, 4, 5, 6, 7, 8, 9, 10 or more days (or any range derivable therein) or until symptoms of the condition have disappeared or been reduced or after 6, 12, 18, or 24 hours or 1, 2, 3, 4, or 5 days after tumor or indications of cancer.

IX. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Adjuvanting Tumor Antigen Using a Polymeric Glyco-Adjuvant for the Induction of Anti-Tumor Immunity B. Summary Here the inventors demonstrate the creation of a therapeutic cancer vaccine using the p(Man-TLR7) glyco-polymer adjuvant. The vaccine material is composed of pManTLR7 conjugated to a tumor-binding moieties, optimizing the adjuvant as an in situ vaccine where the tumor itself is utilized as source of antigen to which immune responses are generated.

The inventors' engineered material seeks to prolong tumor retention of this strong adjuvant to increase APC activation within the tumor microenvironment and enhance T cell priming in the tumor draining lymph node. By increasing intratumoral APC activation, the inventors' vaccination will shift the tumor immune environment from suppressive to inflammatory. The cytokines produced by activated APCs will create a proinflammatory cytokine milieu which will improve T cell functionality within the tumor, as well as enhance T cell priming in the tumor draining lymph node. Extended duration and magnitude of inflammatory conditions to the draining lymph node more closely mimics natural infections and previous studies have reported prolonged antigen availability and delivery to immune cells improves vaccination efficacy through T follicular helper differentiation, appropriate T cell polarization, and humoral responses. Furthermore, prolonged inflammation with adjuvant and antigen has been shown to improve T cell memory differentiation and clonal expansion. Together, the inventors' vaccination strategy seeks to provides an optimal immunostimulatory context for the priming of naïve T cells against cancer antigens and improved functionality of T cells within the tumor microenvironment.

The inventors' vaccine consists of the p(ManTLR7) glyco-polymer, chemically linked to a tumor binding moiety which serves to augment its tissue localization and biodistribution upon intratumoral vaccination. These tumor cell binding moieties can be antibodies (or fAb, scFv, f(ab)2 forms of the original antibody) that are capable of recognizing tumor ligands, or cell surface proteins. The inventors' in situ vaccine can be made broadly applicable to a number of cancers by simply modifying the tumor-binding antibody to suit a given cancer. Specifically, p(ManTLR7) can be chemically conjugated to various antibodies which have been shown to bind ligands expressed or enriched on, the surface of malignant cells. The ligands that can be used as tumor-cell targets for antibody-p(ManTLR7) vaccination are diverse: tumor-specific antigens (i.e. TRP1), integrins, cluster of differentiation antigens (i.e. CD20 or CD19), growth factor receptors (i.e. HER2, EGFR), over-expressed immune inhibitory ligands (i.e. PD-L1), or even glycoproteins (i.e. MUC1). Principally, this antibody component serves as a cell surface anchor, slowing the adjuvant drainage through the tumor as the binds its ligands. In addition to this basic utility of modulating the adjuvant kinetics and biodistribution, each monoclonal antibody may contribute its own additional functional profile such as blocking immune inhibitory-ligand, initiating ADCC of tumor cells, increasing antigen uptake through Fc interactions, or blocking anti-phagocytic signals on tumor cells, which may bring additive effects to pManTLR7 immune activation or vaccine responses.

Here, the inventors performed preliminary testing of their antibody-pManTLR7 vaccination platform in the poorly immunogenic B16F10 murine model of melanoma, using pManTLR7 conjugated to a melanocyte-specific anti-TRP1 antibody. [delete text here] The inventors also explored the modularity of their vaccine to utilize other tumor-binding antibodies, and have created anti-CD47-pManTLR7, which will be used for further testing in a variety of additional tumor models, including B16F10 melanoma, and EMT6 triple negative breast cancer. Antibody conjugation of pManTLR7 prolonged intratumoral retention and treatment with tumor-binding antibody-pManTLR7 conjugates was able to slow tumor growth, prolong survival, and generate tumor-specific T cell responses.

In addition to use as a monotherapy, the inventors plan to evaluate efficacy of their antibody-pManTLR7 vaccine in combination with checkpoint blockade antibodies. Specifically, anti-PD1, anti-PD-L1, anti-CTLA4, or combinations of these antibodies may show therapeutic synergy with the inventors' antibody-pManTLR7 vaccine and increase its efficacy. Intratumoral T regulatory cells (Tregs) have been shown to suppress the activity of effector T cells through a variety of mechanisms so Treg depleting therapies such as anti-CTLA4 may help amplify the functionality of the effector T cells generated by the inventors' vaccine. Secretion of IFNγ by activated T cells has also been shown to increase PD-L1 expression by tumor cells, leading to dampened or dysfunctional T cell responses. It is possible that having an increased density of activated tumor infiltrating lymphocytes post vaccination may lead to PD-L1 upregulation. To combat this, blocking antibodies to PD-L1 or its receptor PD-1 may further enhance anti-tumor T cell responses. Although preliminary results described herein do not show synergistic efficacy, it is possible that alternative antibody combinations or single antibody dosing will be beneficial.

C. Design of p(Man-TLR7) Conjugates with Tumor-Binding Avidity

Figure 1E:
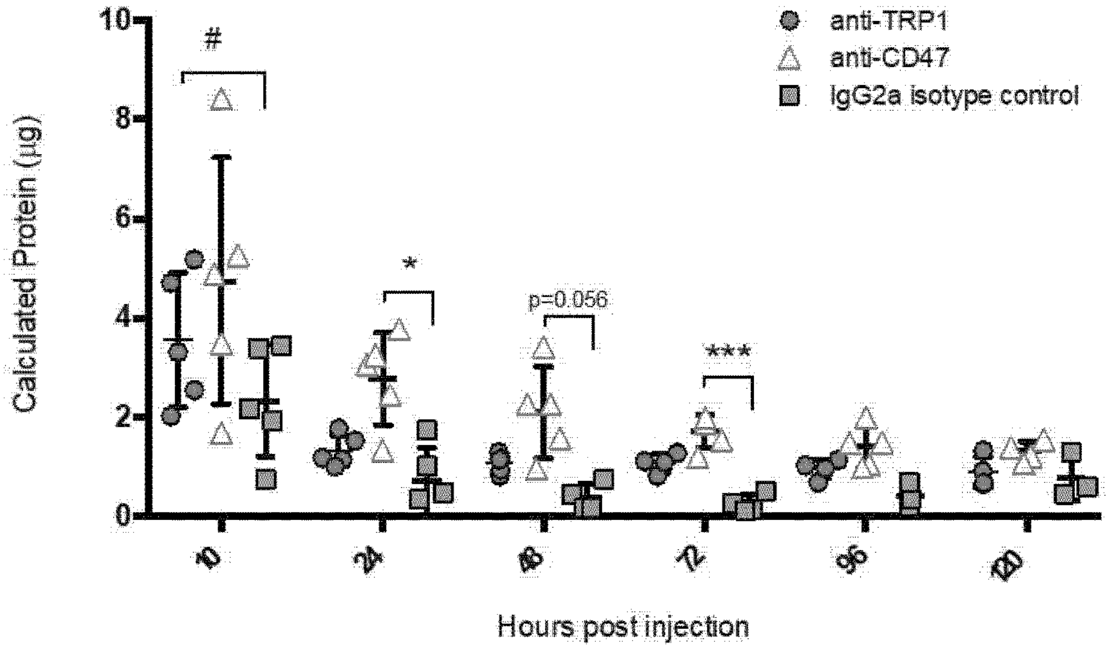
Figure 2C:
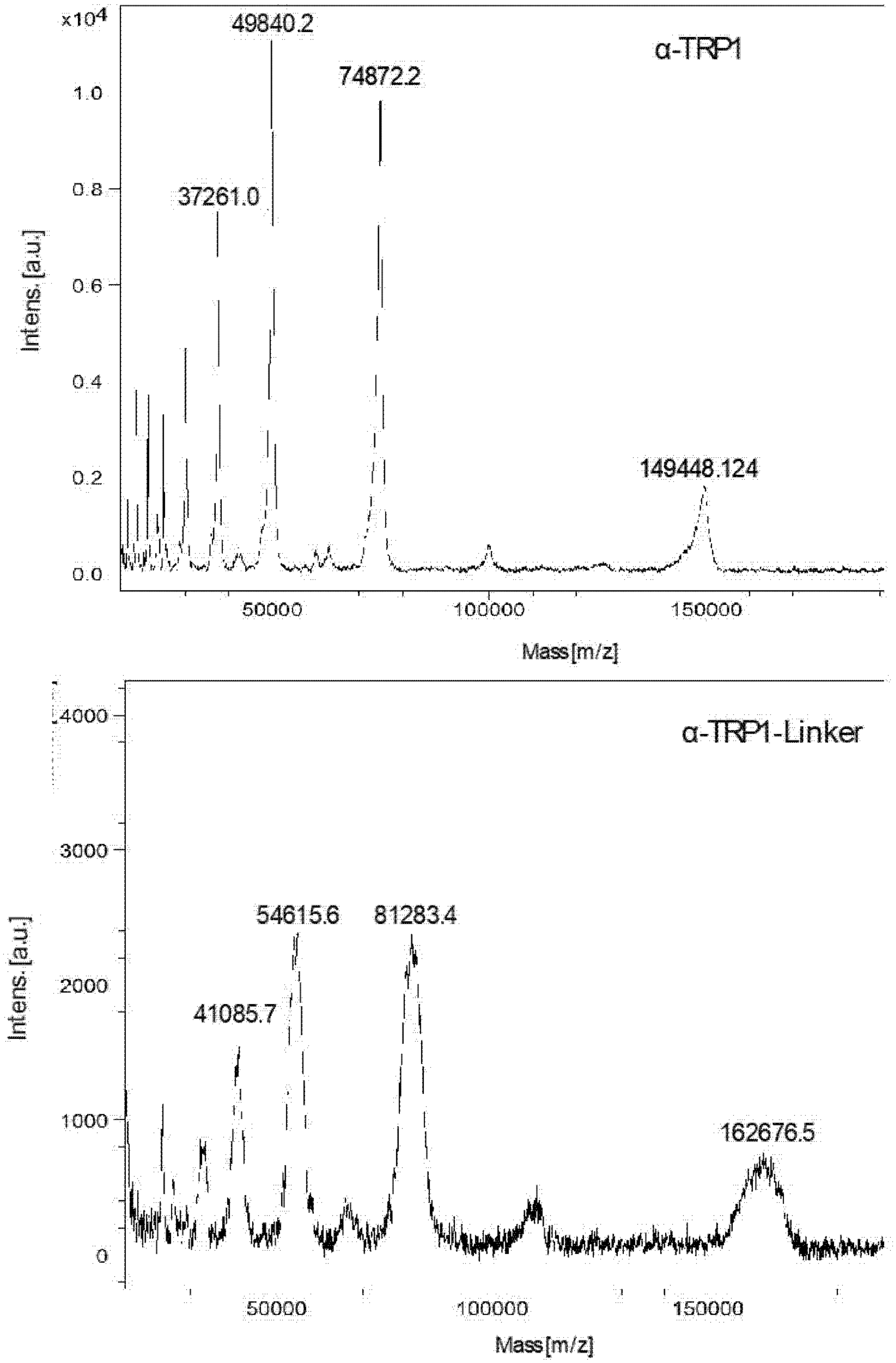
Figure 2D:
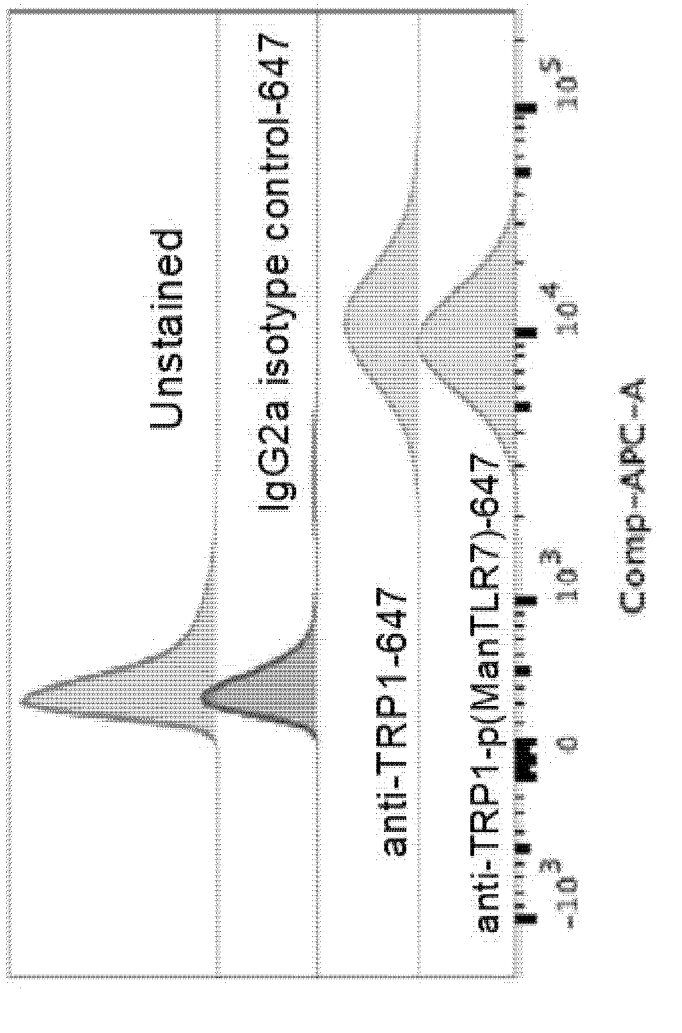
Figure 5D:
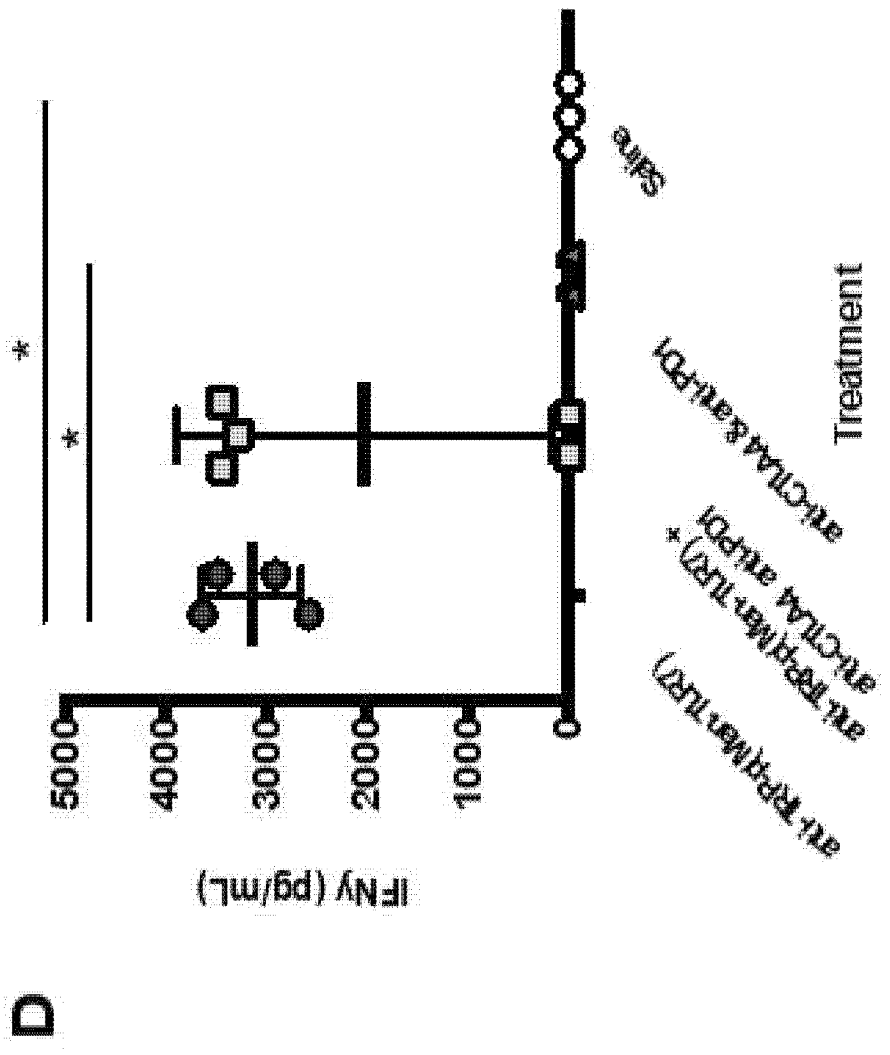

Antibodies specific to tumor-specific antigens, or to surface ligands enriched on tumor cells, were explored for their ability to anchor pManTLR7 within the tumor environment and increase local concentration of adjuvant. For the antibody component of their vaccine the inventors have thus far experimentally explored two tumor-binding antibodies: anti-CD47 and anti-TRP1. Anti-TRP1 (clone TA99) is a well characterized melanocyte-reactive antibody, recognizing tyrosinase-related protein 1, and is a cancer-specific antibody which is reactive to melanoma. The inventors confirmed the ability of anti-TRP1 antibody to bind to both B16F10 cells (FIG. 1A, D) and to tumor tissue from a genetically-engineered murine model of melanoma Tyr:Cre-ER+/LSL-BrafV600E/Ptenfl/fl (referred to as BP) (FIG. 1D). The inventors confirmed the ability of this antibody to bind within the tumor microenvironment in vivo and observed improved tumor retention over a control antibody with irrelevant specificity at 10 hr post injection (FIG. 1E). Increased retention at early timepoints may reduce systemic exposure of the adjuvant, and the potential for toxicity-related side effects. Importantly, when antibodies were chemically conjugated p(ManTLR7) the observed the addition of p(ManTLR7) did not interfere with the ability of anti-TRP1 to associate with B16F10 cells (FIG. 1A, FIG. 2D).

The inventors also adapted an anti-CD47 antibody for use in their vaccine as elevated CD47 expression has been observed for various malignancies, including lymphoma, bladder cancer, breast cancer and colon cancer. This antibody has been tested in the clinical treatment of cancer as blocking CD47 results in clearance of cells by macrophages and dendritic cells, resulting from the loss of inhibitory CD47 interactions with the prophagocytic SIRPα receptor on APCs. Flow cytometric analysis showed anti-CD47 is able to bind a variety of tumor models and subsequently, can be used to adapt the inventors' vaccine for the treatment of B16F10, EMT6, PyMT, and BP (FIG. 1A-D). Similarly to anti-TRP1, the inventors observed anti-CD47 antibody was able to retain within the tumor environment in an antigen-specific manner (FIG. 1E).

In summary, these data demonstrate the modularity of the inventors' antibody-p(ManTLR7) vaccine design and suggests that conjugation to various tumor-binding antibodies allows for adaptation to different tumor models, and through antigen-specific interactions, is able to prolong tumor retention.

D. Preparation of Antibody-pManTLR7 Conjugates

Using their previously published conjugation strategy and bifunctional BCN linker, the inventors were able to chemically link pManTLR7 to free amines on their tumor binding antibody. Through their conjugation strategy, the inventors estimate each antibody will have ~6 p(ManTLR7) polymers attached, based on MALDI analysis of antibody modified with their (BCN)-decorated linker (FIG. 2C). The inventors can estimate that quantitation of BCN-decorated linker conjugated to each antibody corresponds with final quantity of pManTLR per antibody as the cycloaddition reaction of the bicyclononyne moiety which reacts with the terminal azide of pManTLR7 polymer to produce full protein-linker-pManTLR7 conjugates at >95% yield. Production of antibody-p(ManTLR7) conjugates has been reproducible and allows for the consistent generation of vaccine materials with little variability. For each step of conjugation, the inventors observe consistent shifts in protein mobility that correspond with increasing overall kDa of their material following the reaction of antibody to linker and antibody-linker to pManTLR7 (FIG. 2B).

E. Antibody-p(Man-TLR7) Biodistribution and Accumulation in Tumor Microenvironment After confirming that pManTLR7 could be linked to tumor-binding antibodies (tAbs), the inventors next wanted to test if this linkage could modulate the biodistribution and kinetics of lymph node drainage of tAb-pManTLR7 as a vaccine. Importantly, conjugation of pManTLR7 to the anti-TRP1 or anti-CD47 antibodies showed retention within the B16F10 and EMT6 tumor environments post intratumoral administration. tAb-conjugates improved intratumoral halflife by 1.5-3× over non tumor-binding antibodies (FIG. 3B-D). Persistence of the anti-TRP1-p(ManTLR7) within the tumor for several days suggests that conjugation of p(ManTLR7) to a tumor-binding antibody can enhance agonist availability to APCs within the tumor microenvironment and prolong LN drainage. In comparison to a bolus dose that drains immediately to the lymph node, the inventors expect that pManTLR7 persistence among an abundance of tumor antigens would better simulate a natural infection and thus promote a more mature immune response. In addition to modulating biodistribution of their vaccine material, the inventors also predicted that antibody conjugation would simultaneously decrease systemic distribution of their agonist, thereby limiting exposure and subsequent toxicity to peripheral organs.

F. Therapeutic Efficacy

Having demonstrated the ability of antibody-p(ManTLR7) to bind and be retained intratumorally, the inventors then assessed the anti-tumor efficacy of their in-situ p(ManTLR7) vaccine in vivo. Treatment of B16F10 tumor-bearing mice with anti-TRP1-p(ManTLR7) resulted in significantly reduced tumor size as compared to vehicle-treated control animals (FIG. 4B) as well as improved overall survival (FIG. 4C). Additionally, slower tumor growth was observed in anti-Trp1-p(ManTLR7) vaccinated animals than for the unconjugated control, containing free p(ManTLR7) and anti-TRP1 antibody mixed at equimolar amounts to the full conjugate (FIG. 4B), suggesting that antibody linkage is important for the overall vaccine efficacy. Testing tumor-specific T cell responses via antigen restimulation with gp100 melanoma peptide corroborated the inventors' efficacy data. Significantly higher IFNγ secretion upon gp100 peptide restimulation was observed in the tumor-draining lymph node after treatment with anti-TRP1-p(ManTLR7) vaccine as compared to unconjugated pManTLR7 or saline-treated controls (FIG. 4D). Together this data shows anti-TRP1-pManTLR7 vaccination improves anti-tumor T cell responses and shows therapeutic benefit in this poorly immunogenic melanoma model.

To benchmark efficacy and safety profile of p(ManTLR7) against a current standard in the field, the inventors compared their vaccine against a molar equivalent dose of CpG, a TLR9 stimulating adjuvant. Here, anti-TRP1-pManTLR7 vaccination outperformed CpG in its ability to slow tumor growth (FIG. 4B). Because systemic dissemination of agonists is correlated with toxicity and inflammation-related side effects, the inventors quantified serum levels of IL-6 and IL-12p70 24 hours post vaccination as a readout of systemic APC activation via TLR stimulation. CpG-treated animals had detectably increased serum levels of IL-6 and active form of IL-12 cytokines as compared to saline-treated animals. However, vaccination with anti-TRP1-pManTLR7 showed no detectable response over saline-treated animals, suggesting the inventors' vaccine formulation provides reduced potential for off-target effects and overall tolerability in translation (FIG. 4 F, G).

A subset of patients that are refractory or unresponsive to immunotherapy antibodies show minimal T cell infiltration into the tumor. Here, tumors are characterized as "cold" tumor models, with T cells physically excluded to the stromal boundaries of the tumor or few T cells anywhere within the tumor environment. To test our vaccine efficacy in these settings, we tested our anti-CD47-pManTLR7 vaccine in a murine model of triple-negative breast cancer, EMT6 (FIG. 6A-B). Strikingly, we observed complete remission (CR) in 50% of immune-excluded EMT6 breast cancer tumors (FIG. 6C). Intratumorally retained anti-CD47-pManTLR7 showed improved tumor control over equimolar unconjugated mixtures of anti-CD47 antibody and pManTLR7, suggesting linkage of antibody and pManTLR7 is important for maximal therapeutic efficacy (anti-CD47-pManTLR, CR=4 of 8 vs. pManTLR+anti-CD47 mix, CR=1 of 8) (FIG. 6C).

To confirm our vaccination is capable of providing anti-tumor memory, we rechallenged EMT6 survivors 30 days after the primary tumor was no longer palpable with a second tumor on the abscopal mammary fat pad (FIG. 6A). Mice vaccinated with anti-CD47-pManTLR7 either with or without additional anti-PD1 and anti-CTLA4 treatment were resistant to this secondary tumor rechallenge whereas all naïve controls developed tumors (FIG. 6D), thus confirming anti-CD47-pManTLR7 vaccination provided durable, systemic antitumor memory.

We next wanted to assess what immune cell subsets were required for tAb-pManTLR therapeutic efficacy. To test this, we vaccinated mice after depleting macrophage or CD8 T cell subsets, using depletion antibodies and observed therapeutic efficacy via tumor growth. We observed vaccinated mice with macrophage depletion had similar therapeutic efficacy to vaccinated wildtype, non-depleted mice, suggesting macrophages are not required. However, when CD8 T cells were depleted from vaccinated mice, we saw no therapeutic efficacy of vaccination and tumors grew out similar to saline treated animals (FIG. 6E-F).

G. tAb-pManTLR7 Activates APCs and is Endocytosed by Multiple APC Subsets

To determine what antigen presenting cells internalize tAb-pManTLR7, we vaccinated EMT6 tumor-bearing mice with fluorescently labeled anti-CD47647-pManTLR7 and assessed APC subsets in the tumor, and tumor draining lymph node for uptake 24 hours later. In the lymph node, we observed tAb-pManTLR7 was present across all APC subsets and in more than half of the total cross-presenting DC subsets (FIG. 7A). We also observed that anti-CD47-pManTLR vaccination can increase frequencies of macrophages, inflammatory monocytes, $CD11c^+$ DCs and $CD103^+$ DC subsets (FIG. 7B-E). In the tumor 24 hrs post vaccination, we observed significantly more macrophage and cDC2 activation as measured by CD80 upregulation (FIG. 7F). In the lymph node, macrophages and $CD103^+$ DCs were significantly more activated in anti-CD47-pManTLR vaccinated animals than in unconjugated mix of anti-CD47+pManTLR7.

H. Combination with Checkpoint Antibody Therapy

To avoid immune-recognition and destruction, tumors co-opt a variety of mechanisms to suppress immune activity. Due to this, it is likely that the inventors' vaccination will achieve maximal therapeutic efficacy with checkpoint blockade therapy to overcome Treg or PD-L1 mediated immunosuppression. Because inflammation within the tumor microenvironment can increase surface expression of PD-L1 on tumor cells as well as recruit immunosuppressive T regulatory cells (Tregs), the inventors first wanted to explore synergy of their vaccination with a combination anti-PD1 and anti-CTLA4 antibody treatment.

Surprisingly, the inventors found treatment with anti-CTLA4 and anti-PD1 did not improve efficacy of their vaccination. Tumor growth (FIG. 4B), survival (FIG. 4C), and antigen-specific T cell responses (FIG. 4D) were not significantly different between anti-TRP1-pManTLR vaccination alone or in combination with checkpoint blockade antibodies. It is possible that dosing checkpoint blockade antibodies at the same day as vaccination is suboptimal and the inventors will assess additional dosing strategies. More time might be needed to first prime T cell responses via vaccination before checkpoint antibodies can be efficacious in relieving the T cell exhaustion by PD-1 blockade or Treg depletion. Alternatively, vaccination responses to anti-TRP1-pManTLR as an in situ vaccine alone might initiate a sufficiently inflamed tumor environment and further checkpoint blockade therapy might activate and exhaust non-tumor specific T cells, leading to reduced therapeutic efficacy.

I. Materials and Methods

1. Reagents

CpG-B 1826 was purchased from InvivoGen. Mouse anti-rat/mouseTRP1 (Clone TA99), rat anti-mouse CD47 (Clone MIAP301), and mouse IgG2a Isotype control (Clone C1.182) antibodies were purchased from BioXCell. Rat anti-mouse PD-L1 (Clone 10F.9G2, Bio X Cell) and hamster anti-mouse CTLA4 (clone 9H10, Bio X Cell) were used for checkpoint blockade antibody studies. Before administration to mice, endotoxin levels of all in-house prepared formulations were tested via HEK-Blue hTLR4 cells from InvivoGen. NHS Ester Sulfo-Cy7 dye (Lumiprobe), AlexaFluor 647 (Invivogen), or DyLight 800 NHS Ester (ThermoFisher) was used to label antibodies or antibody-pManTLR polymer for flow cytometry, immunofluorescence staining, and in vivo imaging analysis according to manufacturer's recommendations.

2. Production of Antibody-pManTLR7 Conjugates.

Antibody (at >5 mg/mL) was mixed with 10 to 30 molar equivalence of 2 kDa self-immolative PEG linker in 500 μL phosphate buffer (pH 7.7) and reacted for 2 hours mixing at RT. The reaction solution was then purified twice via Zeba spin desalting columns with 30 kDa cutoff to remove unreacted linker (Thermo Fisher). Successful linker conjugation was confirmed using gel electrophoresis and comparison to a size standard of the unmodified antibody. Antibody-linker construct in PBS (pH 7.4) was then reacted with 7 molar excess of p(Man-TLR7) polymer in an endotoxin-free Eppendorf tube for 2 hours, mixing, at RT. Excess p(Man-TLR7) polymer was removed using FPLC size-exclusion chromatography Superdex 200 column (GE). Fractions containing species with MW higher than 150 kDa (as assessed by gel electrophoresis) were then pooled and concentrated in 100 kDa Amicon centrifuge unit. TLR7 content was then determined via absorbance at 327 nm and antibody content was determined via gel electrophoresis, as described below.

3. Determination of TLR7 Content in p(ManTLR7) Conjugates.

To determine the concentration of TLR7 content in polymer and polymer-antibody conjugates, absorbance at 327 nm was measured. Known quantities of mTLR7 in saline was measured (n=3 independent samples) at 327 nm in several concentrations ranging from 8 mg/mL to 1 mg/mL to calculate a standard curve as previously published in Wilson et al. 2019. The determined standard curve [TLR7 (mg/mL) =1.9663*A327+0.0517] was then used to calculate TLR7 concentration in the final antibody-p(ManTLR7) conjugate.

4. Determination of Antibody Content in Antibody-pManTLR7 Conjugates.

SDS-PAGE was performed on 4-20% gradient gels (Bio-Rad) using antibody of a standard curve (2, 1.5, 1, and 0.5 mg/mL) and two dilutions of antibody-pManTLR7 conjugate samples were reduced with 10 mM dithiothreitol. Reducing conditions liberates any conjugated pManTLR7 allowing for the reduced antibody band intensity to be analyzed. Band density of reduced sample and antibody standard curve was then analyzed using ImageJ and antibody concentration of sample was calculated based on intensity, using standard curve generated.

5. Cell Culture

B16F10 cells (ATCC) and EMT6 (ATCC) were cultured in DMEM (Gibco) with 10% FBS (Thermo Fisher Scientific). MMTV-PyMT cells were obtained from spontaneously developed tumors in breast cancer transgenic mice (FVB-Tg(MMTV-PyMT)) after oncogene induction by viral promoter and cultured in vitro. All cell lines were tested to confirm a lack of murine pathogens via IMPACT I PCR testing (IDEXX Laboratories).

6. Animals.

All studies with animals were carried out in accordance to procedures approved by the Institutional Animal Care and Use Committee at the University of Chicago and housed in a specific pathogen-free environment at the University of Chicago. C57BL/6 female mice aged between 8-12 weeks were obtained from Charles River or The Jackson Laboratory. Tyr:Cre-ER+/LSL-BrafV600E/Ptenfl/fl mice, ages 8-16 weeks were provided by T. Gajewski (University of Chicago).

7. B16F10 and EMT6 Tumor Inoculation and Treatment.

$3\times10^5$-$5\times10^5$ B16F10 cells resuspended in 50 uL of PBS were inoculated intradermally on the left side of the back, or left flank, of each C57BL/6 mouse. $5\times10^5$ EMT6 cells resuspended in 50 uL of PBS were inoculated into the mammary fat pad. Tumors were measured every other day starting at day 5 after tumor inoculation with digital caliper. Volumes were calculated as volume V=length×width×height. Mice were sacrificed when tumor volume had reached over 1000 $mm^3$ Treatments were performed on days described in figures and in figure legends. tAb-pManTLR7 vaccination or control treatment was administered in described doses via intratumoral injection in a total volume of 35 μL. 100 μg of anti-PDL1 and 100 μg of anti-CTLA4 treatment was administered intraperitoneally. Prior to initial treatment, mice were randomized into treatment groups with each treatment group split up between cages to reduce cage effects.

8. Tyr:Cre-ER+/LSL-BrafV600E/Ptenfl/fl Melanoma Induction.

Tumors were induced on the back of 8-16 week old Tyr:Cre-ER+/LSL-BrafV600E/Ptenfl/fl mice. Fur was shaved prior to application of 50 μg 4-OH-tamoxifen (Sigma-Aldrich) at 10 mg/mL topically, as previously described (Spranger et al., 2015). Volume was computed as Volume=Surface*Z where surface is computed through ImageJ analysis and Z is depth measured by digital caliper. Mice were sacrificed when the tumor volume reached 1000 mm3.

9. Tissue Processing.

Spleens, lymph nodes, and tumors were collected and kept on ice in IMDM until processing. Tumors were digested in 1 mL DMEM supplemented with 2% FBS, collagenase D (2 mg/mL; Gibco), DNase I (40 μg/mL; Roche) for 45 min at 37° C. mixing. Lymph nodes were mechanically disrupted and digested at 37° C. for 45 min in collagenase D. Digested tumors or lymph nodes, or spleens were processed into single-cell suspensions via mechanical disruption and passaged through a sterile 70 um screen. Red blood cells in tumor cells and splenocytes were lysed by resuspending in ACK lysing buffer (Quality Biological) and incubating for 5 min at room temperature. Lysis reaction was quenched using 15 mL DMEM+10% FBS. The single cell suspensions for tumor, lymph nodes, or splenocytes were then washed once with PBS or DMEM before resuspension in DMEM. These single cell suspensions were then used in restimulation experiments or stained for flow cytometry analysis.

10. Ex Vivo T Cell Stimulation.

Single-cell suspensions from spleen or lymph nodes were prepared as described above. 5×105 cells from spleen or lymph node were restimulated in vitro with the addition of 1.0 μg/mL gp10025-33 CD8-dominant peptide (EGSRNQDWL) epitope (SEQ ID NO: 29) (Genscript) for 72 hrs. Following restimulation, cells were spun down and supernatant was collected for the measurement of secreted cytokines by ELISA. Cytokine ELISAs were performed using the Ready-Set-Go Kit (eBioscience), according to manufacturer's protocol. All cell restimulations were done in duplicate for each biological replicate with an unstimulated (no peptide added) control well to determine background levels of non-specific activation.

11. Immunofluorescence of Tumor Tissue Sections.

Tumors were inoculated as described above for B16F10 and Tyr:Cre-ER+/LSL-BrafV600E/Ptenfl/fl melanoma models. Harvested tumors were fixed with 4% paraformaldehyde (PFA) and flash frozen embedded in OCT medium and stored at −20° C. until sectioning. Serial sections of the tumor (10 um thick) were cut starting from the side until middle of tumor was reached. Slide mounted sections were then blocked with 10% casein solution, then with 20% rat serum prior to incubation with primary antibodies: biotinylated anti-collagen IV Ab (Jackson ImmunoResearch), rat anti-mouse CD47 (Bio X Cell), and Sulfo-Cy7 (Lumican)

labelled mouse anti-mouse TRP1 Ab for 2 hours at room temperature, followed by staining with Alexa Fluor 750-conjugated streptavadin (BioLegend), and goat anti-rat-647 (Invitrogen) (1:400 final concentration for all) for 1 hour. Slides were mounted with ProLong gold antifade medium with DAPI (Invitrogen) before imaging on Olympus confocal microscope. Images were taken with 20× oil lens, composite images and scale bar overlays were made using ImageJ.

12. Serum Cytokine Concentration Analysis.

B16F10 melanoma tumors were inoculated using 3×105 cells and vaccinated every 4 days starting on day 5 post inoculation with 30 μg of TLR7 as anti-TRP1-pManTLR7 and molar equivalent dose of controls CpG, anti-TRP1 and free pManTLR7 polymer, or saline. 24 hours after the 2nd vaccination, 200 μL of blood was collected in heparin-coated tubes and serum was separated by centrifugation and stored at −20° C. Sera was assessed for IL-6 and IL-12p70 using ELISA, Ready-Set-Go Kit (eBioscience), following the manufacturer's instructions.

13. Flow Cytometric Analysis of Tumor-Binding Antibodies.

Flow cytometry analysis was done using a BD FACS LSR Fortessa flow cytometer (BD Biosciences) and analyzed using FlowJo software (Tree Star). For staining, cells were washed twice with PBS, then stained in PBS+0.2% FBS containing Cy7-labeled anti-TRP1, anti-CD47, mouse IgG2a isotype control antibodies at 30 μg/mL or with 5 μg/mL antibody as antibody-pManTLR7 conjugate. Cells were stained for 20 min on ice. Stained cells were washed twice and resuspended in PBS+2% FBS for analysis.

14. Tumor Retention Studies.

C57BL/6 mice B16F10 tumor bearing mice (80 mm3) were injected intratumorally with anti-TRP1-pManTLR7800, anti-TRP1-750, anti-CD47-750, mouse IgG2a isotype control-750, or PBS. At 10 hr. post injection and at every 24 hr timepoint, mice were imaged, and fluorescence was measured via IVIS Spectrum in vivo imaging system (Perkin Elmer). Images were processed and quantified via ROI selection of tumor area using Living Imaging 4.5.5 software (Perkin Elmer). To normalize any differences between fluorescent labelling of anti-TRP1, anti-CD47 and isotype control antibodies a standard curve was determined plating various concentrations of labeled antibody (5 μg, 2.5 μg, 1 μg, 0.5 μg) in duplicate. The calculated standard curve for each antibody was then used to calculate tumor protein from fluorescence reading at each timepoint. For experiments in which no comparisons between materials were made, fluorescent signal was reported directly as radiant efficiency.

15. Matrix-Assisted Laser Desorption/Ionization-Time-of-Flight Mass Spectrometry.

First, saturated solution of the matrix, α-cyano-4-hydroxycinnamic acid (Sigma-Aldrich), was prepared in 50:50 acetonitrile:1% TFA in water as a solvent. The analyte in PBS (5 μl, 0.1 mg/ml) and the matrix solution (25 μl) were then mixed and 1 μl of that mixture was deposited on the MTP 384 ground steel target plate. The drop was allowed to dry in the nitrogen gas flow which resulted in the formation of uniform sample/matrix co-precipitate. All samples were analyzed using high mass linear positive mode method with 2500 laser shots at the laser intensity of 75%.

16. Tissue Processing.

Spleens, lymph nodes, and tumors were collected and kept on ice, in IMDM until processing. Tumors were digested in 1 mL DMEM supplemented with 2% FBS, collagenase D (2 mg/mL; Gibco), DNase I (40 μg/mL; Roche) for 45 min at 37° C. mixing. Lymph nodes were mechanically disrupted and digested at 37° C. for 45 min in collagenase D. Digested tumors or lymph nodes, or spleens were processed into single-cell suspensions via mechanical disruption and passage through a sterile 70 um screen. Red blood cells in tumor cells and splenocytes were lysed by resuspending in ACK lysing buffer (Quality Biological) and incubating for 5 min at room temperature. Lysis reaction was quenched using 15 mL DMEM+10% FBS. The single cell suspensions for tumor, lymph nodes, or splenocytes were then washed once with PBS or DMEM and resuspended in DMEM. These single cell suspensions were then used in restimulation experiments or directly stained for flow cytometry analysis.

17. Flow Cytometric Analysis on Tumors and Tumor-Draining Lymph Nodes

For staining, cells were washed with PBS and stained for 15 min on ice with an eFluor 455UV (eBioscience) fixable viability dye. The cells were washed twice with PBS then stained in PBS+2% fetal bovine serum (FBS) containing the antibody cocktail (BD Biosciences and Biolegend) for 20 min on ice. Stained cells were washed twice with PBS+2% FBS, and the cells were then fixed for 15 min in PBS+2% paraformaldehyde. Cells were washed twice and resuspended in PBS+2% FB S. If required, intracellular staining of FoxP3 was carried out using the eBioscience Foxp3 Transcription Factor Staining Buffer Set, per the manufacturer's instructions. Flow cytometry measurements were performed using a LSR Fortessa flow cytometer (BD Biosciences), and data were analyzed using FlowJo software (Tree Star).

18. Cellular Depletion Experiments

CD8 T cell subsets were depleted by administration of 400 μg anti-CD8a (clone 2.43, BioXCell) depleting antibody i.p. twice per week. Macrophages were depleted by administration of 300 μg of anti-CSF1R (clone AFS98, BioXcell) depletion antibody every other day. Control group (vaccination only) received 300 μg of IgG2a isotype control antibody every other day. Depletion antibodies were administered through the entire vaccination treatment window. Cellular depletions were confirmed via flow cytometry analysis of tumor, spleen, or LN populations.

19. Data Analysis.

Statistical analysis and graphs were generated using Prism software (V7; GraphPad Software). For single comparisons, a two-tailed t test was used. Data were also analyzed using one-way ANOVA with Bonferroni post hoc test. Differences in survival curves were analyzed using log-rank (Mantel Cox) test. Group size (n) used to calculate significance is indicated in figure legend. Significance is reported with respect to vehicle control group, unless stated otherwise in figure legend. For showing statistical significance *P≤0.001; P≤0.01; *P≤0.05, unless otherwise stated.

J. References

The following references and the publications referred to throughout the specification, to the extent that they provide exemplary procedural or other details supplementary to those set forth herein, are specifically incorporated herein by reference.

1. Buchbinder, E. & Stephen Hodi, F. Cytotoxic T lymphocyte antigen-4 and immune checkpoint blockade. Journal of Clinical Investigation (2015). doi:10.1172/JCI80012
2. Appay, V., Douek, D. C. & Price, D. A. CD8+ T cell efficacy in vaccination and disease. Nat. Med. 14, 623-628 (2008).

3. Koup, R. A. & Douek, D. C. Vaccine design for CD8 T lymphocyte responses. Cold Spring Harb. Perspect. Med. 1, (2011).
4. Banchereau, J. & Palucka, K. Immunotherapy: Cancer vaccines on the move. Nat. Rev. Clin. Oncol. (2017). doi:10.1038/nrclinonc.2017.149
5. Sato, E. et al. Intraepithelial CD8+ tumor-infiltrating lymphocytes and a high CD8+/regulatory T cell ratio are associated with favorable prognosis in ovarian cancer. Proc. Natl. Acad. Sci. U.S.A 102, 18538-43 (2005).
6. Yee, C. et al. Adoptive T cell therapy using antigen-specific CD8+ T cell clones for the treatment of patients with metastatic melanoma: in vivo persistence, migration, and antitumor effect of transferred T cells. Proc. Natl. Acad. Sci. U.S.A 99, 16168-73 (2002).
7. van Duikeren, S. et al. Vaccine-induced effector-memory CD8+ T cell responses predict therapeutic efficacy against tumors. J. Immunol. 189, 3397-403 (2012).
8. Ossendorp, F. et al. against Tumors Cell Responses Predict Therapeutic Efficacy T+ Vaccine-Induced Effector-Memory CD8. J Immunol Ref 189, 3397-3403 (2018).
9. Wilson, D. S. et al. Antigens reversibly conjugated to a polymeric glyco-adjuvant induce protective humoral and cellular immunity. Nat. Mater. (2019). doi:10.1038/s41563-018-0256-5
10. Kerrigan, A. M. & Brown, G. D. C-type lectins and phagocytosis. Immunobiology 214, 562-575 (2009).
11. Burgdorf, S., Kautz, A., Bohnert, V., Knolle, P. A. & Kurts, C. Distinct Pathways of Antigen Uptake and Intracellular Routing in CD4 and CD8 T Cell Activation. Science (80-.). 316, 612-616 (2007).
12. Weck, M. M. et al. TLR ligands differentially affect uptake and presentation of cellular antigens. Blood 109, 3890-3894 (2007).
13. Oh, J. Z., Kurche, J. S., Burchill, M. A. & Kedl, R. M. TLR7 enables cross-presentation by multiple dendritic cell subsets through a type I IFN-dependent pathway. Blood (2011). doi:10.1182/blood-2011-04-348839
14. Bachmann, M. F. & Jennings, G. T. Vaccine delivery: a matter of size, geometry, kinetics and molecular patterns. Nat. Rev. Immunol. 10, 787-796 (2010).
15. Tritto, E., Mosca, F. & De Gregorio, E. Mechanism of action of licensed vaccine adjuvants. Vaccine (2009). doi:10.1016/j.vaccine.2009.01.084
16. Moyer, T. J., Zmolek, A. C. & Irvine, D. J. Beyond antigens and adjuvants: Formulating future vaccines. Journal of Clinical Investigation (2016). doi:10.1172/JCI81083
17. Shaulov, A. & Murali-Krishna, K. CD8 T Cell Expansion and Memory Differentiation Are Facilitated by Simultaneous and Sustained Exposure to Antigenic and Inflammatory Milieu. J. Immunol. (2014). doi:10.4049/jimmunol.180.2.1131
18. Sakaguchi, S., Yamaguchi, T., Nomura, T. & Ono, M. Regulatory T Cells and Immune Tolerance. Cell 133, 775-787 (2008).
19. Wing, K. et al. CTLA-4 Control over Foxp3+ Regulatory T Cell Function. Science (80-.). 322, 271-275 (2008).
20. Abiko, K. et al. IFN-γ from lymphocytes induces PD-L1 expression and promotes progression of ovarian cancer. Br. J. Cancer (2015). doi:10.1038/bjc.2015.101
21. Peng, J. et al. Chemotherapy induces programmed cell death-ligand 1 overexpression via the nuclear factor-κBto foster an immunosuppressive tumor microenvironment in Ovarian Cancer. Cancer Res. (2015). doi:10.1158/0008-5472.CAN-14-3098
22. Thomson, T. M., Mattes, M. J., Roux, L., Old, L. J. & Lloyd, K. O. Pigmentation-associated glycoprotein of human melanomas and melanocytes: Definition with a mouse monoclonal antibody. J. Invest. Dermatol. 85, 169-174 (1985).
23. Takechi, Y., Hara, I., Naftzger, C., Xu, Y. & Houghton, A. N. A melanosomal membrane protein is a cell surface target for melanoma therapy. Clin. Cancer Res. 2, 1837-1842 (1996).
24. Bevaart, L. et al. The high-affinity IgG receptor, FcγRI, plays a central role in antibody therapy of experimental melanoma. Cancer Res. 66, 1261-1264 (2006).
25. Majeti, R. et al. CD47 Is an Adverse Prognostic Factor and Therapeutic Antibody Target on Human Acute Myeloid Leukemia Stem Cells. Cell (2009). doi:10.1016/j.cell.2009.05.045
26. Li, Y. et al. Overexpression of CD47 predicts poor prognosis and promotes cancer cell invasion in high-grade serous ovarian carcinoma. Am. J. Transl. Res. (2017).
27. Zhao, H.-J. et al. Prognostic significance of CD47 in human malignancies: a systematic review and meta-analysis. Transl. Cancer Res. 7, 609-621 (2018).
28. Tong, B. & Wang, M. CD47 is a novel potent immunotherapy target in human malignancies: Current studies and future promises. Future Oncology (2018). doi:10.2217/fon-2018-0035
29. Contreras-Trujillo, H. et al. Anti-CD47 antibody-mediated phagocytosis of cancer by macrophages primes an effective antitumor T-cell response. Proc. Natl. Acad. Sci. (2013). doi:10.1073/pnas.1305569110
30. Liu, X. et al. CD47 blockade triggers T cell-mediated destruction of immunogenic tumors. Nat. Med. (2015). doi:10.1038/nm.3931
31. Nielsen, M. C. et al. Cancer vaccine formulation dictates synergy with CTLA-4 and PD-L1 checkpoint blockade therapy. J. Clin. Invest. 128, 1338-1354 (2018).

Example 2—Targeting Polymeric Glyco-Adjuvants to the Tumor Stroma for the Induction of Anti-Tumor Immunity

A. Summary

Here the inventors report the creation of a therapeutic cancer vaccine using the p(Man-TLR7) glyco-polymer adjuvant. The inventors' vaccine material is composed of p(Man-TLR7) conjugated to tumor stroma-binding moieties, optimizing the adjuvant as a targeted vaccine where the tumor itself is utilized as source of antigen to which immune responses are generated.

The inventors' engineered material seeks to localize this strong adjuvant to the tumor microenvironment and prolong tumor retention in order to increase APC activation within the tumor microenvironment and enhance T cell priming in the tumor draining lymph node. By increasing intratumoral APC activation, the vaccination will shift the tumor immune environment from suppressive to inflammatory. The cytokines produced by activated APCs will create a proinflammatory cytokine milieu which will improve T cell functionality within the tumor, as well as enhance T cell priming in the tumor draining lymph node. Extended duration and magnitude of inflammatory conditions in the draining lymph node more closely mimics natural infections. This vaccination strategy seeks to provide an optimal immunostimulatory context for the priming of naïve T cells against cancer antigens and improved functionality of T cells within the tumor microenvironment.

The inventors' vaccine comprises the p(Man-TLR7) glyco-polymer, chemically linked to a tumor stroma-binding moiety which serves to augment its tissue localization and biodistribution upon intravenous or intratumoral vaccination. These tumor cell binding moieties can be antibodies (or Fab, scFv, F(ab')2 forms of the original antibody) that are capable of recognizing tumor stroma extracellular matrix components, or other tumor stroma components. The inventors' in situ vaccine can be made broadly applicable to a number of cancers by simply modifying the tumor stroma-binding antibody to suit a given cancer. Specifically, p(Man-TLR7) can be chemically conjugated to various antibodies which have been shown to bind ligands expressed, uniquely exposed, or enriched within the tumor stroma. The ligands that can be used as tumor stroma targets for antibody-p (Man-TLR7) vaccination are diverse: fibronectin (or alternatively spliced domains of fibronectin, such as the extra domain A), collagens, tenascins, periostins, syndecans, other proteins or proteoglycans, or even tumor stroma cell-specific antigens (i.e. FAP). Principally, this antibody component serves as a means to localize the inventors' adjuvant to the tumor and then slow adjuvant drainage through the tumor as the antibody binds its ligands in the tumor microenvironment. In addition to this basic utility of modulating the adjuvant kinetics and biodistribution, each monoclonal antibody may contribute its own additional functional profile such as blocking immune inhibitory-ligand, initiating ADCC of tumor cells, increasing antigen uptake through Fc interactions, or blocking anti-phagocytic signals on tumor cells, which may bring additive effects to p(Man-TLR7) immune activation or vaccine responses.

Here, the inventors performed preliminary testing of their antibody-p(Man-TLR7) vaccination platform in the poorly immunogenic B16F10 murine model of melanoma, using p(Man-TLR7) conjugated to an antigen binding fragment (Fab) of an antibody specific to the extra domain A (EDA) of fibronectin, which has been found to be over-expressed in many cancers. Treatment of tumor-bearing mice with anti-EDA Fab-p(Man-TLR7) was able to slow tumor growth and prolong survival.

In addition to use as a monotherapy, the inventors plan to evaluate efficacy of their antibody-p(Man-TLR7) vaccine in combination with checkpoint blockade antibodies. Specifically, anti-PD-1, anti-PD-L1, anti-CTLA-4, or combinations of these antibodies may show therapeutic synergy with the inventors' antibody-p(Man-TLR7) vaccine and increase its efficacy. Intratumoral T regulatory cells (Tregs) have been shown to suppress the activity of effector T cells through a variety of mechanisms, so Treg depleting therapies such as anti-CTLA-4 may help amplify the functionality of the effector T cells generated by the vaccine. It is possible that having an increased density of activated tumor infiltrating lymphocytes post vaccination may lead to PD-L1 upregulation. Therefore, it is possible that delivering an adjuvant to the tumor in the presence of immune checkpoint inhibitors will provide a therapeutic effect. Preliminary results described herein show synergistic efficacy when the inventors' antibody-p(Man-TLR7) vaccination was used in combination with anti-PD-1 and anti-CTLA-4 antibodies. This work demonstrates the efficacy of the vaccination strategy and also provides evidence that alternative antibody combinations or single antibody dosing may also provide synergistic efficacy in cancer treatments.

B. Design of p(Man-TLR7) Conjugates with Tumor Localization and Retention

To begin to assess the antibody-p(Man-TLR7) platform, an antibody specific to tumor stroma components was explored for its ability to localize p(Man-TLR7) to the tumor microenvironment and increase local concentration of adjuvant. For this antibody component of their vaccine, the inventors decided to focus on antibodies targeting the extra-domain A (EDA) of fibronectin. For their purposes, the inventors decided to use the antigen binding fragment (Fab) antibody format. The inventors produced the anti-EDA Fab recombinantly (FIG. 8A-B) and then confirmed binding to EDA (FIG. 8C). The inventors also confirmed that EDA is expressed in B16F10 tumors, as they planned to use this model for assessing the in vivo anti-tumor efficacy of their anti-EDA Fab-p(Man-TLR7) conjugates (FIG. 8D).

C. Preparation of Anti-EDA Fab-p(Man-TLR7) Conjugates

Using their previously published conjugation strategy and bifunctional bicyclononyne (BCN) linker, the inventors were able to chemically link p(Man-TLR7) to free amines on their EDA-binding Fab (FIG. 9A). The Fab-p(Man-TLR7) conjugates used herein will have an estimated 1:5 molar ratio of Fab:p(Man-TLR7) polymer based on the initial molar concentrations of the Fab and BCN that were used. The inventors can estimate that quantitation of BCN-decorated linker conjugated to each antibody corresponds with final quantity of p(Man-TLR7) per antibody, as the cycloaddition reaction of the BCN moiety with the terminal azide of the p(Man-TLR7) polymer in order to produce full protein-linker-p(Man-TLR7) conjugates occurs at >95% yield. Production of Fab-p(ManTLR7) conjugates has been reproducible and allows for the consistent generation of vaccine materials with little variability. For each step of conjugation, the inventors observe consistent shifts in protein mobility that correspond with increasing overall kDa of their material following the reaction of antibody to linker and antibody-linker to p(Man-TLR7) (FIG. 9B).

D. Therapeutic Efficacy

Once the inventors had prepared the Fab-p(Man-TLR7) conjugates, they then assessed the anti-tumor efficacy in vivo (FIG. 10A). The inventors decided to assess the anti-tumor efficacy of their vaccination alone and in combination with checkpoint antibody therapy. To avoid immune-recognition and destruction, tumors co-opt a variety of mechanisms to suppress immune activity. Due to this, the inventors hypothesized that their vaccination would achieve maximal therapeutic efficacy with checkpoint blockade therapy to overcome Treg or PD-L1 mediated immunosuppression. Because inflammation within the tumor microenvironment can increase surface expression of PD-L1 on tumor cells as well as recruit immunosuppressive T regulatory cells (Tregs), the inventors first wanted to explore synergy of their vaccination with a combination of anti-PD-1 and anti-CTLA4 antibody treatment.

Treatment of B16F10 tumor-bearing mice with intravenously (i.v.)-delivered human anti-EDA Fab-p(Man-TLR7) resulted in slightly reduced tumor size compared to untreated control animals (FIG. 10B). The inventors observed an improved anti-tumor efficacy and significantly improved overall survival when they combined their Fab-p (Man-TLR7) vaccination with anti-PD-1 and anti-CTLA-4 antibodies (FIG. 10B-C). This data shows that anti-EDA Fab-p(Man-TLR7) vaccination in combination with checkpoint antibody therapy provides therapeutic benefit in this treatment of a poorly immunogenic melanoma model.

In order to begin to assess the immunological mechanisms underlying the anti-tumor efficacy observed, the inventors next looked at the cell types present within the tumor after vaccination with i.v.-delivered human anti-EDA Fab-p(Man-TLR7) (FIG. 11A). Similar to previous results, vaccination with Fab-p(Man-TLR7) in combination with anti-PD-1 and anti-CTLA-4 antibodies significantly slowed B16F10 tumor growth (FIG. 11B). Upon sacrificing the mice, the inventors did not observe any significant differences in numbers of $CD8^+$ T cells in the tumor (FIG. 11C). However, the inventors did see a significant decrease in $CD4^+$ T cells and $CD4^+$ $CD25^+$ $FoxP3^+$ regulatory T cells in the tumor (FIG. 11D-E). Additionally, a significant increase in NK cells in the tumor was observed (FIG. 11F), as was a decrease in macrophages within the tumor (FIG. 11G). These results point towards these cell types playing a role in the observed anti-tumor efficacy.

Because of immunogenicity concerns associated with injecting a human protein (the anti-EDA Fab) along with a strong adjuvant into mice, the inventors subsequently moved to using a chimeric murinized version of the Fab, comprised of murine constant regions and human variable regions. Upon vaccination of B16F10 tumor bearing mice with the murinized anti-EDA Fab conjugated to p(Man-TLR7), delivered i.v. (FIG. 12A), a significant slowing of tumor growth (FIG. 12B) and significantly improved survival (FIG. 12C) were observed when the vaccine was combined with anti-PD-1 and anti-CTLA-4 antibodies, similar to the results observed with the human Fab-p(Man-TLR7) vaccine.

Finally, the inventors assessed two different administration routes for the vaccine: i.v. administration and intratumoral (i.t.) administration (FIG. 13A). A significant slowing of tumor growth (FIG. 13B) and improved survival (FIG. 13C) were observed with both i.v. and i.t. administration of the murinized anti-EDA Fab-p(Man-TLR7) in combination with anti-PD-1 and anti-CTLA-4 antibodies. However, i.t. administration of the vaccine resulted in improved anti-tumor efficacy (FIG. 13B-C) and a trend towards fewer anti-Fab antibodies (FIG. 13D) as compared to i.v. administration. Importantly, systemic levels of the cytokines IL-6, IL-12p70, TNFα, and IFNγ (FIG. 13E-H) were not significantly increased in the serum after vaccination via either administration route, pointing towards the safety of the inventors' vaccine. This data indicates that anti-EDA Fab-p(Man-TLR7) in combination with checkpoint antibody therapy is an effective treatment for the poorly immunogenic B16F10 murine melanoma model with minimal systemic toxicity.

E. Materials and Methods

1. Production and Purification of Anti-EDA Fab Protein

The sequences encoding the human or murinized anti-EDA Fab were synthesized and subcloned into the mammalian expression vector pSecTag A. The murinized anti-EDA Fab is a chimeric Fab composed of murine constant regions and human variable regions. Suspension-adapted HEK-293F cells were routinely maintained in serum-free FreeStyle 293 Expression Medium (Gibco). On the day of transfection, cells were inoculated into fresh medium at a density of $1\times10^6$ cells/mL, 2 μg/mL plasmid DNA, 2 μg/ml linear 25 kDa polyethylenimine (Polysciences), and OptiPRO SFM medium (4% final concentration, Thermo Fisher) were sequentially added. The culture flask was agitated by orbital shaking at 135 rpm at 37° C. in the presence of 5% $CO_2$. 7 days after transfection, the cell culture medium was collected by centrifugation and filtered through a 0.22 μm filter. Culture medium was loaded into a HiTrap Mab Select 5 mL column (GE Healthcare), using an ÄKTA pure 25 (GE Healthcare). After washing the column with PBS, protein was eluted with 0.1 M sodium citrate (pH 3.0). All purification steps were carried out at 4° C. The expression of the anti-EDA Fab was determined by western blotting using anti-human IgG antibody (Jackson ImmunoResearch), and the proteins were verified as >90% pure by SDS-PAGE (performed on 4-20% gradient gels (Bio-Rad)).

2. Production and Purification of EDA Protein

EDA was recombinantly expressed and purified as described previously (Julier et al. 2015).

3. Sodium Dodecyl Sulfate Polyacrylamide Gel Electrophoresis (SDS-PAGE)

SDS-PAGE was performed on 4-20% gradient gels (Bio-Rad). Samples run under reducing conditions were incubated for 5 min at 95° C. with 10 mM diothiothreitol. After electrophoresis, gels were stained with SimplyBlue SafeStain (Thermo Fisher Scientific) according to the manufacturer's instructions. Gel images were acquired with the ChemiDoc XRS+ system (Bio-Rad).

4. Western Blotting

SDS-PAGE gels were run as described above. Subsequently, proteins were transferred onto a PVDF membrane (Millipore Sigma) for 1 hour at 80 V. The membrane was blocked overnight at 4° C. in Tris-Buffered Saline with 0.1% Tween 20 (TBS-T) with 5% skim milk. The membrane was then washed 5 times with TBS-T, followed by incubation for 1 h at room temperature with horseradish peroxidase (HRP)-conjugated antibody against human IgG (Jackson ImmunoResearch) in 2% skim milk. The membrane was washed again 5 times with TBS-T. Clarity Western ECL Substrate (BioRad) was then added to the membrane, per manufacturer instructions, and the Western blot was imaged with the ChemiDoc XRS+ system (Bio-Rad).

5. Binding of Anti-EDA Fab to EDA

Affinity measurements were performed using enzyme-linked immunosorbent assay (ELISA). 96-well ELISA plates (Nunc MaxiSorp flat-bottom plates, Thermo Fisher) were coated with 10 μg/mL EDA (produced in the inventors' lab) in PBS overnight at 4° C. The following day, plates were washed in PBS with 0.05% Tween 20 (PBS-T) and then blocked with 1× casein (Sigma) diluted in PBS for 1 hour at room temperature. Then, wells were washed with PBS-T and further incubated with various dilutions of anti-EDA Fab for 2 hours at room temperature. After 6 washes with PBS-T, wells were incubated for 1 hour at room temperature with horseradish peroxidase (HRP)-conjugated antibody against human IgG (Jackson ImmunoResearch). After 6 washes with PBS-T, bound anti-EDA Fab was detected with tetramethylbenzidine substrate by measurement of the absorbance at 450 nm with subtraction of the measurement at 570 nm. The apparent dissociation constant ($K_d$) values were obtained by nonlinear regression analysis in Prism software (v7, GraphPad Software) assuming one-site specific binding.

6. Reagents for In Vivo Studies

Rat anti-mouse PD-1 (Clone 29F.1A12, Bio X Cell) and hamster anti-mouse CTLA-4 (clone 9H10, Bio X Cell) were used for checkpoint blockade antibody studies. Before administration to mice, endotoxin levels of all formulations were tested via HEK-Blue mTLR4 cells from InvivoGen. A detailed explanation of the synthesis of the p(Man-TLR7) polymer and intermediates is provided in the inventors' previous publication (Wilson et al. 2019).

7. Production of Fab-p(Man-TLR7) Conjugates

Fab (at >3 mg/mL) was mixed with 5 (or up to 30) molar equivalents of 2 kDa self-immolative PEG linker in 500 μL phosphate buffer (pH 7.7) and reacted for 2 hours mixing at RT. The reaction solution was then purified twice via Zeba spin desalting columns with 30 kDa cutoff to remove unreacted linker (Thermo Fisher). Successful linker conjugation was confirmed using gel electrophoresis and comparison to a size standard of the unmodified Fab. Fab-linker construct in PBS (pH 7.4) was then reacted with 7 molar excess of p(Man-TLR7) polymer in an endotoxin-free Eppendorf tube for 2 hours, mixing, at RT. Excess p(Man-TLR7) polymer was removed using FPLC size-exclusion chromatography Superdex 200 column (GE). Fractions containing species with MW higher than 50 kDa (as assessed by gel electrophoresis) were then pooled and concentrated in 30 kDa Amicon centrifuge unit. TLR7 content was then determined via absorbance at 327 nm and Fab content was determined via gel electrophoresis.

8. Determination of TLR7 Content in p(Man-TLR7) Conjugates

To determine the concentration of TLR7 content in polymer and polymer-Fab conjugates, absorbance at 327 nm was measured. Known quantities of mTLR7 in saline was measured (n=3 independent samples) at 327 nm in several concentrations ranging from 8 mg/mL to 1 mg/mL to calculate a standard curve as previously published in Wilson et al. 2019. The determined standard curve [TLR7 (mg/mL) =1.9663*A327+0.0517] was then used to calculate TLR7 concentration in the prepared p(Man-TLR7) conjugate.

9. Determination of Antibody Content in Fab-p(Man-TLR7) Conjugates

SDS-PAGE was performed on 4-20% gradient gels (Bio-Rad) using a standard curve of Fab protein (2, 1.5, 1, and 0.5 mg/mL) and two dilutions of Fab-p(Man-TLR7) conjugate samples were reduced with 10 mM dithiothreitol. Reducing conditions liberates conjugated p(Man-TLR7) allowing for reduced antibody band intensity to be analyzed. Band density of reduced sample and Fab standard curve was then analyzed using ImageJ and the Fab concentration of sample was calculated using standard curve generated.

10. Cell Culture

B16F10 cells (ATCC) were cultured in DMEM (Gibco) with 10% FBS (Thermo Fisher Scientific). Cell line was tested to confirm a lack of murine pathogens via IMPACT I PCR testing (IDEXX Laboratories).

11. Animals

All studies with animals were carried out in accordance to procedures approved by the Institutional Animal Care and Use Committee at the University of Chicago and housed in a specific pathogen-free environment at the University of Chicago. C57BL/6 female mice aged between 8-12 weeks were obtained from Charles River or The Jackson Laboratory.

12. B16F10 Tumor Inoculation and Treatment $3\times10^5$-$5\times10^5$ B16F10 cells resuspended in 50 μL of PBS were inoculated intradermally on the left side of the back of each C57BL/6 mouse. Tumors were measured every other day starting at day 3 or 4 after tumor inoculation with digital caliper. Volumes were calculated as volume V=length×width×height×π/6. Mice were sacrificed when the tumor volume had reached over 500 $mm^3$ or early endpoint criteria were reached. Treatments were performed on days described in figures (FIG. 10A, 11A, 12A, 13A) and in figure legends. Fab-p(Man-TLR7) vaccination or control treatment was administered in described doses and treatments via intravenous injection in a total volume of 100 μL or intratumoral injection in a total volume of 30 μL. 100 μg of anti-PD-1 and 100 μg of anti-CTLA-4 treatment was administered intraperitoneally or intravenously. Prior to initial treatment, mice were randomized into treatment groups with each treatment group split up between cages to reduce cage effects.

13. Immunofluorescence of Tumor Tissue Sections

Tumors were inoculated as described above for the B16F10 melanoma model. Harvested tumors were fixed with 4% paraformaldehyde (PFA) and flash frozen embedded in OCT medium and stored at −20° C. until sectioning. Sectioning was performed by the Human Tissue Resource Center at the University of Chicago. Briefly, serial sections of the tumor (10 um thick) were cut starting from the side until middle of tumor was reached. Slide mounted sections were then blocked with 2% BSA in PBS-T for 1 hour at room temperature. Tissue was incubated with primary antibodies: biotinylated mouse anti-EDA antibody (antibody from Abcam, biotinylated using Biotin-XX Microscale Protein Labeling Kit from Thermo Fisher, 1:500 final concentration) and rat anti-mouse CD31 (BioLegend clone MEC13.3, 1:100 final concentration) for 2 hours at room temperature, followed by staining with Alexa Fluor 488-conjugated streptavadin (BioLegend, 1:1000 final concentration) and goat Alexa Fluor 647-conjugated anti-rat IgG (Jackson ImmunoResearch, 1:500 final concentration) for 1 hour at room temperature. Slides were mounted with ProLong gold antifade medium with DAPI (Invitrogen) before imaging on a Leica DMi8 microscope. Images were taken with 10× lens. Composite images were made using ImageJ (NIH).

14. Serum Cytokine Concentration Analysis

B16F10 melanoma tumors were inoculated as described above, and mice were vaccinated as described above. On day 11 post-tumor inoculation, 50 μL of blood was collected in heparin-coated tubes, and serum was separated by centrifugation and stored at −20° C. Serum was assessed for IL-6, IL-12p70, TNFα, and IFNγ using Ready-Set-Go (eBioscience) or Quantikine (R&D) ELISA kits, following the manufacturer's instructions.

15. Anti-Fab IgG Concentration Analysis

B16F10 melanoma tumors were inoculated as described above, and mice were vaccinated as described above. On day 11 post-tumor inoculation, 50 μL of blood was collected in heparin-coated tubes, and plasma was separated by centrifugation and stored at −20° C. Plasma was assessed for anti-Fab IgGs by ELISA. 96-well ELISA plates (Nunc MaxiSorp flat-bottom plates, Thermo Fisher) were coated with 10 μg/mL anti-EDA Fab in PBS overnight at 4° C. The following day, plates were washed in PBS with 0.05% Tween 20 (PBS-T) and then blocked with 1× casein (Sigma) diluted in PBS for 1 hour at room temperature. Then, wells were washed with PBS-T and further incubated with various dilutions of plasma for 2 hours at room temperature. After 6 washes with PBS-T, wells were incubated for 1 hour at room temperature with horseradish peroxidase (HRP)-conjugated antibody against mouse IgG (Fc region specific, Jackson ImmunoResearch,). After 6 washes with PBS-T, bound anti-EDA Fab was detected with tetramethylbenzidine substrate by measurement of the absorbance at 450 nm with subtraction of the measurement at 570 nm.

16. Flow Cytometric Analysis on Tumors

Tumors were harvested from B16F10 tumor-bearing mice at day 10 post-inoculation, and cell suspensions were prepared. For staining, cells were washed with PBS and stained for 15 min on ice with a eFluor 455UV (eBioscience) fixable viability dye. The cells were washed twice with PBS then stained in PBS+2% fetal bovine serum (FBS) containing the antibody cocktail (BD Biosciences and Biolegend) for 20 min on ice. Stained cells were washed twice with PBS+2% FBS, and the cells were then fixed for 15 min in PBS+2% paraformaldehyde. Cells were washed twice and resuspended in PBS+2% FBS. If required, intracellular staining of FoxP3 was carried out using the eBioscience Foxp3 Transcription Factor Staining Buffer Set, per the manufacturer's instructions. Flow cytometry measurements were performed using a LSR Fortessa flow cytometer (BD Biosciences), and data were analyzed using FlowJo software (Tree Star).

17. Data Analysis

Statistical analysis and graphs were generated using Prism software (V7; GraphPad Software). For single comparisons, a two-tailed t test was used. Data were also analyzed using one-way ANOVA with Tukey's HSD post hoc test. Differences in survival curves were analyzed using log-rank (Mantel Cox) test. Group size (n) used to calculate significance is indicated in figure legend. Significance is reported with respect to vehicle control group, unless stated otherwise in figure legend. For showing statistical significance **P≤0.0001; *P≤0.001; **P≤0.01; *P≤0.05, unless otherwise stated.

F. References

The following references and the publications referred to throughout the specification, to the extent that they provide exemplary procedural or other details supplementary to those set forth herein, are specifically incorporated herein by reference.

1. Buchbinder, E. & Hodi, F. S. Cytotoxic T lymphocyte antigen-4 and immune checkpoint blockade. J. Clin. Invest. 125, 3377-3383 (2015).
2. Appay, V., Douek, D. C. & Price, D. A. CD8+ T cell efficacy in vaccination and disease. Nat. Med. 14, 623-628 (2008).
3. Koup, R. A. & Douek, D. C. Vaccine design for CD8 T lymphocyte responses. Cold Spring Harb. Perspect. Med. 1, a007252 (2011).
4. Banchereau, J. & Palucka, K. Immunotherapy: Cancer vaccines on the move. Nat. Rev. Clin. Oncol. 15, 9-10 (2017).
5. Sato, E. et al. Intraepithelial CD8+tumor-infiltrating lymphocytes and a high CD8+/regulatory T cell ratio are associated with favorable prognosis in ovarian cancer. Proc. Natl. Acad. Sci. U.S.A 102, 18538-43 (2005).
6. Yee, C. et al. Adoptive T cell therapy using antigen-specific CD8+ T cell clones for the treatment of patients with metastatic melanoma: in vivo persistence, migration, and antitumor effect of transferred T cells. Proc. Natl. Acad. Sci. U.S.A 99, 16168-73 (2002).
7. van Duikeren, S. et al. Vaccine-induced effector-memory CD8+ T cell responses predict therapeutic efficacy against tumors. J. Immunol. 189, 3397-403 (2012).
8. Ossendorp, F. et al. Vaccine-Induced Effector-Memory CD8+ T Cell Responses Predict Therapeutic Efficacy against Tumors. J Immunol Ref. 189, 3397-3403 (2012).
9. Wilson, D. S. et al. Antigens reversibly conjugated to a polymeric glyco-adjuvant induce protective humoral and cellular immunity. Nat. Mater. 18, 175-185 (2019).
10. Kerrigan, A. M. & Brown, G. D. C-type lectins and phagocytosis. Immunobiology 214, 562-575 (2009).
11. Burgdorf, S., Kautz, A., Bohnert, V., Knolle, P. A. & Kurts, C. Distinct pathways of antigen uptake and intracellular routing in CD4 and CD8 T cell activation. Science (80-.). 316, 612-616 (2007).
12. Weck, M. M. et al. TLR ligands differentially affect uptake and presentation of cellular antigens. Blood 109, 3890-4 (2007).
13. Oh, J. Z., Kurche, J. S., Burchill, M. A. & Kedl, R. M. TLR7 enables cross-presentation by multiple dendritic cell subsets through a type I IFN-dependent pathway. Blood 118, 3028-3038 (2011).
14. Bachmann, M. F. & Jennings, G. T. Vaccine delivery: a matter of size, geometry, kinetics and molecular patterns. Nat. Rev. Immunol. 10, 787-796 (2010).
15. Tritto, E., Mosca, F. & De Gregorio, E. Mechanism of action of licensed vaccine adjuvants. Vaccine 27, 3331-3334 (2009).
16. Moyer, T. J., Zmolek, A. C. & Irvine, D. J. Beyond antigens and adjuvants: formulating future vaccines. J. Clin. Invest. 126, 799-808 (2016).
17. Shaulov, A. & Murali-Krishna, K. CD8 T cell expansion and memory differentiation are facilitated by simultaneous and sustained exposure to antigenic and inflammatory milieu. J. Immunol. 180, 1131-8 (2008).
18. Lehmann, B. et al. Tumor location determines tissue-specific recruitment of tumor-associated macrophages and antibody-dependent immunotherapy response. Sci. Immunol. 2, eaah6413 (2017).
19. Rodell, C. B. et al. TLR7/8-agonist-loaded nanoparticles promote the polarization of tumor-associated macrophages to enhance cancer immunotherapy. Nat. Biomed. Eng. 2, 578-588 (2018).
20. Bevaart, L. et al. The High-Affinity IgG Receptor, FcγRI, Plays a Central Role in Antibody Therapy of Experimental Melanoma. Cancer Res. 66, 1261-1264 (2006).
21. Borsi, L. et al. Monoclonal antibodies in the analysis of fibronectin isoforms generated by alternative splicing of mRNA precursors in normal and transformed human cells. J. Cell Biol. 104, 595-600 (1987).
22. Oyama, F., Hirohashi, S., Shimosato, Y., Titani, K. & Sekiguchi, K. Deregulation of alternative splicing of fibronectin pre-mRNA in malignant human liver tumors. J. Biol. Chem. 264, 10331-10334 (1989).
23. Rybak, J. N., Roesli, C., Kaspar, M., Villa, A. & Neri, D. The extra-domain A of fibronectin is a vascular marker of solid tumors and metastases. Cancer Res. 67, 10948-10957 (2007).
24. Sakaguchi, S., Yamaguchi, T., Nomura, T. & Ono, M. Regulatory T Cells and Immune Tolerance. Cell 133, 775-787 (2008).
25. Wing, K. et al. CTLA-4 Control over Foxp3+ Regulatory T Cell Function. Science (80-.). 322, 271-275 (2008).
26. Abiko, K. et al. IFN-γ from lymphocytes induces PD-L1 expression and promotes progression of ovarian cancer. Br. J. Cancer 112, 1501-1509 (2015).
27. Peng, J. et al. Chemotherapy Induces Programmed Cell Death-Ligand 1 Overexpression via the Nuclear Factor-kB to Foster an Immunosuppressive Environment in Ovarian Cancer. Cancer Res. 75, 5034-5045 (2015).
28. Villa, A. et al. A high-affinity human monoclonal antibody specific to the alternatively spliced EDA domain of fibronectin efficiently targets tumor neo-vasculature in vivo. Int. J. Cancer 122, 2405-2413 (2008).
29. Julier, Z., Martino, M. M., De Titta, A., Jeanbart, L. & Hubbell, J. A. The TLR4 agonist fibronectin extra domain a is cryptic, Exposed by elastase-2; Use in a fibrin matrix cancer vaccine. Sci. Rep. 5, 1-10 (2015).

Example 3—Engineered Collagen-Binding Serum Albumin as a Polymeric Glyco-Adjuvant Carrier for Cancer Therapy A. Summary Here the inventors report the creation of a targeted therapeutic cancer vaccine using the p(Man-TLR7) glyco-polymer adjuvant. The inventors' vaccine material is composed of p(Man-TLR7) conjugated to a fusion protein consisting of serum albumin (SA) fused to a collagen binding domain (CBD), namely the A3 domain of von Willebrand factor (VWF) (FIG. 14A). CBD-SA combines the active tumor targeting mechanisms of CBD with the passive targeting mechanisms of SA, so the inventors hypothesized that CBD-SA could act to target p(Man-TLR7) to the tumor microenvironment and improve its anti-tumor efficacy.

The inventors' engineered material seeks to localize this strong adjuvant to the tumor microenvironment and prolong tumor retention in order to increase APC activation within the tumor microenvironment and enhance T cell priming in the tumor draining lymph node. In this vaccine approach, the tumor itself is utilized as a source of antigen to which immune responses are generated. By increasing intratumoral APC activation, the inventors' vaccination will shift the tumor immune environment from suppressive to inflammatory. The cytokines produced by activated APCs will create a proinflammatory cytokine milieu which will improve T cell functionality within the tumor, as well as enhance T cell priming in the tumor draining lymph node. This vaccination strategy seeks to provide an optimal immunostimulatory context for the priming of naïve T cells against cancer antigens and improved functionality of T cells within the tumor microenvironment.

By chemically linking the p(Man-TLR7) glyco-polymer to the CBD-SA moiety, the inventors aim to augment the tissue localization and biodistribution upon intravenous or intratumoral vaccination of their polymeric glyco-adjuvant. Principally, the CBD-SA component serves as a means to localize the inventors' adjuvant to the tumor and then slow adjuvant drainage through the tumor as the CBD-SA binds collagen in the tumor microenvironment. Here, the inventors performed preliminary testing of their CBD-SA-p(Man-TLR7) vaccination platform in the poorly immunogenic B16F10 murine model of melanoma. Treatment of tumor-bearing mice with CBD-SA-p(Man-TLR7) was able to slow tumor growth and prolong survival.

In addition to use as a monotherapy, the inventors plan to evaluate efficacy of their CBD-SA-p(Man-TLR7) vaccine in combination with checkpoint blockade antibodies. Specifically, anti-PD-1, anti-PD-L1, anti-CTLA-4, or combinations of these antibodies may show therapeutic synergy with the inventors' CBD-SA-p(Man-TLR7) vaccine and increase its efficacy. Intratumoral T regulatory cells (Tregs) have been shown to suppress the activity of effector T cells through a variety of mechanisms, so Treg depleting therapies such as anti-CTLA-4 may help amplify the functionality of the effector T cells generated by the inventors' vaccine. However, secretion of IFNγ by activated T cells has also been shown to increase PD-L1 expression by tumor cells, leading to dampened or dysfunctional T cell responses. It is possible that having an increased density of activated tumor infiltrating lymphocytes post vaccination may lead to PD-L1 upregulation. To combat this, blocking antibodies to PD-L1 or its receptor PD-1 may further enhance anti-tumor T cell responses. Preliminary results described herein show synergistic efficacy when the inventors' CBD-SA-p(Man-TLR7) vaccination was used in combination with anti-PD-1 and anti-CTLA-4 antibodies. The inventors plan on testing alternative antibody combinations or single antibody dosing in the future to see if further synergistic efficacy can be achieved.

B. Preparation of CBD-SA-p(Man-TLR7) Conjugates

Using the inventors' previously published conjugation strategy and bifunctional bicyclononyne (BCN) linker, the inventors were able to chemically link p(Man-TLR7) to free amines on CBD-SA (FIG. 14A). The CBD-SA-p(Man-TLR7) conjugates used herein will have an estimated 1:5 molar ratio of CBD-SA:p(Man-TLR7) polymer based on the initial molar concentrations of the CBD-SA and BCN that were used. The inventors can estimate that quantitation of BCN-decorated linker conjugated to each CBD-SA molecule corresponds with final quantity of p(Man-TLR7) per CBD-SA, as the cycloaddition reaction of the BCN moiety with the terminal azide of the p(Man-TLR7) polymer in order to produce full protein-linker-p(Man-TLR7) conjugates occurs at >95% yield. Production of CBD-SA-p (ManTLR7) conjugates has been reproducible and allows for the consistent generation of vaccine materials with little variability. For each step of conjugation, the inventors observe consistent shifts in protein mobility that correspond with increasing overall kDa of their material following the reaction of CBD-SA to linker and CBD-SA-linker to p(Man-TLR7) (FIG. 14B-C). Importantly, when CBD-SA was conjugated to p(Man-TLR7), the CBD-SA-p(Man-TLR7) conjugates retained the ability to bind to both collagen I and collagen III (FIG. 14D).

C. Therapeutic Efficacy

Once the inventors had prepared the CBD-SA-p(Man-TLR7) conjugates, they then assessed the anti-tumor efficacy in vivo (FIG. 15A). The inventors decided to assess the anti-tumor efficacy of their vaccination alone and in combination with checkpoint antibody therapy. To avoid immune-recognition and destruction, tumors co-opt a variety of mechanisms to suppress immune activity. Due to this, the inventors hypothesized that their vaccination would achieve maximal therapeutic efficacy with checkpoint blockade therapy to overcome Treg or PD-L1 mediated immunosuppression. Because inflammation within the tumor microenvironment can increase surface expression of PD-L1 on tumor cells as well as recruit immunosuppressive T regulatory cells (Tregs), the inventors first wanted to explore synergy of their vaccination with a combination anti-PD-1 and anti-CTLA4 antibody treatment.

Treatment of B16F10 tumor-bearing mice with intravenously (i.v.)-delivered human CBD-SA-p(Man-TLR7) resulted in reduced tumor size compared to untreated control animals (FIG. 15B). The inventors observed an improved anti-tumor efficacy and improved overall survival when they combined their CBD-SA-p(Man-TLR7) vaccination with anti-PD-1 and anti-CTLA-4 antibodies (FIG. 15B-C). This data shows that CBD-SA-p(Man-TLR7) vaccination in combination with checkpoint antibody therapy provides therapeutic benefit in this treatment of a poorly immunogenic melanoma model.

Because of immunogenicity concerns associated with injecting a human protein (CBD-SA) along with a strong adjuvant into mice, the inventors subsequently moved to using a murine version of CBD-SA. Upon vaccination of B16F10 tumor bearing mice with the murine CBD-SA conjugated to p(Man-TLR7), delivered i.v. (FIG. 16A), a significant slowing of tumor growth (FIG. 16B) and significantly improved survival (FIG. 16C) were observed when the vaccine was combined with anti-PD-1 and anti-CTLA-4 antibodies, similar to the results observed with the human CBD-SA-p(Man-TLR7) vaccine.

Finally, the inventors assessed two different administration routes for the vaccine: i.v. administration and intratumoral (i.t.) administration (FIG. 17A). A significant slowing of tumor growth (FIG. 17B) and improved survival (FIG. 17C) were observed with both i.v. and i.t. administration of the murine CBD-SA-p(Man-TLR7) in combination with anti-PD-1 and anti-CTLA-4 antibodies. However, i.t. administration of the vaccine resulted in improved anti-tumor efficacy (FIG. 17B-C) as compared to i.v. administration. Importantly, systemic levels of anti-CBD-SA antibodies (FIG. 17D) and the cytokines IL-6, IL-12p70, TNFα, and IFNγ (FIG. 17E-H) were not significantly increased in the serum after vaccination via either administration route, pointing towards the safety of the inventors' vaccine. This data indicates that CBD-SA-p(Man-TLR7) in combination with checkpoint antibody therapy is an effective treatment for the poorly immunogenic B16F10 murine melanoma model with minimal systemic toxicity.

D. Materials and Methods

1. Production and Purification of CBD-SA Protein

The sequences encoding for the fusion of human or murine VWF A3 domain residues Cys1670-Gly1874 (907-1111 of mature VWF) and mouse SA without pro-peptide (25-608 amino acids of whole SA) were synthesized and subcloned into the mammalian expression vector pcDNA3.1 (+) by Genscript. A sequence encoding for 6 His (SEQ ID NO: 30) was added at the C-terminus for further purification of the recombinant protein. Suspension-adapted HEK-293F cells were routinely maintained in serum-free FreeStyle 293 Expression Medium (Gibco). On the day of transfection, cells were diluted into fresh medium at a density of $1\times10^6$ cells/mL, 2 μg/mL plasmid DNA, 2 μg/mL linear 25 kDa polyethylenimine (Polysciences), and OptiPRO SFM media (4% final concentration, Thermo fisher scientific) were added. The culture flask was agitated by orbital shaking at 135 rpm at 37° C. in the presence of 5% $CO_2$. 7 days after transfection, the cell culture medium was collected by centrifugation and filtered through a 0.22 um filter. Culture media was loaded into a HisTrap HP 5 mL column (GE Healthcare), using an ÄKTA pure 25 (GE Healthcare). After washing of the column with wash buffer (20 mM imidazole, 20 mM $NaH_2PO_4$, 0.5 M NaCl, pH 7.4), protein was eluted with a gradient of 500 mM imidazole (in 20 mM $NaH_2PO_4$, 0.5 M NaCl, pH 7.4). The eluent was further purified with size exclusion chromatography using a HiLoad Superdex 200PG column (GE Healthcare). All purification steps were carried out at 4° C. The protein was verified as >90% pure by SDS-PAGE.

2. Binding Affinity Assay

Affinity measurements were performed using enzyme-linked immunosorbent assay (ELISA). 96 well ELISA plates (Greiner Bio-One) were coated with collagen I or collagen III (10 μg/mL each in PBS, EMD Millipore) overnight at 37° C., followed by blocking with 2% BSA in PBS with 0.05% Tween 20 (PBS-T) for 1 h at room temperature. Then, wells were washed with PBS-T and further incubated with CBD-SA at increasing concentrations for 2 h at room temperature. After three washes with PBS-T, wells were incubated for 1 h at room temperature with a biotin-conjugated antibody against mouse SA. Following three subsequent washes with PBS-T, the wells were incubated for 30 min at room temperature with avidin-horseradish peroxidase (HRP). After three washes, bound CBD-SA was detected with tetramethylbenzidine substrate by measurement of the absorbance at 450 nm with subtraction of the absorbance at 570 nm. The apparent $K_d$ values were obtained by nonlinear regression analysis in Prism software (version 7, GraphPad) assuming one-site-specific binding.

3. Reagents for In Vivo Studies

Rat anti-mouse PD-1 (Clone 29F.1A12, Bio X Cell) and hamster anti-mouse CTLA-4 (clone 9H10, Bio X Cell) were used for checkpoint blockade antibody studies. Before administration to mice, endotoxin levels of all formulations were tested via HEK-Blue mTLR4 cells from InvivoGen. A detailed explanation of the synthesis of the p(Man-TLR7) polymer and intermediates is provided in the inventors' previous publication (Wilson et al. 2019).

4. Production of CBD-SA-p(Man-TLR7) Conjugates

CBD-SA (at >3 mg/mL) was mixed with 5 (or up to 30) molar equivalents of 2 kDa self-immolative PEG linker in 500 μL phosphate buffer (pH 7.7) and reacted for 2 hours mixing at RT. The reaction solution was then purified twice via Zeba spin desalting columns with 30 kDa cutoff to remove unreacted linker (Thermo Fisher). Successful linker conjugation was confirmed using gel electrophoresis and comparison to a size standard of the unmodified CBD-SA. CBD-SA-linker construct in PBS (pH 7.4) was then reacted with 7 molar excess of p(Man-TLR7) polymer in an endotoxin-free Eppendorf tube for 2 hours, mixing, at RT. Excess p(Man-TLR7) polymer was removed using FPLC size-exclusion chromatography Superdex 200 column (GE). Fractions containing species with MW higher than 90 kDa (as assessed by gel electrophoresis) were then pooled and concentrated in 30 kDa Amicon centrifuge units. TLR7 content was then determined via absorbance at 327 nm and CBD-SA content was determined via gel electrophoresis.

5. Determination of TLR7 Content in p(Man-TLR7) Conjugates

To determine the concentration of TLR7 content in polymer and polymer-CBD-SA conjugates, absorbance at 327 nm was measured. Known quantities of mTLR7 in saline was measured (n=3 independent samples) at 327 nm in several concentrations ranging from 8 mg/mL to 1 mg/mL to calculate a standard curve as previously published in Wilson et al. 2019. The determined standard curve [TLR7 (mg/mL) =1.9663*A327+0.0517] was then used to calculate TLR7 concentration in the prepared p(Man-TLR7) conjugate.

6. Determination of CBD-SA Content in CBD-SA-p(Man-TLR7) Conjugates

SDS-PAGE was performed on 4-20% gradient gels (Bio-Rad) using a standard curve of CBD-SA protein (2, 1.5, 1, and 0.5 mg/mL) and two dilutions of CBD-SA-p(Man-TLR7) conjugate samples were reduced with 10 mM dithiothreitol. Reducing conditions liberates conjugated p(Man-TLR7) allowing for reduced CBD-SA band intensity to be analyzed. Band density of reduced sample and CBD-SA standard curve was then analyzed using ImageJ and the CBD-SA concentration of sample was calculated using standard curve generated.

7. Cell Culture

B16F10 cells (ATCC) were cultured in DMEM (Gibco) with 10% FBS (Thermo Fisher Scientific). Cell line was tested to confirm a lack of murine pathogens via IMPACT I PCR testing (IDEXX Laboratories).

8. Animals

All studies with animals were carried out in accordance to procedures approved by the Institutional Animal Care and Use Committee at the University of Chicago and housed in a specific pathogen-free environment at the University of Chicago. C57BL/6 female mice aged between 8-12 weeks were obtained from Charles River or The Jackson Laboratory.

9. B16F10 Tumor Inoculation and Treatment $5\times10^5$ B16F10 cells resuspended in 50 uL of PBS were inoculated intradermally on the left side of the back of each C57BL/6 mouse. Tumors were measured every other day starting at day 3 or 4 after tumor inoculation with digital caliper. Volumes were calculated as volume V=length×width×height×π/6. Mice were sacrificed when tumor volume had reached over 500 $mm^3$ or early endpoint criteria were reached. Treatments were performed on days described in figures (FIG. 15A, 16A, 17A) and in figure legends. CBD-SA-p(Man-TLR7) vaccination or control treatment was administered in described doses and treatments via intravenous injection in a total volume of 100 μL or intratumoral injection in a total volume of 30 μL. 100 μg of anti-PD-1 and 100 μg of anti-CTLA-4 treatment was administered intraperitoneally or intravenously. Drug administration was performed in a blinded fashion. Prior to initial treatment, mice were randomized into treatment groups with each treatment group split up between cages to reduce cage effects.

10. Serum Cytokine Concentration Analysis

B16F10 melanoma tumors were inoculated as described above, and mice were vaccinated as described above. On day 11 post-tumor inoculation, 50 μL of blood was collected in heparin-coated tubes, and serum was separated by centrifugation and stored at −20° C. Serum were assessed for IL-6, IL-12p70, TNFα, and IFNγ using Ready-Set-Go (eBioscience) or Quantikine (R&D) ELISA kits, following the manufacturer's instructions.

11. Anti-CBD IgG Concentration Analysis

B16F10 melanoma tumors were inoculated as described above, and mice were vaccinated as described above. On day 11 post-tumor inoculation, 50 μL of blood was collected in heparin-coated tubes, and plasma was separated by centrifugation and stored at −20° C. Plasma was assessed for anti-CBD-SA IgGs by ELISA. 96-well ELISA plates (Nunc MaxiSorp flat-bottom plates, Thermo Fisher) were coated with 10 μg/mL CBD-SA in PBS overnight at 4° C. The following day, plates were washed in PBS with 0.05% Tween 20 (PBS-T) and then blocked with 1× casein (Sigma) diluted in PBS for 1 hour at room temperature. Then, wells were washed with PBS-T and further incubated with various dilutions of plasma for 2 hours at room temperature. After 6 washes with PBS-T, wells were incubated for 1 hour at room temperature with a horseradish peroxidase (HRP)-conjugated antibody against mouse IgG (Jackson ImmunoResearch). After 6 washes with PBS-T, bound anti-EDA Fab was detected with tetramethylbenzidine substrate by measurement of the absorbance at 450 nm with subtraction of the measurement at 570 nm.

12. Data Analysis

Statistical analysis and graphs were generated using Prism software (V7; GraphPad Software). For single comparisons, a two-tailed t test was used. Data were also analyzed using one-way ANOVA with Tukey's HSD post hoc test, and variance between groups was found to be similar by Brown-Forsythe test. Differences in survival curves were analyzed using log-rank (Mantel Cox) test. Group size (n) used to calculate significance is indicated in figure legend. Significance is reported with respect to vehicle control group, unless stated otherwise in figure legend. For showing statistical significance **$P \leq 0.0001$; *$P \leq 0.001$; **$P \leq 0.01$; *$P \leq 0.05$; N.S.=not significant, unless otherwise stated.

E. References

The following references and the publications referred to throughout the specification, to the extent that they provide exemplary procedural or other details supplementary to those set forth herein, are specifically incorporated herein by reference.

1. Buchbinder, E. & Hodi, F. S. Cytotoxic T lymphocyte antigen-4 and immune checkpoint blockade. J. Clin. Invest. 125, 3377-3383 (2015).
2. Appay, V., Douek, D. C. & Price, D. A. CD8+ T cell efficacy in vaccination and disease. Nat. Med. 14, 623-628 (2008).
3. Koup, R. A. & Douek, D. C. Vaccine design for CD8 T lymphocyte responses. Cold Spring Harb. Perspect. Med. 1, a007252 (2011).
4. Banchereau, J. & Palucka, K. Immunotherapy: Cancer vaccines on the move. Nat. Rev. Clin. Oncol. 15, 9-10 (2017).
5. Sato, E. et al. Intraepithelial CD8+tumor-infiltrating lymphocytes and a high CD8+/regulatory T cell ratio are associated with favorable prognosis in ovarian cancer. Proc. Natl. Acad. Sci. U.S.A 102, 18538-43 (2005).
6. Yee, C. et al. Adoptive T cell therapy using antigen-specific CD8+ T cell clones for the treatment of patients with metastatic melanoma: in vivo persistence, migration, and antitumor effect of transferred T cells. Proc. Natl. Acad. Sci. U.S.A 99, 16168-73 (2002).
7. van Duikeren, S. et al. Vaccine-induced effector-memory CD8+ T cell responses predict therapeutic efficacy against tumors. J. Immunol. 189, 3397-403 (2012).
8. Ossendorp, F. et al. Vaccine-Induced Effector-Memory CD8+ T Cell Responses Predict Therapeutic Efficacy against Tumors. J Immunol Ref. 189, 3397-3403 (2012).
9. Wilson, D. S. et al. Antigens reversibly conjugated to a polymeric glyco-adjuvant induce protective humoral and cellular immunity. Nat. Mater. 18, 175-185 (2019).
10. Kerrigan, A. M. & Brown, G. D. C-type lectins and phagocytosis. Immunobiology 214, 562-575 (2009).
11. Burgdorf, S., Kautz, A., Böhnert, V., Knolle, P. A. & Kurts, C. Distinct pathways of antigen uptake and intracellular routing in CD4 and CD8 T cell activation. Science (80-.). 316, 612-616 (2007).
12. Weck, M. M. et al. TLR ligands differentially affect uptake and presentation of cellular antigens. Blood 109, 3890-4 (2007).
13. Oh, J. Z., Kurche, J. S., Burchill, M. A. & Kedl, R. M. TLR7 enables cross-presentation by multiple dendritic cell subsets through a type I IFN-dependent pathway. Blood 118, 3028-3038 (2011).
14. Ishihara, J. et al. Targeted antibody and cytokine cancer immunotherapies through collagen affinity. Sci. Transl. Med. In press, (2019).
15. Matsumura, Y. & Maeda, H. A new concept for macromolecular therapeutics in cancer chemotherapy: mechanism of tumoritropic accumulation of proteins and the antitumor agent smancs. Cancer Res. 46, 6387-92 (1986).
16. Bachmann, M. F. & Jennings, G. T. Vaccine delivery: a matter of size, geometry, kinetics and molecular patterns. Nat. Rev. Immunol. 10, 787-796 (2010).
17. Tritto, E., Mosca, F. & De Gregorio, E. Mechanism of action of licensed vaccine adjuvants. Vaccine 27, 3331-3334 (2009).
18. Moyer, T. J., Zmolek, A. C. & Irvine, D. J. Beyond antigens and adjuvants: formulating future vaccines. J. Clin. Invest. 126, 799-808 (2016).
19. Shaulov, A. & Murali-Krishna, K. CD8 T cell expansion and memory differentiation are facilitated by simultaneous and sustained exposure to antigenic and inflammatory milieu. J. Immunol. 180, 1131-8 (2008).
20. Sakaguchi, S., Yamaguchi, T., Nomura, T. & Ono, M. Regulatory T Cells and Immune Tolerance. Cell 133, 775-787 (2008).
21. Wing, K. et al. CTLA-4 Control over Foxp3+ Regulatory T Cell Function. Science (80-.). 322, 271-275 (2008).
22. Abiko, K. et al. IFN-γ from lymphocytes induces PD-L1 expression and promotes progression of ovarian cancer. Br. J. Cancer 112, 1501-1509 (2015).
23. Peng, J. et al. Chemotherapy Induces Programmed Cell Death-Ligand 1 Overexpression via the Nuclear Factor-kB to Foster an Immunosuppressive Environment in Ovarian Cancer. Cancer Res. 75, 5034-5045 (2015).

Although certain embodiments have been described above with a certain degree of particularity, or with reference to one or more individual embodiments, those skilled in the art could make numerous alterations to the disclosed embodiments without departing from the scope of this invention. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments. Any reference to a patent publication or other publication is a herein a specific incorporation by reference of the disclosure of that publication. The claims are not to be interpreted as including means-plus- or step-plus-function limitations, unless such a limitation is explicitly recited in a given claim using the phrase(s) "means for" or "step for," respectively.

The invention claimed is:

1. A method for treating cancer, for targeting a TLR agonist to a tumor in a subject, or for increasing the accumulation of a TLR agonist in a tumor in a subject, the method comprising administering a polypeptide comprising a collagen binding domain covalently linked to p(Man-TLR7), wherein the collagen binding domain comprises:

the amino acid sequence of one of SEQ ID NOS: 1, 2, or 8.

2. The method of claim 1, wherein the subject has cancer.

3. The method of claim 1, wherein the cancer comprises melanoma, lymphoma, bladder, breast, mammary carcinoma, or colon cancer.

4. The method of claim 3, wherein the cancer comprises melanoma, breast cancer, or a mammary carcinoma.

5. The method of claim 1, wherein the polypeptide or composition is administered systemically, by intravenous injection, intratumorally, or peritumorally.

6. The method of claim 1, wherein the polypeptide is further covalently linked to an albumin molecule, wherein the albumin molecule comprises an amino acid sequence having at least 95% sequence identity to one of SEQ ID NOs: 11-14.

7. The method of claim 1, wherein the molar ratio of the tumor targeting agent to p(Man-TLR) is 1:5.

8. The method of claim 1, wherein the polypeptide is further covalently linked to an albumin molecule, wherein the albumin molecule comprises the amino acid sequence of one of SEQ ID NOs: 11-14.

9. The method of claim 1, wherein the cancer comprises a solid tumor.

10. A method for treating melanoma in a subject, the method comprising administering a polypeptide comprising a collagen binding domain covalently linked to p(Man-TLR7), wherein the collagen binding domain comprises the amino acid sequence of one of SEQ ID NOS: 1, 2, or 8.

11. The method of claim 10, wherein the polypeptide is further covalently linked to an albumin molecule and wherein the albumin molecule comprises the amino acid sequence of one of SEQ ID NOs: 11-14.

* * * * *